(12) United States Patent
Lu et al.

(10) Patent No.: US 12,398,182 B2
(45) Date of Patent: Aug. 26, 2025

(54) LENTIVIRAL-BASED VECTORS AND RELATED SYSTEMS AND METHODS FOR EUKARYOTIC GENE EDITING

(71) Applicant: Wake Forest University Health Sciences, Winston-Salem, NC (US)

(72) Inventors: Baisong Lu, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1238 days.

(21) Appl. No.: 17/051,296

(22) PCT Filed: May 1, 2019

(86) PCT No.: PCT/US2019/030198
§ 371 (c)(1),
(2) Date: Oct. 28, 2020

(87) PCT Pub. No.: WO2019/213257
PCT Pub. Date: Nov. 7, 2019

(65) Prior Publication Data
US 2021/0047375 A1    Feb. 18, 2021

Related U.S. Application Data

(60) Provisional application No. 62/665,080, filed on May 1, 2018.

(51) Int. Cl.
*C12N 7/00* (2006.01)
*C07K 14/155* (2006.01)
(Continued)

(52) U.S. Cl.
CPC ............ *C07K 14/155* (2013.01); *C12N 9/22* (2013.01); *C12N 15/113* (2013.01); *C12N 15/86* (2013.01);
(Continued)

(58) Field of Classification Search
None
See application file for complete search history.

(56) References Cited

U.S. PATENT DOCUMENTS

2010/0173365 A1    7/2010  Borns
2017/0037432 A1*   2/2017  Donohoue ............ C12N 15/87
(Continued)

FOREIGN PATENT DOCUMENTS

CN    105861485 A  *  8/2016 ............ C12N 15/09
WO    2007/072056 A2    6/2007
(Continued)

OTHER PUBLICATIONS

WIPO English translation of CN105861485A (Year: 2016).*
(Continued)

*Primary Examiner* — M Franco G Salvoza
(74) *Attorney, Agent, or Firm* — Kilpatrick Townsend & Stockton LLP

(57) ABSTRACT

Provided are compositions, systems, and methods useful for effecting gene editing in eukaryotic cells. Compositions include plasmids that encode one or more viral fusion proteins in which one or more viral proteins are fused with an aptamer-binding protein. Compositions also include plasmids that encode a non-viral nucleic acid sequence, wherein the non-viral nucleic acid sequence encodes a CRISPR system component. In some instances, the non-viral nucleic acid sequence also includes an aptamer sequence. The plasmids can be used to generate viral particles, including lentivirus-like particles that contain a viral fusion protein
(Continued)

and a non-viral RNA sequence. Systems of producing such viral particles are provided. Also provided are methods of using the viral particles of the disclosure to effect gene editing in eukaryotic cells.

15 Claims, 34 Drawing Sheets

Specification includes a Sequence Listing.

(51) Int. Cl.
    *C12N 9/22*         (2006.01)
    *C12N 15/113*       (2010.01)
    *C12N 15/86*        (2006.01)
    *C12P 21/02*        (2006.01)
(52) U.S. Cl.
    CPC .... *C07K 2319/735* (2013.01); *C12N 2310/16* (2013.01); *C12N 2310/20* (2017.05); *C12N 2740/15022* (2013.01)

(56) References Cited

U.S. PATENT DOCUMENTS

| | | |
|---|---|---|
| 2017/0292156 A1 | 10/2017 | Davidson et al. |
| 2020/0308571 A1 | 10/2020 | Joung et al. |
| 2020/0390700 A1 | 12/2020 | Leonard et al. |
| 2021/0047375 A1 | 2/2021 | Lu et al. |

FOREIGN PATENT DOCUMENTS

| | | | | |
|---|---|---|---|---|
| WO | 2015002956 A1 | 1/2015 | | |
| WO | WO-2015089473 A1 * | 6/2015 | ........... | C12N 15/113 |
| WO | WO-2017059902 A1 * | 4/2017 | ............. | A47B 13/02 |
| WO | WO-2017194902 A2 * | 11/2017 | ........... | C07K 14/005 |
| WO | 2018213708 A1 | 11/2018 | | |
| WO | 2019005884 A1 | 1/2019 | | |
| WO | 2019213257 A1 | 11/2019 | | |
| WO | 2021055459 A1 | 3/2021 | | |

OTHER PUBLICATIONS

Zalatan et al., "Engineering Complex Synthetic Transcriptional Programs with CRISPR RNA Scaffolds," Cell 160: 339-350 (Year: 2015).*
WIPO English translation of WO2017194902 (Year: 2017).*
Anonymous, "The WFIRM 2017 Summer Scholars Program Final Research Day & Poster Symposium," 2017, pp. 1-28, Retrieved from the Internet: URL:https://school.wakehealth.edu/-/media/WakeForest/School/Files/Research/WFIRM/Summer-Scholars/2017-Summer-Scholars-Projects.pdf [retrieved on Jul. 24, 2019], p. 12.
Prel, A. et al., "Highly efficient in vitro and in vivo delivery of functional RNAs using new versatile MS2-chimeric retrovirus-like particles", Molecular Therapy-Methods & Clinical Development, vol. 2, Oct. 21, 2015, p. 15039.
Konermann, S. et al., "Genome-scale transcriptional activation by an engineered CRISPR-Cas9 complex", Nature, vol. 517, No. 7536, Jan. 1, 2015, pp. 583-588.
Zalatin, J. et al., "Engineering Complex Synthetic Transcriptional Programs with CRISPR RNA Scaffolds", Cell, vol. 160, No. 1-2, Jan. 1, 2015, pp. 339-350.
Lu, B. et al., "Delivering SaCas9 mRNA by lentivirus-like bionanoparticles for transient expression and efficient genome editing", Nucleic Acids Research, vol. 47, No. 8, Feb. 13, 2019, p. e44.
Javidi-Parsijani P. et al., "No evidence of genome editing activity from Natronobacterium gregoryi Argonaute (NgAgo) in human cells", PLOS One, vol. 12, No. 5, May 11, 2017, p. e0177444.
Lyu, P. et al., "Delivering Cas9/sgRNA ribonucleoprotein (RNP) by lentiviral capsid-based bionanoparticles for efficient 'hit-and-run' genome editing", Nucleic Acids Research, vol. 1, Jul. 12, 2019, pp. 1-13.

PCT Search Report & Written Opinion for PCT/US2019/030198 mailed Oct. 2, 2019.
Tozser et al., In Vitro Processing of HIV-1 Nucleocapsid Protein by the Viral Proteinase: Effects of Amino Acid Substitutions at the Scissile Bond in the Proximal Zinc Finger Sequence, Biochemistry, vol. 43, No. 14, Apr. 13, 2004, pp. 4304-4312.
Abudayyeh et al., "C2c2 is a Single-Component Programmable RNA-Guided RNA-Targeting CRISPR Effector", Science, vol. 353, No. 6299, Aug. 5, 2016, 23 pages.
Alton et al., "Nucleotide Sequence Analysis of the Chloramphenicol Resistance Transposon Tn9", Nature, vol. 282, Dec. 1979, pp. 864-869.
Bae et al., "Cas-OFFinder: A Fast and Versatile Algorithm That Searches for Potential Off-target Sites of Cas9 RNA-guided Endonucleases", Bioinformatics, vol. 30, No. 10, May 15, 2014, pp. 1473-1475.
Barrangou et al., "CRISPR Provides Acquired Resistance Against Viruses in Prokaryotes", Science, vol. 315, No. 5819, Mar. 23, 2007, pp. 1709-1712.
Batzer et al., "Enhanced Evolutionar PCR using Oligonucleotides With Inosine at the 3'-terminus", Nucleic Acids Research, vol. 19, No. 18, 1991, 1 page.
Bertrand et al., "Localization of ASH1 mRNA Particles in Living Yeast", Molecular Cell, vol. 2, Oct. 1998, pp. 437-445.
Bikard et al., "Programmable Repression and Activation of Bacterial Gene Expression Using an Engineered CRISPR-Cas System", Nucleic Acids Research, vol. 41, No. 15, Jun. 12, 2013, pp. 7429-7437.
Briggs et al., "The Stoichiometry of Gag protein in HIV-1", Nature Structural & Molecular Biology, vol. 11, No. 7, Jul. 2004, pp. 672-675.
Cai et al., "Targeted Genome Editing by Lentiviral Protein Transduction of Zinc-finger and TAL-effector Nucleases", Elife, vol. 3, Apr. 24, 2014, 19 pages.
Charlesworth et al., "Identification of Pre-existing Adaptive Immunity to Cas9 Proteins in Humans", Nature Medicine, vol. 25, No. 2, Feb. 2019, pp. 249-254.
Chen et al., "Dynamic Imaging of Genomic Loci in Living Human Cells by an Optimized CRISPR/Cas System", Cell, vol. 155, No. 7, Dec. 19, 2013, pp. 1479-1491.
Cho et al., "Targeted Genome Engineering in Human Cells with the Cas9 RNA-Guided Endonuclease", Nature Biotechnology, vol. 31, No. 3, Mar. 2013, pp. 230-232.
Choi et al., "Lentivirus Pre-packed With Cas9 Protein for Safer Gene Editing", Gene Therapy, vol. 23, No. 7, Jul. 2016, pp. 627-633.
Chylinski et al., "The tracrRNA and Cas9 Families of Type II CRISPR-Cas Immunity Systems", RNA Biology, vol. 10, No. 5, May 2013, pp. 726-737.
Cong et al., "Multiplex Genome Engineering Using CRISPR/Cas Systems", Science, vol. 339, No. 6121, Feb. 15, 2013, pp. 819-823.
Core et al., "Nascent RNA Sequencing Reveals Widespread Pausing and Divergent Initiation at Human Promoters", Science, vol. 322, Dec. 19, 2008, pp. 1845-1848.
Cradick et al., "CRISPR/Cas9 Systems Targeting β-Globin and CCR5 Genes Have Substantial Off-Target Activity", Nucleic Acids Research, vol. 41, No. 20, Nov. 2013, pp. 9584-9592.
De Guzman et al., "Structure of the HIV-1 Nucleocapsid Protein Bound to the Sl3 Psi-RNA Recognition Element", Science, vol. 279, No. 5349, Jan. 16, 1998, pp. 384-388.
Esvelt et al., "Orthogonal Cas9 Proteins for RNA-Guided Gene Regulation and Editing", Nature Methods, vol. 10, No. 11, Nov. 2013, pp. 1116-1121.
Fonfara et al., "The CRISPR-Associated DNA-Cleaving Enzyme Cpf1 Also Processes Precursor CRISPR RNA", Nature, vol. 32, Apr. 2016, pp. 517-522.
Fouts et al., "Functional Recognition of Fragmented Operator Sites by R17/MS2 Coat Protein, a Translational Repressor", Nucleic Acids Research, vol. 25, No. 22, Nov. 15, 1997, pp. 4464-4473.
Friedland et al., "Characterization of *Staphylococcus aureus* Cas9: a Smaller Cas9 for All-in-one Adeno-associated Virus Delivery and Paired Nickase Applications", Genome Biology, vol. 16, No. 1, Nov. 24, 2015, 10 pages.

(56) References Cited

OTHER PUBLICATIONS

Fu et al., "High-frequency Off-Target Mutagenesis Induced by CRISPR-Cas Nucleases in Human Cells", Nature Biotechnology, vol. 31, No. 9, Sep. 2013, pp. 822-826.
Fusco et al., "Single mRNA Molecules Demonstrate Probabilistic Movement in Living Mammalian Cells", Current Biology, vol. 13, No. 2, Jan. 21, 2003, pp. 161-167.
Gilbert et al., "CRISPR-Mediated Modular RNA-Guided Regulation of Transcription in Eukaryotes", Cell, vol. 154, No. 2, Jul. 18, 2013, pp. 442-451.
Gilbert et al., "Genome-Scale CRISPR-Mediated Control of Gene Repression and Activation", Cell, vol. 159, No. 3, Oct. 23, 2014, pp. 647-661.
Grigorov et al., "Intracellular HIV-1 Gag Localization Is Impaired by Mutations in the Nucleocapsid Zinc Fingers", Retrovirology, vol. 4, No. 54, Aug. 3, 2007, 12 pages.
Haeussler et al., "Evaluation of Off-Target and On-Target Scoring Algorithms and Integration into the Guide RNA Selection Tool CRISPOR", Genome Biology, vol. 17, No. 148, Jul. 5, 2016, pp. 1-12.
Hah et al., "Enhancer Transcripts Mark Active Estrogen Receptor Binding Sites", Genome Research, vol. 23, No. 8, Aug. 2013, pp. 1210-1213.
Hall et al., "Expression and Regulation of *Escherichia coli* Lacz Gene Fusions in Mammalian Cells", Journal of Molecular and Applied Genetics, vol. 1, No. 2, 1983, pp. 101-109.
Hayashi et al., "A Method for Stabilizing RNA for Transfection That Allows Control of Expression Duration", Developmental Dynamics, vol. 239, No. 7, Jul. 2010, pp. 2034-2040.
Holtkamp et al., "Modification of Antigen-encoding Rna Increases Stability, Translational Efficacy, and T-cell Stimulatory Capacity of Dendritic Cells", Blood, vol. 108, No. 13, Dec. 15, 2006, pp. 4009-4017.
Hou et al., "Efficient Genome Engineering in Human Pluripotent Stem Cells Using Cas9 From Neisseria MeningitidisEfficient Genome Engineering in Human Pluripotent Stem Cells Using Cas9 From Neisseria Meningitidis", Proceedings of the National Academy of Sciences of the United States of America, vol. 110, No. 39, Sep. 24, 2013, pp. 15644-15649.
Hsu et al., "DNA Targeting Specificity of RNA-Guided Cas9 Nucleases", Nature Biotechnology, vol. 31, No. 9, Sep. 2013, pp. 827-832.
Jalaguier et al., "Efficient Production of HIV-1 Virus-Like Particles from a Mammalian Expression Vector Requires the N-Terminal Capsid Domain", PLoS One, vol. 6, No. 11, Mar. 2011, 13 pages.
Jinek et al., "A Programmable Dual RNA-guided DNA Endonuclease in Adaptive Bacterial Immunity", Science, vol. 337, No. 6096, Aug. 17, 2012, pp. 816-821.
Jinek et al., "RNA-Programmed Genome Editing in Human Cells", eLife Research Article, Genomics and Evolutionary Biology, Human Biology and Medicine, vol. 2, Jan. 29, 2013, 9 pages.
Kaya et al., "Highly Specific Targeted Mutagenesis in Plants Using *Staphylococcus aureus* Cas9", Scientific Reports, vol. 6, No. 26871, May 26, 2016, pp. 1-9.
Kim et al., "Highly Efficient RNA-Guided Genome Editing in Human Cells Via Delivery of Purified Cas9 Ribonucleoproteins", Genome Research, vol. 24, No. 6, Apr. 2, 2014, pp. 1012-1019.
Konnyu et al., "Gag-pol Processing During HIV-1 Virion Maturation: A Systems Biology Approach", PLOS Computational Biology, vol. 9, No. 6, 2013, 15 pages.
Kutluay et al., "Global Changes in the RNA Binding Specificity of HIV-1 Gag Regulate Virion Genesis", Cell, vol. 159, No. 5, Nov. 20, 2014, pp. 1096-1109.
Landt et al., "ChIP-Seq Guidelines and Practices of the ENCODE and modENCODE Consortia", Genome Research, vol. 22, No. 9, 2012, pp. 1813-1831.
Lim et al., "Translational Repression and Specific RNA Binding by the Coat Protein of the Pseudomonas Phage Pp7", Journal of Biological Chemistry, vol. 276, No. 25, Jun. 22, 2001, pp. 22507-22513.
Long et al., "Postnatal Genome Editing Partially Restores Dystrophin Expression in a Mouse Model of Muscular Dystrophy", Science, vol. 351, No. 6271, Jan. 22, 2016, pp. 400-403.
Ma et al., "Multiplexed Labeling of Genomic Loci with dCas9 and Engineered SgRNAs using CRISPRainbow", Nature Biotechnology, vol. 34, No. 5, Apr. 18, 2016, pp. 528-530.
Makarova et al., "An Updated Evolutionary Classification of CRISPR-Cas Systems", Nature Reviews Microbiology, vol. 13, No. 11, Nov. 2015, pp. 722-736.
Makarova et al., "Evolution and Classification of the CRISPR-Cas Systems", Nature Reviews, vol. 9, Jun. 2011, pp. 467-477.
Mali et al., "RNA-Guided Human Genome Engineering Via Cas9", Science, vol. 339, No. 6121, Feb. 15, 2013, pp. 823-826.
Malina et al., "Repurposing CRISPR/Cas9 for in Situ Functional Assays", Genes & Development, vol. 27, No. 23, Dec. 1, 2013, pp. 2602-2614.
Mock et al., "Novel Lentiviral Vectors With Mutated Reverse Transcriptase for Mrna Delivery of Tale Nucleases", Scientific Reports, vol. 4, 2014, 8 pages.
Mout et al., "Direct Cytosolic Delivery of CRISPR/Cas9-ribonucleoprotein for Efficient Gene Editing", ACS Nano, vol. 11, No. 3, Jan. 27, 2017, pp. 2452-2458.
Muller et al., "Human Immunodeficiency Virus Type 1 Vpr Protein is Incorporated Into the Virion in Significantly Smaller Amounts than Gag and is Phosphorylated in Infected Cells", Journal of Virology, vol. 74, No. 20, Oct. 2000, pp. 9727-9731.
Muratori et al., "Lentivirus-Based Virus-Like Particles as a New Protein Delivery Tool", Methods in molecular biology, vol. 614, Nov. 2010, pp. 111-124.
Nelles et al., "Programmable RNA Tracking in Live Cells with CRISPR/Cas9", Cell, vol. 165, No. 2, Apr. 7, 2016, pp. 488-496.
Nelson et al., "In Vivo Genome Editing Improves Muscle Function in a Mouse Model of Duchenne Muscular Dystrophy", Science, vol. 351, No. 6271, Jan. 22, 2016, pp. 403-407.
Newbury et al., "Stabilization of Translationally Active mRNA by Prokaryotic REP Sequences", Cell, vol. 48, No. 2, Jan. 30, 1987, pp. 297-310.
Ohtsuka et al., "An Alternative Approach to Deoxyoligonucleotides as Hybridization Probes by Insertion of Deoxyinosine at Ambiguous Codon Positions", Journal of Biological Chemistry, vol. 260, No. 5, Mar. 10, 1985, pp. 2605-2608.
Ortinski et al., "Integrase-Deficient Lentiviral Vector as an All-in-One Platform for Highly Efficient CRISPR/Cas9-Mediated Gene Editing", Molecular Therapy: Methods & Clinical Development, vol. 5, Apr. 19, 2017, pp. 153-164.
Park et al., "Cas-Analyzer: an Online Tool for Assessing Genome Editing Results Using NGS Data", Bioinformatics, vol. 33, No. 2, Aug. 2017, pp. 286-288.
Peabody et al., "Control of Translational Repression by Protein-protein Interactions", Nucleic Acids Research, vol. 20, No. 7, Apr. 11, 1992, pp. 1649-1655.
Peretti et al., "Cell Death Induced by the Herpes Simplex Virus-1 Thymidine Kinase Delivered by Human Immunodeficiency Virus-1-based Virus-like Particles", Molecular Therapy, vol. 12, No. 6, Dec. 2005, pp. 1185-1196.
Qi et al., "Repurposing CRISPR as an RNA-guided Platform for Sequence-Specific Control of Gene Expression", Cell, vol. 152, No. 5, Feb. 28, 2013, 22 pages.
Ramakrishna et al., "Gene Disruption by Cell-Penetrating Peptide-Mediated Delivery of Cas9 Protein and Guide RNA", Genome Research, vol. 24, No. 6, Jun. 2014, pp. 1020-1027.
Ran et al., "In Vivo Genome Editing Using *Staphylococcus aureus* Cas9", Nature, vol. 520, No. 7546, Apr. 9, 2015, pp. 186-191.
Rolls et al., "Novel Infectious Particles Generated by Expression of the Vesicular Stomatitis Virus Glycoprotein from a Self-Replicating RNA", vol. 79, No. 3, Nov. 1994, pp. 497-506.
Rossolini et al., "Use of Deoxyinosine-containing Primers Vs Degenerate Primers for Polymerase Chain Reaction Based on Ambiguous Sequence Information", Molecular and Cellular Probes, vol. 8, No. 2, Apr. 1994, pp. 91-98.
Rulli et al., "Selective and Nonselective Packaging of Cellular RNAs in Retrovirus Particles", Journal of Virology, vol. 81, No. 12, Jun. 2007, pp. 6623-6631.

(56) References Cited

OTHER PUBLICATIONS

Sampson et al., "A CRISPR-CAS System Mediates Bacterial Innate Immune Evasion and Virulence", Nature, vol. 497, May 9, 2013, pp. 254-257.
Scarlata et al., "Role of HIV-1 Gag Domains in Viral Assembly", Biochimica et Biophysica Acta, vol. 1614, No. 1, 2003, pp. 62-72.
Schrom et al., "Translation of Angiotensin-converting Enzyme 2 upon Liver- and Lung-targeted Delivery of Optimized Chemically Modified mRNA", Molecular Therapy—Nucleic Acids, vol. 7, Jun. 16, 2017, pp. 350-365.
Shalem et al., "Genome-Scale CRISPR-Cas9 Knockout Screening in Human Cells", Science, vol. 343, Issue 6166, Jan. 3, 2014, pp. 84-87.
Shechner et al., "CRISPR Display: A Modular Method for locus-Specific Targeting of long Noncoding RNAs and Synthetic RNA devices in Vivo", Nature Methods, vol. 12, No. 7, Jul. 2015, 20 pages.
Sheng et al., "Cleavage of p15 Protein in Vitro by Human Immunodeficiency Virus Type 1 Protease Is RNA Dependent", Journal of Virology, vol. 68, No. 10, Oct. 1994, pp. 6207-6214.
Tabebordbar et al., "In Vivo Gene Editing in Dystrophic Mouse Muscle and Muscle Stem Cells", Science, vol. 351, No. 6271, Jan. 23, 2016, pp. 407-411.
Toh et al., "Isolation and characterization of a rat liver alkaline phosphate gene: A single gene with two promoters", European Journal of Biochemistry, vol. 182, 1989, pp. 231-237.
Tritch et al., "Mutagenesis of Protease Cleavage Sites in the Human Immunodeficiency Virus Type 1 Gag Polyprotein", Journal of Virology, vol. 65, No. 2, Feb. 1991, pp. 922-930.
Wagner et al., "High Prevalence of *Streptococcus pyogenes* Cas9-reactive T Cells within the Adult Human Population", Nature Medicine, vol. 25, No. 2, Feb. 2019, pp. 242-248.
Wu et al., "Fluorescence Fluctuation Spectroscopy Enables Quantitative Imaging of Single mRNAs in Living Cells", Biophysical Journal, vol. 102, No. 12, Jun. 2012, pp. 2936-2944.
Wu et al., "Targeting Foreign Proteins to Human Immunodeficiency Virus Particles via Fusion With Vpr and Vpx", Journal of Virology, vol. 69, No. 6, Jun. 1995, pp. 3389-3398.
Zetsche et al., "Cpf1 Is a Single RNA-Guided Endonuclease of a Class 2 CRISPR-Cas System", Cell, vol. 163, No. 3, Oct. 22, 2015, pp. 759-771.
Zuris et al., "Cationic Lipid-Mediated Delivery of Proteins Enables Efficient Protein-Based Genome Editing in Vitro and in Vivo", Nature Biotechnology, vol. 33, No. 1, Jan. 2015, pp. 73-80.
International Application No. PCT/US2021/060099, International Search Report and Written Opinion mailed on Mar. 21, 2022, 8 pages.
International Application No. PCT/US2022/016053, International Search Report and Written Opinion mailed on May 3, 2022, 19 pages.
International Application No. PCT/US2023/063954, International Search Report and Written Opinion, mailed on Jul. 31, 2023, 15 pages.
Ling, et al., "Lentiviral Delivery of Co-packaged Cas9 mRNA and a Vegfa-targeting Guide RNA Prevents wet Age-related Macular Degeneration in Mice", Nature Biomedical Engineering, vol. 5, No. 2, Feb. 2021, pp. 144-156.
Lyu, et al., "Adenine Base Editor Ribonucleoproteins Delivered by Lentivirus-Like Particles Show High On-Target Base Editing and Undetectable RNA Off-Target Activities", The CRISPR Journal, vol. 4, No. 1, Feb. 19, 2021, pp. 69-81.
Lyu, et al., "Virus-Like Particle Mediated CRISPR/Cas9 Delivery for Efficient and Safe Genome Editing", Life, vol. 10, No. 12, Dec. 2020, pp. 1-16.
Vamva, et al., "Development of a Novel Competitive qRT-PCR Assay to Measure Relative Lentiviral Packaging Efficiency", Molecular Therapy: Methods & Clinical Development, vol. 19, Dec. 11, 2020, pp. 307-319.
Yao, et al., "Engineered Extracellular Vesicles as Versatile Ribonucleoprotein Delivery Vehicles for Efficient and Safe Crispr Genome Editing", Journal of Extracellular Vesicle, vol. 10, No. 5, Mar. 16, 2021, pp. 1-14.
Yin, et al., "Targeting Herpes Simplex Virus with CRISPR-Cas9 Cures Herpetic Stromal Keratitis in Mice", Nature Biotechnology, vol. 39, No. 5, May 1, 2021, pp. 1-29.

\* cited by examiner

| | | |
|---|---|---|
| SEQ ID NO: 103 | GAAGAGCAAGCGCCATACTCCTGTGTGGAGAAGTCTGCCGTTACTGCCCTGTGGGGCAAGGTG | 13.5% |
| SEQ ID NO: 104 | GAAGAGCAAGCGCCATACTC------------------CTGCCGTTACTGCCCTGTGGGGCAAGGTG | 8.5% |
| SEQ ID NO: 105 | GAAGAGCAAGCGCCATACTCCTGT-GAGAAGTCTGCCGTTACTGCCCTGTGGGGCAAGGTG | 7.9% |
| SEQ ID NO: 106 | GAAGAGCAAGCGCCATACTCCTGT----GAAGTCTGCCGTTACTGCCCTGTGGGGCAAGGTG | 5.6% |
| SEQ ID NO: 107 | GAAGAGCAAGCGCCATACTCCT--------GTCTGCCGTTACTGCCCTGTGGGGCAAGGTG | 5.6% |
| SEQ ID NO: 108 | GAAGAGCAAGCGCCATACTCCT------GAGAAGTCTGCCGTTACTGCCCTGTGGGGCAAGGTG | 5.1% |
| SEQ ID NO: 109 | GAAGAGCAAGCGCCATACTCC---TGGAGAAGTCTGCCGTTACTGCCCTGTGGGGCAAGGTG | 2.6% |
| SEQ ID NO: 110 | GAAGAGCAAGCGCCATACT--------------------CCTGTGGGGCAAGGTG | 1.3% |
| SEQ ID NO: 111 | GAAGAGCAAGCGCCATACTCCTGT----GTCTGCCGTTACTGCCCTGTGGGGCAAGGTG | 1.2% |
| SEQ ID NO: 112 | GAAGAGCAAGC---------------------GCCGTTACTGCCCTGTGGGGCAAGGTG | 1.2% |

FIG. 6

A Targeting SCD mutant sequence in GFP-report

HBB sgRNA1: 3' CACCUCUUCAGACGGCAAUGA 5'

| SEQ ID NO | Sequence | % |
|---|---|---|
| SEQ ID NO: 136 | AGCGCCATACTCCTGTGGAGAAGTCTGCCGTTACTGCCCT | |
| SEQ ID NO: 137 | AGCGCCATACTC------------------------------CTGCCGTTACTGCCT | 13.5% |
| SEQ ID NO: 138 | AGCGCCATACTCCTGT - GAGAAGTCTGCCGTTACTGCCCT | 8.5% |
| SEQ ID NO: 139 | AGCGCCATACTCCTGT --- GAAGTCTGCCGTTACTGCCCT | 7.9% |
| SEQ ID NO: 140 | AGCGCCATACTCCT-----------------GTCTGCCGTTACTGCCCT | 5.6% |
| SEQ ID NO: 141 | AGCGCCATACTCCT------GAGAAGTCTGCCGTTACTGCCCT | 5.6% |
| SEQ ID NO: 142 | AGCGCCATACTCC --- TGGAGAAGTCTGCCGTTACTGCCCT | 5.1% |
| SEQ ID NO: 143 | AGCGCCATACT------------------------------CCT | 2.6% |
| SEQ ID NO: 144 | AGCGCCATACTCCTGT -----------GTCTGCCGTTACTGCCCT | 1.3% |
| SEQ ID NO: 145 | AGC---------------------------------GCCGTTACTGCCCT | 1.2% |
| SEQ ID NO: 146 | | 1.2% |

Total Indel: 86.5%

FIG. 12A

**Targeting *IL2RG***

| | | |
|---|---|---|
| SEQ ID NO: 148 | TTCCTGACACAGACAGACAGACTACAC<u>CCAGGGAATGAAGAGC</u> | 87% |
| SEQ ID NO: 149 | TTCCTGACACAGACAGACAGACTACA-CCAGGGAATGAAGAGC | 3.6% |
| SEQ ID NO: 150 | TTCCTGACACAGACAGACAGACTA------CAGGGAATGAAGAGC | 2.8% |
| SEQ ID NO: 151 | TTCCTGACACAGACAGACAGACTACA---CAGGGAATGAAGAGC | 0.5% |
| SEQ ID NO: 152 | TTCCTGACACAGA---------------------CAGGGAATGAAGAGC | 0.3% |
| SEQ ID NO: 153 | TTCCTGACACAGACAGACAGACTA----CCAGGGAATGAAGAGC | 0.3% |
| SEQ ID NO: 154 | TTCCTGACACAGACAGACAGACTACAC--------GAAGAGC | 0.1% |
| SEQ ID NO: 155 | TTCCTGACACAGACAGACAGACAGA------------CAGGGAATGAAGAGC | 0.1% |

Total Indel: 13%

FIG. 12C

**Targeting *IL2RG***

| | | |
|---|---|---|
| SEQ ID NO: 156 | TTCCTGACACAGACAGACAGACTACAC<u>CCAGGGAATGAAGAGC</u> | 12.4% |
| SEQ ID NO: 157 | TTCCTGACACAGACAGACAGACTACA-CCAGGGAATGAAGAGC | 24.1% |
| SEQ ID NO: 158 | TTCCTGACACAGACAGACAGACTA------CAGGGAATGAAGAGC | 18.1% |
| SEQ ID NO: 159 | TTCCTGACACAGACAGACAGACTACA---CAGGGAATGAAGAGC | 3.5% |
| SEQ ID NO: 160 | TTCCTGACACAGA---------------------CAGGGAATGAAGAGC | 1.8% |
| SEQ ID NO: 161 | TTCCTGACACAGACAGACAGACTA----CCAGGGAATGAAGAGC | 1.6% |
| SEQ ID NO: 162 | TTCCTGACACAGACAGACAGACTACAC--------GAAGAGC | 1.0% |
| SEQ ID NO: 163 | TTCCTGACACAGACAGACAGACAGA------------CAGGGAATGAAGAGC | 0.7% |

Total Indel: 87.6%

FIG. 12D

E Targeting wild-type *HBB*

*HBB* sgRNA1: 3' CACCUCUUCAGACGGCAAUGA 5'

| | | LV | LVLP | IDLV | AAV |
|---|---|---|---|---|---|
| SEQ ID NO: 164 | ATGGTGCACCTGACTCCTGAGGAGAAGTCTGCCGTTACTG | | | | |
| SEQ ID NO: 165 | ATGGTGCACCTGACTCCT----GAGAAGTCTGCCGTTACTG | 39.6% | 1.39% | 11.3% | 4.2% |
| SEQ ID NO: 166 | ATGGTGCACCTGACTCCTGA-GAGAAGTCTGCCGTTACTG | 4.9% | 0.18% | 0.93% | 0.26% |
| SEQ ID NO: 167 | ATGGTGCACCTGACTCCT------GAAGTCTGCCGTTACTG | 1.9% | 0.05% | 0.33% | 0.11% |
| SEQ ID NO: 168 | ATGGTGCACCTGACTCCT---GGAGAAGTCTGCCGTTACTG | 1.8% | 0.06% | 0.30% | 0.13% |
| SEQ ID NO: 169 | ATGGTGCACCTGACTCCTG-------AGTCTGCCGTTACTG | 1.4% | 0.04% | 0.38% | 0.12% |
| SEQ ID NO: 170 | ATGGTGCACCTGACTC--------------CTGCCGTTACTG | 1.2% | 0.03% | 0.28% | 0.11% |
| SEQ ID NO: 171 | ATGGTGCACCT-----------GAGAAGTCTGCCGTTACTG | 0.72% | 0.02% | 0.27% | 0.10% |
| SEQ ID NO: 172 | ATGGTGCACCTGACTC-------GAGAAGTCTGCCGTTACTG | 0.62% | 0.02% | 0.27% | 0.10% |
| SEQ ID NO: 173 | ATGGTGCACCTGACTCCTGAG-------GTCTGCCGTTACTG | 0.62% | 0.02% | 0.12% | 0.05% |
| SEQ ID NO: 174 | ATGGTGCACCTGACTCCTGAG----------TGCCGTTACTG | 0.45% | 0.01% | 0.08% | 0.02% |
| Total Indel: | | 81.8% | 3.0% | 21.1% | 8.7% |

FIG. 12E

Off-target 8: AGTCACAGGCAGACTTCTCCAC*GGGGGGGG*

`|||||| ||||||||||||||`

HBB gRNA 5' ACUAAC-GGCAGACUUCUCCAC 3'

| LV | LV-like particles | IDLV | AAV |
|---|---|---|---|
| Indel: 0.045% | 0.023% | 0.023% | 0.025% |

FIG. 12F

SEQ ID NO: 176
SEQ ID NO: 177

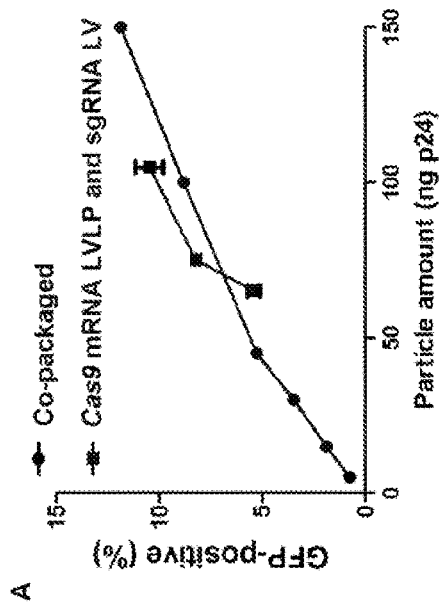
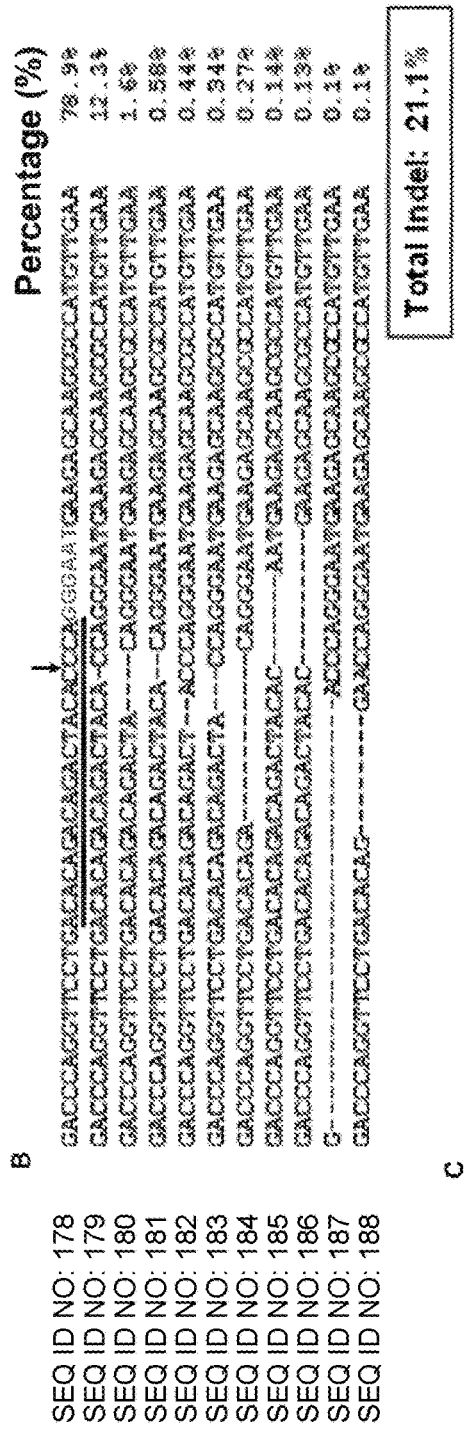
FIGS. 20A-20C

US 12,398,182 B2

LENTIVIRAL-BASED VECTORS AND RELATED SYSTEMS AND METHODS FOR EUKARYOTIC GENE EDITING

PRIOR RELATED APPLICATION

This application claims the benefit of U.S. Provisional Application No. 62/665,080 filed on May 1, 2018, which is hereby incorporated by reference in its entirety.

BACKGROUND

The clustered regularly interspaced short palindromic repeats (CRISPR)/CRISPR-associated (Cas) system discovered in bacteria can be used as a tool to modify mammalian and human genomes, for gene therapy, gene expression regulation, DNA and RNA labeling. In CRISPR/Cas systems, a CRISPR-associated nuclease is targeted to a genomic site by complexing with a guide RNA (gRNA) that hybridizes to a target site in the genome. This results in a double stranded break that initiates either non-homologous end joining (NHEJ) or homology-directed repair (HDR) of genomic DNA via a double-stranded or single-stranded DNA template. Modified systems using a nickase (modified CRISPR-associated nuclease) that introduces a single stranded break have also been developed.

Currently, the common practice is to deliver CRISPR-associated nuclease expressing DNA by plasmid DNA, lentivirus, or adeno-associated virus. All of these delivery systems suffer from a risk of inducing mutagenesis due to the possibility of off-targets and prolonged nuclease expression. Thus, there is a need for efficient, transient delivery of the CRISPR/Cas9 components.

SUMMARY

The present disclosure is directed to compositions, systems, and methods useful for effecting gene editing in eukaryotic cells. In some instances, the compositions, systems and methods can be used to package a CRISPR-associated endonuclease mRNA into a viral particle, for example, a lentiviral-particle. In some instances, the compositions, systems and methods can be used to package a CRISPR-associated endonuclease and a gRNA sequence, for example, as a ribonucleoprotein complex, into a viral particle. Compositions include plasmids that encode one or more viral fusion proteins in which one or more viral proteins are fused with an aptamer-binding protein. Compositions also include plasmids that encode a non-viral nucleic acid sequence, wherein the non-viral nucleic acid sequence encodes a CRISPR system component. In some instances, the non-viral nucleic acid sequence also includes an aptamer sequence. In some instances, a nucleic acid encoding a CRISPR-associated endonuclease comprises at least one aptamer sequence. In some cases, a gRNA coding sequence comprises at least one aptamer sequence. The plasmids can be used to generate viral particles, including lentivirus-like particles Systems of producing such viral particles are provided. Also provided are methods of using the viral particles described herein to effect gene editing in eukaryotic cells.

Also provided is a lentiviral packaging plasmid comprising a eukaryotic promoter operably linked to a Gag nucleotide sequence, wherein the Gag nucleotide sequence comprises a nucleocapsid (NC) coding sequence and a matrix protein (MA) coding sequence, wherein one or both of the NC coding sequence or the MA coding sequence comprises at least one non-viral aptamer-binding protein (ABP) nucleotide sequence, and wherein the packaging plasmid does not encode a functional integrase protein.

Further provided is a mammalian expression plasmid comprising an eukaryotic promoter operably linked to a Viral Protein R (VPR) coding sequence or a Negative Regulatory Factor (NEF) coding sequence, wherein the VPR coding sequence or the NEF coding sequence comprises at least one non-viral aptamer-binding protein (ABP) nucleotide sequence.

Also provided is a mammalian expression plasmid comprising an eukaryotic promoter operably linked to a non-viral nucleic acid sequence, wherein the non-viral nucleic acid sequence comprises at least one aptamer coding sequence, and wherein the non-viral nucleic acid sequence comprises (i) one or both of a CRISPR-associated endonuclease coding sequence or a guide RNA (gRNA) coding sequence, and (ii) at least one aptamer coding sequence.

Further provided is a lentiviral packaging system comprising: a) a packaging plasmid comprising a eukaryotic promoter operably linked to a Gag nucleotide sequence, wherein the Gag nucleotide sequence comprises a nucleocapsid (NC) coding sequence and a matrix protein (MA) coding sequence, wherein one or both of the NC coding sequence or the MA coding sequence comprises at least one non-viral aptamer-binding protein (ABP) nucleotide sequence, and wherein the packaging plasmid does not encode a functional integrase protein; b) at least one mammalian expression plasmid comprising a eukaryotic promoter operably linked to a non-viral nucleic acid sequence, wherein the non-viral nucleic acid sequence comprises a CRISPR-associated endonuclease coding sequence, a guide RNA (gRNA) coding sequence, or both a CRISPR-associated endonuclease coding sequence and a gRNA coding sequence; and c) an envelope plasmid comprising an envelope glycoprotein coding sequence.

Also provided is a lentiviral packaging system comprising: a) a packaging plasmid, and wherein the packaging plasmid does not encode a functional integrase protein; b) at least one mammalian expression plasmid comprising a eukaryotic promoter operably linked to a Viral Protein R (VPR) coding sequence or a Negative Regulatory Factor (NEF) coding sequence, wherein one or both of the VPR coding sequence or the NEF coding sequence comprises at least one non-viral aptamer-binding protein (ABP) nucleotide sequence; c) at least one mammalian expression plasmid comprising a eukaryotic promoter operably linked to a non-viral nucleic acid sequence, wherein the non-viral nucleic acid sequence comprises a CRISPR-associated endonuclease coding sequence, a guide RNA (gRNA) coding sequence, or both a CRISPR-associated endonuclease coding sequence and a gRNA coding sequence; and d) an envelope plasmid comprising an envelope glycoprotein coding sequence.

Further provided is a lentivirus-like particle comprising: a) a fusion protein comprising a nucleocapsid (NC) protein or a matrix (MA) protein, wherein the NC protein or MA protein comprises at least one non-viral aptamer binding protein (ABP); and b) at least one non-viral RNA molecule, wherein the non-viral RNA sequence comprises a CRISPR-associated endonuclease mRNA, a guide RNA (gRNA), or both a CRISPR-associated endonuclease mRNA and a gRNA; wherein the lentivirus-like particle does not comprise a functional integrase protein.

Also provided is a lentivirus-like particle comprising: a) a fusion protein comprising a Viral Protein R (VPR) protein or a Negative Regulatory Factor (NEF) protein, wherein VPR protein or the NEF protein comprises at least one non-viral aptamer binding protein (ABP); and b) at least one non-viral RNA molecule, wherein the non-viral RNA sequence comprises a CRISPR-associated endonuclease mRNA, a guide RNA (gRNA), or both a CRISPR-associated endonuclease mRNA and a gRNA; wherein the lentivirus-like particle does not comprise a functional integrase protein.

Further provided is a lentivirus-like particle comprising: a) a fusion protein comprising a Viral Protein R (VPR) protein or a Negative Regulatory Factor (NEF) protein, wherein VPR protein or the NEF protein comprises at least one non-viral aptamer binding protein (ABP); and b) a ribonucleotide protein (RNP) complex comprising a CRISPR-associated endonuclease and a guide RNA; wherein the lentivirus-like particle does not comprise a functional integrase protein.

Also provided is a method of producing a lentiviral particle, the method comprising: a) transfecting a plurality of eukaryotic cells with the packaging plasmid, the at least one mammalian expression plasmid, and the envelope plasmid of any one of the systems described herein; and b) culturing the transfected eukaryotic cells for sufficient time for lentiviral particles to be produced.

Further provided is a method of producing a lentiviral particle, the method comprising: a) transfecting a plurality of eukaryotic cells with the plasmids of any one of the systems described herein; and b) culturing the transfected eukaryotic cells for sufficient time for lentiviral particles to be produced.

Also provided is a method of modifying a genomic target sequence in a cell, the method comprising transducing a plurality of eukaryotic cells with a plurality of viral particles, wherein the plurality of viral particles comprise: i) any lentivirus-like particle described herein, wherein which the non-viral RNA sequence comprises a CRISPR-associated endonuclease mRNA and a gRNA, or ii) any lentivirus-like particle described herein, wherein the non-viral RNA sequence comprises a CRISPR-associated endonuclease mRNA and a second viral particle comprises a gRNA or a gRNA coding sequence, wherein a CRISPR-associated endonuclease is expressed from the CRISPR-associated endonuclease mRNA in cells transduced with the lentivirus-like particle, wherein, if the second viral particle comprises a gRNA coding sequence, a gRNA is expressed from the gRNA coding sequence in cells transduced with the second viral particle, and wherein the CRISPR-associated endonuclease and the gRNA form a complex that binds to the genomic target sequence in genomic DNA of the cell and the CRISPR-associated endonuclease cleaves the genomic DNA of the cell, thereby triggering cellular DNA repair mechanisms causing modification of the genomic target sequence.

Further provided is a method of modifying a genomic target sequence in a cell, the method comprising transducing a plurality of eukaryotic cells with a plurality of viral particles, wherein the plurality of viral particles comprise: i) a lentivirus-like particle comprising a ribonucleotide protein (RNP) complex (a CRISPR-associated endonuclease complexed with at least one gRNA), wherein the RNP binds to the genomic target sequence in genomic DNA of the cell and the CRISPR-associated endonuclease cleaves the genomic DNA of the cell, thereby triggering cellular DNA repair mechanisms causing modification of the genomic target sequence. Cells modified by any of the genomic modification described herein are also provided. Also provided are cells containing any of the lentivirus-like particles described herein.

Further provided is a method for treating a disease in a subject comprising: a) obtaining cells from the subject; b) modifying the cells of the subject using any of the methods of modifying a genomic target sequence described herein; and c) administering the modified cells to the subject. In some instances, the disease is cancer. In some instances the cells are T cells.

BRIEF DESCRIPTION OF THE DRAWINGS

The present disclosure includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

As shown in FIG. 1A, a plasmid is used to express a lentivirus protein fused with an aptamer-binding protein (ABP), referred to in the figures as a viral protein-ABP fusion protein. The plasmid encoding the viral protein-ABP fusion protein coding sequence may be a lentivirus packaging plasmid (e.g., for NC or MA fusion proteins) or a mammalian expression vector (e.g., for NEF or VPR fusion proteins). FIG. 1A also shows mammalian expression plasmids containing non-viral nucleic acid sequences encoding CRISPR system components (i.e. CRISPR-associated endonuclease and sgRNA) that are used together with a packaging plasmid and an envelope plasmid to transfect eukaryotic cells and generate lentivirus-like particles that contain the viral protein-ABP fusion protein and non-viral RNA molecules (i.e. CRISPR-associated endonuclease mRNA, sgRNA, or both). Optionally, the non-viral RNA molecules encoded by the mammalian expression plasmid(s) may comprise an aptamer sequence. If the viral protein-ABP fusion protein coding sequence is provided on a mammalian expression plasmid (e.g., for NEF and VPR fusion proteins), a lentiviral packaging plasmid is also used to transfect the eukaryotic cells. The mammalian expression plasmids may be lentiviral transfer plasmids encoding various viral genes. The packaging plasmids, whether they contain the viral protein-ABP fusion protein coding sequence or not, and the transfer plasmid, if used, may be modified to remove viral sequences so as to generate lentivirus-like particles. The lentivirus-like particles are collected from the eukaryotic cells. Optionally, sgRNA may be packaged in lentivirus particles or sgRNA coding sequence may packaged in DNA viruses instead of in lentivirus-like particles.

As shown in FIG. 1B, the lentivirus-like particles may be used to transduce eukaryotic cells thereby providing CRISPR-associated endonuclease mRNA, from which active protein is translated in the cells, and sgRNA molecules. These non-viral RNA molecules may be provided in the same lentivirus-like particle or in different viral particles. The CRISPR-associated endonuclease protein and the sgRNA interact to form a ribonucleoprotein complex that binds to a genomic target site (as directed by the sgRNA) and introduces breaks into the DNA. The breaks may be repaired by homology-directed repair (HDR) or non-homologous end-joining (NHEJ) mechanisms. If HDR is desired, the eukaryotic cells may also be transduced with a viral particle containing a target template sequence that can be used as the template for modification of the genomic target site. As the amount of CRISPR-associated endonuclease mRNA introduced into the cells is finite, eventually it will be degraded, as will proteins expressed from the mRNA. Optionally, the sgRNA may be provided in a lentiviral particle or DNA virus particle or, when the cells are in culture, as synthetic RNA molecules introduced into the cells via transfection. While FIG. 1B shows in vitro or ex vivo transduction of eukaryotic cells, the viral particles described may be administered to a subject to effect gene editing in vivo.

FIG. 5A shows expression of SaCas9 mRNA from adeno-associated virus (AAV) and integration defective lentivirus (IDLV) vectors. FIG. 5B shows expression of SaCas9 mRNA from lentivirus-like particles containing SaCas9$^{1 \times PP7}$, SaCas9$^{1 \times MS2}$, or SaCas9$^{1 \times PP7-3'UTR}$. RNA levels were measured by quantitative RT-PCR at 24, 48, 72 and 96 hours post transduction. * indicates $p<0.05$ between SaCas9$^{1 \times MS2}$ and SaCas9$^{1 \times MS2}$-2x3'UTR by two-way ANOVA.

FIG. 6 shows Indels observed in the HBB sgRNA1 target sequence of GFP reporter cells transduced with lentivirus-like particles according to aspects of this disclosure. The GFP-reporter cells were co-transduced with lentivirus-like particles containing SaCas9$^{1 \times MS2}$-3'UTR mRNA and lentivirus expressing HBB-sgRNA1. The DNA was amplified by PCR and sequenced by Next Generation Sequencing. The top 10 most observed sequences are listed as SEQ ID NOs:103-112 (top to bottom). 13.5% of the alleles were unmodified and the rest all had Indels. The target sequence is underlined and the PAM sequence is the 6 nucleotides preceding the target sequence. The arrow indicates the predicted cleavage position. The wild type HBB sequence has an "A" at the second position of the target sequence; the "T" at that position indicates the nucleotide difference relative to the wild type HBB sequence. The data were from 5774277 sequence readings.

FIG. 7A shows MCP-viral protein fusion proteins and SaCas9-MS2 aptamer fusion RNA (SaCas9 fused to SEQ ID NO: 211) for packaging SaCas9 mRNA in LVLPs. MCP: MS2 coat protein; VPR: viral protein R, NEF: negative regulatory factor; NC, nucleocapsid protein; MA: matrix protein. Dashed line indicates the deleted region in MA. FIG. 7B shows plasmids for making lentivirus and LVLP. The aptamer-binging protein MCP and the MS2 aptamer are shown. LTR: long terminal repeats; 'I': lentivirus packaging signal. FIG. 7C shows the effects of MCP-fusion proteins on lentivirus production. $5 \times 10^5$ cells in 6-well plates were transfected with the indicated plasmids (5 μg total DNA). 24 hours after transfection the medium was replaced with 2 ml fresh medium and p24 was assayed after 24 hours. Individual data points and mean±SEM are shown. Only MA-MCP modification decreased virus production ($p<0.05$). FIG. 7D shows that the best gene editing activity was obtained when MCP was fused to NC. SaCas9$^{1 \times MS2}$ was expressed during LVLP production. 250 μl LVLP-containing supernatant and 250 μl IDLV-expressing HBB sgRNA1 were co-transduced into $2.5 \times 10^4$ GFP-reporter cells. ** indicates $p<0.01$ when LVLPs from NC-MCP fusion was compared with other particles; * indicates $p<0.05$ compared with any other particles. FIG. 7E shows flow cytometry analysis of GFP reporter cells transduced with particles made with or without NC-MCP modified packaging plasmid. Increasing volumes of supernatants were co-transduced with 50 ng of HBB sgRNA1-expressing IDLV into GFP reporter cells. When producing particles without packaging plasmid, the packaging plasmid was replaced with pKanCMV-mRuby3-10aa-H2B expressing mRuby. *, $p<0.001$ when the GFP-positive rates of the two conditions were compared (Bonferroni posttests following ANOVA). FIG. 7F shows that plasmid DNA contributed little in generating GFP-positive reporter cells. pSaCas9$^{1 \times MS2}$ (first column) or pSaCas9$^{1 \times MS2}$-HBB sgRNA1 plasmid DNA (second column) was transfected into GFP reporter cells to observe GFP-positive cells. pSaCas9$^{1 \times MS2}$-HBB sgRNA1 was also used to make LVLPs to transduce into GFP reporter cells alone (100 ng p24, the third column) or with 50 ng p24 of IDLV expressing HBB sgRNA1 (the fourth column). * indicates $p<0.001$. For FIGS. 7C, 7D and 7F, Tukey's multiple comparison tests were performed following ANOVA analysis.

FIG. 9A shows the effects of MS2 aptamers on SaCas9 mRNA level. Plasmid DNA expressing SaCas9$^{n \times MS2}$ (250 ng) was co-transfected into GFP-reporter cells grown in 24-well plates with plasmid DNA expressing HBB sgRNA1 (250 ng). SaCas9 mRNA level was compared by RT-qPCR with HBB sgRNA1 as a control. *** and ### indicate $p<0.001$ when SaCas9$^{0 \times MS2}$ was compared with SaCas9$^{1 \times MS2}$, and when SaCas9$^{1 \times MS2}$ was compared with SaCas9 with more than one MS2 aptamer. FIG. 9B shows the effects of MS2 aptamers on SaCas9 gene editing activity.

GFP-reporter cells were transfected as in FIG. 9A. Flow cytometry was performed 72 hours after transfection. *** indicates p<0.001 when SaCas9$^{0 \times MS2}$ was compared with SaCas9 with at least one MS2 aptamer. FIG. 9C shows the effects of aptamer numbers on LVLP gene editing activity. LVLP-containing supernatants (titer determined by p24 ELISA) were co-transduced with 50 ng HBB sgRNA1-expressing IDLV into 2.5×10$^4$ GFP-reporter cells. Flow cytometry was performed 72 hours after transduction. "a" indicates that 45 ng p24 of SaCas9$^{1 \times MS2}$ LVLPs obtained significantly higher GFP-positive rate (p<0.001) than all other LVLPs at the same dosage; "b" indicates that 45 ng p24 of SaCas9$^{12 \times MS2}$ LVLPs obtained significantly lower GFP-positive rate (p<0.001) than SaCas9$^{2 \times MS2}$ or SaCas9$^{3 \times MS2}$ LVLPs; "c" indicates that 15 ng p24 of SaCas9$^{12 \times MS2}$ LVLPs obtained significantly lower GFP-positive rate (p<0.05) than all other LVLPs at the same dosage. Each data point is the mean of three replicates. FIG. 9D shows flow cytometry analysis of GFP-positive cells generated after transducing various SaCas9-containing LVLPs. Designated amounts of SaCas9-containing LVLPs were co-transduced with 60 ng p24 HBB sgRNA1-expressing IDLV into 2.5×10$^4$ GFP-reporter cells. Each point was the average of indicated replicates (numbers in parentheses). * indicates p<0.05 when SaCas9$^{1 \times MS2}$-HBB 3' UTR LVLP was compared with any other particles of the same dosage; * indicates p<0.001 when LVLPs generated without ABP and aptamers were compared with any other particles of the same dosage. FIG. 9E shows RT-qPCR comparisons of SaCas9 mRNA copy numbers in different types of LVLPs. RNA was purified from lentivirus or LVLPs containing 30 ng p24. 30 ng p24 of GFP-lentivirus was added in each sample for experimental control. Copy numbers were compared to normal lentiviral vectors known to contain 2 RNA genomes/LV particle. Shown are individual data points and mean±SEM. ns, no significant difference; *, p<0.001 compared with any other groups. For FIGS. 9A, 9B and 9E, Tukey's multiple comparison tests were performed following ANOVA analysis. For FIG. 9C and FIG. 9D, Bonferroni posttests were performed following two-way ANOVA.

FIG. 10A shows transient expression of SaCas9 mRNA from LVLPs. SaCas9-expressing IDLV (35 ng p24) or LVLPs (35 ng p24) were transduced into 2.5×10$^4$ HEK293T cells. SaCas9 mRNA levels were assayed at different time points. SaCas9 mRNA levels 24 h post transduction were normalized by housekeeping gene GAPDH and RPLP0 to obtain the relative SaCas9 mRNA expression level. No normalization was performed thereafter so that possible cell replication does not affect evaluation of mRNA degradation since no new mRNA was generated in LVLP transduced cells. *** indicates p<0.001 when SaCas9$^{1 \times MS2}$-HBB 3'UTR was compared with other particles at the same time. ### indicates p<0.001 when SaCas9$^{1 \times MS2}$ was compared with other particles at the same time. FIG. 10B shows a time course of SaCas9 mRNA level from the same particle. mRNA levels of each particle 24 h post transduction were set as 1. Shown are mean±SEM of indicated replicates. * and ** indicate p<0.05 and p<0.01 when compared with other particles at the same time point. For FIGS. 10A and 10B, Bonferroni posttests were performed following two-way ANOVA. FIG. 10C shows Western blot analysis of SaCas9 protein. The four lanes were lysates from mock transfected HREK293T cells (lane 1), GFP-reporter cells co-transduced with 300 ng p24 of Cas9 LVLP and 50 ng p24 of HBB sgRNA1 IDLV (lane 2), HEK293T cells overexpressing Cas9$^{1 \times MS2}$ (lane 3) or Cas9 mRNA (lane 4) by transfecting 0.25 μg DNA to 1.25×10$^5$ cells. A very faint band in LVLP transduced cells was indicated by an arrow. FIG. 10D is a diagram showing the processing of Gag precursor by HIV protease. The wideness of the arrows is proportional to the processing speed at that site (1-5). The estimated sizes of the p15-ABP fusion proteins were listed. FIG. 10E shows Western blot analysis of lentiviral proteins. 200 ng p24 of GFP lentivirus, NC-MCP and NC-PCP modified LVLPs were analyzed.

FIGS. 12A-F shows genome editing by SaCas9 LVLP. FIG. 12A shows that SaCas9 LVLPs efficiently generated Indels in the perfectly matched HBB sgRNA1 target sequence. The most frequently observed sequences and their percentages from next-generation sequencing are listed. The "T" in red is the mutation in HBB causing Sickle cell disease. FIG. 12B shows the frequency of Indels at each position obtained from sequencing data in FIG. 12A. FIG. 12C shows Indels in the IL2RG gene of HEK293T cells generated by SaCas9 LVLPs. 2.5×10$^4$ cells were co-transduced with 30 ng p24 of SaCas9$^{1 \times MS2}$-HBB 3'UTR LVLPs and 60 ng of IDLV expressing IL2RG sgRNA. FIG. 12D shows Indels in the IL2RG gene of lymphoblasts generated by 500 ng p24 of SaCas9$^{1 \times MS2}$-HBB 3'UTR LVLPs (500 ng p24 LVLPs on 2×10$^5$ cells). FIG. 12E shows Indel rates in the wild-type HBB locus of the GFP reporter cells. There was one mismatch between the HBB sgRNA1 (highlighted in red) and the target sequence. FIG. 12F shows Indel rates in predicted off-target 8 of the GFP reporter cells. Off-target 8 has one mismatch with HBB sgRNA1 (underlined), one DNA bulge (in blue) and a non-typical PAM (a "G" instead of a "T" at the last position, in italics). For FIGS. 12A-12F: The protospacer adjacent motif (PAM) or its complementary sequence is in green. For FIGS. 12A-12E: The target sequences are underlined. Vertical lines indicate complementarity between HBB sgRNA1 and the target. 3-4 million readings were obtained for each sample.

FIG. 14A is a diagram illustrating the different Cas9 mRNA LVLP (left) and Cas9/sgRNA RNP LVLP (right) as immature virions. Only one GAG precursor and one mRNA or RNP were shown for simplicity. ABP may bind to aptamer as dimers. FIG. 14B shows the locations for MS2 aptamer insertion in sgRNA scaffold. The original sgRNA was shown on the left (SEQ ID NO: 212). The "N"s indicate guide sequence. The three locations tested for MS2 aptamer insertion was indicated by the dashed black boxes. The inserted sequences were shown on the right (SEQ ID NO: 213 (aptamer at tetraloop) and SEQ ID O: 214 (aptamer at the 3'end). The blue letters in dashed blue boxes were the MS2 aptamers and the black letters were added linkers. Complementary ribonucleotides were indicated by vertical lines and atypical base-pairings were indicated by dots. FIG. 14C shows the effects of MS2 aptamer position on gene editing activity of the RNP with the modified sgRNA. Plasmid DNA co-expressing SaCas9 mRNA and various modified HBB sgRNA1 were transfected into the GFP-reporter cells and the GFP-positive percentage was determined by flow cytometry. Each data point indicates one independent experiment. *,  and * indicate p<0.05, p<0.01 and p<0.001 (Tukey's Multiple Comparison Test following ANOVA) when compared with unmodified HBB sgRNA1. FIG. 14D shows the effects of MS2 aptamer position on gene editing activity of modified sgRNA packaged in LVLPs. Indicated amounts of LVLPs containing MS2-modified HBB sgRNA1 and SaCas9 protein (or mRNA) were used to transduce $2.5 \times 10^4$ GFP reporter cells and the GFP-positive percentages were determined by flow cytometry. Each data point is the average of three replicates. ***, p<0.001 when HBB sgRNA1$^{Tetra\ MS2}$ was compared with HBB sgRNA1$^{3'MS2}$; ###, p<0.001 when HBB sgRNA1$^{3'MS2}$ was compared with HBB sgRNA1$^{ST2\ MS2}$.

FIG. 15A shows the replacement of the Tetraloop in SEq ID NO: 215 with different aptamers for sgRNA packaging. The boxed Tetra loop (GAAA) sequence was replaced with sequences containing various aptamers (underlined) ((MS2 (SEQ ID NO: 216), com (SEQ ID NO: 217), PP7 (SEQ ID NO: 218) and BoxB (SEQ ID NO: 219)) with or without linkers (not underlined). FIG. 15B shows a comparison of gene editing activities after the Tetraloop was replaced by different aptamers. Various amounts of plasmid DNA co-expressing SaCas9 and aptamer-modified HBB shRNA1 was transfected into $1.25 \times 10^5$ GFP reporter cells. 48 hours after transfection the GFP-positive cells were analysed by flow cytometry. Each point was the average of three replicates. * indicates p<0.001 when sgRNA without modification or with com modification was compared with PP7, BoxB or MS2 modified sgRNAs (Bonferroni posttests following ANOVA). FIG. 15C provides a comparison of gene editing activities of LVLPs made by different aptamer/ABP pairs. 400 ul of un-concentrated LVLPs were used to transduce $2.5 \times 10^4$ GFP reporter cells, and the GFP-positive rate was determined by flow cytometry. Each point indicates one independent assay. * indicates p<0.001 between the indicated pairs in Tukey's Multiple Comparison Test following ANOVA analysis. ns, not significant.

FIG. 18A shows that HBB sgRNA1 expressed from transfected plasmid DNA was functional. Indicated amounts of DNA were transfected into $1.25 \times 10^5$ GFP reporter cells and the cells were analysed by flow cytometry 48 hour after transfection. In co-transfection experiments, the DNA amount indicated each of the Cas9 expressing- and the sgRNA expressing-plasmid DNA. Each point was the average of three replicates. FIG. 18B shows the importance of Cas9 co-packaging and com-aptamer modification of sgRNA on gene editing activity of the LVLPs. LVLPs packaged in the absence of Cas9 expression were inactive when co-transduced into GFP-reporter cells with functional Cas9-HBB-3'UTR$^{MS2}$ mRNA LVLPs. $2.5 \times 10^4$ GFP-reporter cells were transduced with Cas9/HBB sgRNA1 LVLPs (com$^-$ RNP LVLPs), Cas9/HBB sgRNA1$^{tetra-com}$ LVLPs (com$^+$ RNP LVLPs), or co-transduced with 45 ng p24 of Cas9-HBB-3'UTR$^{MS2}$ mRNA LVLPs and various amounts of HBB sgRNA1$^{tetra-com}$ LVLPs (com$^+$ sgRNA LVLPs). GFP-positive cells were determined by flow cytometry 48 hours after transduction. Each point is the average of 3 replicates. *** indicates p<0.001 when GFP-positive rates of cells treated with com$^+$ RNP LVLPs were compared with cells treated with similar amounts of other particles (Bonferroni posttests following ANOVA). FIG. 18C shows that co-expressing Cas9 increased HBB sgRNA1 level. Plasmids expressing only HBB sgRNA1$^{Tetra-com}$ (200 ng) and only SaCas9 (200 ng) were transfected into HEK293T cells alone or together, and the sgRNA level was compared by RT-qPCR. A GFP-expressing plasmid (50 ng) was co-transfected so that GFP expression could be used to normalize transfection efficiency. Total plasmid DNA was brought to 450 ng by pCDNA3 plasmid DNA. * indicates p<0.05 when sgRNA level without Cas9 co-expression was compared with that of with Cas9 co-expression. FIG. 18D shows Western blot analysis of Cas9 protein in isolated lentiviral vectors and LVLPs. 200 ng p24 of GFP lentivirus (lane 1), NC-MCP modified Cas9-HBB-3' UTR$^{MS2}$ LVLPs (without sgRNA, lane 2), NC-unmodified Cas9$^{MS2}$ LVLPs (without sgRNA, lane 3), NC-COM modified Cas9/HBB sgRNA1$^{tetra-com}$ LVLPs (lane 4), NC-COM modified Cas9/IL2RG sgRNA1$^{tetra-com}$ LVLPs (lane 5), and NC-COM modified Cas9/HBB sgRNA1 LVLPs (sgRNA without Tetra-com aptamer, lane 6) were loaded. FIG. 18E shows that a Tetra-com modification of sgRNA increased the Cas9 protein content in LVLPs. FIG. 18F show that Cas9 proteins in LVLPs with com-modified sgRNA are more detergent-resistant than Cas9 proteins in LVLPs with unmodified sgRNA. The same amount of starting LVLPs (200 ng of p24) was centrifuged through 1 ml of 10% sucrose with or without 0.5% Triton X-100. For (FIGS. 18E and 18F), Cas9 level was normalized by CA protein, based on dosimetry analysis (IMAGE J). FIG. 18G shows that packaging of sgRNA in LVLPs is com-aptamer but not Cas9 protein dependent. See FIG. 18E for evidence of similar particle input (CA) for RNA isolation. Each point indicates one repeat. *** indicates p<0.001 between the indicated pairs in Tukey's Multiple Comparison Test following ANOVA analysis.

FIG. 20A-20E show that Cas9/sgRNA RNP LVLPs are efficient and specific in gene editing. FIG. 20A shows that Cas9/sgRNA RNP LVLPs has comparable gene editing activity as Cas9 mRNA LVLPs. For Cas9 mRNA LVLPs, the particle amount was the sum of Cas9 mRNA LVLPs and 60 ng p24 of HBB sgRNA1-expressing LVs. FIG. 20B shows that Indels generated by Cas9/IL2RG sgRNA1 RNP LVLPs on the endogenous IL2RG target sequence. The protospacer adjacent motif (PAM) is in grey and the target sequence is underlined. The predicted cleavage site is indicated by an arrow. The dashed lines indicate deletions. FIG. 20C is a diagram showing the sequence of HBB sgRNA1, the Sickle mutant sequence perfectly matching the gRNA, and the endogenous HBB sequence with one mismatch with the gRNA. The mutation causing Sickle cell disease is underlined. FIG. 20D is a comparison of on target and off-target Indel rate of Cas9/HBB sgRNA1 RNP LVLPs with those of other delivery vehicles. The on target to off-target Indel rate ratios ("on/off" ratios) are the results of on-target Indel rates divided by off-target Indel rates. Cells were harvested 72 hours after treatment. For cells grown in 24-well plates, $1.25 \times 10^5$ and $2.5 \times 10^4$ cells were used for transfection and transduction respectively. For RNP LVLPs, 150 ng p24 were used; for mRNA LVLPs, 45 ng p24 of Cas9 mRNA LVLPs and 60 ng p24 of HBB sgRNA1-expressing IDLV were used; for LV co-expressing Cas9 and HBB sgRNA1, 30 ng p24 were used; for IDLV co-expressing Cas9 and HBB sgRNA1, 30 ng p24 were used; for Cas9-expressing AAV6 and HBB sgRNA1-expressing AAV6, $10^4$ virus genome/cell were used for each virus. On-target Indel rates are all normalized to 100 for comparison. Original data are in FIG. 22. FIG. 20E shows that Cas9 RNP LVLPs showed faster actions than Cas9 mRNA LVLPs. 50 ng p24 of Cas9/IL2RG sgRNA1 RNP LVLPs, or 100 ng p24 of Cas9 mRNA LVLPs plus 100 ng p24 of IDLV expressing IL2RG sgRNA1 were transduced into $2.5 \times 10^4$ GFP reporter cells and incubated in IncuCyte for scanning. * indicates the time point from which RNP-treated cells showed significantly higher GFP-positive area/phase area than negative control or mRNA LVLP-treated cells (p<0.05). # indicates the time point from which mRNA LVLP-treated cells showed significantly higher GFP-positive area/phase area than negative control cells (p<0.05). The line shows the time lag in Cas9 mRNA LVLP treated cells to reach the same level of GFP-positive area/phase area as RNP-treated cells.

FIG. 22A is a diagram showing the design of the donor template and the PCR strategies for detection of homologous recombination. FIG. 22B shows detection of homologous recombination events by NGS. The PAM is in green. The target sequence is underlined. The inserted IL2RG cDNA was in orange. The original start codon and the start codon for the inserted cDNA are in red. In the cDNA, the lower case letters are identical to the original cDNA sequence while the capital letters are different from the original sequence but the encoded protein is the same.

DEFINITIONS

Figure 1A:
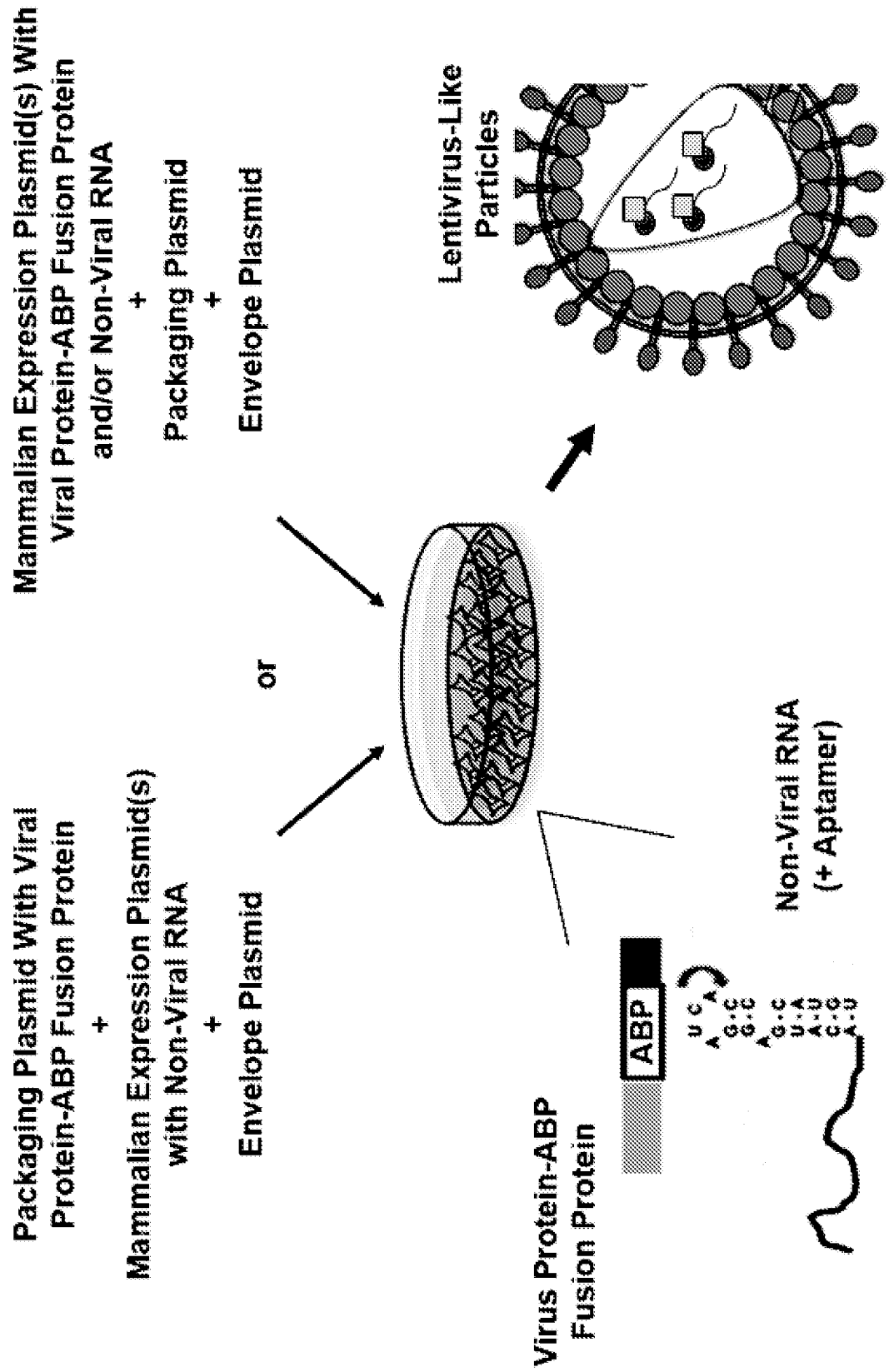
FIGS. 1A-1B show schematics illustrating compositions, systems, and methods according to aspects of this disclosure.

As used in this specification and the appended claims, the singular forms "a," "an," and "the" include plural reference unless the context clearly dictates otherwise.

The term "nucleic acid" or "nucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with gene, cDNA, and mRNA encoded by a gene.

The term "gene" can refer to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, guide RNA, or micro RNA "Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present disclosure to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods of the present disclosure includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition. The term "treatment," as used herein, includes preventative (e.g., prophylactic), curative, or palliative treatment.

A "promoter" is defined as one or more a nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass full-length proteins, truncated proteins, and fragments thereof, and amino acid chains, wherein the amino acid residues are linked by covalent peptide bonds.

As used herein, the term "complementary" or "complementarity" refers to specific base pairing between nucleotides or nucleic acids. Complementary nucleotides are, generally, A and T (or A and U), and G and C.

As used throughout, by subject is meant an individual. For example, the subject is a mammal, such as a primate, and, more specifically, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical uses and formulations are contemplated herein. The term does not denote a particular age or sex. Thus, adult and newborn subjects, whether male or female, are intended to be covered. As used herein, patient or subject may be used interchangeably and can refer to a subject afflicted with a disease or disorder.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter, followed by a transcription termination signal sequence. An expression cassette may or may not include specific regulatory sequences, such as 5' or 3' untranslated region from human globin genes.

A "reporter gene" encodes proteins that are readily detectable due to their biochemical characteristics, such as enzymatic activity or chemifluorescent features. These reporter proteins can be used as selectable markers. One specific example of such a reporter is green fluorescent protein. Fluorescence generated from this protein can be detected with various commercially-available fluorescent detection systems. Other reporters can be detected by staining. The reporter can also be an enzyme that generates a detectable signal when contacted with an appropriate substrate. The reporter can be an enzyme that catalyzes the formation of a detectable product. Suitable enzymes include, but are not limited to, proteases, nucleases, lipases, phosphatases and hydrolases. The reporter can encode an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton and Vapnek (1979) Nature 282: 864-869); luciferase (lux); β-galactosidase; LacZ; β.-glucuronidase; and alkaline phosphatase (Toh, et al. (1980) Eur. J. Biochem. 182: 231-238; and Hall et al. (1983) J. Mol. Appl. Gen. 2: 101), each of which are incorporated by reference herein in its entirety. Other suitable reporters include those that encode for a particular epitope that can be detected with a labeled antibody that specifically recognizes the epitope.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types.

The CRISPR/Cas system classification as described in by Makarova, et al. (Nat Rev Microbiol. 2015 November; 13(11):722-36) defines five types and 16 subtypes based on shared characteristics and evolutionary similarity. These are grouped into two large classes based on the structure of the effector complex that cleaves genomic DNA. The Type II CRISPR/Cas system was the first used for genome engineering, with Type V following in 2015. Wild-type type II CRISPR/Cas systems utilize an RNA-mediated nuclease Cas protein or homolog (referred to herein as a "CRISPR-associated endonuclease") in complex with guide RNA to recognize and cleave foreign nucleic acid. Cas9 proteins also use an activating RNA (also referred to as a transactivating or tracr RNA). Guide RNAs having the activity of either a guide RNA or both a guide RNA and an activating RNA, depending on the type of CRISPR-associated endonuclease used therewith, are also known in the art. In some cases, such dual activity guide RNAs are referred to as a single guide RNA (sgRNA). Synthetic guide RNAs that do not contain an activating RNA sequence may also be referred to as sgRNAs. In this disclosure, the terms sgRNA and gRNA are used interchangeably to refer to an RNA molecule that complexes with a CRISPR-associated endonuclease and localizes the ribonucleoprotein complex to a target DNA sequence. Methods and compositions for controlling inhibition and/or activation of transcription of target genes, populations of target genes (e.g., controlling a transcriptome or portion thereof) are described, e.g., in Cell. 2014 Oct. 23; 159(3):647-61, the contents of which are incorporated by reference in its entirety herein for all purposes.

As used herein, "activity" in the context of CRISPR/Cas activity, CRISPR-associated endonuclease activity, sgRNA activity, sgRNA:CRISPR-associated endonuclease nuclease activity and the like refers to the ability to bind to a target genetic element. Typically, activity also refers to the ability of the sgRNA:CRISPR-associated endonuclease nuclease complex to make double-strand breaks at a target genomic region. In some instances, the activity may refer to the ability to modulate transcription at or near a target genomic region. Such activity can be measured in a variety of ways as known in the art. For example, expression, activity, or level of a gene containing or adjacent to the target genomic region can be measured. In another example, the generation of insertions and deletions (Indels) in the genome of cells at a target genomic region can be measured.

As used herein, the phrase "editing" in the context of editing of a genome of a cell refers to inducing a structural change in the sequence of the genome at a target genomic region. For example, the editing can take the form of inserting a nucleotide sequence into or deleting a nucleotide sequence from the genome of the cell. The nucleotide sequence can encode a polypeptide or a fragment thereof. Such editing can be performed by inducing a double stranded break within a target genomic region, or a pair of single stranded nicks on opposite strands and flanking the target genomic region. Methods for inducing single or double stranded breaks at or within a target genomic region include the use of a CRISPR-associated endonuclease nuclease domain and a guide RNA, or pair of guide RNAs, directed to the target genomic region.

As used herein, non-homologous end joining (NHEJ) refers to a cellular process in which cut or nicked ends of a DNA strand can be directly ligated without the need for a homologous template nucleic acid. NHEJ can lead to the addition, the deletion, substitution, or a combination thereof, of one or more nucleotides at the repair site.

As used herein, the term homology directed repair (HDR) refers to a cellular process in which cut or nicked ends of a DNA strand are repaired by polymerization from a homologous template nucleic acid. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid can be introduced to obtain a specific HDR-induced change of the sequence at the target site. In this way, specific mutations can be introduced at the cut site.

As used herein, a "target template sequence" refers to a DNA oligonucleotide that can be used by a cell as a template for HDR. A target template sequence may be a single-stranded DNA template or a double-stranded DNA template. Generally, the target template sequence has at least one region of homology to a target site in the genome of a cell (genomic target sequence or target genomic region). In some cases, the target template sequence has two homologous regions flanking a region that contains a heterologous sequence to be inserted at a target cut site in the genome of a cell (genomic target sequence or target genomic region).

As used herein, the term "ribonucleoprotein complex" "RNPs", and the like refers to a complex between a CRISPR-associated endonuclease, for example, Cas9 protein, and a crRNA (e.g., guide RNA or single guide RNA), the Cas9 protein and a trans-activating crRNA (tracrRNA), the Cas9 protein and a guide RNA, or a combination thereof (e.g., a complex containing the Cas9 protein, a tracrRNA, and a crRNA guide.

DETAILED DESCRIPTION

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art; therefore, information well known to the skilled artisan is not necessarily included.

Provided herein are compositions, systems, methods of manufacture, and methods for efficient delivery of CRISPR/Cas system components to eukaryotic cells using viral particles. For example, components, systems, methods of manufacture, and methods for efficient delivery to cells of CRISPR-associated endonuclease mRNA or RNPs via lentivirus-like particles are provided. The CRISPR-associated endonuclease produced by the systems described herein is functional for gene editing in eukaryotic cells. CRISPR-associated endonuclease mRNA is delivered into eukaryotic cells and has a limited half-life, reducing the risk of off-target mediated mutagenesis. Delivery of RNPs into eukaryotic cells allows for efficient delivery, for example, in cells that are difficult to transfect, such as primary cells while reducing off-target effects.

Figure 1B:
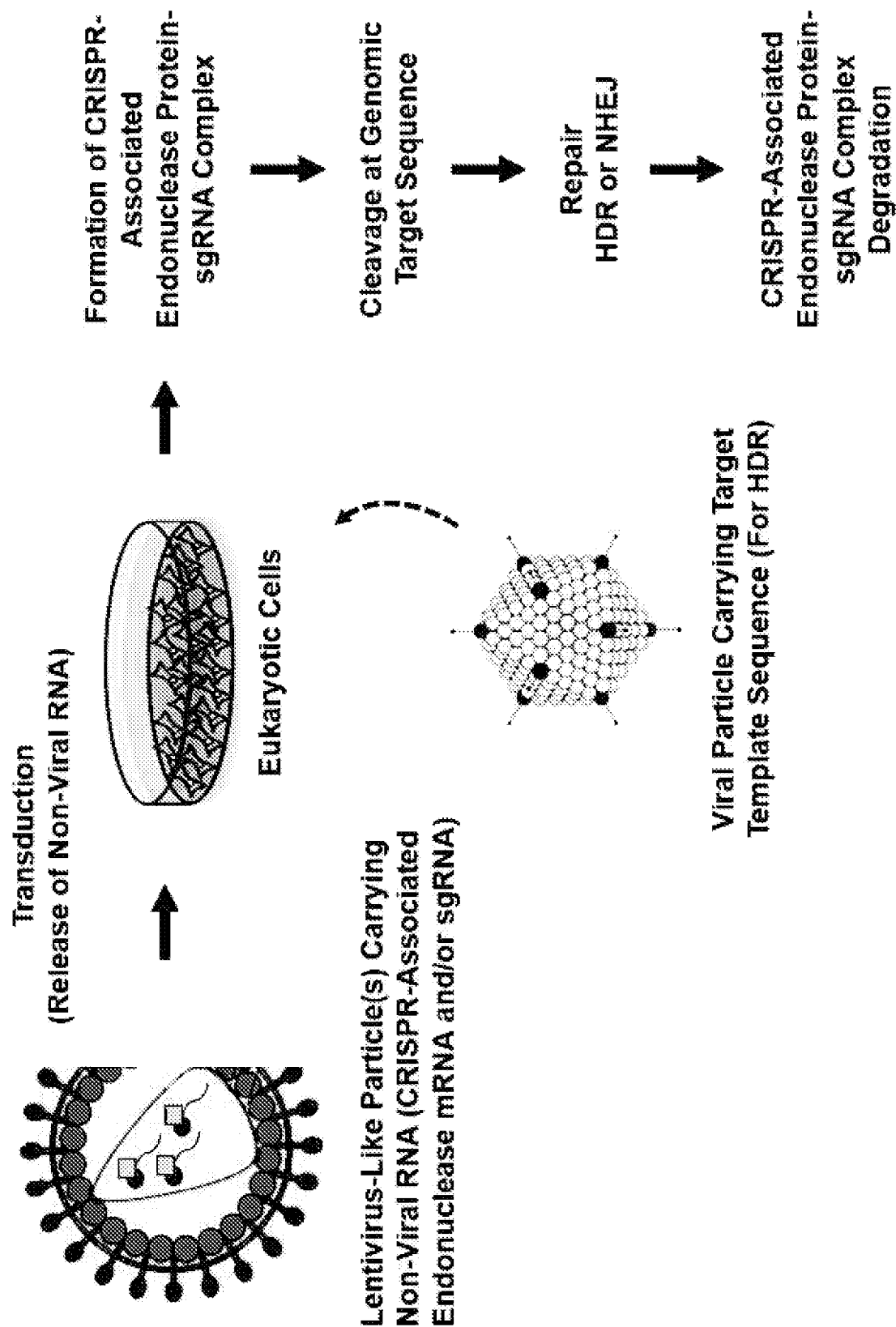

The lentivirus-like particles contain a modified viral protein that is a fusion protein with an aptamer-binding protein. The modified viral protein may be structural or non-structural. In particular, the modified viral protein may be lentiviral regulatory proteins (VPR and NEF), nucleocapsid (NC) protein or matrix (MA) protein with the aptamer-binding protein be fused to the protein. The lentivirus-like particles also contain a non-viral nucleic acid sequence; specifically, one or both of a CRISPR-associated endonuclease coding sequence (a CRISPR-associated endonuclease mRNA) or a guide RNA (gRNA). These CRISPR/Cas system components are packaged within the lentivirus-like particles and delivered into the eukaryotic cells as shown in FIG. 1A and FIG. 1B. In some instances, the gRNA is delivered using lentivirus-like particles. For example, in some instances, the CRISPR-associated endonuclease coding sequence and gRNA may be packaged together into lentivirus-like particles. Alternatively, the CRISPR-associated endonuclease coding sequence and gRNA may be packaged into separate lentivirus-like particles. Additionally, other delivery mechanisms may be used to deliver the gRNA into the eukaryotic cells (such as, for example, lentivirus, adenovirus, adeno-associated virus, plasmids, gRNA transfection or electroporation).

Figures 14A, 14B, 14C, 14D:
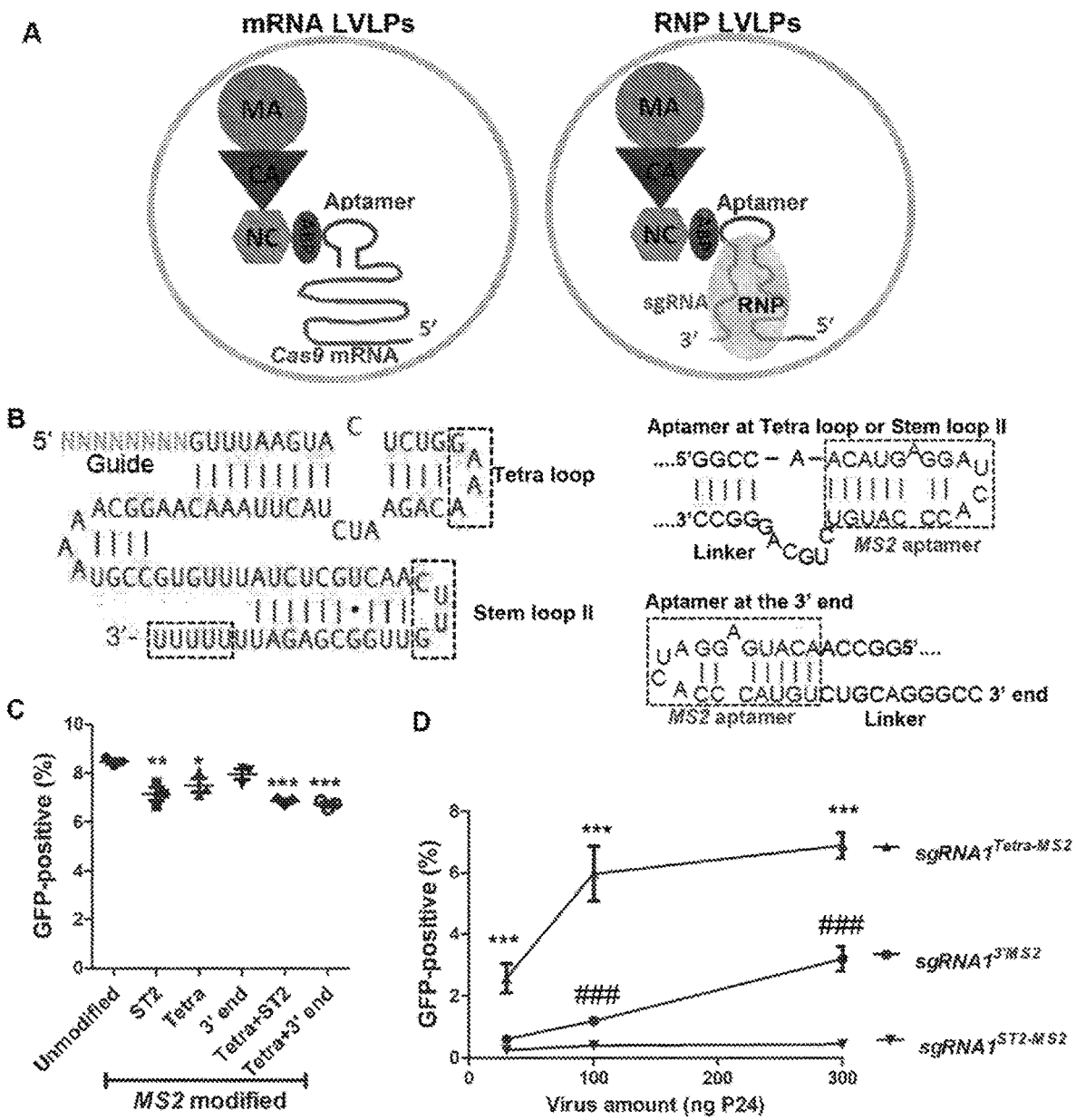
FIG. 14A-14D show packaging of sgRNA in LVLPs.

The non-viral nucleic acid sequence may be modified with the addition of an aptamer sequence that is specifically bound by the aptamer-binding protein that is fused to the modified viral protein. In some embodiments, the aptamer sequence is attached to a nucleic acid encoding a CRISPR-associated endonuclease mRNA. The interaction between the aptamer sequence and the aptamer-binding protein that is fused to the modified viral protein facilitates packaging of the endonuclease mRNA into the lentiviral particle. FIG. 14A illustrates the packaging of a CRISPR-associated endonuclease mRNA in a lentiviral particle via the interaction between an aptamer attached to a Cas mRNA and an aptamer binding protein fused to a viral protein. In some embodiments, the aptamer sequence is attached to or inserted into a gRNA sequence. When the aptamer sequence attached to or inserted into the gRNA sequence interacts with the aptamer-binding protein, the gRNA sequence complexed with a CRISPR-associated endonuclease (RNP) is packaged in the lentiviral particle. FIG. 14B illustrates the packaging of an RNP (i.e., CRISPR-associated endonuclease complexed with gRNA) in a lentiviral particle via the association of an aptamer attached to the gRNA and an aptamer binding protein fused to a viral protein.

The presence of the viral fusion protein may increase packaging of non-viral nucleic acid sequence or RNPs within the lentivirus-like particles. In some instances, addition of an aptamer sequence to the non-viral nucleic acid sequence, for example, addition of an aptamer sequence to a nucleic acid sequence encoding a CRISPR-associated endonuclease mRNA, may further increase the amount of RNA packaged. In other instances, the non-viral nucleic acid sequence comprises a gRNA sequence and sequence encoding a CRISPR-associated endonuclease, wherein addition of an aptamer sequence to the gRNA sequence, may further increase the amount of RNPs packaged. This disclosure provides lentivirus-like particles as described above; other virus particles components; plasmids for generating such lentivirus-like particles; methods and systems using such plasmids to generate the lentivirus-like particles; and methods of using the lentivirus-like particles to modify a genomic target sequence in a cell.

I. Introduction

Class 2 Clustered Regularly Interspaced Short Palindromic Repeat (CRISPR) systems, which form an adaptive immune system in bacteria, have been modified for genome engineering. Engineered CRISPR/Cas systems contain two components: a guide RNA (gRNA, also referred to as single guide RNA (sgRNA)) and a CRISPR-associated endonuclease. The gRNA is a short synthetic RNA composed of a scaffold sequence necessary for binding with the CRISPR-associated endonuclease and a user-defined ~20 nucleotide spacer that defines the genomic target to be modified. Thus, one can change the genomic target of the CRISPR-associated endonuclease by simply changing the target sequence present in the gRNA. CRISPR was originally employed to knock out target genes in various cell types and organisms, but modifications to various CRISPR-associated endonucleases have extended CRISPR to selectively activate/repress target genes, purify specific regions of DNA, image DNA in live cells, and precisely edit DNA and RNA. Where homology-directed repair (HDR) of the genomic target is desired, such as when the aim is to correct a mutated genomic sequence, the system includes a target template sequence that provides the desired sequence to be introduced into the genome in place of the mutated genomic sequence. When non-homologous end joining (NHEJ) is the repair mechanism used to repair the break in the genomic DNA, no target template sequence is used and repair generally results in deletions or insertions at the site of repair. This mechanism is useful where the desired outcome from gene editing is to inactivate and/or impair the function of a genomic sequence, or restoring the reading frame of a gene disrupted by deletions or insertions.

Various mammalian expression systems have been used to deliver CRISPR/Cas systems into cells. These include lentiviral transduction, adeno-associated virus (AAV) transduction, mammalian expression vectors, direct delivery of CRISPR-associated endonuclease mRNA and gRNA, and direct delivery of CRISPR-associated endonuclease/gRNA ribonucleoprotein complexes.

In the case of lentiviral systems, the CRISPR-associated endonuclease and gRNA can be present in a single lentiviral vector or separate lentiviral vectors. The viral vectors may contain a reporter gene (such as GFP) to identify and enrich positive cells. Often the lentiviral vector will also contain a selection marker to generate stable cell lines. A safety feature of lentivirus systems is that the components necessary to produce an infectious viral particle (a virion) are generally divided among multiple plasmids. Packaging plasmids and envelope plasmids encode components of the viral capsid and envelope and are used in conjunction with a transfer plasmid that encodes the viral genome and one or both of the CRISPR-associated endonuclease or gRNA. These plasmids are simultaneously transfected into cells (such as 293 human embryonic kidney cells), the cells are allowed to incubate, and then the supernatant containing the viral particles is collected. These viral particles can then be used to transduce cells of interest. Portions of the lentiviral vector genome can then integrate into the genome of target cells, modulating target genes and their expression. However, use of lentiviral vector systems to deliver a CRISPR-associated endonuclease has the potential to cause oncogenic, infectious, and other transformative changes to infected cells.

Different types of lentiviral vector systems have been developed that seek to improve lentiviral vector system safety and efficacy. Second generation lentiviral systems contain a single packaging plasmid encoding the Gag, Pol, Rev, and Tat genes. Without an internal promotor, transgene expression is driven by the genomic 5' LTR, which is a weak promoter and requires the presence of Tat to activate expression. Third generation systems improve on the safety of the second generation system in two ways. First, the packaging system is split into two packaging plasmids: one encoding Rev and one encoding Gag and Pol. Second, Tat is eliminated from the third generation system; expression of the transgene from this promoter is no longer dependent on Tat transactivation. A third generation transfer plasmid can be packaged by either a second or a third generation packaging system. While the second and third generation systems address concerns related to unintentional generation of replication-competent viruses, the systems are still vulnerable to causing mutagenesis and off target effects in transduced cells.

An AAV system can be used in which the CRISPR-associated endonuclease and/or gRNA are inserted into an AAV transfer vector and used to generate AAV particles. The packaging limit of the AAV particle is only approximately 4.5 kb, which limits which CRISPR-associated endonuclease can be used and the size of the gRNA.

When mammalian expression vectors are used, a heterologous promoter is used to drive CRISPR-associated endonuclease expression. The promoter can be constitutive or inducible. Often, U6 promoter is used for gRNA. The expression vectors may contain a reporter gene (such as green fluorescent protein; GFP) to identify and enrich positive cells or a selection marker to generate stable cell lines. Mammalian expression vectors can be used for transient or stable expression of the CRISPR-associated endonuclease and/or gRNA in a mammalian cell line that can be transfected at high efficiency.

CRISPR-associated endonuclease mRNA and gRNA (synthesized from plasmids using vitro transcription reactions) can be delivered to target cells using microinjection or electroporation. Similarly, purified CRISPR-associated endonuclease protein and in vitro transcribed gRNA can be combined in vitro to form a ribonucleoprotein complex that is delivered to cells using cationic lipids. Both direct delivery methods result in transient expression of CRISPR components as expression decreases as the CRISPR-associated endonuclease mRNA or protein and/or gRNA are degraded within the cell.

Aspects of this disclosure include modified lentiviral vector systems and components and, in some instances, may also include one or more of lentiviral components, AAV components, or mammalian expression vectors. In some instances, the modified lentiviral vector systems and components provided have been modified to eliminate all or a substantial portion of the lentiviral genome. Additionally, lentivirus-like particles produced from the modified system and components have a reduced risk of generating infection particles and causing mutagenesis and off target effects in transduced cells.

II. Plasmid Components

Various plasmid compositions are provided in this disclosure. These include modified lentiviral packaging plasmids, modified lentiviral transfer plasmids, and mammalian expression plasmids.

A. Modified Viral Protein Plasmids

An aspect of the disclosure are plasmids comprising a polynucleotide sequence that encodes a modified lentiviral protein that is a fusion protein of a lentiviral protein fused with an aptamer-binding protein. In the context of this disclosure, the modified viral protein may be structural or non-structural. In some instances, the modified viral protein is a structural protein and may be provided by a lentiviral packaging plasmid. In some instances, the modified viral protein is a non-structural protein and may be provided by a mammalian expression vector. Exemplary structural proteins are lentiviral nucleocapsid (NC) protein and matrix (MA) protein. Exemplary non-structural proteins are viral protein R (VPR) and negative regulatory factor (NEF).

In some embodiments, the modified viral protein is nucleocapsid (NC) protein. In other embodiments, the modified viral protein is matrix (MA) protein. Both the NC protein and the MA protein are encoded by the lentiviral Gag gene. In some instances, the coding sequence of the viral protein may be one of SEQ ID NO:1, SEQ ID NO:3, SEQ ID NO:5, or SEQ ID NO:7. In some instances, the amino acid sequence of the viral protein may be one of SEQ ID NO:2, SEQ ID NO:4, SEQ ID NO:6, or SEQ ID NO:8. In some instances, the lentiviral packaging plasmid comprises a sequence encoding at least one of SEQ ID NO:2, SEQ ID NO:4, SEQ ID NO:6, or SEQ ID NO:8 operably linked to a eukaryotic promoter. In some instances, if the viral protein is NEF, the polypeptide may comprise three mutations that enhances packaging in the viral capsid such as, for example, the following substitution mutations: G3C, V153L, and E177G.

The polynucleotide encoding the modified lentiviral protein comprises an aptamer-binding protein (ABP) coding sequence. In some instances, the ABP coding sequence is at the 5' end or 3' end of the viral protein coding sequence. In some instances, the ABP coding sequence may be inserted into the viral protein coding sequence such that the encoded ABP is fused to the viral protein. The ABP coding sequence may be inserted in frame at an internal position within the viral protein coding sequence. When positioned in frame at an internal position near the 5' or 3' end of the viral protein coding sequence, the ABP coding sequence is positioned so as not to disrupt processing sequences such as those described in J. Virol. 65(2):922-30 (1991) and Biochimica et Biophysica Acta—Biomembranes 1614(1):62-72 (2003), which are incorporated herein by reference in their entirety. For example, the Gag nucleotide sequence encodes, inter alia, the NC coding sequence and the MA coding sequence, and the Gag precursor protein is processed by proteolytic cleavage into separate mature viral proteins. The in frame insertion of the ABP coding sequence would not disrupt the nucleotides encoding the processing sequences for proteolytic cleavage. In some instances, nucleotides in the viral protein coding sequence may be replaced with the ABP protein coding sequence. In some instances, a linker sequence encoding 3-6 amino acids may be positioned between the viral protein coding sequence and the ABP coding sequence, or flanking the ABP coding sequence, to help facilitate proper folding of the protein domains upon expression.

In one example, the modified viral protein is NC and the ABP coding sequence is inserted at the 5' end or the 3' end of the NC coding sequence. In another example, the modified viral protein is NC and the ABP coding sequence is inserted before or after one of the zinc finger (ZF) domains. For example, the ABP coding sequence may be inserted after the last codon of the second ZF (ZF2) domain. In another example, the ABP coding sequence may be inserted before the first codon of the ZF2 domain. In another example, the ABP coding sequence may be inserted before the first codon of the first ZF (ZF1) domain. In another example, the ABP coding sequence may be inserted after the last codon of the first ZF (ZF1) domain. In some instances, the ABP coding sequence is inserted into the NC coding sequence in a manner that does not disrupt the highly positive stretch of amino acids in the NC protein.

In another example, the modified viral protein is MA and the ABP coding sequence is inserted at the 5' end or the 3' end of the MA coding sequence. In another example, the ABP coding sequence is inserted in frame at an internal position within the MA coding sequence. In some instances, nucleotides in the MA coding sequence may be replaced with the ABP protein coding sequence. For example, the nucleotides encoding amino acids 44-132 of the MA protein may be replaced with the ABP coding sequence. In another example, the ABP coding sequence is inserted prior to the codon encoding amino acid 44 of the MA protein. In another example, the ABP coding sequence is inserted after the codon encoding amino acid 132 of the MA protein.

In another example, the modified viral protein is VPR and the ABP coding sequence is inserted at the 5' end or the 3' end of the VPR coding sequence. In one example, the ABP coding sequence is inserted at the 5' end of the VPR coding sequence.

In another example, the modified viral protein is NEF and the ABP coding sequence is inserted at the 5' end or the 3' end of the NEF coding sequence. In one example, the ABP coding sequence is inserted at the 3' end of the NEF coding sequence.

In one aspect, provided is a lentiviral packaging plasmid comprising a eukaryotic promoter operably linked to a Gag nucleotide sequence, wherein the Gag nucleotide sequence comprises a nucleocapsid (NC) coding sequence and a matrix protein (MA) coding sequence, and one or both of the NC coding sequence or the MA coding sequence comprises at least one non-viral aptamer-binding protein (ABP) nucleotide sequence. In some instances, the packaging plasmid does not encode a functional integrase protein. In some instances, lentiviral packaging plasmid comprises at least one non-viral ABP nucleotide sequence immediately downstream the second zinc finger domain of the NC coding sequence. In such instances, the NC coding sequence may comprises two functional zinc finger protein domains and functional native protease processing sequences. Retention of the zinc finger protein domains and native protease processing sequences ensures that the modified NC fusion protein expressed from the lentiviral packaging plasmid is processed correctly into a functional protein. In some instances, lentiviral packaging plasmid comprises at least one non-viral ABP nucleotide sequence in the MA coding sequence.

In some instances, the plasmids may encode one or more viral proteins that comprise two or more aptamer-binding proteins fused thereto. In certain instances, the Gag nucleotide sequence of the lentiviral packaging plasmid may comprise a NC coding sequence and a MA coding sequence and where one or both of the NC coding sequence or the MA coding sequence comprises a first non-viral ABP nucleotide sequence and a second non-viral ABP nucleotide sequence. The first non-viral ABP nucleotide sequence and the second non-viral ABP nucleotide sequence may both encode the same ABP. Alternatively, the first non-viral ABP nucleotide sequence and the second non-viral ABP nucleotide sequence encode different ABPs. In some instances, the Gag nucleotide sequence of the lentiviral packaging plasmid may comprise a NC coding sequence comprising at least one first non-viral ABP nucleotide sequence and a MA coding sequence comprising at least one second non-viral ABP nucleotide sequence. The at least one first non-viral ABP nucleotide sequence and the at least one second non-viral ABP nucleotide sequence may both encode the same ABP. Alternatively, the at least one first non-viral ABP nucleotide sequence and the at least one second non-viral ABP nucleotide sequence encode different ABPs.

In certain instances, the mammalian expression vector may encode a VPR coding sequence or a NEF coding sequence and where the VPR coding sequence or the NEF coding sequence comprises a first non-viral ABP nucleotide sequence and a second non-viral ABP nucleotide sequence. The first non-viral ABP nucleotide sequence and the second non-viral ABP nucleotide sequence may both encode the same ABP. Alternatively, the first non-viral ABP nucleotide sequence and the second non-viral ABP nucleotide sequence encode different ABPs.

A non-viral aptamer-binding protein (ABP) nucleotide sequence encodes a polypeptide sequence that binds to an RNA aptamer sequence. Several non-viral ABPs are suitable for use in this disclosure. In particular, suitable ABPs include bacteriophage RNA-binding proteins that bind specifically to RNA sequences that form stem-loop structures referred to as RNA aptamer sequences. Exemplary non-viral aptamer binding protein include MS2 coat protein, PP7 coat protein, lambda N peptide, and COM (Control of mom) protein. The lambda N peptide may be amino acids 1-22 of the lambda N protein, which are the RNA-binding domain of the protein. In some instances, the ABPs bind to their aptamers as dimers. Information about these ABP and the apatamer sequences to which they bind is provided below in Table 1. In some embodiments, the at least one non-viral ABP nucleotide sequence encodes a polypeptide having the sequence set forth in any of SEQ ID NO:10, SEQ ID NO:12, SEQ ID NO:14, or SEQ ID NO:16. In some embodiments, the at least one non-viral ABP nucleotide sequence comprises any of SEQ ID NO:9, SEQ ID NO:11, SEQ ID NO:13, or SEQ ID NO:15.

functional integrase protein and they are used in the systems and methods described herein, there is substantially reduced risk the nucleic acid molecules carried by the lentivirus-like particles produced using these packaging plasmids will integrate into the genome of the transduced eukaryotic cell. In some instances, the lentiviral packaging plasmid comprises an integrase coding sequence with an integrase-inactivating mutation therein. For example, the integrase-inactivating mutation may be an aspartic acid to valine mutation at amino acid position 64 (D64V) of the integrase protein encoded by the integrase coding sequence. In some instances, the lentiviral packaging plasmid comprises a deletion of all or a portion of an integrase coding sequence.

The lentiviral packaging plasmids comprise a eukaryotic promoter operably linked to the Gag nucleotide sequence. The mammalian expression plasmids comprise a eukaryotic promoter operably linked to the VPR coding sequence or the NEF coding sequence. In some instances, the eukaryotic promoter is a RNA polymerase II promoter. The RNA polymerase II promoter sequence is selected from a mammalian species. For example, the promoter sequence can be selected from a human, cow, sheep, buffalo, pig, or mouse, to name a few. In some examples, the RNA polymerase II promoter sequence is a CMV, FE1α, or SV40 sequence. In

TABLE 1

Aptamer-Binding Proteins and Corresponding Aptamer Sequences

| | Aptamer-Binding Proteins | | | |
|---|---|---|---|---|
| | MS2 coat protein | PP7 coat protein | lambda N peptide (amino acids 1-22) | COM protein |
| Nucleic Acid Sequence | SEQ ID NO: 9 | SEQ ID NO: 11 | SEQ ID NO: 13 | SEQ ID NO: 15 |
| Amino Acid Sequence | SEQ ID NO: 10 | SEQ ID NO: 12 | SEQ ID NO: 14 | SEQ ID NO: 16 |
| Aptamer (RNA) | SEQ ID NO: 17 | SEQ ID NO: 19 | SEQ ID NO: 21 (Box-B aptamer) | SEQ ID NO: 23 |
| Aptamer (DNA) | SEQ ID NO: 18 | SEQ ID NO: 20 | SEQ ID NO: 22 | SEQ ID NO: 24 |

As discussed above, the lentiviral packaging plasmid may encode various lentiviral proteins. In some instances, the packaging plasmid contains only a Gag nucleotide sequence (gene), a Pol nucleotide sequence (gene), a Rev nucleotide sequence (gene), and a Tat nucleotide sequence (gene), which may be referred to as a second generation packaging plasmid. In some instances, the packaging plasmid contains only the Gag nucleotide sequence (gene) and Pol nucleotide sequence (gene), which may be referred to as a third generation packaging plasmid. In some instances, the lentiviral packaging plasmid may encode only those proteins needed for the viral shell (capsid). In some instances, coding sequences for one or more lentiviral proteins may be excluded in full or in part from the packaging plasmid. For example, in some instances, the packaging plasmid contains only the Gag nucleotide sequence (gene). In another example, the lentiviral packaging plasmid may comprise a deletion of all or a portion of a Pol nucleotide sequence (gene). In another example, the lentiviral packaging plasmid may comprise a deletion of all or a portion of an integrase (Int) coding sequence. In another example, the lentiviral packaging plasmid may comprise a deletion of all or a portion of a reverse transcriptase (RT) coding sequence.

A feature of the lentiviral packaging plasmids provided herein is that they may not encode a functional integrase protein. When the packaging plasmids do not encode a some examples, the RNA polymerase II sequence is a modified RNA polymerase II sequence. For example, the RNA polymerase II sequences having at least 80%, 85%, 90%, 95%, or 99% identity to a wild-type RNA polymerase II promoter sequence from any mammalian species can be used in the constructs provided herein. Those of skill in the art readily understand how to determine the identity of two polypeptides or nucleic acids. For example, the identity can be calculated after aligning the two sequences so that the identity is at its highest level. Another way of calculating identity can be performed by published algorithms. For example, optimal alignment of sequences for comparison can be conducted using the algorithm of Needleman and Wunsch, J. Mol. Biol. 48: 443 (1970). In some instances, the eukaryotic promoter is an inducible promoter.

Coding sequences transcribed from a RNA pol II promoter include a poly(A) signal and a transcription terminator sequence downstream of the coding sequence. Commonly used mammalian terminators (SV40, hGH, BGH, and rbGlob) include the sequence motif AAUAAA which promotes both polyadenylation and termination. The role of the terminator, a sequence-based element, is to define the end of a transcriptional unit (such as a gene) and initiate the process of releasing the newly synthesized RNA from the transcription machinery. Terminators are found downstream of the gene to be transcribed, and typically occur directly after any 3' regulatory elements, such as the polyadenylation or poly (A) signal.

In some instances, the lentiviral packaging plasmids may comprise an expression cassette. In some instances, the mammalian expression plasmids may comprise an expression cassette.

B. CRISPR System Component Plasmids

Provided herein are mammalian expression plasmids that are used to deliver CRISPR component coding sequences into mammalian cells being used to generate the lentivirus-like particles of this disclosure. Once introduced into the mammalian cells together with the lentiviral packaging plasmids or the mammalian expression plasmids described in Section IIA, these mammalian expression plasmids act as template for generating non-viral CRISPR component RNA molecules that are packaged into the lentivirus-like particles. In some instances, the mammalian expression plasmids are lentiviral transfer vectors. Lentiviral transfer vectors generally encode the viral genome in addition to exogenous genes of interest. In some instances, any mammalian expression plasmid may be suitable for expression of CRISPR component coding sequences in the cells used to produce the lentivirus-like particles.

An aspect of this disclosure are mammalian expression plasmids that comprise the coding sequence for one or more CRISPR components. In some instances, the CRISPR component coding sequence comprises at least one aptamer sequence coding sequence. When the CRISPR component coding sequence is transcribed from the mammalian expression vector, the aptamer sequence is transcribed as well. The resulting transcribed RNA molecule comprises a CRISPR component RNA sequence and at least one aptamer sequence. As discussed in more detail below, the CRISPR component coding sequence may be a CRISPR-associated endonuclease coding sequence, a gRNA coding sequence, or both. In some instances, the CRISPR component coding sequence may be a CRISPR-associated endonuclease coding sequence. In some instances, the CRISPR-associated endonuclease coding sequence may comprise at least one aptamer coding sequence after the stop codon for CRISPR-associated endonuclease coding sequence but before any poly(A) signal and/or transcription terminator. In some instances, the CRISPR component coding sequence may be a gRNA coding sequence. In some instances, the gRNA coding sequence comprises at least one aptamer coding sequence. In some instances, the at least one aptamer coding sequence may be positioned at the 5' end or the 3' end of the gRNA. In some instances, the at least one aptamer coding sequence may be inserted at an internal position within the gRNA such as, for example, at one or more of the loops formed in the folded gRNA. For example, where the gRNA is for the SaCas9 protein, the at least one aptamer coding sequence may be positioned at the tetra loop, the stem loop 2, or the 3' end of the gRNA. In some instances, the aptamer sequence is inserted as a tetraloop.

In some instances, the aptamer coding sequence attached to or inserted to a gRNA sequence is selected from the group consisting of an aptamer that binds an MS2 coat protein sequences, an aptamer that binds a PP7 coat protein, an aptamer that binds a lambda N peptide and an aptamer that binds a COM protein. In some instances, the aptamer coding sequence is an MS2 coat protein aptamer sequence, for example, SEQ ID NO: 17 (RNA) or SEQ ID NO: 18 (DNA). In some instances, the aptamer coding sequence is a PP7 coat protein aptamer sequence, for example, SEQ ID NO: 19 (RNA) or SEQ ID NO: 20 (DNA). In some instances, the aptamer coding sequence is a lambda N peptide aptamer sequence, for example, SEQ ID NO: 21 (RNA) or SEQ ID NO: 22 (DNA). In some instances, the aptamer coding sequence is a COM protein protein aptamer sequence, for example, SEQ ID NO: 17 (RNA) or SEQ ID NO: 18 (DNA).

In some instances, the mammalian expression plasmid comprises a CRISPR-associated endonuclease coding sequence and a gRNA coding sequence. In some instances, each of the CRISPR-associated endonuclease coding sequence and the gRNA coding sequence may comprise at least one aptamer coding sequence. In some instances, the CRISPR-associated endonuclease coding sequence comprises at least one aptamer coding sequence downstream thereof. In some instances, the gRNA coding sequence comprises at least one aptamer coding sequence. In some instances, a spacer of 1-30 nucleotides may be positioned between the CRISPR component coding sequence and the at least one aptamer coding sequence, or flanking the at least one aptamer coding sequence.

An aspect of this disclosure are mammalian expression plasmids that comprise the coding sequence for one or more CRISPR components. In some instances, the CRISPR component coding sequence comprises at least one aptamer sequence coding sequence As used throughout, a sgRNA is a single guide RNA sequence that interacts with a CRISPR-associated endonuclease (a CRISPR site-directed nuclease) and specifically binds to or hybridizes to a target nucleic acid within the genome of a cell (genomic target sequence), such that the sgRNA and the CRISPR-associated endonuclease co-localize to the target nucleic acid in the genome of the cell. Each sgRNA includes a DNA targeting sequence or protospacer sequence of about 10 to 50 nucleotides in length that specifically binds to or hybridizes to a target DNA sequence in the genome. For example, the DNA targeting sequence may be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. For example, the DNA targeting sequence may be about 15-30 nucleotides, about 15-25 nucleotides, about 10-25 nucleotides, or about 18-23 nucleotides. In one example, the DNA targeting sequence is about 20 nucleotides. In some embodiments, the sgRNA comprises a crRNA sequence and a transactivating crRNA (tracrRNA) sequence. In some embodiments, the sgRNA does not comprise a tracrRNA sequence.

Generally, the DNA targeting sequence is designed to complement (e.g., perfectly complement) or substantially complement (e.g., having 1-4 mismatches) to the target DNA sequence. In some cases, the DNA targeting sequence can incorporate wobble or degenerate bases to bind multiple genetic elements. In some cases, the 19 nucleotides at the 3' or 5' end of the binding region are perfectly complementary to the target genetic element or elements. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%). In some cases, the binding region, can be selected to begin with a sequence that facilitates efficient transcription of the sgRNA. For example, the binding region can begin at the 5' end with a G nucleotide. In some cases, the binding region can contain modified nucleotides such as, without limitation, methylated or phosphorylated nucleotides.

As used herein, the term "complementary" or "complementarity" refers to base pairing between nucleotides or nucleic acids, for example, and not to be limiting, base pairing between a sgRNA and a target sequence. Complementary nucleotides are, generally, A and T (or A and U), and G and C. The guide RNAs described herein can comprise sequences, for example, DNA targeting sequence that are perfectly complementary or substantially complementary (e.g., having 1-4 mismatches) to a genomic sequence.

The sgRNA includes a sgRNA constant region that interacts with or binds to the CRISPR-associated endonuclease. In the constructs provided herein, the constant region of an sgRNA can be from about 75 to 250 nucleotides in length. In some examples, the constant region is a modified constant region comprising one, two, three, four, five, six, seven, eight, nine, ten or more nucleotide substitutions in the stem, the stem loop, a hairpin, a region in between hairpins, and/or the *nexus* of a constant region. In some instances, a modified constant region that has at least 80%, 85%, 90%, or 95% activity, as compared to the activity of the natural or wild-type sgRNA constant region from which the modified constant region is derived, may be used in the constructs described herein. In particular, modifications should not be made at nucleotides that interact directly with a CRISPR-associated endonuclease, for example, a Cas9 polypeptide, or at nucleotides that are important for the secondary structure of the constant region.

The CRISPR-associated endonuclease encoded on mammalian expression plasmids as described herein are RNA-guided site-directed nucleases. Examples include, but are not limited to, nucleases present in any bacterial species that encodes a Type II or a Type V CRISPR/Cas system. For example, and not to be limiting, the CRISPR-associated endonuclease can be a Cas9 polypeptide (Type II) or a Cpf1 polypeptide (Type V). See, for example, Abudayyeh et al., Science 2016 Aug. 5; 353(6299):aaf5573; Fonfara et al. Nature 532: 517-521 (2016), and Zetsche et al., Cell 163(3): p. 759-771, 22 Oct. 2015. As used throughout, the term "Cas9 polypeptide" means a Cas9 protein, or a fragment or derivative thereof, identified in any bacterial species that encodes a Type II CRISPR/Cas system. See, for example, Makarova et al. Nature Reviews, Microbiology, 9: 467-477 (2011), including supplemental information, hereby incorporated by reference in its entirety. CRISPR-associated endonucleases, such as Cas9 and Cas9 homologs, are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein (SpCas9). Another exemplary Cas9 protein is the *Staphylococcus aureus* Cas9 protein (SaCas9). Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. The Cas9 nuclease domains can be optimized for efficient activity or enhanced stability in the host cell. Other CRISPR-associated endonucleases include Cpf1 (See, e.g., Zetsche et al., Cell, Volume 163, Issue 3, p759-771, 22 Oct. 2015) and homologs thereof.

Full-length Cas9 is an endonuclease comprising a recognition domain and two nuclease domains (HNH and RuvC, respectively) that creates double-stranded breaks in DNA sequences. In the amino acid sequence of Cas9, HNH is linearly continuous, whereas RuvC is separated into three regions, one left of the recognition domain, and the other two right of the recognition domain flanking the HNH domain. Cas9 is targeted to a genomic site in a cell by interacting with a guide RNA that hybridizes to a 20-nucleotide DNA sequence that immediately precedes an NGG motif recognized by Cas9. This results in a double-strand break in the genomic DNA of the cell. In some examples, a Cas9 nuclease that requires an NGG protospacer adjacent motif (PAM) immediately 3' of the region targeted by the guide RNA can be utilized. As another example, Cas9 proteins with orthogonal PAM motif requirements can be utilized to target sequences that do not have an adjacent NGG PAM sequence. Exemplary Cas9 proteins with orthogonal PAM sequence specificities include, but are not limited to those described in Esvelt et al., Nature Methods 10: 1116-1121 (2013).

In some embodiments, the Cas9 protein can be in an active endonuclease form, such that when bound to target nucleic acid as part of a complex with a guide RNA or part of a complex with a DNA template, a double strand break is introduced into the target nucleic acid. The double strand break can be repaired by NHEJ to introduce random mutations, or HDR to introduce specific mutations. Various Cas9 nucleases can be utilized in the methods described herein. For example, a Cas9 nuclease that requires an NGG protospacer adjacent motif (PAM) immediately 3' of the region targeted by the guide RNA, such as SpCas9, can be utilized. Such Cas9 nucleases can be targeted to any region of a genome that contains an NGG sequence. In another example, a Cas9 nuclease that requires an NNGRRT or NNGRR(N) PAM immediately 3' of the region targeted by the guide RNA, such as SaCas9, can be utilized. As another example, Cas9 proteins with orthogonal PAM motif requirements can be utilized to target sequences that do not have an adjacent NGG PAM sequence. Exemplary Cas9 proteins with orthogonal PAM sequence specificities include, but are not limited to those described in Nature Methods 10, 1116-1121 (2013), and those described in Zetsche et al., Cell, Volume 163, Issue 3, p'759-'7'71, 22 Oct. 2015.

In some cases, the Cas9 protein is a nickase, such that when bound to target nucleic acid as part of a complex with a guide RNA, a single strand break or nick is introduced into the target nucleic acid. A pair of Cas9 nickases, each bound to a structurally different guide RNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation.

In some instances, the CRISPR-associated endonuclease is a deactivated site-directed nuclease. For example, the CRISPR-associated endonuclease may be a dCas9 polypeptide. As used throughout this disclosure, a dCas9 polypeptide is a deactivated or nuclease-dead Cas9 (dCas9) that has been modified to inactivate Cas9 nuclease activity. Modifications include, but are not limited to, altering one or more amino acids to inactivate the nuclease activity or the nuclease domain. For example, and not to be limiting, D10A and H840A mutations can be made in Cas9 from *Streptococcus pyogenes* to inactivate Cas9 nuclease activity. Other modifications include removing all or a portion of the nuclease domain of Cas9, such that the sequences exhibiting nuclease activity are absent from Cas9. Accordingly, a dCas9 may include polypeptide sequences modified to inactivate nuclease activity or removal of a polypeptide sequence or sequences to inactivate nuclease activity. The dCas9 retains the ability to bind to DNA even though the nuclease activity has been inactivated. Accordingly, dCas9 includes the polypeptide sequence or sequences required for DNA binding but includes modified nuclease sequences or lacks nuclease sequences responsible for nuclease activity. It is understood that similar modifications can be made to inactivate nuclease activity in other site-directed nucleases, for example in Cpf1 or C2c2. In some examples, the dCas9 protein is a full-length Cas9 sequence from *S. pyogenes* lacking the polypeptide sequence of the RuvC nuclease domain and/or the HNH nuclease domain and retaining the DNA binding function. In other examples, the dCas9 protein sequences have at least 30%, 40%, 50%, 60%, 70%, 80%, 90%, 95%, 98% or 99% identity to Cas9 polypeptide sequences lacking the RuvC nuclease domain and/or the HNH nuclease domain and retains DNA binding function.

In some examples, the deactivated CRISPR-associated endonuclease is linked to an effector protein. Optionally, the site-directed nuclease is linked to the effector protein via a peptide linker. The linker can be between about 2 and about 25 amino acids in length. The effector protein can be a transcriptional regulatory protein or an active fragment thereof. The transcriptional regulatory protein can be a transcriptional activator or a transcriptional repressor protein or a protein domain of the activator protein or the inhibitor protein. Examples of transcriptional activators include, but are not limited to VP16, VP48, VP64, VP192, MyoD, E2A, CREB, KMT2A, NF-KB (p65AD), NFAT, TET1, p300Core and p53. Examples of transcriptional inhibitors include, but are not limited to KRAB, MXI1, SID4X, LSD1, and DNMT3A/B. The effector protein can also be an epigenome editor, such as, for example, histone acetyltransferase, histone demethylase, DNA methylase etc. The effector protein or an active fragment thereof can be operatively linked, in series, to the amino-terminus or the carboxy-terminus of the CRISPR-associated endonuclease. Optionally, two or more activating effector proteins or active domains thereof can be operatively linked to the amino-terminus or the carboxy-terminus of the CRISPR-associated endonuclease. Optionally, two or more repressor effector proteins or active domains thereof can be operatively linked, in series, to the amino-terminus or the carboxy-terminus of the CRISPR-associated endonuclease. Optionally, the effector protein can be associated, joined or otherwise connected with the nuclease, without necessarily being covalently linked to the CRISPR-associated endonuclease.

In some embodiment, the CRISPR-associated endonuclease is a Cpf1 polypeptide. Cpf1 protein is a Class II, Type V CRISPR/Cas system protein. Cpf1 is a smaller and simpler endonuclease than Cas9 (such as the spCas9). The Cpf1 protein has a RuvC-like endonuclease domain that is similar to the RuvC domain of Cas9 but does not have a HNH endonuclease domain. The N-terminal domain of Cpf1 also does not have the alpha-helical recognition lobe like the Cas9 protein. When cleaving DNA, Cpf1 introduces a sticky-end-like DNA double-stranded break with a 4 or 5 nucleotide overhang. The Cpf1 protein does not need a tracrRNA; rather, the Cpf1 protein functions with only a crRNA. In the context of this disclosure, where the CRISPR-associated endonuclease is a Cpf1 protein, the sgRNA does not comprise a tracr sequence. The sgRNA used with the Cpf1 protein may comprise only a crRNA sequence (constant region). In some examples, a Cpf1 protein that requires an TTTN or TTN PAM (depending on the species, where "N" is an nucleobase) immediately 5' of the region targeted by the guide RNA can be utilized. Known Cpf1 proteins and derivatives thereof may be used in the context of this disclosure. For example, in some instances, the CRISPR-associated endonuclease is FnCpf1p and the PAM is 5' TTN, where N is A/C/G or T. In some instances, the CRISPR-associated endonuclease is PaCpf1p and the PAM is 5' TTTV, where V is A/C or G In certain instances, the CRISPR-associated endonuclease is FnCpf1p and the PAM is 5' TTN, where N is A/C/G or T, and the PAM is located upstream of the 5' end of the protospacer. In certain instances, the CRISPR-associated endonuclease is FnCpf1p and the PAM is 5' CTA and is located upstream of the 5' end of the protospacer or the target locus. In one example, the CRISPR-associated endonuclease is AsCpf1p and the PAM is 5' TTTN.

The mammalian expression plasmids comprise a eukaryotic promoter operably linked to the non-viral nucleic acid sequence. In some instances, the eukaryotic promoter is a RNA polymerase II promoter and the non-viral nucleic acid sequence is a CRISPR-associated endonuclease coding sequence. In other instances, the eukaryotic promoter is a RNA polymerase III promoter and the non-viral nucleic acid sequence is a gRNA coding sequence. In some instances, wherein the non-viral nucleic acid sequence comprises both a CRISPR-associated endonuclease coding sequence and a gRNA coding sequence, and wherein a RNA polymerase II promoter is operably linked to the CRISPR-associated endonuclease coding sequence and a RNA polymerase III promoter operably linked to the gRNA coding sequence.

The RNA polymerase II promoter sequence is selected from a mammalian species. The RNA polymerase III promoter sequences is selected from a mammalian species. For example, these promoter sequences can be selected from a human, cow, sheep, buffalo, pig, or mouse, to name a few. In some examples, the RNA polymerase II promoter sequence is a CMV, FE1α, or SV40 sequence. In some examples, the RNA polymerase III promoter sequence is a U6 or an H1 sequence. In some examples, the RNA polymerase II sequence is a modified RNA polymerase II sequence. For example, the RNA polymerase II sequences having at least 80%, 85%, 90%, 95%, or 99% identity to a wild-type RNA polymerase II promoter sequence from any mammalian species can be used in the constructs provided herein. In some examples, the RNA polymerase III sequence is a modified RNA polymerase III sequence. For example, the RNA polymerase III sequences having at least 80%, 85%, 90%, 95%, or 99% identity to a wild-type RNA polymerase III promoter sequence from any mammalian species can be used in the constructs provided herein. Those of skill in the art readily understand how to determine the identity of two polypeptides or nucleic acids. For example, the identity can be calculated after aligning the two sequences so that the identity is at its highest level. Another way of calculating identity can be performed by published algorithms. For example, optimal alignment of sequences for comparison can be conducted using the algorithm of Needleman and Wunsch, J. Mol. Biol. 48: 443 (1970). In some instances, the eukaryotic promoter is an inducible promoter.

Coding sequences transcribed from a RNA pol II promoter include a poly(A) signal and a transcription terminator sequence downstream of the coding sequence. Commonly used mammalian terminators (SV40, hGH, BGH, and rbGlob) include the sequence motif AAUAAA which promotes both polyadenylation and termination. Coding sequences transcribed from a RNA pol III promoter include a simple run of T residues downstream of the coding sequence as a terminator sequence. The role of the terminator, a sequence-based element, is to define the end of a transcriptional unit (such as a gene) and initiate the process of releasing the newly synthesized RNA from the transcription machinery. Terminators are found downstream of the gene to be transcribed, and typically occur directly after any 3' regulatory elements, such as the polyadenylation or poly (A) signal.

In some instances, the mammalian expression vector comprises at least one aptamer coding sequence that encodes an aptamer sequence that is bound specifically by an aptamer-binding protein (ABP). In the context of this disclosure, an aptamer sequence is an RNA sequence that forms a tertiary loop structure that is specifically bound by an ABP. ABPs are RNA-binding proteins or RNA-binding protein domains. Suitable aptamer coding sequences include polynucleotide sequences that encode known bacteriophage aptamer sequences. Exemplary aptamer coding sequences include those encoding the aptamer sequences provided above in Table 1. In some instances, the aptamers are bound by a dimer of ABP. These aptamer sequences are RNA sequences known to be bound specifically by bacteriophage proteins. In some circumstances, the at least one aptamer coding sequence encodes an aptamer sequence bound specifically by an ABP selected from the group consisting of MS2 coat protein, PP7 coat protein, lambda N RNA-binding domain, or COM protein.

In some instances, the mammalian expression vector comprises a CRISPR component coding sequence that comprises one aptamer coding sequence downstream thereof. In other instances, the CRISPR component coding sequence may comprise 1, 2, 3, 4, 5, 6, 7, 8, 9, 10, 11, or 12 aptamer coding sequences. For example, in some instances, the CRISPR component coding sequence may comprise two aptamer coding sequences in tandem. Where the mammalian expression vector includes both a CRISPR-associated endonuclease coding sequence and a gRNA coding sequence, either or both may comprise one or more aptamer coding sequences. In one example, where the vector comprises both a CRISPR-associated endonuclease coding sequence and a gRNA coding sequence, the CRISPR-associated endonuclease coding sequence may comprise one or more aptamer coding sequences. In another example, where the vector comprises both a CRISPR-associated endonuclease coding sequence and a gRNA coding sequence, the gRNA coding sequence may comprise one or more aptamer coding sequences. In another example, where the vector comprises both a CRISPR-associated endonuclease coding sequence and a gRNA coding sequence, both the CRISPR-associated endonuclease coding sequence and the gRNA coding sequence may each comprise one or more aptamer coding sequences. Where the vector comprises both a CRISPR-associated endonuclease coding sequence and a gRNA coding sequence and both comprise one or more aptamer coding sequences, the one or more aptamer coding sequences of the CRISPR-associated endonuclease coding sequence and the one or more aptamer coding sequences of the gRNA coding sequence may be the same aptamer coding sequence or may be different aptamer coding sequences. In some instances, the mammalian expression plasmid comprises a CRISPR component coding sequence, and the CRISPR component coding sequence does not comprise an aptamer coding sequence.

In some instances, the mammalian expression plasmid comprises a CRISPR-associated endonuclease coding sequence comprising at least one first aptamer coding sequence and a gRNA coding sequence comprising at least one second aptamer coding sequence. In one example, the at least one first aptamer coding sequence and the at least one second coding aptamer sequence are the same aptamer coding sequence. In some instances, the at least one first aptamer coding sequence encodes an aptamer sequence bound specifically by a first ABP and the at least one second aptamer coding sequence encodes an aptamer sequence bound specifically by a second ABP, wherein the at least one first aptamer coding sequence and the at least one second aptamer coding sequence encode aptamer sequences bound by different first and second ABPs. For example, the at least one first aptamer coding sequence and the at least one second aptamer coding sequence may encode an aptamer sequence bound specifically by an ABP selected from the group consisting of MS2 coat protein, PP7 coat protein, lambda N protein RNA binding domain, and COM protein. In another example, the at least one first aptamer coding sequence and the at least one second aptamer coding sequence may encode aptamer sequence that are each bound specifically by a different ABP selected from the group consisting of MS2 coat protein, PP7 coat protein, lambda N protein RNA binding domain, and COM protein.

In some instances, the mammalian expression plasmid may also include at least one polynucleotide sequence encoding a RNA-stabilizing sequence positioned downstream of the CRISPR component coding sequence or the aptamer coding sequence if positioned downstream of the CRISPR component coding sequence. The polynucleotide sequence encoding the RNA-stabilizing sequence is transcribed downstream of the CRISPR/Cas system component coding sequence and stabilizes the longevity of the transcribed RNA sequence. In one example, the polynucleotide sequence encoding the RNA-stabilizing sequence is positioned downstream of the CRISPR-associated endonuclease coding sequence. In another example, the polynucleotide sequence encoding the RNA-stabilizing sequence is positioned downstream of the gRNA coding sequence. An exemplary RNA-stabilizing sequence is the sequence of the 3' UTR of human beta globin gene as set forth in SEQ ID NO:25 (DNA) and SEQ ID NO:26 (RNA). Other RNA-stabilizing sequences are described in Hayashi, T. et al., Developmental Dynamics 239(7):2034-2040 (2010) and Newbury, S. et al., Cell 48(2):297-310 (1987). In some instances, a spacer of 1-30 nucleotides may be positioned between the CRISPR component coding sequence and the at least one polynucleotide sequence encoding RNA-stabilizing sequence.

In some instances, the mammalian expression plasmid may comprise an expression cassette. In some instances, the mammalian expression plasmid may also comprise a reporter gene.

III. Systems

Another aspect of this disclosure are lentiviral packaging systems. Such systems include the lentiviral packaging plasmids and mammalian expression plasmids described in this disclosure. These systems are useful in providing components for introduction into mammalian cells to generate the lentivirus-like particles described in this disclosure.

In some instances, the system includes a lentiviral packaging plasmid comprising a eukaryotic promoter operably linked to a Gag nucleotide sequence, wherein the Gag nucleotide sequence comprises a nucleocapsid (NC) coding sequence and a matrix protein (MA) coding sequence, wherein one or both of the NC coding sequence or the MA coding sequence comprise at least one non-viral aptamer-binding protein (ABP) nucleotide sequence, and wherein the packaging plasmid does not encode a functional integrase protein. The lentiviral packaging plasmid may have any of the configurations described above in Section II.A. The system may include a second generation packaging plasmid or third generation packaging plasmids or modified versions thereof. In some instances, the packaging plasmid includes the Gag nucleotide sequence as described above and further comprises a Rev nucleotide sequence and a Tat nucleotide sequence. In other instances, the system includes a first packaging plasmid including a Gag nucleotide sequence as described above and a second packaging plasmid comprising a Rev nucleotide sequence. In each of the packaging plasmids, the viral protein coding sequences are operably linked to a eukaryotic promoter for example, each individually or one promoter for multiple protein coding sequences.

In other instances, the system includes mammalian expression plasmids comprising a eukaryotic promoter operably linked to a NEF coding sequence or a VPR coding sequence, wherein the NEF coding sequence or the VPR coding sequence comprises at least one non-viral ABP nucleotide sequence. The mammalian expression plasmid may have any of the configurations described above in Section II.A. The system may include a second generation packaging plasmid or third generation packaging plasmids or modified versions thereof. In some instances, the packaging plasmid includes a Gag nucleotide sequence, a Rev nucleotide sequence, and a Tat nucleotide sequence. In other instances, the system includes a first packaging plasmid including a Gag nucleotide sequence and a second packaging plasmid comprising a Rev nucleotide sequence.

The system also can include at least one mammalian expression plasmid comprising a eukaryotic promoter operably linked to a non-viral nucleic acid sequence, wherein the non-viral nucleic acid sequence comprises a CRISPR-associated endonuclease coding sequence, a guide RNA (gRNA) coding sequence, or both a CRISPR-associated endonuclease coding sequence and a gRNA coding sequence. The mammalian expression plasmid may have any of the configurations described above in Section II.B. In some instances, the system includes a mammalian expression plasmid that includes a eukaryotic promoter operably linked to a CRISPR-associated endonuclease coding sequence and a eukaryotic promoter operably linked to a gRNA coding sequence. In other instances, the system includes a first mammalian expression plasmid that includes a eukaryotic promoter operably linked to a CRISPR-associated endonuclease coding sequence and a second mammalian expression plasmid that includes a eukaryotic promoter operably linked to a gRNA coding sequence. In some instances, the non-viral nucleic acid in the at least one mammalian expression plasmid does not include an aptamer sequence. In other instances, the non-viral nucleic acid in the at least one mammalian expression plasmid comprises at least one aptamer sequence.

The system also can include an envelope plasmid having an envelope coding sequence that encodes a viral envelope glycoprotein. For example, the Env nucleotide sequence may encode VSV-G. The envelope coding sequence is operably linked to a eukaryotic promoter. In some instances, the eukaryotic promoter is a RNA pol II promoter. Appropriate eukaryotic promoters are described in Section II.

Also provided herein are kits the include the components of the systems described in this disclosure. In some embodiments, the kits include one or more of the plasmids described herein.

IV. Production of Lentivirus-Like Particles

Provided herein are methods of producing lentivirus-like particles using the plasmids and systems described in this disclosure.

In one aspect, provided is a method of producing a lentiviral particle, the method including the steps of transfecting a plurality of eukaryotic cells with a packaging plasmid, at least one mammalian expression plasmid, and an envelope plasmid as described above in Sections II and III, and culturing the transfected eukaryotic cell for sufficient time for lentiviral particles to be produced. The method may employ a second generation packaging plasmid or third generation packaging plasmids. In some instances, a first and a second packaging plasmid as described in Section III are used. The plurality of eukaryotic cells may be mammalian cells. For example, the mammalian cells may be 293 human embryonic kidney cells or another suitable mammalian expression cell line.

In some instances, the fusion of one or more ABP nucleotide sequences to a viral protein coding sequence, such as the NC coding sequence, the MA coding sequence, or both, does not interfere with viral particle assembly when the plasmid encoding the viral fusion protein, the at least one mammalian expression plasmid encoding a non-viral nucleotide sequence, and the envelope plasmid are transfected into eukaryotic cells. In some instances, a lentiviral packaging plasmid encoding a NC-ABP fusion protein, a MA-ABP fusion protein, or both a NC-ABP fusion protein and a MA-ABP fusion protein does not interfere with viral particle assembly. In some instances, a mammalian expression plasmid encoding either a NEF-ABP fusion protein or a VPR-ABP fusion protein does not interfere with viral particle assembly.

Different lentivirus-like particles will be generated by the provided method depending on the plasmids used to transfect the eukaryotic cells. In some instances, the eukaryotic cells are transfected with a mammalian expression plasmid containing a CRISPR-associated endonuclease coding sequence. Cells transfected with this plasmid will produce lentivirus-like particles containing a CRISPR-associated endonuclease mRNA. In some instances, the eukaryotic cells are transfected with a mammalian expression plasmid containing a gRNA coding sequence. Cells transfected with this plasmid will produce lentivirus-like particles containing a gRNA. In some instances, the cells may be transfected with a first mammalian expression plasmid that contains a CRISPR-associated endonuclease coding sequence and a second mammalian expression plasmid that contains a gRNA coding sequence. Cells transfected with these plasmids will produce lentivirus-like particles containing both a CRISPR mRNA and a gRNA. In some instances, the cells may be transfected with a mammalian expression plasmid that contains a CRISPR-associated endonuclease coding sequence and a gRNA coding sequence. Cells transfected with this plasmid will produce lentivirus-like particles containing both a CRISPR mRNA and a gRNA.

Generally, the plasmids are simultaneously transfected into eukaryotic cells, the cells are allowed to incubate, and then the supernatant containing the virus-like particles is collected. The medium may be changed following transfection and prior to the incubation. The collected virus-like particles may be stored or centrifuged to concentrate particles. Routine cell transfection methods are used for generating lentiviral particles. Crude or concentrated virus-like particles can then be used to transduce the cells of interest. Viral titer may also be determined using known protocols.

A feature of the provided method is the amount of non-viral RNA molecules that can be packaged within the lentivirus-like particles. In a native lentivirus, the viral shell (capsid) contains two copies of the single stranded RNA genome. For example, wild-type HIV-1 viral particles contain two copies of the approximately 9.7 kb single stranded RNA genome. In the methods provided by this disclosure, many non-viral RNA molecules may be packaged within the viral shell. In some instances, the method may produce lentivirus-like particles containing up to 100 non-viral RNA molecules. For example, the lentivirus-like particles may contain about 5, 10, 15, 20, 25, 30, 35, 40, 45, 50, 55, 60, 65, 70, 75, 80, 85, 90, 95, or 100 non-viral RNA molecules. For example, the method may produce particles containing 5-25 non-viral RNA molecules, 25-50 non-viral RNA molecules, 50-75 non-viral RNA molecules, or 75-100 non-viral RNA molecules. For example, the method may produce particles containing approximately 50-100 non-viral RNA molecules. In some instances, the method may produce particles containing up to 100 copies of CRISPR-associated endonuclease mRNA (such as, for example, SaCas9 mRNA). In some instances, the method may produce lentivirus-like particles containing several copies of a CRISPR-associated endonuclease mRNA, a gRNA, or a combination thereof. In some instances, the mammalian expression plasmid used in the method may comprise a non-viral nucleic acid sequence that comprises at least one aptamer coding sequence. In other instances, the mammalian expression plasmid used in the method may contain a non-viral nucleic acid sequence that does not comprise at least one aptamer sequence. In some instances, the mammalian expression plasmid does not require an aptamer coding sequence downstream of the non-viral nucleic acid sequence to generate lentiviral-particles containing several copies of non-viral RNA molecules.

In some instances, the mammalian expression plasmid contains a non-viral nucleic acid sequence encoding a CRISPR-associated endonuclease mRNA, wherein an aptamer coding sequence is attached to the nucleic acid encoding a CRISPR-associated endonuclease mRNA. The interaction between the aptamer sequence and an aptamer-binding protein in a viral fusion protein described herein facilitates packaging of the CRISPR-associated endonuclease mRNA into a lentiviral particle. In some instances, the mammalian expression plasmid contains a non-viral nucleic acid sequence encoding a CRISPR-associated endonuclease mRNA and a gRNA, wherein an aptamer coding sequence is attached to or inserted into the gRNA. The interaction between the aptamer sequence attached to or inserted into the gRNA with the aptamer-binding protein in a viral fusion protein described herein, facilitates packaging of the gRNA complexed with the CRISPR-associated endonuclease (RNP) into a lentiviral particle.

V. Lentivirus-Like Particles

In another aspect, provided are lentivirus-like particles. The lentivirus-like particles contain a modified lentiviral protein that is a fusion protein in which at least one aptamer-binding protein is fused to one or more viral proteins. In the context of this disclosure, the modified viral protein may be structural or non-structural. Exemplary structural proteins are lentiviral nucleocapsid (NC) protein and matrix (MA) protein. Exemplary non-structural proteins are viral protein R (VPR) and negative regulatory factor (NEF). In some instances, the particles contain a fusion protein comprising a NC protein and a MA protein where one or both thereof are fused with at least one non-viral aptamer binding protein (ABP). The NC protein of the particles may have two functional zinc finger protein domains. In particular, retention of the second NC zinc finger domain may preserve the efficiency of viral assembly and budding. In some instances, the particles contain a fusion protein comprising a VPR protein or a NEF protein where the VPR protein or the NEF protein are fused with at least one non-viral ABP. The particles also contain at least one non-viral RNA sequence, wherein the non-viral RNA sequence comprises a CRISPR-associated endonuclease mRNA, a guide RNA (gRNA), or both a CRISPR-associated endonuclease mRNA and a gRNA. In some instances, the lentivirus-like particles do not contain a functional integrase protein. These virus-like particles are useful to transduce eukaryotic cells of interest.

The particles may comprise a viral fusion protein comprising one or more ABPs. In some instances, the particles contain a NC protein, a MA protein, or both, where one or both of the NC protein or MA protein are fused with one or more non-viral ABP. In some instances, lentivirus-like particles comprise a NC protein fused with at least one non-viral ABP. In some instances, lentivirus-like particles comprise a MA protein fused with at least one non-viral ABP. In some instances, the lentivirus-like particles may comprise a NC protein and a MA protein, where one or both of the NC protein or the MA protein may be fused with two non-viral ABP proteins, a first non-viral ABP and a second non-viral ABP fused to a C' terminal end of the first non-viral ABP (i.e. in tandem). In certain instances, the particles may contain one or both of a NC protein or a MA protein fused with a first non-viral ABP and a second non-viral ABP. In some instances, the lentivirus-like particle contains a VPR protein or a NEF protein, where the VPR protein or the NEF protein is fused to one or more non-viral ABP. In some instances, the lentivirus-like particle contains a VPR protein or a NEF protein fused to two non-viral ABP, a first non-viral ABP and a second non-viral ABP fused to a C' terminal end of the first non-viral ABP (i.e. in tandem). In some instances, the lentivirus-like particle contains a VPR protein or a NEF protein fused to a first non-viral ABP and a second non-viral ABP. The first non-viral ABP and the second non-viral ABP may both be the same ABP. Alternatively, the first non-viral ABP and the second non-viral ABP may be different ABPs. In some instances, the lentivirus-like particles may comprise a NC protein with at least one first non-viral ABP fused to MA protein with at least one second non-viral ABP fused to its C' terminal end. The at least one first non-viral ABP and the at least one second non-viral ABP both be the same ABP. Alternatively, the at least one first non-viral ABP protein and the at least one second non-viral ABP may be different ABPs. The first non-viral ABP and the second non-viral ABP may both be the same ABP. Alternatively, the first non-viral ABP and the second non-viral ABP may be different ABPs.

A non-viral ABP is a polypeptide sequence that binds to an RNA aptamer sequence. Several non-viral ABPs are suitable for use in this disclosure. In particular, suitable ABPs include bacteriophage RNA-binding proteins that bind specifically to known RNA aptamer sequences, which are RNA sequences that form stem-loop structures. Exemplary non-viral aptamer binding protein include MS2 coat protein, PP7 coat protein, lambda N peptide, and COM (Control of mom) protein. The lambda N peptide may be amino acids 1-22 of the lambda N protein, which are the RNA-binding domain of the protein. Information about these ABP and the apatamer sequences to which they bind is provided above in Table 1. In some embodiments, the at least one non-viral ABP protein is a polypeptide having the sequence set forth in any of SEQ ID NO:10, SEQ ID NO:12, SEQ ID NO:14, or SEQ ID NO:16.

The lentivirus-like particles may comprise various lentiviral proteins. However, in some instances, the lentivirus-like particles do not comprise all of the types of proteins or nucleic acids found in native lentiviruses. In some instances, the particles may contain NC, MA, CA, SP1, SP2, P6, POL, ENV, TAT, REV, VIF, VPU, VPR, and/or NEF proteins, or a derivative, combination, or portion of any thereof. In some instances, the particles may contain NC, MA, CA, SP1, SP2, P6, and POL. In some instances, the lentivirus-like particles may comprise only those proteins that form the viral shell (capsid). In some instances, one or more lentiviral proteins may be excluded in full or in part from the lentivirus-like particles. For example, in some instances, the lentivirus-like particles may not contain a POL protein or may comprise a non-functional version of a POL protein such as, for example, a POL protein with an inactivating point mutation or an inactivating truncation. In another example, the lentivirus-like particles may not contain an integrase protein or may comprise a non-functional version of an integrase protein such as, for example, an integrase protein with an inactivating point mutation or an inactivating truncation. For example, the lentivirus-like particle may contain a non-functional integrase protein comprising an aspartic acid to valine mutation at amino acid position 64 (D64V). In another example, the lentivirus-like particles may not contain a reverse transcriptase protein or may comprise a non-functional version of a reverse transcriptase protein such as, for example, a reverse transcriptase protein with an inactivating point mutation or an inactivating truncation.

In some instances, the lentivirus-like particles contain at least one non-viral RNA molecule. The non-viral RNA molecule is at least one of a CRISPR/Cas system component or encodes a CRISPR/Cas system component. In some instances, the non-viral RNA molecule may be an mRNA that encode a CRISPR-associated endonuclease. Suitable CRISPR-associated endonucleases are discussed throughout this disclosure. In one example, the non-viral RNA molecule may be an mRNA that encodes a Cas9 protein or derivative thereof. In another example, the non-viral RNA molecule may an mRNA that encodes a Cpf1 protein or derivative thereof. In some instances, the non-viral RNA molecule may comprise a gRNA. Features of suitable gRNAs are discussed throughout this disclosure. The gRNA generally comprises a DNA targeting sequence and a constant region that interacts with the CRISPR-associated endonuclease. In some instances, the gRNA may comprise a transactivating crRNA (tracrRNA) sequence. For example, the gRNA may comprise a tracrRNA where it is to be used in conjunction with a Cas9 protein or derivative. In other instances, the gRNA does not comprise a tracrRNA sequence. For example, the gRNA may not comprise a tracrRNA sequence where it is to be used in conjunction with a Cpf1 protein or derivative. In some instances, the lentivirus-like particles contain both an mRNA encoding a CRISPR-associated endonuclease and a gRNA. In some instances, the particles may contain one of an mRNA encoding a CRISPR-associated endonuclease or a gRNA.

In some instances, the at least one non-viral RNA molecule may have at least one aptamer sequence positioned at the 3' end thereof. The aptamer sequence is a sequence known to be bound specifically by the aptamer-binding protein (ABP) that is fused to the viral protein as described above. As discussed above, an aptamer sequence is an RNA sequence that forms a tertiary loop structure that is specifically bound by an ABP. Suitable aptamer sequences include known bacteriophage aptamer sequences. Exemplary aptamer sequences are provided above in Table 1. These aptamer sequences are RNA sequences known to be bound specifically by bacteriophage proteins. In some circumstances, the at least one aptamer sequence is bound specifically by an ABP selected from the group consisting of MS2 coat protein, PP7 coat protein, lambda N RNA-binding domain, or COM protein.

In some instances, the non-viral RNA molecule may be a CRISPR-associated endonuclease mRNA. In some instances, the CRISPR-associated endonuclease mRNA may comprise at least one aptamer sequence at its 3' end. In some instances, the non-viral RNA molecule may be a gRNA coding sequence. In some instances, the gRNA comprises at least one aptamer sequence. In some instances, the at least one aptamer sequence may be positioned at the 5' end or the 3' end of the gRNA. In some instances, the at least one aptamer sequence may be inserted at an internal position within the gRNA such as, for example, at one or more of the loops formed in the folded gRNA. For example, where the gRNA is for the SaCas9 protein, the at least one aptamer sequence may be positioned at the tetra loop, the stem loop 2, or the 3' end of the gRNA. In some instances, the at least one non-viral RNA molecule comprises a CRISPR-associated endonuclease mRNA and a gRNA. In some instances, each of the CRISPR-associated endonuclease mRNA and the gRNA may comprise at least one aptamer coding sequence. In some instances, the CRISPR-associated endonuclease mRNA comprises at least one aptamer sequence at its 3' end. In some instances, the gRNA comprises at least one aptamer sequence. In some instances, a spacer of 1-30 ribonucleotides may be positioned between the CRISPR-associated endonuclease mRNA or the gRNA and the at least one aptamer sequence, or flanking the at least one aptamer sequence. In certain instances, at least one aptamer sequence does not interfere with lentivirus-like particle transduction of eukaryotic cells. For example, at least one non-viral ABP fused to one or more of the NC protein, the MA protein, the VPR protein, or the NEF protein may not interfere with lentivirus-like particle transduction of eukaryotic cells.

In some instances, the at least one non-viral RNA molecule comprises one aptamer sequence. In other instances, the at least one non-viral RNA molecule may comprise 1, 2, 3, 4, 5, 6, 7, 8, 9, 10, 11, or 12 aptamer sequences. For example, in some instances, lentivirus-like particles comprises at least one non-viral RNA molecule comprising two aptamer sequences. Where the lentivirus-like particle includes both a CRISPR-associated endonuclease mRNA and a gRNA, either or both may comprise one or more aptamer sequences. In one example, where the particles comprise both a CRISPR-associated endonuclease mRNA and a gRNA, the CRISPR-associated endonuclease mRNA may comprise one or more aptamer sequences positioned at the 3' end. In another example, where the particles comprise both a CRISPR-associated endonuclease mRNA and a gRNA, the gRNA may comprise one or more aptamer sequences. In another example, where the particles comprise both a CRISPR-associated endonuclease mRNA and a gRNA, both the CRISPR-associated endonuclease mRNA and the gRNA may comprise one or more aptamer sequences. Where the particles comprise both a CRISPR-associated endonuclease mRNA and a gRNA and both comprise one or more aptamer sequences, the CRISPR-associated endonuclease mRNA and the gRNA may comprise the same aptamer sequence or may comprise different aptamer sequences.

In some instances, the lentivirus-like particles contain CRISPR-associated endonuclease mRNA with at least one first aptamer sequence positioned at the 3' end thereof and a gRNA comprising at least one second aptamer sequence. In one example, the at least one first aptamer sequence and the at least one second aptamer sequence are the same aptamer sequence. In some instances, the at least one first aptamer sequence is an aptamer sequence bound specifically by a first ABP and the at least one second aptamer sequence as an aptamer sequence bound specifically by a second ABP, wherein the at least one first aptamer sequence and the at least one second aptamer sequence are bound by different first and second ABPs. For example, the at least one first aptamer sequence and the at least one second aptamer sequence may be bound specifically by an ABP selected from the group consisting of MS2 coat protein, PP7 coat protein, lambda N protein RNA binding domain, and COM protein. In another example, the at least one first aptamer sequence and the at least one second aptamer sequence may be each bound specifically by a different ABP selected from the group consisting of MS2 coat protein, PP7 coat protein, lambda N protein RNA binding domain, and COM protein.

In some instances, the non-viral RNA molecule may also include a RNA-stabilizing sequence positioned at the 3' end of the CRISPR-associated endonuclease mRNA, at the 3' end of the CRISPR-associated endonuclease mRNA, or after the at least one aptamer sequence if the at least one aptamer sequence is positioned at the 3' end of the non-viral RNA molecule. The RNA-stabilizing sequence stabilizes the longevity of the non-viral RNA molecule. In one example, the non-viral RNA molecule comprises a CRISPR-associated endonuclease mRNA with one or more aptamer sequences and a RNA-stabilizing sequence after the one or more aptamer sequences. In another example, the non-viral RNA molecule comprises a gRNA and a RNA-stabilizing sequence downstream a the 3' end of the gRNA (after any aptamer sequence positioned at the 3' end of the gRNA). An exemplary RNA-stabilizing sequence is the sequence of the 3' UTR of human beta globin gene as set forth in SEQ ID NO:25 (DNA) and SEQ ID NO:26 (RNA). Other RNA-stabilizing sequences are described in Hayashi, T. et al., Developmental Dynamics 239(7):2034-2040 (2010) and Newbury, S. et al., Cell 48(2):297-310 (1987).

A feature of the lentivirus-like particles provided is the amount of non-viral RNA molecules that can be packaged within the particles. In a native lentivirus, the viral shell (capsid) contains two copies of the single stranded RNA genome. For example, wild-type HIV-1 viral particles contain two copies of the approximately 9.7 kb single stranded RNA genome. In the lentivirus-like particles of this disclosure, up to 100 copies of non-viral RNA molecules may be packaged within the viral shell. For example, the lentivirus-like particles may contain about 5, 10, 15, 20, 25, 30, 35, 40, 45, 50, 55, 60, 65, 70, 75, 80, 85, 90, 95, or 100 non-viral RNA molecules. For example, the particles may contain 5-25 non-viral RNA molecules, 25-50 non-viral RNA molecules, 50-75 non-viral RNA molecules, or 75-100 non-viral RNA molecules. For example, the particles may contain approximately 50-100 non-viral RNA molecules. In some instances, the lentivirus-like particles contain up to 100 copies of CRISPR-associated endonuclease mRNA (such as, for example, SaCas9 mRNA). In some instances, the lentivirus-like particles may contain several copies of a CRISPR-associated endonuclease mRNA, a gRNA, or a combination thereof. In some instances, the lentivirus-like particles comprise several copies of non-viral RNA molecules that comprise at least one aptamer sequence. In other instances, the lentivirus-like particles comprise several copies of non-viral RNA molecules that do not comprise at least one aptamer sequence. In some instances, an aptamer sequence is not required to generate lentiviral-particles containing several copies of non-viral RNA molecules.

In some instances, the lentivirus-like particles contain RNP(s), wherein the RNP is a complex between a CRISPR-associated endonuclease and a gRNA. In some instances, the lentivirus-like particle comprises a) a fusion protein comprising a nucleocapsid (NC) protein or a matrix (MA) protein, wherein the NC protein or MA protein comprises at least one non-viral aptamer binding protein (ABP); and b) a ribonucleotide protein (RNP) complex comprising a CRISPR-associated endonuclease and a guide RNA. In some instances, the lentivirus-like particle comprises a fusion protein comprising a Viral Protein R (VPR) protein or a Negative Regulatory Factor (NEF) protein, wherein VPR protein or the NEF protein comprises at least one non-viral aptamer binding protein (ABP); and b) a ribonucleotide protein (RNP) complex comprising a CRISPR-associated endonuclease and a guide RNA. In lentivirus-like particles that contain RNPs, the guide RNA comprises an apatamer that binds to the non-viral aptamer binding protein of the fusion protein.

Any of the mammalian expression plasmids described herein comprising a non-viral nucleic acid sequence, wherein the non-viral nucleic acid sequence encodes a CRISPR-associated endonuclease and a gRNA sequence, and wherein at least one aptamer is attached or inserted into the gRNA sequence, can be used to generate lentivirus-like particles containing RNPs. As described above, the interaction between the aptamer sequence attached to or inserted into the gRNA with the aptamer-binding protein in a viral fusion protein described herein, facilitates packaging of the gRNA complexed with the CRISPR-associated endonuclease (RNP) into a lentiviral particle.

VI. Cells

Also provided are cells including the compositions described herein and cells modified by the compositions described herein. Cells or populations of cells comprising one or more nucleic acid constructs (plasmids) described herein are also provided. For example, a cell comprising a lentiviral packaging plasmid as described above are provided herein. For example, a cell comprising a mammalian expression plasmid as described above are provided herein. In another example, a cell comprising both a lentiviral packaging plasmid and a mammalian expression plasmid as described above are provided herein. In this way, lentivirus-like particles comprising CRISPR components of the systems described herein may be generated. In another example, a cell comprising a lentivirus-like particle as described above are provided herein. In this way, modification of target DNA sequences in a cell genome can be effected by the CRISPR components of the systems described herein. Cells or populations of cells comprising the lentiviral packaging systems described herein are also provided. Cells or populations of cells comprising the lentivirus-like particles described herein are also provided.

Cells include, but are not limited to, eukaryotic cells, prokaryotic cells, human cells, non-human animal cells, and fungal cells. Optionally, the cells are in a cell culture. Optionally, the cell is a mammalian cell, for example, a human cell. The cell can be in vitro, ex vivo or in vivo. The cell can also be a primary cell, a germ cell, a stem cell or a precursor cell. The precursor cell can be, for example, a pluripotent stem cell or a hematopoietic stem cell. Introduction of the composition into cells can be cell cycle dependent or cell cycle independent. Methods of synchronizing cells to increase a proportion of cells in a particular phase are known in the art. Depending on the type of cell to be modified, one of skill in the art can readily determine if cell cycle synchronization is necessary. In some cases, cells are removed from a subject, modified using any of the methods described herein and administered to the subject.

Optionally, the cells are T cells. T cells include, but are not limited to, naïve T cells, stimulated T cells, primary T cells (e.g., uncultured), cultured T cells, immortalized T cells, helper T cells, cytotoxic T cells, memory T cells, regulatory T cells, natural killer T cells, combinations thereof, or sub-populations thereof. T cells can be $CD4^+$, $CD8^+$, or $CD4^+$ and $CD8^+$. T cells can be helper cells, for example helper cells of type $T_H1$, $T_H2$, $T_H3$, $T_H9$, $T_H17$, or $T_{FH}$. T cells can be cytotoxic T cells. A T cell can be a recombinant T cell that has been genetically manipulated, for example a T cell expressing a chimeric antigen receptor or a recombinant T cell receptor

VII. Gene Editing Methods

Described herein are methods of using the plasmids and systems provided in this disclosure in CRISPR/Cas systems for editing DNA targets or modulating transcription of one or more DNA targets. These methods can be used to repress, mutate, or activate a target genomic sequence, such as a gene, in the genome of a eukaryotic cell.

In the methods provided herein, eukaryotic cells comprising a target genomic sequence of interest to be modified are transduced with lentivirus-like particles that contain a viral fusion protein comprising a viral protein fused to at least one aptamer-binding protein (ABP) and a CRISPR-associated endonuclease mRNA. A feature of the described methods is that the eukaryotic cells do not stably express a CRISPR-associated endonuclease. The CRISPR-associated endonuclease is not constitutively expressed; rather, a finite amount of CRISPR-associated endonuclease mRNA is provided to the transduced cells via the lentivirus-like particles. An advantage of the provided methods is reduced off-target gene editing events because the CRISPR-associated endonuclease is not present and, as such, not active for a long period of time in the cells. Also, when lentivirus-like particles lacking integrase activity are used in the method, there is reduced risk of integration into the cell genome of any of the nucleic acids carried by the particles, particularly the CRISPR-associated endonuclease coding sequence. In some instances, the lentiviral-particles used lack portions of the lentiviral genomic sequences that are essential for viral replication and, as such, reduce the risk of continued particle production. Another advantage of the provided components is that the viral fusion protein may increase packaging of non-viral RNA molecules, such as CRISPR-associated endonuclease mRNA, into the lentivirus-like particles, which in turn increase genome editing efficiency. In some instances, the non-viral RNA molecules packaged in the lentivirus-like particles include at least one aptamer sequence positioned at the 3' end.

In some instances, the transduced eukaryotic cells are mammalian cells. In some instances, the eukaryotic cells may be in vitro cultured cells. In some instances, the eukaryotic cells may ex vivo cells obtained from a subject.

In other instances, the eukaryotic cells are present in a subject. As used throughout, by subject is meant an individual. For example, the subject is a mammal, such as a primate, and, more specifically, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical uses and formulations are contemplated herein. The term does not denote a particular age or sex. Thus, adult and newborn subjects, whether male or female, are intended to be covered. As used herein, patient or subject may be used interchangeably and can refer to a subject afflicted with a disease or disorder. The viral particles of the system provided by this disclosure may be injected into a subject according to known, routine methods. In some instances, the viral particles of the system are injected intravenously (IV), intraperitoneally (IP), intramuscularly, or into a specific organ.

In some instances, the provided methods are for modifying a target locus of interest, the method comprising transducing a plurality of eukaryotic cells with a plurality of viral particles, wherein the plurality of viral particles comprise a fusion protein comprising a Viral Protein R (VPR) protein or a Negative Regulatory Factor (NEF) protein, wherein VPR protein or the NEF protein comprises at least one non-viral aptamer binding protein (ABP); and a ribonucleotide protein (RNP) complex comprising a CRISPR-associated endonuclease and a guide RNA, wherein the RNP binds to the genomic target sequence in genomic DNA of the cell and the CRISPR-associated endonuclease cleaves the genomic DNA of the cell, thereby triggering cellular DNA repair mechanisms causing modification of the genomic target sequence. In some instances, the plurality of viral particles comprise a) a fusion protein comprising a nucleocapsid (NC) protein or a matrix (MA) protein, wherein the NC protein or MA protein comprises at least one non-viral aptamer binding protein (ABP); and b) a ribonucleotide protein (RNP) complex comprising a CRISPR-associated endonuclease and a guide RNA, wherein the RNP binds to the genomic target sequence in genomic DNA of the cell and the CRISPR-associated endonuclease cleaves the genomic DNA of the cell, thereby triggering cellular DNA repair mechanisms causing modification of the genomic target sequence.

As described above, the RNPs are packaged into the viral particles via the interaction of an aptamer sequence attached to or inserted into a gRNA sequence that binds to at least one non-viral aptamer binding protein in a fusion protein described herein. The gRNA sequence binds to at least one non-viral aptamer binding protein in a fusion protein described herein and interacts with the CRISPR-associated endonuclease to form a complex (RNP).

In some instances, the provided methods are for modifying a target locus of interest, the method comprising delivering to said locus a CRISPR-associated endonuclease and one or more nucleic acid components, wherein the CRISPR-associated endonuclease forms a complex with the one or more nucleic acid components and upon binding of the said complex to the locus of interest the CRISPR-associated endonuclease induces the modification of the target locus of interest. In a preferred embodiment, the modification is the introduction of a strand break. In the context of this disclosure, a lentivirus-like particle containing a CRISPR-associated endonuclease mRNA is used to transduce cells containing a target locus of interest to be modified, and a CRISPR-associated endonuclease is expressed in the cells from the CRISPR-associated endonuclease mRNA.

In the provided methods, lentivirus-like particles containing CRISPR-associated endonuclease mRNA can be used to effect genome editing in conjunction with other viral particles that provide the gRNA component of the editing system. In some instances, the plurality of eukaryotic cells are transduced with a lentivirus-like particle that contains both CRISPR-associated endonuclease mRNA and gRNA. In some instances, the plurality of eukaryotic cells are transduced with a lentivirus-like particle containing CRISPR-associated endonuclease mRNA and a second viral particle that provides a gRNA or a gRNA coding sequence. Where the second viral particle is a type of virus that comprises an RNA genome, the viral particle may contain a gRNA or a gRNA coding sequence. For example, the second viral particle may be a lentivirus-like particle that contains a gRNA. In another example, the second viral particle may be a lentiviral particle that contains a gRNA coding sequence. Where the second viral particle is a type of virus that comprises a DNA genome, the viral particle contains a gRNA coding sequence in which the gRNA coding sequence is operably linked to a eukaryotic promoter. In another example, the second viral particle may be an adenovirus or an adeno-associated virus that contains a gRNA coding sequence that is operably linked to a eukaryotic promoter.

In some instances, the provided methods of genome editing or modifying sequences associated with or at a target locus of interest comprises introducing CRISPR/Cas system components including a CRISPR-associated endonuclease mRNA into a eukaryotic cell, whereby the CRISPR/Cas system components effectively function to integrate a DNA insert into the genome of the eukaryotic cell. In certain embodiments, the genome is a mammalian genome. In some instances, the integration of the DNA insert is facilitated by non-homologous end joining (NHEJ) or homology-directed recombination (HDR). In some instances, the DNA insert is an exogenously introduced target template sequence, such as a DNA template or a repair template. The target template sequence comprises a nucleic acid sequence with a desired insertion or modification to the genomic target sequence present in the eukaryotic cells. The target template sequence also comprises nucleic acid sequences homologous to genomic DNA flanking the genomic target sequence.

The target template sequence may be introduced into the eukaryotic cells by transducing the cells with an adenovirus particle, adeno-associated virus, or integration defective lentivirus particle containing the target template sequence. In some instances, the adenovirus particle, adeno-associated virus, or integration defective lentivirus particle may also comprise a gRNA coding sequence operably linked to a eukaryotic promoter.

In homology-directed repair, the target template sequence acts as a donor template, and the natural DNA-repair mechanisms of the cell result in insertion of the nucleic acid sequence with the desired insertion or modification to the genomic target sequence. Genome modification carried out in this way can be used to insert novel genes or knock out existing genes. NHEJ-mediated repair of CRISPR/Cas system breaks can be useful if the intent is to make a null allele ("knockout") in the genomic target of interest, as it is prone to generating indel errors. Indel errors generated in the course of repair by NHEJ are typically small (1-10 bp) but extremely heterogeneous. There is consequently about a two-thirds chance of the NHEJ-mediated repair causing a frameshift mutation. NHEJ does not obligatorily introduce indels. Given the end structure of the double stranded break (blunt or near-blunt ends without nucleotide damage), indels are rare; in some instances, accounting for less than 5% of repair events. However, the products of accurate repair are easily re-cleaved while indel products are not (no longer pair with the gRNA), so extended exposure of the genomic DNA to the CRISPR system components will favor accumulation of the latter products. In some instances, a pair of gRNAs that flank regions of hundreds of base pairs or more can simultaneously introduce a pair of chromosome breaks to result in deletion of the intervening DNA ("pop-out" deletions) if NHEJ joins the distal ends together. Similarly, it may be possible to direct insertion of an exogenous DNA fragment at a CRISPR-associated endonuclease targeted break (or pair of breaks) by NHEJ-dependent repair ("pop-in" insertion) provided a target template sequence containing compatible overhangs is used.

The methods described can be used with any CRISPR-associated endonuclease that requires a constant region of an sgRNA for function. These include, but are not limited to RNA-guided site-directed nucleases. Examples include nucleases present in any bacterial species that encodes a Type II or V CRISPR/Cas system. Suitable CRISPR-associated endonucleases are described throughout this disclosure. For example, and not to be limiting, the site-directed nuclease can be a Cas9 polypeptide or a Cpf1 polypeptide, or derivatives thereof.

In some instances, CRISPR-associated endonuclease can be in an active Cas9 polypeptide, such that when bound to target nucleic acid as part of a complex with a gRNA or part of a complex with a DNA template, a double strand break is introduced into the target nucleic acid. The double strand break can be repaired by NHEJ to introduce random mutations or HDR to introduce specific mutations. Various Cas9 nucleases can be utilized in the methods described herein. For example, a Cas9 nuclease that requires an NGG protospacer adjacent motif (PAM) immediately 3' of the region targeted by the guide RNA can be utilized. Such Cas9 nucleases can be targeted to any region of a genome that contains an NGG sequence. As another example, Cas9 proteins with orthogonal PAM motif requirements can be utilized to target sequences that do not have an adjacent NGG PAM sequence. Exemplary Cas9 proteins with orthogonal PAM sequence specificities include, but are not limited to, Cpf1 protein and fragments and derivatives thereof, those described in Esvelt et al., Nature Methods 10 (11):1116-1121 (2013), and those described in Zetsche et al., Cell 163 (3):759-771 (2015).

In some cases, the CRISPR-associated endonuclease is a modified Cas9 protein that is a nickase, such that when bound to target nucleic acid as part of a complex with a gRNA, a single strand break or nick is introduced into the target nucleic acid. A pair of Cas9 nickases, each bound to a structurally different guide RNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation.

In one example, where the lentivirus-like particles encode a Cas9 polypeptide, which generates blunt ended double-stranded cuts, the method may be used to disable genes, as repair may readily proceed by NHEJ. In another example, where the lentivirus-like particles encode a Cpf1 polypeptide, which generates sticky ends, the method may aid in the incorporation of new sequences of DNA, such as to insert a gene or generate a knock-in. In some instances, a Cpf1 protein may be used to produce gene introductions. However, either CRISPR-associated endonuclease may be used to either introduce genetic sequences or remove (and disable) genes. In some instances, modified Cas9 nickase can be used to introduced single strand breaks near each other in opposite strands to result in a DSB with long overhangs.

Generally, the sgRNA is targeted to specific regions at or near a gene. In some instances, the sgRNA is targeted to regions to affect transcription of a gene. For example, a sgRNA can be targeted to a region at or near the 0-750 bp region 5' (upstream) of the transcription start site of a gene. In some cases, the 0-750 bp targeting of the region can provide or provide increased, transcriptional activation by an sgRNA:deactivated CRISPR-associated endonuclease. For example, the sgRNA can form a complex with a deactivated CRISPR-associated endonuclease, such as dCas9 polypeptide, to a transcriptional activator to provide, or provide increased transcriptional activation of a gene by the complex. As another example, a sgRNA can be targeted to a region at or near the 0-1000 bp region 3' (downstream) of the transcription start site of a gene. In some cases, targeting this region may be done to provide increased transcriptional repression by an sgRNA:deactivated CRISPR-associated endonuclease complex. For example, the sgRNA can form a complex with a CRISPR-associated endonuclease, such as dCas9 polypeptide, linked to a transcriptional inhibitor to provide, or provide increased transcriptional repression of a gene by the complex.

In some examples, the sgRNA is targeted to a genomic region that is predicted to be relatively free of nucleosomes. The locations and occupancies of nucleosomes can be assayed through use of enzymatic digestion with micrococcal nuclease (MNase), such as by MNase-seq analysis. Thus, in some examples, the sgRNA is targeted to a genomic region that has a low MNase-Seq signal. In some cases, the sgRNA is targeted to a region predicted to be highly transcriptionally active. For example, the sgRNA can be targeted to a region predicted to have a relatively high occupancy for RNA polymerase II (Pol II). Such regions can be identified by Pol II chromatin immunoprecipitation sequencing (ChIP-seq). Thus, in some cases, the sgRNA is targeted to regions having a high Pol II ChIP-seq signal as disclosed in the ENCODE-published Pol II ChIP-seq database (Landt, et al., Genome Research 22(9):1813-1831 (2012)). As another example, the sgRNA can be targeted to a region predicted to be highly transcriptionally active as identified by run-on sequencing or global run-on sequencing (GRO-seq). Thus, in some cases, sgRNAs are targeted to regions having a high GRO-seq signal as disclosed in a published GRO-seq data (e.g., Core et al., Science. 2008 Dec. 19; 322(5909):1845-8; and Hah et al., Genome Res. 2013 August; 23(8):1210-23).

In some instances, the modifications to the system components as described in this disclosure do not impair how the system components function following transduction into eukaryotic cells. Rather, the components may function similarly or better than unmodified components upon transduction into eukaryotic cells. For example, the viral fusion proteins in the lentivirus-like particles may not interfere with the lentivirus-like particle transduction of eukaryotic cells. Similarly, if the non-viral RNA molecule packaged in the lentivirus-like particles comprises at least one aptamer sequence, the at least one aptamer sequence may not interfere with the lentivirus-like particle transduction of eukaryotic cells. For example, where the non-viral RNA molecule is a CRISPR-associated endonuclease mRNA, the presence of at least one aptamer sequence may not impair expression of the CRISPR-associated endonuclease from the mRNA molecule. In another example, the CRISPR-associated endonuclease expressed from the CRISPR-associated endonuclease mRNA with the at least one aptamer sequence immediately downstream thereof may be as functional as if expressed from an mRNA molecule lacking the at least one aptamer sequence. In another example, the gRNA comprising at least one aptamer sequence may be as functional as a gRNA lacking any aptamer sequence. In some instances, the lentivirus-like proteins containing viral fusion protein may result in greater gene editing upon transduction into eukaryotic cells relative to lentivirus-like particles that do not comprise a viral fusion protein. In one example the viral fusion protein may be a NC-ABP fusion protein, such as a NC-MS2 fusion protein or NC-PP7 fusion protein. In one example, the NC fusion protein is fused to one or two ABPs, such as one or two MS2 proteins, one or two PP7 proteins, or one MS2 protein and one PP7 protein.

The eukaryotic cells can be in vitro, ex vivo or in vivo. In some embodiments, the cell is a primary cell (isolated from a subject). As used herein, a primary cell is a cell that has not been transformed or immortalized. Such primary cells can be cultured, sub-cultured, or passaged a limited number of times (e.g., cultured 0, 1, 2, 3, 4, 5, 6, 7, 8, 9, 10, 11, 12, 13, 14, 15, 16, 17, 18, 19, or 20 times). In some cases, the primary cells are adapted to in vitro culture conditions. In some cases, the primary cells are isolated from an organism, system, organ, or tissue, optionally sorted, and utilized directly without culturing or sub-culturing. In some cases, the primary cells are stimulated, activated, or differentiated. In some embodiments, the cells are cultured under conditions effective for expanding the population of modified cells. In some embodiments, cells modified by any of the methods provided herein are purified. In some cases, cells are removed from a subject, modified using any of the methods described herein and re-administered to the patient.

In some instances, once the cells have been transduced with the viral particles described above, the cells are cultured for a sufficient amount of time to allow for gene editing to occur, such that a pool of cells expressing a detectable phenotype can be selected from the plurality of transduced cells. The phenotype can be, for example, cell growth, survival, or proliferation. In some examples, the phenotype is cell growth, survival, or proliferation in the presence of an agent, such as a cytotoxic agent, an oncogene, a tumor suppressor, a transcription factor, a kinase (e.g., a receptor tyrosine kinase), a gene (e.g., an exogenous gene) under the control of a promoter (e.g., a heterologous promoter), a checkpoint gene or cell cycle regulator, a growth factor, a hormone, a DNA damaging agent, a drug, or a chemotherapeutic. The phenotype can also be protein expression, RNA expression, protein activity, or cell motility, migration, or invasiveness. In some examples, the selecting the cells on the basis of the phenotype comprises fluorescence activated cell sorting, affinity purification of cells, or selection based on cell motility.

In some examples, the selecting the cells comprises analysis of the genomic DNA of the cells such as by amplification, sequencing, SNP analysis, etc. Sequencing methods include, but are not limited to, shotgun sequencing, bridge PCR, Sanger sequencing (including microfluidic Sanger sequencing), pyrosequencing, massively parallel signature sequencing, nanopore DNA sequencing, single molecule real-time sequencing (SMRT) (Pacific Biosciences, Menlo Park, CA), ion semiconductor sequencing, ligation sequencing, sequencing by synthesis (Illumina, San Diego, Ca), Polony sequencing, 454 sequencing, solid phase sequencing, DNA nanoball sequencing, heliscope single molecule sequencing, mass spectroscopy sequencing, pyrosequencing, Supported Oligo Ligation Detection (SOLiD) sequencing, DNA microarray sequencing, RNAP sequencing, tunneling currents DNA sequencing, and any other DNA sequencing method identified in the future. One or more of the sequencing methods described herein can be used in high throughput sequencing methods. As used herein, the term "high throughput sequencing" refers to all methods related to sequencing nucleic acids where more than one nucleic acid sequence is sequenced at a given time.

Others have assessed the utility of using lentiviral particles to deliver CRISPR/Cas components to eukaryotic cells. Choi et al., Gene Therapy 23(7): 627-633 (2016) described a system in which Cas9 coding sequence was inserted into the lentiviral genome, resulting in lentiviral particles containing Cas9 protein. That system has low virus titer and low gene editing activity. Compared to Choi et al.'s system, the advantages of the systems and components described herein include: 1) production of lentivirus-like particles at titers similar to conventional lentiviral system; 2) the packaging of multiple CRISPR-associated endonuclease mRNA molecules into each lentivirus-like particle, each mRNA useful for translation of multiple CRISPR-associated endonuclease proteins; and 3) the CRISPR-associated endonuclease expressed from the mRNA molecules packaged in the lentivirus-like particles are fully active and do not require post translational processing. For instance, Choi et al. describe obtaining an Indel rate of 30% (using particles reflecting 150 ng of P24). In contrast, an Indel rate of over 80% was observed by the inventors of this disclosure when using lentivirus-like particles described in this disclosure (particles reflecting 45 ng of P24; $2 \times 10^4$ HEK293T cells; sickle cell mutation correction).

Others have assessed the utility of using lentiviral particles to deliver mRNA to eukaryotic cells (Mock et al., Scientific Reports 4: 6409 (2014) and Prel et al., Molecular Therapy Methods & Clinical Development 2: 15039 (2015)). Neither group assessed the effectiveness of using lentivirus-like particles to introduce CRISPR/Cas system components into eukaryotic cells. Mock et al. used the lentiviral genome to deliver TALEN mRNA molecules. In this system, only two copies of TALEN mRNA molecules were packaged per viral particle. The extent of translation from the TALEN mRNA was relatively low, leading to inefficient gene editing activity. The inventors of this disclosure tested Mock et al.'s system to deliver SaCas9 mRNA molecules to GFP reporter eukaryotic cells useful for detecting gene editing events. Lentivirus with a SaCas9 coding sequence inserted in the genome was packaged using a packaging plasmid encoding an inactivated reverse transcriptase. The resulting lentivirus particles were co-transduced into the GFP reporter cells described in the Examples with a lentivirus expressing HBB sgRNA1. No GFP+ reporter cells could be detected, indicating that gene editing was not occurring. As such, the system described by Mock et al. was not useful for CRISPR/Cas system gene editing. Prel et al. used lentiviral particles to deliver Cre mRNA molecules into eukaryotic cells in vivo and in vitro. The lentivirus-like particles contained a NC fusion protein in which the second zinc finger domain of the NC protein was replaced with an MS2 protein. The Cre mRNA also had 12 copies of the MS2 aptamer sequence added to the 3' UTR. That system had inefficient viral particle production and low copy number packaging of Cre mRNA molecules into the viral particles. Compared to Prel et al.'s system, the system of this disclosure generates viral particles efficiently and with high copy number of non-viral RNA molecules per viral particle. Prel et al. reported observing packaging of 5 to 6 copies of Cre mRNA per particle. In contrast, using lentivirus-like particles described in this disclosure made to express NC-MS2 fusion protein (Plasmid No. 11 as packaging plasmid), the inventors of this disclosure observed 100 copies of SaCas9 mRNA per particle when SaCas9 mRNA was modified with human HBB 3' UTR (Plasmid No. 36) or 30 copies of SaCas9 mRNA per particle when the human HBB 3' UTR was not added (Plasmid No. 16).

VIII. Methods of Treatment

Any of the methods and compositions described herein can be used to treat a disease (e.g., cancer, a blood disorder (for example, sickle cell anemia or beta thalassemia), an infectious disease, an autoimmune disease, transplantation rejection, graft vs. host disease or other inflammatory disorder) in a subject.

In some methods, the cancer to be treated is selected from a cancer of B-cell origin, breast cancer, gastric cancer, neuroblastoma, osteosarcoma, lung cancer, colon cancer, chronic myeloid cancer, leukemia (e.g., acute myeloid leukemia, chronic lymphocytic leukemia (CLL) or acute lymphocytic leukemia (ALL)), prostate cancer, colon cancer, renal cell carcinoma, liver cancer, kidney cancer, ovarian cancer, stomach cancer, testicular cancer, rhabdomyosarcoma, and Hodgkin's lymphoma. In some embodiments, the cancer of B-cell origin is selected from the group consisting of B-lineage acute lymphoblastic leukemia, B-cell chronic lymphocytic leukemia, and B-cell non-Hodgkin's lymphoma In some methods, the cells of the subject are modified in vivo. In some methods, the method of treating a disease in a subject comprises: a) obtaining cells from the subject; b) modifying the cells using any of the methods provided herein; and c) administering the modified cells to the subject. Optionally, the disease is selected from the group consisting of cancer, a blood disorder (for example, sickle cell anemia or beta thalassemia), an infectious disease, an autoimmune disease, transplantation rejection, graft vs. host disease or other inflammatory disorder in a subject. In some methods for treating cancer, the cells obtained form the subject are modified to express a tumor specific antigen. As used throughout, the phrase "tumor-specific antigen" means an antigen that is unique to cancer cells or is expressed more abundantly in cancer cells than in non-cancerous cells. Optionally, the cells obtained from the subject are T cells. Optionally, the modified cells are expanded prior to administration to the subject.

All patents, patent publications, patent applications, journal articles, books, technical references, and the like discussed in the instant disclosure are incorporated herein by reference in their entirety for all purposes.

It is to be understood that the figures and descriptions of the disclosure have been simplified to illustrate elements that are relevant for a clear understanding of the disclosure. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

Where a range of values is provided, it is understood that each intervening value, to the smallest fraction of the unit of the lower limit, unless the context clearly dictates otherwise, between the upper and lower limits of that range is also specifically disclosed. Any narrower range between any stated values or unstated intervening values in a stated range and any other stated or intervening value in that stated range is encompassed. The upper and lower limits of those smaller ranges may independently be included or excluded in the range, and each range where either, neither, or both limits are included in the smaller ranges is also encompassed within the technology, subject to any specifically excluded limit in the stated range. Where the stated range includes one or both of the limits, ranges excluding either or both of those included limits are also included.

Different arrangements of the components depicted in the drawings or described above, as well as components and steps not shown or described are possible. Similarly, some features and sub-combinations are useful and may be employed without reference to other features and sub-combinations. Embodiments of the disclosure have been described for illustrative and not restrictive purposes, and alternative embodiments will become apparent to readers of this patent. Accordingly, the present disclosure is not limited to the embodiments described above or depicted in the drawings, and various embodiments and modifications can be made without departing from the scope of the claims below.

EXAMPLES

Example 1. Materials and Methods

Next-Generation Sequencing and Data Analysis. Genomic DNA was isolated from cells with the QIAamp DNA Mini Kit (Qiagen, Germantown, MD) according to the manufacturer's instructions. Two DNA regions were amplified for Next Generation Sequencing analysis. To amplify the endogenous HBB target sequence for sequencing, a nested PCR strategy was used to avoid amplifying the sequence from the viral vector template. First, primers HBB-1849F and HBB-5277R (SEQ ID NOs: 96 and 97) were used to amplify the 3.4 kb region from the HBB gene locus. These two primers are unable to amplify sequence from the templates in the viral vectors. Then HBB-MUT-F and the HBB-MUT-R primers were used to amplify the target DNA for sequencing (Table 3; SEQ ID NOs: 34-40). To amplify the HBB target sites from the integrated EGFP reporter for sequencing, Reporter-mut-F and Reporter-mut-R primers were used (Table 3; SEQ ID NOs: 98-102). The proofreading HotStart® ReadyMix from KAPA Biosystems (Wilmington, MA) was used for PCR. The PCR products were analyzed by next-generation sequencing using the Illumina NextSeq 500 as described before by Javidi-Parsijani, P. et al., *PLoS One* 2017; 12(5): e0177444. The Cas-Analyzer online software described by Park, J. et al., Bioinformatics 33(2):286-288 (2017) was used for mutation analysis of the sequencing data.

Plasmids. pRSV-Rev (Addgene Cat. No. 12253), pMD2.G (Addgene Cat. No. 12259), pMDLg/pRRE (Addgene Cat. No. 12251), psPAX2 (Addgene Cat. No. 12260), psPAX2-D64V (Addgene Cat. No. 63586), pSL-MS2×12 (Addgene Cat. No. 27119), and pX601-AAV-CMV::NLS-SaCas9-NLS-3×HA-bGHpA; U6::BsaI-sgRNA (Addgene Cat. No. 61591). pCDH-GFP was purchased from Systems Biosciences Inc. (Cat. No. CD513B-1). The plasmids described in Table 2 were produced by the inventors of this disclosure and used in the following examples. Synthetic DNA sequences as identified below were synthesized by GenScript based on custom orders. The primers listed in Table 3 below were synthesized by Eurofins Genomics based on custom orders.

TABLE 2

Plasmids Used in Examples

| No. | Name | Purpose | Generation strategy |
|---|---|---|---|
| 1 | pCDNA3.1/MS2x2-VPR | Expressing MS2x2-VPR fusion protein | Synthesized DNA coding for MS2x2-VPR (Genscript, Piscataway, NJ) was inserted between the NheI and NotI sites of pCDNA3.1(+) (Genscript). The inserted DNA sequence is SEQ ID NO: 61 and the corresponding amino acid sequence is SEQ ID NO: 62. |
| 2 | pCDNA3.1/NEF-MS2x2 | Expressing NEF-MS2x2 fusion protein. Three AA of NEF were mutated: $Gly^3$, $Val^{153}$ and $Gly^{177}$ were changed to Cyc, Leu and Glu, respectively. | Synthesized DNA coding for NEF-MS2x2 was inserted between the NheI and NotI sites of pCDNA3.1(+) (Genscript). The inserted DNA sequence is SEQ ID NO: 63 and the corresponding amino acid sequence is SEQ ID NO: 64. |
| | | Packaging Plasmids | |
| 3 | pMDLg/pRRE-D64V | Third generation lentivirus packaging plasmid for generating integration defective lentivirus. | AflII-AgeI fragment of pMDLg/pRRE was replaced by the AflII-AgeI fragment of psPAX2-D64V. |
| 4 | pMDLg/pRRE-D64V-NC-MS2x1 | Third generation lentivirus packaging plasmid with MCP inserted after NC ZF2. | AvrII-SbfI fragment of pMDLg/pRRE-D64V was replaced by a synthetic AvrII-SbfI DNA fragment encoding a modified NC sequence in which one copy of MCP coding DNA (stop codons removed) was inserted |

TABLE 2-continued

Plasmids Used in Examples

| No. | Name | Purpose | Generation strategy |
|---|---|---|---|
| 5 | pMDLg/pRRE-D64V-NC-MS2x2 | Third generation lentivirus packaging plasmid with two copies of MCP inserted after NC ZF2. | in frame after the last codon of the NC zinc finger 2 domain. The inserted DNA sequence is SEQ ID NO: 65 and the corresponding amino acid sequence is SEQ ID NO: 66.<br>AvrII-SbfI fragment of pMDLg/pRRE-D64V was replaced by a synthetic AvrII-SbfI DNA fragment encoding a modified NC sequence in which two copies of MCP coding DNA (stop codons removed) were inserted in frame after the last codon of NC zinc finger 2 domain. The inserted DNA sequence is SEQ ID NO: 67 and the corresponding amino acid sequence is SEQ ID NO: 68. |
| 6 | pMDLg/pRRE-D64V-NC-PP7x1 | Third generation lentivirus packaging plasmid with one copy of PP7 coat protein (PCP) inserted after NC ZF2. | AvrII-SbfI fragment of pMDLg/pRRE-D64V was replaced by a synthetic AvrII-SbfI DNA fragment encoding a modified NC sequence in which one copy of PCP coding DNA (stop codons removed) was inserted in frame after the last codon of NC zinc finger 2 domain. The inserted DNA sequence is SEQ ID NO: 69 and the corresponding amino acid sequence is SEQ ID NO: 70. |
| 8 | pMDLg/pRRE-D64V-MA-MS2x2 | Third generation lentivirus packaging plasmid with two copies of MCP replacing AA 44-132 of MA. | The PmlI-SphI fragment of pMDLg/pRRE-D64V was replaced by a synthetic PmlI-SphI DNA fragment encoding a modified MA in which two copies of MCP coding DNA (stop codons removed) replaced DNA coding for AA 44-132 of MA. The inserted DNA sequence is SEQ ID NO: 71 and the corresponding amino acid sequence is SEQ ID NO: 72. |
| 9 | pMDLg/pRRE-D64V-MA-PP7x1 | Third generation lentivirus packaging plasmid with one copy of PCP replacing AA 44-132 of MA. | The PmlI-SphI fragment of pMDLg/pRRE-D64V was replaced by a synthetic PmlI-SphI DNA fragment encoding a modified MA in which one copy of PCP coding DNA (stop codons removed) replaced DNA coding for AA 44-132 of MA. The inserted DNA sequence is SEQ ID NO: 73 and the corresponding amino acid sequence is SEQ ID NO: 74. |
| 10 | pMDLg/pRRE-D64V-MA-PP7x2 | Third generation lentivirus packaging plasmid with two copies of PCP replacing AA 44-132 of MA. | The PmlI-SphI fragment of pMDLg/pRRE-D64V was replaced by a synthetic PmlI-SphI DNA fragment encoding a modified MA in which two copies of PCP coding DNA (stop codons removed) replaced DNA coding for AA 44-132 of MA. The inserted DNA sequence is SEQ ID NO: 75 and the corresponding amino acid sequence is SEQ ID NO: 76. |
| 11 | psPAX2-D64V-NC-MS2 | Second generation lentivirus packaging plasmid with MCP inserted after NC ZF2. | The SphI-SbfI fragment of psPAX2-D64V (without NC-MS2) was replaced by the SphI-SbfI fragment of pMDLg/pRRE-D64V-NC-MS2x1 (with one copy of MS2) to make psPAX2-D64V-NC-MS2. This is the second generation packaging plasmid with NC-MS2 insertion, corresponding to pMDLg/pRRE-D64V-NC-MS2x1 (Plasmid No. 4), which is the third generation packaging plasmid. |
| 12 | psPAX2-D64V-NC-PP7 | Second generation lentivirus packaging plasmid with one copy of PCP inserted after NC ZF2. | The SphI-SbfI fragment of psPAX2-D64V (without NC-PP7) was replaced by the SphI-SbfI fragment of pMDLg/pRRE-D64V-NC-PP7x1 (with one copy of PP7). |
| 13 | psPAX2-D64V-NC-MS2X2 | Second generation lentivirus packaging plasmid with 2 copies of MS2 inserted after NC ZF2 | The SphI-SbfI fragment of psPAX2-D64V (without NC-MS2x2) was replaced by the SphI-SbfI fragment of pMDLg/pRRE-D64V-NC-MS2X2 (with NC-MS2x2), so that now we added NC-MS2 to pspAX2-D64V. This is to make the second generation packaging plasmid with NC-MS2x2. |
| 14 | psPAX2-D64V-MA-MS2X2 | Second generation lentivirus packaging plasmid with two copies of MS2 replacing AA 44-132 of MA | The PvuI-SphI fragment of psPAX2-D64V was replaced by the PvuI-SphI fragment of pMDLg/pRRE-D64V-MA-MS2X2. |
| | | Mammalian Expression Plasmids | |
| 15 | pSaCas9 | Adeno associated viral (AAV) plasmid expressing SaCas9 | pX601-AAV-CMV::NLS-SaCas9-NLS-3xHA-bGHpA; U6::BsaI-sgRNA (Addgene Cat. No. 61591) was cut with NotI and Acc65I (to remove the Sa sgRNA expression cassette) treated with DNA Pol I Klenow polymerase, and re-ligated by T4 DNA ligase. |
| 16 | pSaCas9$^{1xms2}$ | Plasmid expressing SaCas9 mRNA with a MS2 stem loop at the 3' untranslated region (UTR) | A synthetic dsDNA oligo was generated by annealing oligo 1xloop-F (SEQ ID NO: 41) and oligo 1xloop-R (SEQ ID NO: 42), which was then inserted by Infusion™ reaction (Clontech) into the EcoRI site (after the stop codon) of pSaCas9. |

TABLE 2-continued

Plasmids Used in Examples

| No. | Name | Purpose | Generation strategy |
|-----|------|---------|---------------------|
| 17 | pSaCas9$^{2xms2}$ | Plasmid expressing SaCas9 mRNA with two MS2 stem loops at the 3' UTR | A synthetic dsDNA oligo was generated by annealing oligo 2xloop-F (SEQ ID NO: 43) and oligo 2xloop-R (SEQ ID NO: 44), which was then inserted by Infusion™ reaction (Clontech) into the EcoRI site of pSaCas9. |
| 18 | pSaCas9$^{3xms2}$ | Plasmid expressing SaCas9 mRNA with three MS2 stem loops at the 3' UTR | A synthetic dsDNA oligo was generated by annealing oligo 3xloop-F (SEQ ID NO: 45) and oligo 3xloop-R (SEQ ID NO: 46), which was then inserted by Infusion™ reaction (Clontech)into the EcoRI site of pSaCas9-2xMS2. |
| 19 | pSaCas9$^{12xms2}$ | Plasmid expressing SaCas9 mRNA with twelve MS2 stem loops at the 3' UTR | The EcoR1-Xho1 fragment from pSL-MS2-12X (Addgene Cat. No. 27119), encoding the 12 MS2 stem loops, was inserted between the EcoR1-SalI sites of pSaCas9-1xMS2, which is after the stop codon of SaCas9 but before the polyA signal sequence. The original fragment coding for 1 MS2 stem loop was replaced with the 12 MS2 step loop fragment. |
| 20 | pSaCas9$^{1xPP7}$ | Plasmid expressing SaCas9 mRNA with one PP7 stem loop after the stop codon of saCas9. | pSaCas9-$^{1xPP7}$-HBB-sgRNA1$^{3'MS2}$ was cut with Acc65I and NotI to excise the HBB sgRNA cassette. The plasmid was treated with DNA Pol I Klenow polymerase, and re-ligated with T4 DNA ligase. The starting plasmid had a PP7 aptamer coding sequence after the stop codon of the SaCas9 coding sequence and a MS2 aptamer coding sequence after the sgRNA coding sequence. The sgRNA cassette was removed to make a plasmid with a SaCas9 coding sequence followed by a PP7 aptamer coding sequence. |
| 21 | pSaCas9$^{12xpp7}$ | Plasmid expressing SaCas9 mRNA with 12 PP7 stem loops at the 3' UTR. | The BglII-BamHI fragment of pDZ617 pKAN 12xPP7 V4 (Addgene Cat. No. 72237), encoding the 12 PP7 loops, was inserted into the BamHI site of pSaCas9 (after the coding sequence of Sacas9 but before the HA tag, so that the HA tag is removed but the Sacas9 is complete). |
| 22 | pSaCas9-HBB-sgRNA1 | Plasmid expressing SaCas9 mRNA and HBB sgRNA1 targeting the region causing sickle cell disease. | A dsDNA oligo was generated by annealing oligo Sickle-g1F (SEQ ID NO: 49) and oligo Sickle-g1R (SEQ ID NO: 50), which was then inserted into the BsaI site of pX601-AAV-CMV::NLS-SaCas9-NLS-3xHA-bGHpA; U6::BsaI-sgRNA by T4 DNA ligase. |
| 23 | pSaCas9-HBB-sgRNA2 | Plasmid expressing SaCas9 mRNA and HBB sgRNA2 targeting the region causing sickle cell disease. | A synthetic DNA fragment was generated by annealing oligo Sickle-g2F (SEQ ID NO: 47) and oligo Sickle-g2R (SEQ ID NO: 48), which was then inserted into the BsaI site of pX601-AAV-CMV::NLS-SaCas9-NLS-3xHA-bGHpA; U6::BsaI-sgRNA by T4 DNA ligase. |
| 24 | pSaCas9-HBB-sgRNA1$^{3'ms2}$ | Plasmid expressing SaCas9 mRNA and the guide RNA for HBB; the 3' of the sgRNA has a MS2 stem loop. | A synthetic DNA fragment (by Genscript) (SEQ ID NO: 77) was cut with BsaI and NotI and inserted between the BsaI-NotI sites of pX601-AAV-CMV::NLS-SaCas9-NLS-3xHA-bGHpA; U6::BsaI-sgRNA. This DNA fragment encodes a HBB sgRNA1 with a MS2 aptamer at the 3' end. |
| 25 | pSaCas9-HBB-sgRNA1$^{Tetrams2}$ | Plasmid expressing SaCas9 mRNA and the guide RNA for HBB; a MS2 stem loop was inserted into the tetra loop of the sgRNA. | A synthetic DNA fragment (by Genscript Inc) (SEQ ID NO: 78) was cut with BsaI and NotI and inserted between the BsaI-NotI sites of pX601-AAV-CMV::NLS-SaCas9-NLS-3xHA-bGHpA; U6::BsaI-sgRNA. This DNA fragment encodes a HBB sgRNA1 with a MS2 aptamer at the Tetra loop position. |
| 26 | pSaCas9-HBB-sgRNA1$^{ST2ms2}$ | Plasmid expressing SaCas9 mRNA and the guide RNA for HBB; a MS2 stem loop was inserted into the stem loop 2 of the sgRNA. | A synthetic DNA fragment (by Genscript Inc) (SEQ ID NO: 79) was cut with BsaI and NotI and inserted between the BsaI-NotI sites of pX601-AAV-CMV::NLS-SaCas9-NLS-3xHA-bGHpA; U6::BsaI-sgRNA. This DNA fragment encodes a HBB sgRNA1 with a MS2 aptamer at the ST2 loop position. |
| 27 | pSaCas9-HBB-sgRNA1$^{Tetra-ST2ms2}$ | Plasmid expressing SaCas9 mRNA and the guide RNA for HBB; a MS2 stem loop was inserted into the stem loop 2 of the sgRNA. and a MS2 stem loop was inserted into the tetra loop of the sgRNA. | A synthetic DNA fragment (SEQ ID NO: 80) was cut with BsaI and NotI and inserted between the BsaI-NotI sites of pX601-AAV-CMV::NLS-SaCas9-NLS-3xHA-bGHpA; U6::BsaI-sgRNA. This DNA fragment includes a HBB sgRNA1 with one MS2 loop at the Tetra loop position and one at the ST2 loop position. |
| 28 | pSaCas9$^{1ms2}$-HBB-sgRNA1$^{3'ms2}$ | Plasmid expressing SaCas9-1MS2 mRNA and the guide RNA for HBB sgRNA-3'MS2. | A single MS2 stem loop dsDNA oligo was generated by annealing synthetic DNA oligo 1xloop-F (SEQ ID NO: 41) and oligo 1xloop-R (SEQ ID NO: 42) and inserted into the EcoRI site of pSaCas9-HBB-sgRNA1-3'MS2 (after the stop codon of SaCas9 and before the PolyA signal sequence). |

TABLE 2-continued

Plasmids Used in Examples

| No. | Name | Purpose | Generation strategy |
|---|---|---|---|
| 29 | pSaCas9$^{1PP7}$-HBB-sgRNA1$^{3'ms2}$ | Plasmid expressing SaCas9$^{1PP7}$ mRNA and the guide RNA for HBB sgRNA$^{3'MS2}$. | A single PP7 stem loop dsDNA oligo was generated by annealing synthetic DNA oligo PP7-F (SEQ ID NO: 51) and oligo PP7-R (SEQ ID NO: 52) and inserted into the EcoRI site of pSaCas9-HBB-sgRNA1-3'MS2 (after the stop codon of SaCas9 and before the PolyA signal sequence). |
| 30 | pSaCas9$^{1PP7}$-HBB-sgRNA1$^{3'PP7}$ | Plasmid expressing SaCas9$^{1PP7}$ mRNA and the guide RNA for HBB, the 3' region of the sgRNA has a PP7 stem loop. | A synthetic DNA oligo (SEQ ID NO: 81) was cut with KpnI and NotI and inserted between the KpnI-NotI sites of pSaCas9$^{1PP7}$-HBB-sgRNA1$^{3'MS2}$. This results in excision of the U6-HBB sgRNA1-MS2 aptamer and replacing it with the U6-HBB sgRNA1-PP7 aptamer coding sequence. |
| 31 | pCK002-HBB-sgRNA1 | Lentiviral vector expressing SaCas9 and the sgRNA1 for HBB to treat sickle cell disease. | A dsDNA oligo was generated by annealing oligo sickle-g1-LV-F (SEQ ID NO: 53) and oligo sickle-g1-LV-R (SEQ ID NO: 54), which was then inserted into the BsmBI site of pCK002_U6-Sa-sgRNA(mod)_EFS-SaCas9-2A-Puro_WPRE (Addgene Cat. No. 85452). The dsDNA oligo is the guide sequence for HBB sgRNA1. |
| 32 | pAAV-HBB-sgRNA2 | Adeno associated viral (AAV) vector containing the HBB template for homologous recombination to correct the Sickle Cell Disease mutation causing sickle cell disease. The SaCas9 target sites were removed but the encoding amino acids were identical to the wild type. The vector also contains the cassette for U6 driven expression of sgRNA2, targeting the HBB gene close to the mutation causing sickle cell disease. | A synthetic DNA encoding the human HBB target template sequence and the U6 driven HBB sgRNA2 expression cassette (SEQ ID NO: 82) was inserted into the NotI site of pAAV-MCS (Agilent Genomics, Cat. No. 240071). |
| 33 | pAAV-HBB-sgRNA1 | Adeno associated viral vector containing the HBB template for homologous recombination to correct the mutation causing sickle cell disease. The vector also contains the cassette for U6 driven expression of sgRNA1, targeting the HBB gene close to the mutation causing sickle cell disease. Since we found that sickle-sgRNA1 outperformed sickle-sgRNA2. | Primer Sickle-g1HD-F (SEQ ID NO: 55) and Primer Sickle-g1HD-R (SEQ ID NO: 56) were used to amplify the sickle-sgRNA1 expression cassette from pSaCas9-HBB-sgRNA1 using high fidelity DNA polymerase. The amplified DNA was inserted into the XhoI and XbaI sites of pAAV-HBB-sickle-sgRNA2 by Infusion (Clontech). |
| 34 | pAAV-HBB(n)-sgRNA1 | Adeno associated viral vector containing the HBB template for homologous recombination to change the wild type HBB gene into the version causing sickle cell disease. This will facilitate the detection of gene editing events in normal cells. The Sacas9 target sites were removed but the encoded amino acids were still wild type except for the disease causing mutation. The vector also contains the cassette for U6 driven expression of sgRNA1 | pAAV-HBB-sgRNA2 was cut with XhoI and XbaI, treated with Klenow DNA polymerase and the DNA was ligated to remove the cassette expressing sickle-sgRNA2. Then the NcoI-PasI fragment of the resulted plasmid was replaced by the annealed DNA from oligo HBB-tem-F (SEQ ID NO: 57) and oligo HBB-tem-R (SEQ ID NO: 58) to modify the template. Finally, the NcoI-BstxI of the plasmid was replaced by the NcoI-BstxI fragment from pAAV-HBB-sgRNA1 to add the HBB sgRNA1 expression cassette. |

TABLE 2-continued

Plasmids Used in Examples

| No. | Name | Purpose | Generation strategy |
|---|---|---|---|
| | | for HBB, targeting the sequences close to the mutation causing sickle cell disease. | |
| 35 | pFCK-HBB-sgRNA1 | Lentiviral vector containing the human HBB template (containing the mutation causing sickle cell disease) and the U6 driven HBB sgRNA1 expression cassette. | The sequences for human HBB template and the U6 driven HBB sgRNA1 expression cassette were amplified from pAAV-HBB(n)-sgRNA1 with primer HBB-LT-F (SEQ ID NO: 57) and primer HBB-LT-R (SEQ ID NO: 58) using high fidelity DNA polymerase (proofreading HotStart Ready Mix from KAPA Biosystems (Wilmington, MA)). The DNA was cut with XbaI and EcoRV and inserted into XbaI and EcoRV sites of FCK-ChR2-GFP (Addgene Cat. No. 15814). |
| 36 | pSaCas9$^{1xms2}$-2x3'UTR | Plasmid having two copies 3' untranslated region (UTR) from human HBB gene were inserted after the Sacas9 coding sequences and before the SM2 stem loop of pSaCas9$^{1xms2}$. | A synthetic DNA of two copies of the human HBB 3' UTR sequences (SEQ ID NO: 83) was inserted between the BamHI-EcoRI sites of pSaCas9$^{1xms2}$. The synthetic DNA was designed with a NheI site between the two human HBB 3' UTR sequences. |
| 37 | pSaCas9$^{1xms2}$-1x3'UTR | Plasmid having one copy of HBB gene 3' untranslated region (UTR) was after the Sacas9 coding sequences and before the SM2 stem loop of pSaCas9$^{1xms2}$. | pSaCas9$^{1xms2}$-2x3'UTR was cut with NheI and EcoRI to remove one copy of HBB 3' UTR. The backbone was treated with Klenow DNA polymerase and re-ligated with T4 DNA ligase. |
| 38 | pspCas9$^{1xms2}$ | Plasmid having one copy of MS2 stem loop was added after the stop codon of sp. Cas9 mRNA. | A dsDNA oligo was generated by annealing oligo sp-loop1F (SEQ ID NO: 88) and oligo sp-loop1R (SEQ ID NO: 89) was inserted between the HindIII and EcoRI sites of pU6-sgRosa26-1_CBh-Cas9-T2A-BFP (Addgene Cat. No. 64216) by Infusion™ reaction (Takara, In-Fusion® HD Cloning Plus, Cat. 638909). |
| 39 | pLH-IL2RG-sp-sgRNA | A lentiviral expression plasmid expressing a spCas9 sgRNA targeting the start codon region of human IL2RG gene. | A dsDNA oligo was generated by annealing oligo Il2RG-sp-g1F1 (SEQ ID NO: 90) and oligo Il2RG-sp-g1R (SEQ ID NO: 91) was inserted into the BbsI site of pLH-sgRNA1 (Addgene Cat. No. 75388) by T4 DNA ligase. |
| 40 | pSaCas9$^{1xMS2}$-HBB-sgRNA1 | A plasmid expressing SaCas9$^{1xMS2}$ and HBB sgRNA1. | A synthetic dsDNA oligo was generated by annealing oligo 1xloop-F (SEQ ID NO: 41) and oligo 1xloop-R (SEQ ID NO: 42), which was then inserted by infusion into the EcoRI site of pSaCas9-HBB-sgRNA1. |
| 41 | pSaCas9$^{1xMS2}$-2x3'UTR-HBB sgRNA$^{3'PP7}$1x3'UTR | SaCas9 has a MS2 aptamer and two copies of HBB 3' UTR, the HBB sgRNA1 has one copy of PP7 aptamer and one copy of HBB 3' UTR. | A dsDNA oligo synthesized by Genscript (SEQ ID NO: 84) was inserted into the EagI site of pSaCas91xMS2-2x3'UTR by T4 DNA ligase. The oligo contains in 5' to 3' order: a U6 promoter, a HBB sgRNA coding sequence (for Sickle mutation (g1)), a PP7 aptamer coding sequence, and a HBB 3' UTR coding sequence. The U6 promoter direction is the same as the CMV promoter in the construct. |
| 42 | pSaCas99$^{1xMS2}$-2x3'UTR-HBB sgRNA$^{3'PP7}$2x3'UTR | SaCas9 has a MS2 aptamer and two copies of HBB 3' UTR, the HBB sgRNA1 has one copy of PP7 aptamer and two copy of HBB 3' UTR. | A dsDNA oligo synthesized by Genscript (SEQ ID NO: 85) was inserted between the EcoRV and NotI sites of pSaCas9$^{1xMS2}$-2x3'UTR-HBB sgRNA$^{3'PP7}$ 1x3'UTR (Plasmid No. 41). The sequence encoding one PP7 aptamer followed by one HBB 3' UTR was replaced with a sequence encoding one PP7 aptamer followed by two HBB 3' UTR sequences. |
| 43 | pSaCas9$^{1xms2}$-2x3'UTR-HBB-sgRNA1$^{3'MS2}$-2x3'UTR | One aptamer and 2 copies of HBB 3' UTR sequences were added to both SaCas9 and HBB sgRNA1. | Synthetic oligo MS2-F1 (SEQ ID NO: 92) and oligo MS2-R1 (SEQ ID NO: 93) were annealed and the dsDNA oligo was inserted between the AfeI and EvoRV sites of pSaCas9$^{1xMS2}$-2x3'UTR-HBB sgRNA$^{3'PP7}$ 2x3'UTR (Plasmid No. 42) by Infusion™ reaction (Takara. In-Fusion® HD Cloning Plus. Cat. 638909). |
| 44 | pLVX-ad-IL2RG-rep | Lentivirus vector to express the sgRNA2 targeting IL2RG gene. It also contains the homologous recombination arms for the insertion of IL2RG cDNA into the target site. | pLVX-EF1α-IRES-zsGreen1 was digested with MluI and ClaI to remove the zsGreen1-expression cassette and ligated with an adaptor to introduce the NotI site. Then the synthetic NotI DNA fragment containing the IL2RG sgRNA2 expression cassette and the homologous recombination template were inserted into the NotI site of the modified vector (see SEQ ID 103). |

TABLE 2-continued

Plasmids Used in Examples

| No. | Name | Purpose | Generation strategy |
|---|---|---|---|
| 45 | pLVX-HBB-correct | Lentivirus vector to express the HBB sgRNA1. It also contains the homologous recombination arms for the correction of the Sickle mutation to the wild type HBB gene. | pLVX-EF1α-IRES-zsGreen1 was digested with MluI and ClaI to remove the zsGreen1-expression cassette and ligated with an adaptor to introduce the NotI site. Then the synthetic NotI DNA fragment (see SEQ ID 104) containing the HBB sgRNA1 expression cassette and the homologous recombination template (to change the Sickle mutation to the wild type HBB) were inserted into the NotI site of the modified vector. |
| 46 | pSpCas9-1loop-3'UTR | Plasmid for the expression of sp. Cas9 mRNA, with 2 copies of HBB 3'UTR and one copy of MS2 aptamer after the Cas9 stop codon. | pspCas9-1loop was cut with FseI + NotI to remove the sequence containing the 1x MS2 aptamer and the bGH polyA signal, and the vector backbone was recovered. Then the 600 bp FseI + Eag1 fragment from pX601-1loop-2x3'UTR (containing 2xHBB 3'UTR, 1xMS2 aptamer, and the bGH polyA signal) was ligated into the linearized the vector. |

TABLE 3

Primers Used in Examples

| Primer name | SEQ ID NO | Use |
|---|---|---|
| SaCas9-2576F | SEQ ID NO: 28 | SaCas9 QPCR |
| SaCas9-2713R | SEQ ID NO: 29 | SaCas9 QPCR |
| SgRNA-F1 | SEQ ID NO: 30 | sgRNA QPCR |
| sgRNA-R1 | SEQ ID NO: 31 | sgRNA QPCR |
| EGFP-RT-F | SEQ ID NO: 32 | EGFP QPCR |
| EGFP-RT-R | SEQ ID NO: 33 | EGFP QPCR |
| HHB-mut-F1 | SEQ ID NO: 34 | Next generation sequencing for the HBB target site. |
| HHB-mut-F2 | SEQ ID NO: 35 | Next generation sequencing for the HBB target site |
| HHB-mut-F3 | SEQ ID NO: 36 | Next generation sequencing for the HBB target site |
| HHB-mut-F4 | SEQ ID NO: 37 | Next generation sequencing for the HBB target site |
| HHB-mut-F5 | SEQ ID NO: 38 | Next generation sequencing for the HBB target site |
| HHB-mut-F6 | SEQ ID NO: 39 | Next generation sequencing for the HBB target site |
| HHB-mut-R1 | SEQ ID NO: 40 | Next generation sequencing for the HBB target site |
| HBB-1849F | SEQ ID NO: 96 | PCR amplification of the endogenous HBB locus |
| HBB-5277R | SEQ ID NO: 97 | PCR amplification of the endogenous HBB locus |
| Reporter-mut-F1 | SEQ ID NO: 98 | PCR amplification of the HBB target sequence in the GFP expression cassette together with Reporter-mut-R1 |
| Reporter-mut-F2 | SEQ ID NO: 99 | PCR amplification of the HBB target sequence in the GFP expression cassette together with Reporter-mut-R1 |
| Reporter-mut-F3 | SEQ ID NO: 100 | PCR amplification of the HBB target sequence in the GFP expression cassette together with Reporter-mut-R1 |
| Reporter-mut-F4 | SEQ ID NO: 101 | PCR amplification of the HBB target sequence in the GFP expression cassette together with Reporter-mut-R1 |
| Reporter-mut-R1 | SEQ ID NO: 102 | PCR amplification of the HBB target sequence in the GFP expression cassette together with Reporter-mut-F1, Reporter-mut-F2, Reporter-mut-F3 or Reporter-mut-F4. |

Assays for Assessing Gene Editing Activity. To assess gene editing, the mutated sequence causing sickle cell disease was chosen as the genomic target sequence for editing. The gene defect that cause sickle cell disease is a point mutation of A nucleotide to T nucleotide of the human beta hemoglobin gene (converts a GAG codon into GUG), which results in glutamic acid (E/Glu) being substituted by valine (V/Val) at amino acid position 6 of the β-globin protein. The sequence of the targeted strand is ACTCCTGTGGAGAAGTCTGCCGTTACT (SEQ ID NO: 94); the first 6 nucleotides of this sequence (underlined) correspond to the protospacer adjacent motif. Two assays were used to detect gene editing activities: (1) a GFP-reporter assay and (2) the Surveyor® Mutation Detection Kit (Integrated DNA Technologies, Cat. No. 706020).

For the GFP-reporter assay, enhanced green fluorescent protein (EGFP) reporter cells described in Javidi-Parsijani, P. et al., *PLoS One* 2017; 12(5): e0177444 (referred to throughout the Examples as "GFP reporter cells" or "reporter cells") were used for the detection of genome editing activities by microscopic observation or flow cytometry analysis of GFP-positive cells. This cell line does not express EGFP due to disruption of the EGFP reading frame by the insertion of a 119-base pairs sequence between the start codon ATG and the second codon of EGFP cDNA (insertion is missing 1 bp to make 40 in-frame codons). The 119 bp insertion is gaacccaggttcctgacacagacagactacacccagg-gaatgaagagcaagcgccatACTCCTGTGGAGAAGTCTGC CGTTACTGCCCTGTGGGGCAAGGTGAACGTGGAT- TGGCTAGC (SEQ ID NO: 95), and contains a 57 bp IL2RG target sequence (underlined) and a 62 bp HBB target sequence (capitalized). Without genome editing, EGFP will not be expressed due to the presence of the insertion, which disrupts the EGFP reading frame. This was confirmed by the absence of EGFP-positive cells in the non-transfected reporter cells and in the reporter cells transfected with plasmid DNA expressing SaCas9 without any sgRNA. Upon genome editing in the inserted sequence, the double strand breaks are repaired by non-homologous end joining. Due to the possibility of introducing insertion or deletion (IN-DELs), deletions of 3N+2 or insertions of 3N+1 base pairs will restore the EGFP reading frame and, thus, EGFP protein expression.

To test whether the reporter cells were functional, the cells were transduced with adeno-associated virus particles containing SaCas9 mRNA and sgRNA for HBB (made from pSaCas9-HBB-sgRNA1; Plasmid No. 22). Flow cytometry analysis showed that 4.5% to 15% of the cells were EGFP-positive 24 hours post-transfection. The genomic DNA from the reporter cells was purified three days after the transduction, amplified the reporter region by PCR with high-fidelity DNA polymerase, and sequenced the target region by next-generation sequencing. The percentage of sequences with INDELs was analyzed. 68% of the reads were found to have INDELs. As only some INDELs will restore EGFP expression, and analysis was performed 72 hours after transfection, it is not surprising that a lower EGFP-positive rate than INDEL rate was observed. These data indicate that the reporter cells are functional and useful for analysis of gene editing events in the context of this disclosure.

The Surveyor® Mutation Detection Kit was used according to the kit's manual to detect gene editing activities. The key component of the kit, Surveyor Nuclease, a member of the CEL family of mismatch-specific nucleases, recognizes and cleaves mismatches due to the presence of single nucleotide polymorphisms (SNPs) or small insertions or deletions. Briefly, target sequences were amplified using the proofreading HotStart ReadyMix from KAPA Biosystems (Wilmington, MA), a high fidelity, thermostable DNA polymerase, to minimize the incorporation of errors that would result in background mismatches. The amplified DNA was denatured for 5 mins at 95° C. and renatured by slowly lowing the temperature to room temperature. The DNA was then treated with the Surveyor Nuclease to cleave mismatches. The cleaved DNA fragments were separated by agarose gel electrophoresis, stained with ethidium bromide and observed under UV light.

Packaging Cas9 mRNA in Lentivirus-like Particles. Lentivirus-like particles with genomes were produced with Addgene second or the third generation packaging systems as described in Javidi-Parsijani, P. et al., *PLoS One* 2017; 12(5): e0177444. To package SaCas9 mRNA into the lentivirus-like particles, HEK293T cells were transfected with the desired combination of plasmids. Transfection was mediated by Polyethylenimine (PEI, Polysciences Inc.) using a DNA:PEI ratio of 1:2 (mass:mass). Table 4 provides exemplary conditions used to generate certain Cas9 mRNA packaged lentivirus-like particles. Cell culture and DNA transfection were performed as described in Javidi-Parsijani, P. et al., *PLoS One* 2017; 12(5): e0177444. The viral particles were either used without concentration or after concentration by one of the three different methods: 1) by laying the supernatant containing the viral particles on 10 ml 20% sucrose cushion, and then centrifuge at 20000 g 4° C. for 4 hours, 2) by using the Lenti-X™ Concentrator using the manufacturers protocol (Clontech, Cat. No. 631232), 3) by using the KR2i TFF System [KrosFlo® Research 2i Tangential Flow Filtration System] (Spectrum Lab, Cat. No. SYR2-U20). Transduction experiments found that virus produced by the third method worked the best (judged by the percentage of GFP positive cells generated in GFP reporter assays), so most data were generated with viral particles concentrated by this method.

TABLE 4

Plasmid DNA used to transfect HEK293T cells to make lentiviral particles loaded with SaCas9 mRNA[a]

|  | MCP-fused second generation packaging system | MCP-fused third generation packaging system | PCP-fused second generation packaging system | PCP-fused third generation packaging system | VPR or NEF mediated SaCas9 mRNA packaging |
|---|---|---|---|---|---|
| Gag-pol packaging plasmid (16.5 μg) | pspAX2-D64V-NC-MS2 | pMDLg/pRRE-D64V-NC-MS2 | pspAX2-D64V-NC-PP7 | pMDLg/pRRE-D64V-NC-PP7 | pspAX2-D64V |
| SaCas9 plasmid (12 μg) | pSaCas9$^{1xMS2}$ | pSaCas9$^{1xMS2}$ | pSaCas9$^{1xPP7}$ | pSaCas9$^{1xPP7}$ | pSaCas9$^{1xMS2}$ |
| pMD2G (8 μg) | + | + | + | + | + |
| pRSV-REV (4.5 μg) | − | + | − | + | − |
| VPR or NEF MCP fusion plasmid (12 μg) | − | − | − | − | + |

[a] $13 \times 10^6$ cells were seeded in 15-cm dishes 24 hours before transfection.

Viral titer detection. Viral titer was determined by measuring p24 by enzyme-linked immunosorbent assay (ELISA) using the QuickTiter™ Lentivirus Titer Kit (Cell Biolabs, Cat. No. VPK-107). As per manufacturer's instructions, the viral particles were precipitated prior to the ELISA analysis so that the soluble p24 protein was not detected.

Viral RNA Isolation and Quantification. Two methods were used to isolate viral RNA. In one method, the viral particles were centrifuged at 120,000 g for 90 mins, and then the viral RNA was purified with the miRNeasy Mini Kit (QIAGEN®, Cat No. 217004). Alternatively, viral RNA was isolated directly from 140 μl viral supernatant with the QIAamp Viral RNA Mini Kit (QIAGEN®, Cat. No. 52904). Reverse transcription of viral RNA was done with the QuantiTect® Reverse Transcription Kit (QIAGEN). Custom designed TaqMan™ probes were used for quantitative PCR (QPCR). Quantitation was performed by QPCR or by digital PCR. Absolute QPCR using the standard curve method was performed using SYBR™ Green qPCR master mixture (ThermoFisher). A standard curve was prepared with 50, 500, 5000, 50000 and 500000 copies of pSacas9-HBB-sgRNA1 (for SaCas9 and sgRNA) or pCDH-GFP (for EGFP) plasmid DNA. The concentration of plasmid DNA used for preparing standards was determined using a Nano-Drop™ 2000 (Cat. No. ND-2000) spectrophotometer (ThermoFisher). PCR was run on an ABI 7500 instrument (Applied Biosystems, ThermoFisher). Dissociation analysis was performed after the amplification to determine the specificity of the PCR product (if only one peak was observed in the dissociation curve, the amplification was specific). Alternatively, digital PCR was performed for quantification with the QuantStudio™ 3D Digital PCR System (ThermoFisher Scientific).

Lentivirus-like Particle and Lentiviral Particle Transduction. Various amount of concentrated viral particles (equivalent to 10~200 ng p24 protein) were added to GFP-reporter cells ($2 \times 10^4$) as described above and grown in 24-well plates, with 8-12 μg/ml polybrene in DMEM/10% FBS. Supernatant containing non-concentrated virus was used to transduce GFP-reporter cells with half fresh medium and half virus containing supernatant. The cells were incubated with the virus-containing medium for 12 hours, after which the medium was replaced with fresh DMEM medium with 10% FBS.

Genomic DNA Extraction From Human cells. Genomic DNA was isolated from cells with the QIAamp DNA Mini Kit (Qiagen, Germantown, MD) according to the manufacturer's instructions.

Western blotting. Lentivirus or lentivirus-like particles (200 ng) were directly lysed in 50 μl of 1×SDS loading buffer, heated at 95° C. for 5 min. The proteins were separated by SDS-PAGE, transferred to PVDF membranes and immunoblotted for MA (p17) with anti-p17 antibody (Fisher Scientific, Cat # PA14954, 1:1000), for CA (p24) with anti-p24 antibody (Cell Biolabs, Cat. No. 310810, 1:1000), and for NC with anti-p15 antibody (Abcam, Cat. No. ab66951, 1:1000). Horseradish peroxidase (HRP)-conjugated secondary antibodies and chemiluminescent reagents were purchased from Thermofisher Scientific. The LAS-3000 system (Fujifilm) was used to capture Western blotting images. Densitometry of protein bands was analyzed with Image J software.

Example 2. Fusing MS2 Coat Protein (MCP) to Lentiviral Proteins for SaCas9 mRNA Packaging The aim was to package SaCas9 mRNA in lentivirus-like particles using the high affinity interaction between bacteriophage coat proteins and their respective RNA aptamers. Aptamer-binding proteins were fused with various lentiviral proteins. The corresponding aptamer sequence was added to the 3' untranslated region (UTR) of SaCas9 (see FIG. 2). Four different lentiviral proteins were tested as the fusion recipient for MS2 coat protein (MCP), a commonly used aptamer-binding protein. These fusion proteins were HIV accessory proteins Viral Protein R (VPR) (Wu, Liu et al., J. Virol. 69(6):3389-3398 (1995)) and Negative Regulatory Factor and HIV structure proteins Nucleocapsid Protein (NC) and Matrix Protein (MA) (referred to as MCPx2-VPR, NEF-MCPx2, NC-MCPx2, and MA-MCPx2, respectively). The NEF protein included three mutations (G3C, V153L and G177E) to increase incorporation into lentivirus-like particles as described in Muratori, C., et al., *Methods Mol Biol* 2010; 614: 111-124. Two tandem copies of MCPs were fused to the N-terminus of VPR and the C-terminus of NEF following published studies Wu, X., et al., *J Virol* 1995; 69(6): 3389-3398 and Muratori, C., et al., *Methods Mol Biol* 2010; 614: 111-124. For the NC fusion protein, two copies of MCPs were inserted after NC zinc finger 2 of the Gag precursor protein in packaging plasmids pMDLg/pRRE$^{D64V}$ (third generation packaging plasmid) and psPAX2$^{D64V}$ (second generation packaging plasmid), preserving the NC/P1 protease cleavage site. For the MA fusion protein, amino acids 44-132 of MA in these packaging plasmids were replaced with two copies of MCP. Deleting this region in MA is known not interfere with viral particle assembly or budding (Jalaguier, P., et al., *PLoS One* 2011; 6(11): e28314). Fusing MCP to MA or NC did not disrupt the reading frame of the Gag precursor protein or the protease processing sites.

Neither expressing MCPx2-VPR or NEF-MCPx2 during lentiviral vector production, nor fusing MCP with NC or MA impaired the efficiency of lentiviral particle production. P24 ELISA revealed that in these situations the lentiviral production was equally efficient as virus production by the packaging plasmids without MCP fusion (Table 5). The control used was the unmodified packaging plasmid without MCP fusion. The plasmid name is pspAX2-D64V.

TABLE 5

Viral production efficiency and gene editing activities of packaging plasmids with various fusion proteins.

| Constructs | No MCP fusion | VPR-MCP | NEF-MCP | MA-MCP | NC-MCP |
|---|---|---|---|---|---|
| Viral production efficiency$^a$ (ng/ml) | 100.0 ± 3.2 (8) | 104 ± 14.2 (3) | 120.3 ± 2.7 (3) | 142.0 ± 14.8 (6) | 100.1 ± 26.7 (7) |
| GFP$^+$ percentage$^b$ | 2.46 ± 0.06 (4) | 3.17 ± 0.35 (3) | 3.74 ± 0.33 (3) | 2.87 ± 0.68 (3) | 5.22 ± 0.11 (3)*** |

$^a$The GFP-expressing lentivirus vector pCDH-GFP was packaged. The viral production efficiency of the control packaging plasmid without fusion proteins was set as 100%. Mean ± Sem was shown. Numbers in parentheses mean number of repeats for each group. No difference was noted between groups by ANOVA analysis.
$^b$SaCas9$^{1xMS2}$ was expressed during lentivirus-like particle production. 250 μl of un-concentrated lentivirus-like particles were co-transduced into $4 \times 10^4$ GFP-reporter cells with a lentiviral vector expressing HBB sgRNA1.
***indicates p < 0.0001 when viral particles from NC-MCP fusion was compared with viral particles by packaging plasmid without MCP fusion.

The impact of these fusion proteins on gene editing was then assessed. One copy of MS2 aptamer was added after the stop codon of SaCas9 mRNA (SaCas9$^{1\times MS2}$) as described in Table 2. Lentivirus-like particles were made and packaged with SaCas9$^{1\times MS2}$ as described in Example 1. SaCas9$^{1\times MS2}$ mRNA was transcribed in HEK293T cells during lentivirus-like particle production in the presence of any one of the four different fusion proteins (see Table 4 for how the viral particles were made). The unconcentrated viral-like particles (collected medium) were co-transduced with a lentiviral vector expressing human beta hemoglobin (HBB) sgRNA1 (Plasmid No. 35, pFCK-HBB-sgRNA1) into the GFP-reporter cells as described in Example 1. Gene editing in these reporter cells results insertions or deletions (Indels) in the HBB target sequence inserted after the EGFP start codon, which restore the EGFP reading frame. Viral-like particles produced from unmodified packaging plasmid produced about 2.5% GFP$^+$ reporter cells. Viral-like particles expressing VPR-MCP, NEF-MCP and MA-MCP fusion proteins did not significantly increase the GFP$^+$ reporter cells, while NC-MCP fusion generated over 5% GFP$^+$ reporter cells (see Table 5). As only one third of the Indels in the reporter cells could restore the EGFP reading frame, only a third of gene editing events are detectable using these reporter cells (see Javidi-Parsijani, P., et al., *PLoS One* 2017; 12(5): e0177444). As such, un-concentrated lentivirus-like particles expressing NC-MCP fusion protein were able to generate Indels in over 15% of the reporter cells (3×the detected rate of 5%). In addition, GFP$^+$ cells could only be observed when the lentivirus-like particles were co-transduced with the lentiviral vector expressing HBB sgRNA1. Thus, gene editing events were limited only to cells transduced both by the fusion protein lentivirus-like particles and the virus particles carrying the HBB sgRNA1. As such, the rate of gene editing occurring when the NC-MCP fusion protein particles is used in the system is likely greater than 15%. In view of these results, further experiments were performed using NC as the recipient protein for fusion with RNA-binding aptamer proteins.

The performance of packaging plasmids with one or two copies of MCP fused to NC was compared (Plasmid Nos. 11 and 13). SaCas9$^{1\times MS2}$ containing viral-like particles generated by NC-MCPx1 packaging plasmid produced more GFP+ cells in GFP reporter assays than particles generated by NC-MCPx2 packaging plasmid (NC-MCPx1: 6.2%±0.1%, N=4; NC-MCPx2: 4.8%±0.4%, N=4; p<0.05). In view of these results, the NC-MCPx1 packaging plasmid was used in subsequent experiments unless otherwise specified.

As the lentiviral Env protein VSV-G promotes extracellular vesicle production (Rolls, M. M., et al., *Cell* 1994; 79(3): 497-506), it was possible that SaCas9$^{1\times MS2}$ mRNA could be being introduced into the reporter cells from extracellular vesicles rather than increased packaging into the lentivirus-like particles. To test this, an experiment was conducted comparing the gene editing rate induced by lentivirus-like particles expressing NC-MCPx1 (using psPAX2-D64V-NC-MS2, Plasmid No. 11) or a control generated using an mRuby-expressing plasmid (pKanCMV-mRuby3-10aa-H2B; Addgene Cat. No. 74258) that did not express any of the lentiviral packaging proteins (mRuby is a red fluorescent protein). The mRuby expressing plasmid does not express any lentivirus packaging proteins so no lentivirus will be produced from it alone. If extracellular vesicles but not lentivirus-like particles are the structures mediating Cas9 mRNA transfer, then mRuby mRNA or plasmid should be similarly incorporated into the extracellular vesicles and the mRuby protein should be expressed with similar efficiency as Cas9 protein. The particles were produced as described in Example 1 and were concentrated by ultracentrifugation, which was expected to precipitate both lentivirus-like particles and extracellular vesicles. To measure gene editing, the precipitate was used to transduce GFP reporter cells together with lentivirus particles containing HBB sgRNA1. Particles generated with the NC-MCP modified packaging plasmid generated over 10% GFP$^+$ reporter cells, while particles generated with the mRuby plasmid instead generated less than 1% GFP$^+$ reporter cells as well as less than 1% mRuby$^+$ reporter cells. The precipitate containing lentivirus-like particles containing NC-MCPx1 also containing Cas9 mRNA, which led to the high GFP+ reporter cell rate observed. Without the NC-MS2 packaging plasmid (replaced by mRuby plasmid), the precipitate only contained extracellular vesicles, which led to the low GFP+ reporter cell rate observed. This showed that extracellular vesicles did not have much Cas9 mRNA or mRuby mRNA (mRuby also low percentage). As VSV-G was expressed in both conditions, the key difference was whether the NC-MCP modified packaging plasmid was used. The results suggest that extracellular vesicles do not play a major role in generating GFP$^+$ reporter cells in this system.

To test whether GFP+ reporter cells were simply generated by the plasmid DNA left over from the lentivirus-like particle production, a plasmid expressing both SaCas9$^{1\times MS2}$ RNA and HBB sgRNA1 (Plasmid No. 40, pSaCas9$^{1\times MS2}$-HBB-sgRNA1) was transfected into the packaging cells during lentivirus-like particle production with the NC-MCP modified packaging plasmid (Plasmid No. 11). The sgRNA1 does not include an aptamer sequence. As such, although both SaCas9$^{1\times MS2}$ mRNA and HBB sgRNA1 are transcribed from the plasmid, only SaCas9$^{1\times MS2}$ mRNA could be packaged into lentivirus-like particles with detectable efficiency. The resulting lentivirus-like particles were used to transduce the GFP reporter cells alone (condition 1) or in combination with lentiviral particles containing HBB sgRNA1 (made using Plasmid No. 35) (condition 2). In condition 2, 10% GFP+ reporter cells were observed, while less than 3% GFP+ cells were observed in condition 1. Simply transfecting the GFP-reporter cells with pSaCas9$^{1\times MS2}$-HBB-sgRNA1 DNA generated over 10% GFP reporter cells. The data suggest that plasmid DNA left over during lentivirus-like particle production is not a major contribution to the SaCas9$^{1\times MS2}$ mRNA and support a conclusion that SaCas9$^{1\times MS2}$ mRNA is packaged into lentivirus-like particles.

Example 3. Effects of MS2 Aptamer on SaCas9 mRNA Stability

Two possible mechanisms might contribute to the packaging of SaCas9$^{0\times MS2}$ mRNA in lentivirus-like particles. First, cellular mRNA (including the SaCas9 mRNA) could be packaged into the lentivirus-like particles non-specifically, as described by Rulli, S. J., et al., *J Virol* 2007; 81(12): 6623-6631. Second, SaCas9 mRNA might have some RNA structures that could be bound by the NC-MCP fusion protein or other lentiviral proteins. When the genome editing activity of un-concentrated lentivirus-like particles containing either SaCas9$^{1\times MS2}$ or SaCas9$^{0\times MS2}$ by GFP cell reporter assay was compared, the percentages of GFP+ cells generated by the two showed hardly any difference (9.4%±0.1%, N=4; 9.1%±0.2%, N=4; p=0.17). Although the aptamer is not essential for SaCa9 mRNA to be packaged in the lentivitus-like particles, NC-MCP fusion greatly enhanced the packaging of SaCas9 mRNA by 10 times compared with the amount of SaCas9 mRNA packaged by unmodified packaging plasmid.

To examine the effects of MS2 aptamers on SaCas9 mRNA level in the cells, an experiment was conducted to assess the effects of 0, 1, 2, 3 and 12 copies of MS2 aptamers added to the 3' end of the SaCas9 mRNA (Plasmids Nos. 15-19) on mRNA level. Equal amounts of plasmid DNA encoding SaCas9$^{n \times MS2}$ (n indicates 0, 1, 2, 3 or 12) was transfected into HEK293T cells, and the steady-state level of SaCas9 mRNA was compared by real time RT-PCR. It was found that addition of 1 aptamer after the SaCas9 coding sequence slightly decreased the steady-state level of SaCas9 mRNA, while the addition of 2 or more aptamers significantly decreased the steady-state level of SaCas9 mRNA (Table 6). Consistent with the mRNA level decrease, when the SaCas9$^{n \times MS2}$-encoding plasmids (n indicates 0, 1, 2, 3 or 12) (250 ng) were co-transfected with a plasmid expressing the HBB sgRNA1 (250 ng) into the GFP reporter cells (24-well plates), one aptamer slightly decreased the percentage of GFP$^+$ reporter cells observed, while more aptamers further decreased the number observed (Table 6). Flow cytometry and qRT-PCR were performed 72 hours after transfection. HBB sgRNA1 was used as the transfection efficiency control for qRT-PCR. The data suggest that addition of the MS2 aptamer decreased SaCas9 stability. This mRNA stability decrease could have a measurable effect on genome editing activity because SaCas9 mRNA cannot be replaced (regenerated) once they are released from the lentivirus-like particles.

TABLE 6

Effects of MS2 aptamers on SaCas9 expression

| | No aptamer | 1 aptamer | 2 aptamers | 3 aptamers | 12 aptamers |
|---|---|---|---|---|---|
| SaCas9 mRNA level | 1.0 ± 0.03 | 0.76 ± 0.03$^{\#}$ | 0.18 ± 0.01$^{\#\#}$ | 0.19 ± 0.01$^{\#\#}$ | 0.27 ± 0.03$^{\#\#}$ |
| GFP$^+$ percentage | 9.9 ± 0.15** | 8.3 ± 0.12* | 6.7 ± 0.15 | 7.5 ± 0.38 | 7.3 ± 0.39 |

Mean ± s.e.m of 4 replicates were presented.
$^{\#}$p < 0.0001 compared with no aptamer;
$^{\#\#}$p < 0.0001 compared with 1 aptamer;
*p < 0.05 when 1 aptamer was compared to 2 aptamer;
**p < 0.01 when No aptamer was compared with 1, 2, 3, or 12 aptamers.

Example 4. Human HBB Gene 3' UTR Sequence Increased SaCas9 mRNA Stability

Figure 3:
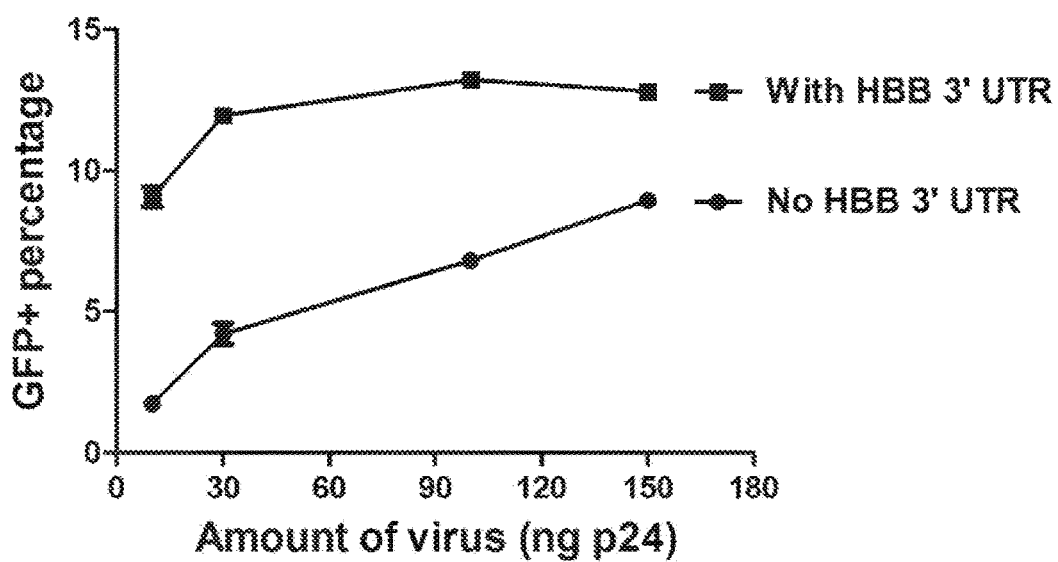
FIG. 3 shows a graph illustrating that addition of a HBB 3' UTR sequence to the SaCas9 mRNA improved the gene editing activity of the viral like particles according to some aspects of this disclosure. Different amount of concentrated viral-like particles containing SaCas9 mRNA with a MS2 aptamer sequence followed by two copies of a HBB 3' UTR sequence were co-transduced into $2.5 \times 10^4$ GFP-reporter cells with equal amounts of lentivirus-like vectors expressing HBB sgRNA1. The GFP-positive cells were detected by flow cytometry. Each data point was the average of two repeats.

An experiment was conducted to assess whether addition of one or two copies of human HBB gene 3' UTR sequences after the MS2 aptamer of SaCas9$^{1 \times MS2}$ could enhance SaCas9 mRNA stability and translatability in the presence of aptamer. Plasmid pSaCas9$^{1 \times ms2}$ and pSaCas9$^{1 \times ms2}$-2×3'UTR was transfected into HEK293T cells (Plasmid Nos. 16 and 36). The steady-state level of SaCas9 mRNA in the cells was assessed by real time RT-PCR. The addition of two human HBB gene 3' UTR sequences was found to increase the steady-state level of SaCas9 mRNA level by 30% (1.0±0.03 versus 1.3±0.08, n=4, p<0.05). GFP reporter cells were co-transduced with lentivirus-like particles containing SaCas9$^{1 \times MS2}$-2×3'UTR mRNA or lentivirus-like particles containing SaCas9$^{1 \times MS2}$ mRNA (no stabilizing sequences), and lentivirus particles containing HBB sgRNA1 (generated using Plasmid No. 35). Transduction with the lentivirus-like particles containing SaCas9$^{1 \times MS2}$-2×3'UTR mRNA resulted in a significantly increased percentage of GFP$^+$ reporter cells than lentivirus-like particles containing SaCas9$^{1 \times MS2}$ mRNA (see FIG. 3). Thus, addition of 2 copies of HBB 3' UTR sequences to SaCas9$^{1 \times MS2}$ improved the performance of the system.

Example 5. SaCas9 Lentivirus-Like Particles Based on PP7 Coat Protein and its Aptamer Showed High Genome Editing Activity PP7 coat protein (PCP) is another RNA aptamer-binding protein (see Lim, F., et al., *J Biol Chem* 2001; 276(25): 22507-22513 and Wu, B., et al., *Biophysical Journal* 2012; 102(12): 2936-2944). An experiment was conducted to compare the utility of the PP7 protein and its cogent aptamer sequence in this system in place of the MCP and its aptamer sequence. A packaging plasmid was produced in which MCP was replaced with PCP thereby creating a NC-PCP fusion. Also constructed was a SaCas9 mRNA expression plasmid in which the MS2 aptamer coding sequence was replaced by the PP7 aptamer coding sequence (Plasmid No. 20, pSaCas9$^{1 \times PP7}$). These plasmids were used to make SaCas9$^{1 \times PP7}$ mRNA packaged lentivirus-like particles. Upon co-transducing GFP reporter cells with lentiviral vectors expressing the HBB targeting sgRNA1, using SaCas9$^{1 \times PP7}$-containing lentivirus-like particles resulted more GFP+ reporter cells than SaCas9$^{1 \times MS2}$-containing lentivirus-like particles (9.4%±0.14%, N=4; 8.1%±0.04%, N=4, p<0.01).

The amount of SaCas9 mRNA packaged into the lentivirus-like particles was assessed by real time RT-PCR, as summarized in Table 7. The types of particles included lentivirus (column 2), lentivirus-like particles produced by packaging plasmid with no ABP fusion (column 3), by NC-MCP fusion packaging plasmid (columns 4-6), and by NC-PCP fusion packaging plasmid (columns 7-9). The SaCas9 mRNA contained no aptamer (columns 2, 3, 4 and 7), one aptamer (columns 5 and 8), or one aptamer and 2 copies of HBB 3' UTR (columns 6 and 9). RNA was purified from various lentivius or lentivirus-like particles containing 200 ng of p24. Equal amount of GFP-lentivirus was included in each sample to normalize the RNA purification, RT, and PCR. Copy number estimation is based on the assumption that each lentivirus particle contains 2 copies of the lentivirus genome. By comparing the SaCas9 mRNA levels in the same amount of SaCas9-expressing lentivirus (known to have 2 copies of genome per particle) or lentivirus-like particles, we calculated the average copy numbers of SaCas9 mRNA per particle in each condition. In Table 7, means±SEM are shown, and the numbers in the parentheses are the numbers of replicates.

TABLE 7

QRT-PCR comparison of the copy number of SaCas9 in various lentivirus-like particles

| | No ABP | | NC-MCP packaged | | | NC-PCP packaged | | |
|---|---|---|---|---|---|---|---|---|
| | Lentivirus | No aptamer | 0 MS2 | 1 MS2 | 1 MS2 3'UTR | 0 PP7 | 1 PP7 | 1 PP7 3' UTR |
| Relative SaCas9 mRNA level | 1 (3) | 0.71 ± 0.06 (2) | 15.8 ± 1.1 (3) | 13.3 ± 0.3 (3) | 50.1 ± 2.6 (3) | 7.9 ± 1.5 (3) | 6.6 ± 0.6 (3) | 21.8 ± 0.1 (2) |
| SaCas9 mRNA copy number | 2 | 1.4 | 31.6 | 26.6 | 100.2 | 15.8 | 13.2 | 43.6 |

Without ABP fused to NC and without aptamer after the stop codon of SaCas9, lentivirus-like particles were found to have less than two copies of SaCas9 mRNA per particle. This could be the result of randomly packaging highly expressed cellular RNA by the virus-like particles. With ABP (MCP or PCP) fused to NC, the SaCas9 mRNA copy number per particle increased 10 to 20 times regardless whether an aptamer sequence is appended to SaCas9. Addition of HBB 3' UTR increased the copy numbers 3 fold with both ABPs, which is most likely the result of increasing the RNA stability before and after packaging. Adding one aptamer to SaCas9 mRNA did not increase SaCas9 mRNA copy number per particle compared with SaCas9 mRNA without aptamers, which is most likely the combined result of aptamer increasing the binding of SaCas9 mRNA to the NC-ABP fusion proteins but decreasing the stability of SaCas9 mRNA. These effects of aptamers on SaCas9 mRNA are also consistent with the observation of HBB 3' UTR addition increasing SaCas9 mRNA copy number per particle, as HBB 3' UTR increases mRNA stability although unable to increase the binding to ABPs.

Figure 4:
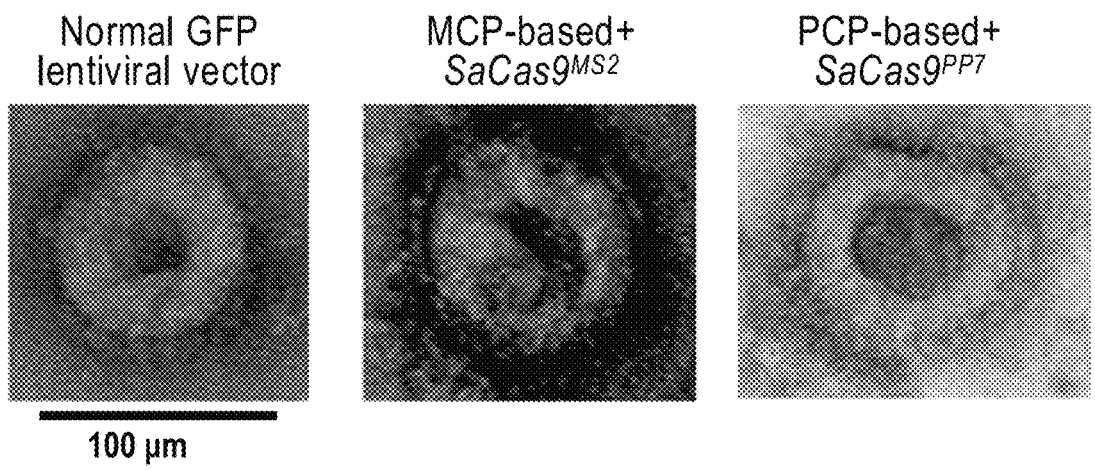
FIG. 4 shows images illustrating the production of lentivirus-like particles from MCP- and PCP-based lentiviral packaging plasmids according to aspects of this disclosure. The control lentiviral particle had the lentiviral genome expressing GFP. The MCP- and PCP-based lentivirus-like particles contained SaCas9$^{1 \times MS2}$ mRNA and SaCas9$^{1 \times PP7}$ mRNA, respectively. Means±sem of control, MCP- and PCP-based particles were 98.5±10.5, 105.7±3.1 and 123.9±5.8 nm respectively, n≥11.

The expression of viral proteins MA, CA, and p15 (where NC is processed from) was also assessed in normal GFP lentiviral vectors and in MCP and PCP-based lentivirus-like particles by Western blotting. The NC-PCP fusion protein was found to migrate as a single band with the expected size of about 22 kDa, while an additional small band of about 14 kDa was observed for the NC-MCP fusion protein, indicating partial degradation. The MA and CA proteins were observed to migrate at the expected sizes from all of the particles, suggesting that the insertion of MCP or PCP into NC protein did not affect the processing of other lentiviral proteins. Electron microscopy analyses of the MCP- and PCP-based lentivirus-like particles revealed similar particles sizes (see FIG. 4).

Example 6. Transient Expression of SaCas9 mRNA From Lentivirus-like Particles

Figure 5A:
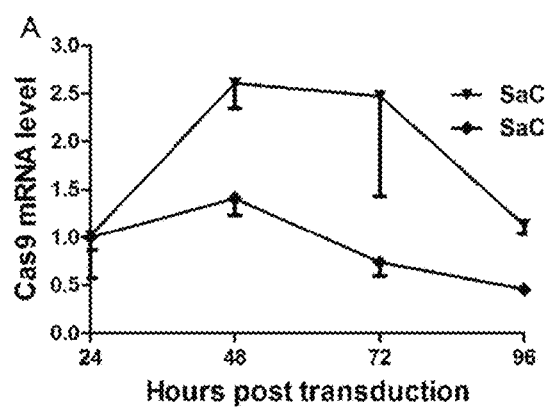
FIG. 5A and FIG. 5B show graphs illustrating the transient expression of SaCas9 mRNA in HEK293T cells transduced with different viral vectors according to aspects of this disclosure.
Figure 5B:
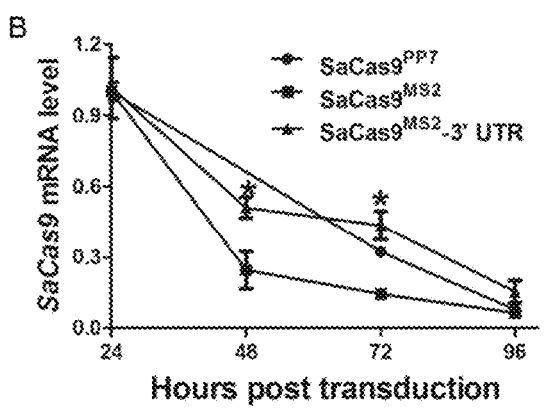

To determine the duration of the SaCas9 mRNA released from lentivirus-like particles, lentivirus-like particles containing SaCas9$^{1\times PP7}$ mRNA (Plasmid No. 20), SaCas9$^{1\times MS2}$ mRNA (Plasmid No. 16), or SaCas9$^{1\times MS2}$-2×3'UTR mRNA (Plasmid No. 36) were transduced into HEK293T cells and the level of SaCas9 mRNA at 24, 48, 72 and 96 hours post transduction was measured by quantitative RT-PCR. As controls, the SaCas9 mRNA levels expressed from adeno associated virus (AAV, made using Plasmid No. 15) and integration defective lentivirus (IDLV, made using Plasmid No. 31) were also assessed. All DNA was eliminated before reverse transcription, thus all SaCas9 nucleic acid detected was mRNA. For both AAV and IDLV, SaCas9 mRNA was increased 48 hours after transduction, consistent with the start of transcription from the DNA templates as shown in FIG. 5A. The level of SaCas9 mRNA in AAV-transduced cells was still higher at 96 hour post-transduction than at 24 hours post-transduction. The SaCas9 mRNA level in IDLV-transduced cells started to decrease after 72 hours but expression at 96 hours after transduction was still about half of that at 24 hour post transduction. In cells transduced with lentivirus-like particles packaged with modified SaCas9, the level of SaCas9 mRNA decreased after 24 hours post-transduction as shown in FIG. 5B. At 96 hours post-transduction, the level of SaCas9 mRNA was less than 25% of that of 24 hours post-transduction. The addition of the HBB 3' UTR to the SaCas9 mRNA slowed its degradation.

Example 7. Efficient Genome Editing Activity From Transient Expression of SaCas9 mRNA Lentivirus-like particles containing SaCas9$^{1\times MS2}$-2×3' UTR mRNA (made using Plasmid No. 36) and lentivirus particles expressing HBB sgRNA1 (made using Plasmid No. 35) were made and concentrated by Tangential Flow Filtration as described in Example 1. The virus concentration was determined by p24 ELISA. The lentivirus-like particles and lentivirus particles (30 ng p24 protein of each) were co-transduced into 2.5×10$^4$ GFP reporter cells as described in Example 1. The HBB sgRNA1 was designed against a mutated HBB sequence known to cause Sickle Cell Disease that has a one nucleotide mismatch with the endogenous HBB sequence in the reporter cells as described in Example 1. The target sequence of HBB sgRNA1 inserted between the first and second codon of the GFP coding sequence in the transduced GFP reporter cells was amplified and Next Generation Sequencing was performed to detect Indels. Sequence analysis found that 86.5% of the alleles had Indels. Thus, the described system was very efficient in editing the Sickle Cell Disease mutation. A close examination of the positions of the Indels found that most of the Indels were around the expected cleavage site (3 nt from the PAM) (see FIG. 6, listing SEQ ID NOs:103-112 from top to bottom), suggesting that the Indels observed were from gene editing guided by HBB sgRNA1.

Example 8. Packaging sgRNA in Lentivirus-like Particles

An experiment was conducted to determine whether sgRNA could also be packaged into lentivirus-like particles via the interactions between coat proteins and their respective aptamers. Other studies have found that aptamer sequences can be added at the stem loop II, tetra loop, or after the 3' end of SpCas9 sgRNA (Shechner, D. M., et al., Nat Methods 2015; 12(7): 664-670 and Konermann, S., et al., Nature 2015; 517(7536): 583-588). However, no information was available about the locations that can tolerate aptamer addition in SaCas9 sgRNA. Modified plasmids were generated by adding one or two MS2 aptamers in the SaCas9 sgRNA at stem loop II (ST2), tetra loop (Tetra), or after the 3' end in plasmid pSaCas9-HBB-sgRNA1 (Plasmid No. 22), which expresses both SaCas9 mRNA and the HBB sgRNA1. The modified plasmid DNA was transfected into GFP reporter cells. The addition of one aptamer at the 3' end of sgRNA showed the least decrease in percentage of GFP+ reporter cells (Table 8). In view of these results, sgRNA with a 3' addition of aptamer was used in subsequent experiments.

TABLE 8

Effects of Aptamer addition on sgRNA performance

| | No aptamer | ST2 | Tetra | Tetra + ST2 | 3' end | Tetra + 3' end |
|---|---|---|---|---|---|---|
| GFP+ (%) | 8.5 ± 0.1 | 7.2 ± 0.3 | 7.5 ± 0.3 | 6.9 ± 0.1* | 8.4 ± 0.6 | 6.7 ± 0.1* |

Shown are mean ± sem (N = 3).
*indicates significantly lower than control (No aptamer) by ANOVA and Tukey's Multiple Comparison Test (p < 0.05).

Another experiment was performed to assess whether the 3' MS2 aptamer-modified HBB sgRNA1 (HBB sgRNA1$^{3'MS2}$) could be packaged in lentivirus-like particles expressing NC-MCP fusion protein using packaging plasmid. Plasmid DNA expressing modified and unmodified HBB sgRNA1 (Plasmid No. 22 for sgRNA without aptamer, Plasmid No. 24 for sgRNA with a 3' MS2 aptamer) were co-transfected into HEK293T cells during lentivirus-like particle production using MCP-based packaging plasmids (pspAX2-D64V-NC-MCP; Plasmid No. 11). Real-time PCR detected 30 times more HBB sgRNA$^{3'MS2}$ than unmodified HBB sgRNA after normalized by lentivirus-like particle input. In agreement with previous data, NC-MCPx1 packaged 5 times more HBB sgRNA1$^{3'MS2}$ than did NC-MCPx2.

To tested whether SaCas9 mRNA and HBB sgRNA could be simultaneously packaged into lentiviral particles, plasmid DNA expressing both SaCas9$^{1\times MS2}$ and HBB sgRNA$^{3'MS2}$ (Plasmid No. 28) was co-transfected into HEK293T cells during lentivirus-like particle production with MCP-based packaging plasmid (psPAX2-D64V-NC-MS2, Plasmid No. 11). Transducing the resulted lentivirus-like particles (70 ng p24 for 2.5×10$^4$ cells) into GFP reporter cells as described in Example 1 produced up to 3.6% GFP-positive cells. However, co-transducing the GFP reporter cells with HBB sgRNA1 containing lentivirus (made using Plasmid No. 35) increased the percentage of GFP+ cells to over 10%. These experiments indicated that the sgRNA could be packaged into lentivirus-like particles but that the amount of sgRNA packaged resulted in low editing efficiency. Another experiment was performed using lentivirus-like particles packaged with sgRNA having two copies of the HBB 3' UTR sequences at the 3' end (made using Plasmid No. 43). This modification was found not to improve the packaging/ functionality of the sgRNA. Thus, for high efficiency gene editing, the sgRNA may need to be expressed from lentivirus or AAV.

Example 9. Lentivirus-Like Particles Delivery of SaCas9 mRNA Reduced Risks of Off-Target Gene Editing Events The HBB sgRNA1 was designed to target the Sickle mutation and has one nucleotide mismatch with the wild type HBB sequence. As such, the corresponding wild type HBB gene sequence in the GFP reporter cells can be regarded as the "off target" for SaCas9/HBB sgRNA1. An experiment was conducted to determine if the provided lentivirus-like delivery system offers lower off target gene editing rates. The GFP reporter cells were transduced with four different combinations of virus/virus-like particles and the Indel rates in the wild type HBB locus of the GFP-reporter cells was determined and compared. The virus or lentivirus-like particles used were as follows: Condition 1: the lentivirus-like particles containing SaCas9$^{1\times MS2}$ mRNA (made using Plasmid No. 16); Condition 2: AAV containing SaCas9 mRNA (made using Plasmid No. 15, pSaCas9); Condition 3: integration defective lentivirus (made using Plasmid No. 31, pCK002-HBB-sgRNA, and packaged using pspAX2-D64V (Addgene Cat No. 63586), which contains the inactive integrase), the IDLV expressing both SaCas9 mRNA and HBB sgRNA1; and Condition 4: integration competent lentivirus (Plasmid No. 31, pCK002-HBB-sgRNA1, and packaged with plasmid pspAX2 (Addgene Cat No. 12260), which contains an active integrase. For Conditions 1 and 2, The GFP reporter cells were co-transduced with lentivirus (pFCK-HBB-sgRNAL Plasmid No. 35) in Condition 1 or AAV (pAAV-HBB(n)-sgRNA1, Plasmid No. 34) in Condition 2 to express HBB sgRNA1. Results are shown in Table 9. Due to the generation of Indels in the Sickle mutation in the GFP cassette of the GFP reporter cells, variant percentages of the GFP reporter cells in all four treatments were observed. The transduced cells were sorted by GFP-activated sorting. The GFP-positive cell percentage was 89-95%, indicating the presence of functional SaCas9/HBB sgRNA1 in majority of the cells in each of the four conditions. The DNA from the endogenous HBB locus was amplified and sequenced by Next Generation Sequencing. The lentivirus-like particle system described in Condition 1 had the lowest Indel rate, demonstrating that delivering SaCas9 mRNA by lentivirus-like particles for gene editing is safer than other virus delivery systems.

TABLE 9

Indel rates in the wild type HBB locus of the GFP reporter cells

| Group name | Condition 1 | Condition 2 | Condition 3 | Condition 4 |
|---|---|---|---|---|
| Vector delivering SaCas9 | Lentivirus-Like Particles | AAV Particles | IDLV Particles | Lentivirus Particles |
| GFP+ (%) | 88.9 | 90.8 | 93.3 | 95.4 |
| Total sequence readings | 3432717 | 3865920 | 3444935 | 4023043 |
| Indel in wild type HBB (%) | 3.0 | 8.7 | 21.1 | 81.8 |

TABLE 10

| | | SEQUENCE LISTING |
|---|---|---|
| SEQ ID NO | Sequence Type | Sequence |
| SEQ ID NO: 1 | HIV-1 Nucleocapsid (NC) DNA Sequence | ATACAGAAAGGCAATTTTAGGAACCAAAGAAAGACTGTTA<br>AGTGTTTCAATTGTGGCAAAGAAGGGCACATAGCCAAAAA<br>TTGCAGGGCCCCTAGGAAAAAGGGCTGTTGGAAATGTGGA<br>AAGGAAGGACACCCAAATGAAAGATTGTACTGAGAGACAG<br>GCTAAT |
| SEQ ID NO: 2 | HIV-1 Nucleocapsid (NC) Amino Acid Sequence | IQKGNFRNQRKTVKCFNCGKEGHIAKNCRAPRKKGCWKCG<br>KEGHQMKDCTERQAN |
| SEQ ID NO: 3 | HIV-1 Matrix protein (MA) DNA Sequence | atgggtgcgagagcgtcagtattaagcgggggagaattagatcgatgggaaaaaattcggt<br>taaggccaggggggaaagaaaaaatataaattaaaacatatagtatgggcaagcagggagct<br>agaacgattcgcagttaatcctggcctgttagaaacatcagaaggctgtagacaaatactg<br>ggacagctacaaccatcccttcagacaggatcagaagaacttagatcattatataatacag<br>tagcaaccctctattgtgtgcatcaaaggatagagataaaagacaccaaggaagctttaga<br>caagatagaggaagagcaaaacaaaagtaagaaaaaagcacagcaagcagcagctgacaca<br>ggacacagcaatcaggtcagccaaaattac |
| SEQ ID NO: 4 | HIV-1 Matrix protein (MA) Amino Acid Sequence | GARASVLSGGELDRWEKIRLRPGGKKKYKLKHIVWASRELE<br>RFAVNPGLLETSEGCRQILGQLQPSLQTGSEELRSLYNTVATL<br>YCVHQRIEIKDTKEALDKIEEEQNKSKKKAQQAAADTGHSN<br>QVSQNY |
| SEQ ID NO: 5 | HIV-1 Viral Protein (VPR) DNA Sequence | ATGGAACAAGCCCCAGAAGACCAGGGACCGCAGAGGGAA<br>CCATACAATGAATGGACACTAGAACTTTTAGAGGAACTCA<br>AGCGGGAAGCAGTCAGACACTTTCCTAGACCATGGCTTCA<br>TGGCTTAGGACAACATATCTATGAAACCTATGGAGATACT<br>TGGACGGGGGTGGAAGCTATAATAAGAATTCTGCAACGAC<br>TACTGTTTGTCCATTTCAGAATTGGGTGCCAGCATAGCCGA<br>ATAGGCATTCTAAGACAGAGAAGAGCAAGAAATGGAGCC<br>AGTAGATCCTAA |
| SEQ ID NO: 6 | HIV-1 Viral Protein (VPR) Amino Acid Sequence | MEQAPEDQGPQREPYNEWTLELLEELKREAVRHFPRPWLHG<br>LGQHIYETYGDTWTGVEAIIRILQRLLFVHFRIGCQHSRIGILR<br>QRRARNGASRS |
| SEQ ID NO: 7 | HIV-1 Negative Regulatory Factor (NEF) DNA Sequence with codon changes to enhance packaging in the virus core (G3C, V153L, and E177G mutations: underlined) | atgggtTgcaagtggtcaaaaagtagtgtgattggatggcctgctgtaagggaaagaatga<br>gacgagctgagccagcagcagatggggtgggagcagtatctcgagacctagaaaaacatgg<br>agcaatcacaagtagcaatacagcagctaacaatgctgcttgtgcctggctagaagcacaa<br>gaggaggaagaggtgggttttccagtcacacctcaggtaccttttaagaccaatgacttaca<br>aggcagctgtagatcttagccacttttttaaaagaaaagggggggactggaagggctaattca<br>gctcccaaagaagacaaatatccttgatctgtggatctaccacacacaaggctacttccct<br>gattggcagaactacacaccagggccaggggtcagatatccactgacctttggatggtgct<br>acaagctagtaccagttgagccagataagCtGgaagaggccaataaaggagaagaccaag<br>cttgttacaccctgtgagcctgcatggaatgaccctgGAagagaagtgttagagtgg<br>aggtttgacagccgcctagcatttcatcacgtggcccgagagctgcatccggagtacttca<br>agaactgc(The yellow positions are changed to code for the changes explained in seq ID. 8. |
| SEQ ID NO: 8 | HIV-1 Negative Regulatory Factor (NEF) Amino Acid Sequence with mutation to enhance packaging in the virus core (G3C, V153L, and E177G mutations: underlined) | MGCKWSKSSVIGWPAVRERMRRAEPAADGVGAVSRDLEKH<br>GAITSSNTAANNAACAWLEAQEEEEVGFPVTPQVPLRPMTY<br>KAAVDLSHFLKEKGGLEGLIHSQRRQDILDLWIYHTQGYFPD<br>WQNYTPGPGVRYPLTFGWCYKLVPVEPDKLEEANKGENTSLL<br>HPVSLHGMDDPGREVLEWRFDSRLAFHHVARELHPEYFKNC |
| SEQ ID NO: 9 | MS2 coat protein (MCP) DNA Sequence | ATGGCTTCTAACTTTACTCAGTTCGTTCTCGTCGACAATGG<br>CGGAACTGGCGACGTGACTGTCGCCCCAAGCAACTTCGCT<br>AACGGGATCGCTGAATGGATCAGCTCTAACTCGCGTTCAC<br>AGGCTTACAAAGTAACCTGTAGCGTTCGTCAGAGCTCTGC<br>GCAGAATCGCAAATACACCATCAAAGTCGAGGTGCCTAAA<br>GGCGCCTGGCGTTCGTACTTAAATATGGAACTAACCATTC<br>CAATTTTCGCCACGAATTCCGACTGCGAGCTTATTGTTAAG<br>GCAATGCAAGGTCTCCTAAAAGATGGAAACCCGATTCCCT<br>CAGCAATCGCAGCAAACTCCGGCATCTAC |

TABLE 10-continued

SEQUENCE LISTING

| SEQ ID NO | Sequence Type | Sequence |
|---|---|---|
| SEQ ID NO: 10 | MS2 coat protein (MCP) Amino Acid Sequence | MASNFTQFVLVDNGGTGDVTVAPSNFANGIAEWISSNSRSQA YKVTCSVRQSSAQNRKYTIKVEVPKGAWRSYLNMELTIPIFA TNSDCELIVKAMQGLLKDGNPIPSAIAANSGIY |
| SEQ ID NO: 11 | PP7 coat protein (PCP) DNA Sequence | tccaaaacaatagtcctctccgtaggggaggcaacacggactttgaccgaaatccagtcaa ccgctgaccgacaaatcttttgaagagaaagtagggcctcttgtgggccgactgcgcttgac tgcaagcttgcgacaaaacggcgcaaagactgcctatagggtcaaccttaaactcgaccaa gccgacgtggtcgatagcggtctccctaaggttcggtatacgcaggtctggagtcatgacg taacaatcgtagcaaacagcacagaagcctcccgaaaaagcctctacgatctgacgaaatc cttggtggctacgtcacaggtggaagacctcgttgtcaaccttgtacctctgggtcga |
| SEQ ID NO: 12 | PP7 coat protein (PCP) Amino Acid Sequence | SKTIVLSVGEATRTLTEIQSTADRQIFEEKVGPLVGRLRLTASL RQNGAKTAYRVNLKLDQADVVDSGLPKVRYTQVWSHDVTI VANSTEASRKSLYDLTKSLVATSQVEDLVVNLVPLGR |
| SEQ ID NO: 13 | lambda N RNA-binding domain (positions (1-22) DNA Sequence | ATGGATGCACAAACACGCCGCCGCGAACGTCGCGCAGAG AAACAGGCTCAATGGAAAGCAGCAAAT |
| SEQ ID NO: 14 | lambda N RNA-binding domain (positions (1-22) Amino Acid Sequence | MDAQTRRRERRAEKQAQWKAAN |
| SEQ ID NO: 15 | COM Protein DNA Sequence | atgaaatcaattcgctgtaaaaactgcaacaaactgttatttaaggcggattcctttgatc acattgaaatcaggtgtccgcgttgcaaacgtcacatcataatgctgaatgcctgcgagca tcccacggagaaacattgtgggaaaagagaaaaaatcacgcattctgacgaaaccgtgcgt tattgagtat |
| SEQ ID NO: 16 | COM Protein Amino Acid Sequence (GenBank AAF01130.1) | MKSIRCKNCNKLLFKADSFDH1EIRCPRCKRHIIMLNACEHPT EKHCGKREKITHSDETVRY |
| SEQ ID NO: 17 | MS2 aptamer sequence (RNA) | ACAUGAGGAUCACCCAUGU |
| SEQ ID NO: 18 | MS2 aptamer sequence (DNA) | ACATGAGGATCACCCATGT |
| SEQ ID NO: 19 | PP7 aptamer sequence (RNA) | GGAGCAGACGAUAUGGCGUCGCUCC |
| SEQ ID NO: 20 | PP7 aptamer sequence (DNA) | GGAGCAGACGATATGGCGTCGCTCC |
| SEQ ID NO: 21 | Box-B: lambda N RNA-binding domain aptamer sequence (RNA) | GGGCCCUGAAGAAGGGCCC |
| SEQ ID NO: 22 | Box-B: lambda N RNA-binding domain aptamer sequence (DNA) | GGGCCCTGAAGAAGGGCCC |
| SEQ ID NO: 23 | COM aptamer RNA sequence | CUGAAUGCCUGCGAGCAUC |
| SEQ ID NO: 24 | COM aptamer DNA sequence | CTGAATGCCTGCGAGCAT |
| SEQ ID NO: 25 | human beta hemoglobin (HBB) 3' UTR (DNA) | gctcgctttcttgctgtccaatttctattaaaggttcctttgttccctaagtccaactact aaactgggggatattatgaagggccttgagcatctggattctgcctaataaaaaacattta ttttcattgc |
| SEQ ID NO: 26 | human beta hemoglobin | gcucgcuuucuugcugucccaauuucuauuaaagguuccuuuguucccuaaguccaacu acuaaacugggggauauuaugaagggccuugagcaucuggauucugccuaauaaaaaa |

TABLE 10-continued

SEQUENCE LISTING

| SEQ ID NO | Sequence Type | Sequence |
|---|---|---|
| | (HBB) 3' UTR (RNA) | cauuuauuuucauugc |
| SEQ ID NO: 27 | human hemoglobin alpha (HBA) 5' UTR (DNA) | Ctcttctggtccccacagactcagagagaac |
| SEQ ID NO: 28 | SaCas9-2576F | AAACCGGGAACTACCTGACC |
| SEQ ID NO: 29 | SaCas9-2713R | TCACGACCTTGTTTCTGCTG |
| SEQ ID NO: 30 | SgRNA-F1 | GAGTAACGGCAGACTTCTCCA |
| SEQ ID NO: 31 | sgRNA-R1 | CGGCATTTTGCCTTGTTTAAG |
| SEQ ID NO: 32 | EGFP-RT-F | CAGTGCTTCAGCCGCTACCC |
| SEQ ID NO: 33 | EGFP-RT-R | AGCTCGATGCGGTTCACCAG |
| SEQ ID NO: 34 | HHB-mut-F1 | TCGTCGGCAGCGTCAGATGTGTATAAGAGACAGTGTTCAC TAGCAACCTCAAACAG |
| SEQ ID NO: 35 | HHB-mut-F2 | TCGTCGGCAGCGTCAGATGTGTATAAGAGACAGATGTTCA CTAGCAACCTCAAACAG |
| SEQ ID NO: 36 | HHB-mut-F3 | TCGTCGGCAGCGTCAGATGTGTATAAGAGACAGGATGTTC ACTAGCAACCTCAAACAG |
| SEQ ID NO: 37 | HHB-mut-F4 | TCGTCGGCAGCGTCAGATGTGTATAAGAGACAGCGATGTT CACTAGCAACCTCAAACAG |
| SEQ ID NO: 38 | HHB-mut-F5 | TCGTCGGCAGCGTCAGATGTGTATAAGAGACAGTCGATGT TCACTAGCAACCTCAAACAG |
| SEQ ID NO: 39 | HHB-mut-F6 | TCGTCGGCAGCGTCAGATGTGTATAAGAGACAGATCGATG TTCACTAGCAACCTCAAACAG |
| SEQ ID NO: 40 | HHB-mut-R1 | GTCTCGTGGGCTCGGAGATGTGTATAAGAGACAGTCCAAT AGGCAGAGAGAGTCAGTG |
| SEQ ID NO: 41 | Oligo 1xloop-F | TTACGCTTAAGAATTCTAGAAAACATGAGGATCACCCATG TCTGCAGGTCGACTCTAGAAAATTCCTAGAGCTCG |
| SEQ ID NO: 42 | Oligo 1xloop-R | CGAGCTCTAGGAATTTTCTAGAGTCGACCTGCAGACATGG GTGATCCTCATGTTTTCTAGAATTCTTAAGCGTAA |
| SEQ ID NO: 43 | Oligo 2xloop-F | TTACGCTTAAGAATTCTAGAAAACATGAGGATCACCCATG TCTGCAGGTCGACTCTAGAAAACATGAGGATCACCCATGT CTGCAAAATTCCTAGAGCTCG |
| SEQ ID NO: 44 | Oligo 2xloop-R | CGAGCTCTAGGAATTTTGCAGACATGGGTGATCCTCATGTT TTCTAGAGTCGACCTGCAGACATGGGTGATCCTCATGTTTT CTAGAATTCTTAAGCGTAA |
| SEQ ID NO: 45 | Oligo 3xloop-F | TTACGCTTAAGAATTCTAGAAAACATGAGGATCACCCATG TCTGCAGGTCGACTCTAGAAAACATGAGGATCACCCATGT CTGCAAAATTCTAGAAAACAT |
| SEQ ID NO: 46 | Oligo 3xloop-R | ATGTTTTCTAGAATTTTGCAGACATGGGTGATCCTCATGTT TTCTAGAGTCGACCTGCAGACATGGGTGATCCTCATGTTTT CTAGAATTCTTAAGCGTAA |
| SEQ ID NO: 47 | Oligo Sickle-g2F | CACCGCCCTGTGGGGCAAGGTGAAC |
| SEQ ID NO: 48 | Oligo Sickle-g2R | AAACGTTCACCTTGCCCCACAGGGC |

TABLE 10-continued

SEQUENCE LISTING

| SEQ ID NO | Sequence Type | Sequence |
|---|---|---|
| SEQ ID NO: 49 | Oligo Sickle-g1F | CACCGAGTAACGGCAGACTTCTCCAC |
| SEQ ID NO: 50 | Sickle-g1R | AAACGTGGAGAAGTCTGCCGTTACTC |
| SEQ ID NO: 51 | Oligo PP7-F | TTACGCTTAAGAATTCGGAGCAGACGATATGGCGTCGCTC CGAATTCCTAGAGCTCG |
| SEQ ID NO: 52 | Oligo PP7-R | CGAGCTCTAGGAATTCGGAGCGACGCCATATCGTCTGCTC CGAATTCTTAAGCGTAA |
| SEQ ID NO: 53 | Oligo Sickle-g1-LV-F | caccGAGTAACGGCAGACTTCCCAC |
| SEQ ID NO: 54 | Oligo sickle-g1-LV-R | gaacGTGGAGAAGTCTGCCGTTACTC |
| SEQ ID NO: 55 | Primer Sickle-g1HD-F | TTGCAATGATCTCGAGGGCCTATTTCCCATGATTC |
| SEQ ID NO: 56 | Primer Sickle-g1HD-R | CTGCGGCCGCTCTAGAAAAATCTCGCCAACAAGTTG |
| SEQ ID NO: 57 | oligo HBB-tcm-F | CATGGTGCATCTGACACCTGTGGAGAAGTCTGCCGTTACT GCCCTGTGGGGCAAGGTGAACGTGGATGAAGTTGGTGGTG AGGCC |
| SEQ ID NO: 58 | oligo FIBB-tem-R | CAGGGCCTCACCACCAACTTCATCCACGTTCACCTTGCCCC ACAGGGCAGTAACGGCAGACTTCTCCACAGGTGTCAGATG CAC |
| SEQ ID NO: 59 | HHB-LT-F | CTTCTGATTTTCTAGATTGTGTAATCGTAGTTTCAGAG |
| SEQ ID NO: 60 | HHB-LT-R | GCTTGATATCGAATTAAAAAATCTCGCCAACAAGTTGAC |
| SEQ ID NO: 61 | pCDNA3.1/MS2x 2-VPR DNA Oligo Insert | GCTAGCcaccATGGCTTCTAACTTTACTCAGTTCGTTCTCGTCGA CAATGGCGGAACTGGCGACGTGACTGTCGCCCCAAGCAACTT CGCTAACGGGATCGCTGAATGGATCAGCTCTAACTCGCGTTCA CAGGCTTACAAAGTAACCTGTAGCGTTCGTCAGAGCTCTGCGC AGAATCGCAAATACACCATCAAAGTCGAGGTGCCTAAAGGCGC CTGGCGTTCGTACTTAAATATGGAACTAACCATTCCAATTTTCG CCACGAATTCCGACTGCGAGCTTATTGTTAAGGCAATGCAAGG TCTCCTAAAAGATGGAAACCCGATTCCCTCAGCAATCGCAGCA AACTCCGGCATCTACGGTGGTGGAGGAGGAATGGCGTCCAAT TTCACGCAGTTCGTCCTGGTTGACAACGGGGGGACTGGGGAC GTTACGGTCGCTCCGAGCAACTTTGCCAATGGTATTGCGGAGT GGATTTCTTCTAATTCACGGTCCCAAGCTTACAAAGTGACCTGT TCCGTGCGGGAAAGTTCTGCTCAGAATAGAAAGTACACTATAA AGGTCGAAGTCCCTAAGGGGGCCTGGCGATCATATCTCAATAT GGAGCTTACCATCCCAATATTTGCCACTAATTCTGATTGTGAAT TGATTGTCAAAGCAATGCAAGGACTCTTGAAAGACGGAAACCC AATCCCCAGCGCAATCGCAGCCAACTCCGGTATATACGGAGG TGGTGGAGGAATGGAACAAGCCCCAGAAGACCAGGGACCGCA GAGGGAACCATACAATGAATGGACACTAGAACTTTTAGAGGAA CTCAAGCGGGAAGCAGTCAGACACTTTCCTAGACCATGGCTTC ATGGCTTAGGACAACATATCTATGAAACCTATGGAGATACTTGG ACGGGGGTGGAAGCTATAA1AAGAAlTCTGCAACGACTACTGT TTGTCCATTTCAGAATTGGGTGCCAGCATAGCCGAATAGGCAT TCTAAGACAGAGAAGAGCAAGAAATGGAGCCAGTAGATCCTAA gcggccgc |
| SEQ ID NO: 62 | pCDNA3.1/MS2x 2-VPR Oligo Insert Amino Acid Sequence | MASNFTQFVLVDNGGTGDVTVAPSNFANGIAEWISSNSRSQAYKV TCSVRQSSAQNRKYTIKVEVPKGAWRSYLNMELTIPIFATNSDCEL IVKAMQGLLKDGNPIPSAIAANSGIYGGGGMASNFTQFVLVDN GGTGDVTVAPSNFANGIAEWISSNSRSQAYKVTCSVRQSSAQNRK YTIKVEVPKGAWRSYLNMELTIPIFATNSDCELIVKAMQGLLXDG NPIPSAIAANSGIYGGGGGMEQAPEDQGPQREPYNEWTLELLEE LKREAVRHFPRPWLHGLGQHIYETYGDTWIGVEAIIRILQRLLFV HFRIGCQHSRIGILRQRRARNGASRS |
| SEQ ID NO: 63 | pCDNA3.1/NEF-MS2x2 DNA | GCTAGCcaccatgggtTgcaagtggtcaaaaagtagtgtgattggcttggcctgctgtaag ggaaagaatgagctcgagctgagccagcagcagatggggtgggagcagtatctcgagacct |

TABLE 10-continued

SEQUENCE LISTING

| SEQ ID NO | Sequence Type | Sequence |
|---|---|---|
| | Oligo Insert | agaaaaacatggagcaatcacaagtagcaatacagcagctactcaatgctgcttgtgcctg gctagaagcacaagaggaggaagaggtgggttttccagtcacacctcaggtacctttaaga ccaatgacttacaaggcagctgtagatcttagccactttttaaaagaaaaggggggactgg aagggctaattcactcccaaagaagacaagatatccttgatctgtggatctaccacacaca aggctacttccctgattggcagaactacacaccagggccagggg tcagatatccactgacc tttggatggtgctacaagctagtaccagttgagccagataagCtGgaagaggcaataaag gagagaacaccagcttgttctcaccctgtgctgcctgcatggaatggatgaccctgGAaga gaagtgttagagtggaggtttgacagccgcctagcatttcatcacgtggcccgagagctgc atccggagtacttcaagaactgcGGAGGTGGTGGAGGAATGGCTTCTAACTTTACTC AGTTCGTTCTCGTCGACAATGGCGGAACTGGCGACGTGACTG TCGCCCCAAGCAACTTCGCTAACGGGATCGCTGAATGGATCA GCTCTAACTCGCGTTCACAGGCTTACAAAGTAACCTGTAGCGT TCGTCAGAGCTCTGCGCAGAATCGCAAATACACCATCAAAGTC GAGGTGCCTAAAGGCGCCTGGCGTTCGTACTTAAATATGGAAC TAACCATTCCAATTTTCGCCACGAATTCCGACTGCGAGCTTATT GTTAAGGCAATGCAAGGTCTCCTAAAAGATGGAAACCCGATTC CCTCAGCAATCGCAGCAAACTCCGGCATCTACGGTGGTGGAG GAGGAATGGCGTCCAATTTCACGCAGTTCGTCCTGGTTGACAA CGGGGGGACTGGGGACGTTACGGTCGCTCCGAGCAACTTTGC CAATGGTATTGCGGAGTGGATTTCTTCTAATTCACGGTCCCAA GCTTACAAAGTGACCTGTTCCGTGCGGCAAAGTTCTGCTCAGA ATAGAAAGTACACTATAAAGGTCGAAGTCCCTAAGGGGGCCTG GCGATCATATCTCAATATGGAGCTTACCATCCCAATATTTGCCA CTAATTCTGATTGTGAATTGATTGTCAAAGCAATGCAAGGACTC TTGAAAGACGGAAACCCAATCCCCAGCGCAATCGCAGCCAACT CCGGTATATACTGAgcggccgc |
| SEQ ID NO: 64 | pCDNA3.1/NEF-MS2x2 Oligo Insert Amino Acid Sequence | TMGCKWSKSSVIGWPAVRERMRRAEPAADGVGAVSRDLEK HGAITSSNTAANNAACAWLEAQEEEEVGFPVTPQVPLRPMT YKAAVDLSHFLKEKGGLEGLIHSQRRQDILDLWIYHTQGYFP DWQNYTPGPGVRYPLTFGWCYKLVPVEPDKLEEANKGENTS LLHPVSLHGMDDPGREVLEVVRFDSRLAFHHVARELHPEYFK NCGGGGGMASNFTQFVLVDNGGTGDVTVAPSNFANGIAEWI SSNSRSQAYKVTCSVRQSSAQNRKYTIKVEVPKGAWRSYLN MELTIPIFATNSDCELIVKAMQGLLKDGNPIPSAIAANSGI YGGGGGMASNFTQFVLVDNGGTGDVTVAPSNFANGIAEWIS SNSRSQAYKVTCSVRQSSAQNRKYTIKVEVPKGAWRSYLNM ELTIPIFATNSDCELIVKAMQGLLKDGNPIPSAIAANSGIY |
| SEQ ID NO: 65 | pMDLg/pRRE-D64V-NC-MS2x1 DNA Oligo Insert | cctaggaaaaagggctgttggaaatgtggaaaggaaggacaccaaatgaaagattgttccg gtggaggtggatccggtggaggttccatggcgtccaatttcacgcagttcgtcctggttga caacggggggactggggacgttacggtcgctccgagcaactttgccaatggtattgcggag tggatttcttctaattcacggtcccaagcttacaaagtgacctgttccgtgcggcaaagtt ctgctcagaatagaaagtacactataaaggtcgaagtccctaagggggcctggcgatcata tctcaatatggagcttaccatcccaatatttgccactaattctgattgtgaatttgattgtc aaagcaatgcaaggactcttgaaagacggaaacccaatccccagcgcaatcgcagccaact ccggtatatactccggaggtggaggtggaactgagagacaggctaattttttagggaagat ctggccttcccacaagggaaggccagggaattttcttcagagcagaccagagccaacagcc ccaccagaagagagcttcaggtttgggggaagagacaacaactccctctcagaaggcaggagc cgatagacaaggaactgtatcctttagcttccctcagatcactctttggcagcgaccccctc gtcacaataaagatagggggcaattaaaggaagctctattagatacaggagcagatgata cagtattagaagaaatgaatttgccaggaagatggaaaccaaaaatgatagggggaattgg aggttttatcaaagtaagacagtatgatcagatactcatagaaatctgcggacataaagct ataggtacagtattagtaggacctacacctgtcaacataattggaagaaatctgttgactc agattggctgcactttaaattttcccattagtcctattgagactgtaccagtaaaattaaa gccaggaatggatggcccaaaagttaaacaatggccattgacagaagaaaaaataaaagca ttagtagaaatttgtacagaaatggaaaaggaaggaaaaatttcaaaaattgggcctgaaa atccatacaatactccagtatttgccataaagaaaaaagacagtactaaatggagaaaatt agtagatttcagagaacttaataagagaactcaagatttctgggaagttcaattaggaata ccacatcctgcagg |
| SEQ ID NO: 66 | pMDLg/pRRE-D64V-NC-MS2x1 Oligo Insert Amino Acid Sequence | PRKKGCWKCGKEGHQMKDCSGGGGSGGGSMASNFTQFVLV DNGGTGDVTVAPSNFANGIAEWISSNSRSQAYKVTCSVRQSS AQNRKYTIKVEVPKGAWRSYLNMELTIPIFATNSDCELIVKA MQGLLKDGNPIPSAIAANSGIYSGGGGGTERQANFLGKIWPS HKGRPGNFLQSRPEPTAPPEESFRFGEETTTPSQKQEPIDKELY PLASLRSLFGSDPSSQ |
| SEQ ID NO: 67 | pMDLg/pRRE-D64V-NC-MS2x2 DNA Oligo Insert | CCTAGGAAAAAGGGCTGTTGGAAATGTGGAAAGGAAGGA CACCAAATGAAAGATTGTTCCGGTGGAGGTGGATCCATGG CTTCTAACTTTACTCAGTTCGTTCTCGTCGACAATGGCGGA ACTGGCGACGTGACTGTCGCCCCAAGCAACTTCGCTAACG GGATCGCTGAATGGATCAGCTCTAACTCGCGTTCACAGGC TTACAAAGTAACCTGTAGCGTTCGTCAGAGCTCTGCGCAG AATCGCAAATACACCATCAAAGTCGAGGTGCCTAAAGGCG |

TABLE 10-continued

SEQUENCE LISTING

| SEQ ID NO | Sequence Type | Sequence |
|---|---|---|
|  |  | CCTGGCGTTCGTACTTAAATATGGAACTAACCATTCCAATT<br>TTCGCCACGAATTCCGACTGCGAGCTTATTGTTAAGGCAAT<br>GCAAGGTCTCCTAAAAGATGGAAACCCGATTCCCTCAGCA<br>ATCGCAGCAAACTCCGGCATCTACGGATCCGGTGGAGGTT<br>CCATGGCGTCCAATTTCACGCAGTTCGTCCTGGTTGACAAC<br>GGGGGGACTGGGGACGTTACGGTCGCTCCGAGCAACTTTG<br>CCAATGGTATTGCGGAGTGGATTTCTTCTAATTCACGGTCC<br>CAAGCTTACAAAGTGACCTGTTCCGTGCGGCAAAGTTCTG<br>CTCAGAATAGAAAGTACACTATAAAGGTCGAAGTCCCTAA<br>GGGGGCCTGGCGATCATATCTCAATATGGAGCTTACCATC<br>CCAATATTTGCCACTAATTCTGATTGTGAATTGATTGTCAA<br>AGCAATGCAAGGACTCTTGAAAGACGGAAACCCAATCCCC<br>AGCGCAATCGCAGCCAACTCCGGTATATACTCCGGAGGTG<br>GAGGTGGAACTGAGAGACAGGCTAATTTTTTAGGGAAGAT<br>CTGGCCTTCCCACAAGGGAAGGCCAGGGAATTTTCTTCAG<br>AGCAGACCAGAGCCAACAGCCCCACCAGAAGAGAGCTTC<br>AGGTTTGGGGAAGAGACAACAACTCCCTCTCAGAAGCAGG<br>AGCCGATAGACAAGGAACTGTATCCTTTAGCTTCCCTCAG<br>ATCACTCTTTGGCAGCGACCCCTCGTCACAATAAAGATAG<br>GGGGGCAATTAAAGGAAGCTCTATTAGATACAGGAGCAG<br>ATGATACAGTATTAGAAGAAATGAATTTGCCAGGAAGATG<br>GAAACCAAAAATGATAGGGGGAATTGGAGGTTTTATCAAA<br>GTAAGACAGTATGATCAGATACTCATAGAAATCTGCGGAC<br>ATAAAGCTATAGGTACAGTATTAGTAGGACCTACACCTGT<br>CAACATAATTGGAAGAAATCTGTTGACTCAGATTGGCTGC<br>ACTTTAAATTTTCCCATTAGTCCTATTGAGACTGTACCAGT<br>AAAATTAAAGCCAGGAATGGATGGCCCAAAAGTTAAACA<br>ATGGCCATTGACAGAAGAAAAAATAAAAGCATTAGTAGA<br>AATTTGTACAGAAATGGAAAAGGAAGGAAAAATTTCAAA<br>AATTGGGCCTGAAAATCCATACAATACTCCAGTATTTGCC<br>ATAAAGAAAAAAGACAGTACTAAATGGAGAAAATTAGTA<br>GATTTCAGAGAACTTAATAAGAGAACTCAAGATTTCTGGG<br>AAGTTCAATTAGGAATACCACATCCTGCAGG |
| SEQ ID NO: 68 | pMDLg/pRRE-<br>D64V-NC-MS2x2<br>Oligo Insert<br>Amino Acid<br>Sequence | PRKKGCWKCGKEGHQMKDCSGGGGSMASNFTQFVLVDNG<br>GTGDVTVAPSNFANGIAEWISSNSRSQAYKVTCSVRQSSAQN<br>RKYTIKVEVPKGAWRSYLNMELTIPIFATNSDCELIVKAMQG<br>LLKDGNPIPSAIAANSGIYGSGGGSMASNFTQFVLVDNGGTG<br>DVTVAPSNFANGIAEWISSNSRSQAYKVTCSVRQSSAQNRKY<br>TIKVEVPKGAWRSYLNMELTIPIFATNSDCELIVKAMQGLLK<br>DGNPIPSAIAANSGIYSGGGGGTERQANFLGKIWPSHKGRPG<br>NFLQSRPEPTAPPEESFRFGEETTTPSQKQEPIDKELYPLASLR<br>SLFGSDPSSQ |
| SEQ ID NO: 69 | pMDLg/pRRE-<br>D64V-NC-PP7x1<br>DNA Oligo Insert | cctaggaaaaagggctgttggaaatgtggaaaggaaggacaccaaatgaaagattgttccg<br>gtggaggtggatcctccaaaacaatagtcctctccgtaggggaggcaacacggactttgac<br>cgaaatccagtcaaccgctgaccgacaaatctttgaagagaaagtagggcctcttgtgggc<br>cgactgcgcttgactgcaagcttgcgacaaaacggcgcaaagactgcctataggtcaacc<br>ttaaactcgaccaagccgacgtggtcgatagcggtctccctaaggttcggtatacgcaggt<br>ctggagtcatgacgtaacaatcgtagcaaacagcacagaagcctcccgaaaaagcctctac<br>gatctgacgaaatccttggtggctacgtcacaggtggaagacctcgttgtcaaccttgtac<br>ctctgggtcggtccggaggtggaggtggaactgagagacaggctaattttttagggaagat<br>ctggccttcccacaagggaaggccagggaattttcttcagagcagaccagagccaacagcc<br>ccaccagaagagagcttcaggtttggggaagagacaacaactccctctcagaagcaggagc<br>cgatagacaaggaactgtatcctttagcttccctcagatcactctttggcagcgaccc ctc<br>agtcacaataaagatagggggcaattaaaggaagctctttagatacaggagcagatgata<br>cagtattagaagaaatgaatttgccaggaagatggaaaccaaaaatgatagggggaattgg<br>aggttttatcaaagtaagacagtatgatcagatactcatagaaatctgcggacataaagct<br>ataggtacagtattagtaggacctacacctgtcaacataattggaagaaatctgttgactc<br>agattggctgcactttaaattttcccattagtcctattgagactgtaccagtaaaattaaa<br>gccaggaatggatggcccaaaagttaaacaatggccattgacagaagaaaaaataaaagca<br>ttagtagaaatttgtacagaaatggaaaaggaaggaaaaatttcaaaaattgggcctgaaa<br>atccatacaatactccagtatttgccataaagaaaaaagacagtactaaatggagaaaatt<br>agtagatttcagagaacttaataagagaactcaagatttctgggaagttcaattaggaata<br>ccacatcctgcaga |
| SEQ ID NO: 70 | pMDLg/pRRE-<br>D64V-NC-PP7x1<br>Oligo Insert<br>Amino Acid<br>Sequence | PRKKGCWKCGKEGHQMKDCSGGGGSSKTIVLSVGEATRTLT<br>EIQSTADRQIFEEKVGPLVGRLRLTASLRQNGAKTAYRVNL<br>KLDQADVVDSGLPKVRYTQVWSHDVTIVANSTEASRKSLYD<br>LTKSLVATSQVEDLVVNLVPLGRSGGGGGTERQANFLGKIW<br>PSHKGRPGNFLQSRPEPTAPPEESFRFGEETTTPSQKQEPI<br>DKELYPLASLRSLFGSDPSSQ |
| SEQ ID NO: 71 | pMDLg/pRRE-<br>D64V-MA- | CACGTGAGATCTGAATTCGAGATCTGCCGCCGCCATGGGT<br>GCGAGAGCGTCAGTATTAAGCGGGGGAGAATTAGATCGAT |

TABLE 10-continued

SEQUENCE LISTING

| SEQ ID NO | Sequence Type | Sequence |
|---|---|---|
| | MS2x2 DNA Oligo Insert | GGGAAAAAATTCGGTTAAGGCCAGGGGGAAAGAAAAAAT<br>ATAAATTAAAACATATAGTATGGGCAAGCAGGGAGCTAG<br>AACGAGGAGGTGGTGGAGGAATGGCTTCTAACTTTACTCA<br>GTTCGTTCTCGTCGACAATGGCGGAACTGGCGACGTGACT<br>GTCGCCCCAAGCAACTTCGCTAACGGGATCGCTGAATGGA<br>TCAGCTCTAACTCGCGTTCACAGGCTTACAAAGTAACCTGT<br>AGCGTTCGTCAGAGCTCTGCGCAGAATCGCAAATACACCA<br>TCAAAGTCGAGGTGCCTAAAGGCGCCTGGCGTTCGTACTT<br>AAATATGGAACTAACCATTCCAATTTTCGCCACGAATTCC<br>GACTGCGAGCTTATTGTTAAGGCAATGCAAGGTCTCCTAA<br>AAGATGGAAACCCGATTCCCTCAGCAATCGCAGCAAACTC<br>CGGCATCTACGGTGGTGGAGGAGGAATGGCGTCCAATTTC<br>ACGCAGTTCGTCCTGGTTGACAACGGGGGGACTGGGGACG<br>TTACGGTCGCTCCGAGCAACTTTGCCAATGGTATTGCGGA<br>GTGGATTTCTTCTAATTCACGGTCCCAAGCTTACAAAGTGA<br>CCTGTTCCGTGCGGCAAAGTTCTGCTCAGAATAGAAAGTA<br>CACTATAAAGGTCGAAGTCCCTAAGGGGGCCTGGCGATCA<br>TATCTCAATATGGAGCTTACCATCCCAATATTTGCCACTAA<br>TTCTGArrGTGAATrGATTGTCAAAGCAATGCAAGGACTCT<br>TGAAAGACGGAAACCCAATCCCCAGCGCAATCGCAGCCA<br>ACTCCGGTATATACCAGGTCAGCCAAAATTACCCTATAGT<br>GCAGAACATCCAGGGGCAAATGGTACATCAGGCCATATCA<br>CCTAGAACTTTAAATGCATGGGTAAAAGTAGTAGAAGAGA<br>AGGCTTTCAGCCCAGAAGTGATACCCATGTTTTCAGCATTA<br>TCAGAAGGAGCCACCCCACAAGATTTAAACACCATGCTAA<br>ACACAGTGGGGGGACATCAAGCAGCCATGCAAATGTTAA<br>AAGAGACCATCAATGAGGAAGCTGCAGAATGGGATAGAG<br>TGCATCCAGTGCATGC |
| SEQ ID NO: 72 | pMDLg/pRRE-D64V-MA-MS2x2 Oligo Insert Amino Acid Sequence | MGARASVLSGGELDRWEKIRLRPGGKKKYKLKHIVWASREL<br>ERGGGGGMASNFTQFVLVDNGGTGDVTVAPSNFANGIAEWI<br>SSNSRSQAYKVTCSVRQSSAQNRKYTIKVEVPKGAWRSYLN<br>MELTIPIFATNSDCELIVKAMQGLLKDGNPIPSAIAANSGI<br>YGGGGGMASNFTQFVLVDNGGTGDVTVAPSNFANGIAEWIS<br>SNSRSQAYKVTCSVRQSSAQNRKYTIKVEVPKGAWRSYLNM<br>ELTIPIFATNSDCELIVKAMQGLLKDGNPIPSAIAANSGIY<br>QVSQNYPIVQNIQGQMVHQAISPRTLNAWVKVVEEKAFSPE<br>VIPMFSALSEGATPQDLNTMLNTVGGHQAAMQMLKETINEE<br>AAEWDRVHPVH |
| SEQ ID NO: 73 | pMDLg/pRRE-D64V-MA-PP7x1 DNA Oligo Insert | Cacgtgagatctgaattcgagatctgccgccgccatgggtgcgagagcgtcagtattaagc<br>gggggagaattagatcgatgggaaaaaattcggttaaggccaggggggaaagaaaaaatata<br>aattaaaacatatagtatgggcaagcagggagctagaacgaggaggtggtggaggaatggc<br>ttctaactttactcagttcgttctcgtcgactccaaaacaatagtcctctccgtaggggag<br>gcaacacggactttgaccgaaaiccagtcaaccgctgaccgacaaatctttgaagagaaag<br>tagggcctcttgtgggccgactgcgcttgactgcaagcttgcgacaaaacggcgcaaagac<br>tgcctatagggtcaaccttaaactcgaccaagccgacgtggtcgatagcggtctccctaag<br>gttcggtatacgcaggtctggagtcatgacgtaacaatcgtagcaaacagcacagaagcct<br>cccgaaaaagcctctacgatctgacgaaatccttggtggctacgtcacaggtggaagacct<br>cgttgtcaaccttgtacctctgggtcgaaaccaggtcagccaaaattaccctatagtgcag<br>aacatccaggggcaaatggtacatcaggccatatcacctagaactttaaatgcatgggtaa<br>aagtagtagaagagaaggctttcagcccagaagtgatacccatgttttcagcattatcaga<br>aggagccaccccacaagatttaaacaccatgctaaacacagtgggggggacatcaagcagcc<br>atgcaaatgttaaaagagaccatcaatgaggaagctgcagaatgggatagagtgcatccag<br>tgcatgc |
| SEQ ID NO: 74 | pMDLg/pRRE-D64V-MA-PP7x1 Oligo Insert Amino Acid Sequence | MGARASVLSGGELDRWEKIRLRPGGKKKYKLKHIVWASREL<br>ERGGGGGMASNFTQFVLVDSKTIVLSVGEATRTLTEIQSTAD<br>RQIFEEKVGPLVGRLRLTASLRQNGAKTAYRVNLKLDQADV<br>VDSGLPKVRYTQVWSHDVT1VANSTEASRKSLYDLTKSLVA<br>TSQVEDLVVNLVPLGRNQVSQNYPIVQNIQGQMVHQAISPRT<br>LNAWVKVVEEKAFSPEVIPMFSALSEGATPQDLNTMLNTVG<br>GHQAAMQMLKETINEEAAEWDRVHPVH |
| SEQ ID NO: 75 | pMDLg/pRRE-D64V-MA-PP7x2 DNA Oligo Insert | cacgtgagatctgaattcgagatctgccgccgccatgggtgcgagagcgtcagtattaagc<br>gggggagaattagatcgatgggaaaaaattcggttaaggccaggggggaaagaaaaaatata<br>aattaaaacatatagtatgggcaagcagggagctagaacgaggaggtggtggaggaatggc<br>ttctaactttactcagttcgttctcgtcgactccaaaacaatagtcctctccgtaggggag<br>gcaacacggactttgaccgaaatccagtcaaccgctgaccgacaaatctttgaagagaaag<br>tagggcctcttgtgggccgactgcgcttgactgcaagcttgcgacaaaacggcgcaaagac<br>tgcctatagggtcaaccttaaactcgaccaagccgacgtggtcgatagcggtctccctaag<br>gttcggtatacgcaggtctggagtcatgacgtaacaatcgtagcaaacagcacagaagcct<br>cccgaaaaagcctctacgatctgacgaaatccttggtggctacgtcacaggtggaagacct<br>cgttgtcaaccttgtacctctgggtcgagcggatccgctcgcatcaaaaactattgtgctc<br>tccgtgggagaagccacccgcacgcttaccgaaattcaatcaacggcagacagacaaatct |

TABLE 10-continued

SEQUENCE LISTING

| SEQ ID NO | Sequence Type | Sequence |
|---|---|---|
| | | ttgaggagaaagtaggtccgttggtgggtcggttgcgcttgaccgcaagcctccgccaaaa<br>cggagcgaaaaccgcataccgcgtaaacttgaagctggaccaagccgatgttgttgactcc<br>ggcttgcccaaagtgcgatatactcaggtctggtctcatgatgtcacaatcgtcgctaatt<br>ccactgaggctagtcgcaaaagtctgtatgacttgacaaagtccttggtagccacgtcaca<br>ggtggaagatttggtggtgaacctcgttccactgggaagaaaccaggtcagccaaaattac<br>cctatagtgcagaacatccaggggcaaatggtacatcaggccatatcacctagaactttaa<br>atgcatgggtaaaagtagtagaagagaaggctttcagcccagaagtgatacccatgttttc<br>agcattatcagaaggagccaccccacaagatttaaacaccatgciaaacacagtgggggga<br>catcaagcagccatgcaaatgttaaaagagaccatcaatgaggaagctgcagaatgggata<br>gagtgcatccagtgcatgc |
| SEQ ID NO: 76 | pMDLg/pRRE-D64V-MA-PP7x2 Oligo Insert Amino Acid Sequence | MGARASVLSGGELDRWEKIRLRPGGKKKYKLKHIVWASREL<br>ERGGGGGMASNFTQFVLVDSKTIVLSVGEATRTLTEIQSTAD<br>RQIFEEKVGPLVGRLRLTASLRQNGAKTAYRVNLKLDQADV<br>VDSGLPKVRYTQVWSHDVTIVANSTEASRKSLYDLTKSLVA<br>TSQVEDLVVNLVPLGRADPLASKTIVLSVGEATRTLTEIQSTA<br>DRQIFEEKVGPLVGRLRLTASLRQNGAKTAYRVNLKLDQAD<br>VVDSGLPKVRYTQVVVSHDVTIVANSTEASRKSLYDLTKSLV<br>ATSQVEDLVVNLVPLGRNQVSQNYPIVQNIQGQMVHQAISPR<br>TLNAWVKVVEEKAFSPEVIPMFSALSEGATPQDLNTMLNTV<br>GGHQAAMQMLKETINEEAAEWDRVHPVH |
| SEQ ID NO: 77 | DNA oligo cloned into Plasmid No. 24 (pSaCas9-HBB-sgRNA1$^{3'ms2}$) encoding a HBB-sgRNA1 with a MS2 aptamer at the 3' end of the sgRNA | GGTCTCGCACCGAGTAACGGCAGACTTCTCCACGTTTAAG<br>TACTCTGGAAACAGAATCTACTTAAACAAGGCAAAATGCC<br>GTGTTTATCTCGTCAACTTGTTGGCGAGATGGCCAACATGA |
| SEQ ID NO: 78 | DNA oligo cloned into Plasmid No. 25 (pSaCas9-HBB-sgRNA1$^{Tetrams2}$) encoding a HBB-sgRNA1 with a MS2 aptamer inserted into the Tetra loop of the sgRNA | GGTCTCGCACCGAGTAACGGCAGACTTCTCCACGTTTAAG<br>TACTCTGGGCCAACATGAGGATCACCCATGTCTGCAGGGC<br>CCAGAATCTACTTAAACAAGGCAAAATGCCGTGTTTATCT<br>CGTCAACTTGTTGGCGAGATTTTTTTGCGGCCGC |
| SEQ ID NO: 79 | DNA oligo cloned into Plasmid No. 26 (pSaCas9-HBB-sgRNA1$^{ST2ms2}$) encoding a HBB-sgRNA1 with a MS2 aptamer inserted into the stem loop 2 of the sgRNA | GGTCTCGCACCGAGTAACGGCAGACTTCTCCACGTTTAAG<br>TACTCTGGAAACAGAATCTACTTAAACAAGGCAAAATGCC<br>GTGTTTATCTCGTCAAGGCCAACATGAGGATCACCCATGT<br>CTGCAGGGCCTTGGCGAGATTTTTTTGCGGCCGC |
| SEQ ID NO: 80 | DNA oligo cloned into Plasmid No. 27 (pSaCas9-HBB-sgRNA1$^{ST2ms2}$) encoding a HBB-sgRNA1 with one MS2 aptamer inserted into the Tetra loop position and one at the ST2 loop position | GGTCTCGCACCGAGTAACGGCAGACTTCTCCACGTTTAAG<br>TACTCTGGGCCAACATGAGGATCACCCATGTCTGCAGGGC<br>CCAGAATCTACTTAAACAAGGCAAAATGCCGTGTTTATCT<br>CGTCAAGGCCAACATGAGGATCACCCATGTCTGCAGGGCC<br>TTGGCGAGATTTTTTTGCGGCCGC |
| SEQ ID NO: 81 | DNA oligo cloned into Plasmid No. 30 (pSaCas9$^{1PP7}$-HBB-sgRNA1$^{3'PP7}$) encoding the U6 promoter, HBB sgRNA1 and PP7 aptamer | GGTACCGAGGGCCTATTTCCCATGATTCCTTCATATTTGCA<br>TATACGATACAAGGCTGTTAGAGAGATAATTGGAATTAAT<br>TTGACTGTAAACACAAAGATATTAGTACAAAATACGTGAC<br>GTAGAAAGTAATAATTTCTTGGGTAGTTTGCAGTTTTAAAA<br>TTATGTTTTAAAATGGACTATCATATGCTTACCGTAACTTG<br>AAAGTATTTCGATTTCTTGGCTTTATATATCTTGTGGAAAG<br>GACGAAACACCGAGTAACGGCAGACTTCTCCACGTTCTAG<br>TACTCTGGAAACAGAATCTACTAGAACAAGGCAAAATGCC |

TABLE 10-continued

SEQUENCE LISTING

| SEQ ID NO | Sequence Type | Sequence |
|---|---|---|
| | | GTGTTTATCTCGTCAACTTGTTGGCGAGATGGAGCAGACG<br>ATATGGCGTCGCTCCTTTTTTGCGGCCGC |
| SEQ ID NO: 82 | DNA oligo cloned into Plasmid No. 32 (pAAV-HBB-sgRNA2) encoding the human HBB target template sequence and the U6 driven HBB sgRNA2 expression cassette | gcggccgcttgtgtaatcgtagtttcagagtgttagagctgaaaggaagaagtaggagaaa<br>catgcaaagtaaaagtataacactttccttactaaaccgacatgggtttccaggtaggggc<br>aggattcaggatgactgacagggcccttagggaacactgagaccctacgctgacctcataa<br>atgcttgctacctttgctgttttaattacatctttaatagcaggaagcagaactctgcac<br>ttcaaaagttttcctcacctgaggagttaatttagtacaaggggaaaaagtacagggga<br>tgggagaaaggcgatcacgttgggaagctatagagaaagaagagtaaattttagtaaagga<br>ggtttaaacaaacaaaatataaagagaaataggaacttgaatcaaggaaatgattttaaaa<br>cgcagtattcttagtggactagaggaaaaaataatctgagccaagtagaagacctttcc<br>cctcctacccctactttctaagtcacagagggctttttgttccccagacactcttgcagat<br>tagtccaggcagaaacagttagatgtccccagttaacctcctatttgacaccactgattac<br>cccattgatagtcacactttgggtgtaagtgacttttatttatttgtatttttgactgc<br>attaagaggtctctagttttttatctcttgtttcccaaaacctaataagtaactaatgcac<br>agagcacattgatttgtatttattctatttttagacataatttattagcatgcatgagcaa<br>attaagaaaaacaacaacaaatgaatgcatatatatgtatatgtatgtgtgtatatataca<br>ccacatatatatatatatttttcttttcttaccagaaggtttaatccaaataaggagaa<br>gatatgcttagaaccgaggtagagttttcatccattctgtctgtaagtattttgcatattc<br>tggagacgcaggaagagatccatctacatatcccaaagctgaattatggtagacaaaactc<br>ttccactttagtgcatcaacttcttatttgtgtaataagaaaattgggaaaacgatcttc<br>aaatatgcttaccaagctgtgattccaaatattacgtaaatacacttgcaaaggaggatgtt<br>tttagtagcaatttgtactgatggtatggggccaagagatatatcttagagggagggctga<br>gggtttgaagtccaactcctaagccagtgccagaagagccaaggacaggtacggctgtcat<br>cacttagacctcaccctgtggagccacacccctaggggttggccaatctactcccaggagcag<br>ggagggcaggagccagggctgggcataaaagtcagggcagagccatctattgcttacatttt<br>gcttctgacacaactgtgttcactagcaacctcaaacagacaccatggtgcatctgactcc<br>tgaggagaaaagcgctgtgacagctctctgggaaaagtcaatgtcgacgaagttggtggt<br>gaggcctgggcaggttggtatcaaggttacaagacaggtttaaggagaccaatagaaact<br>gggcatgtggagacagagaagactcttgggtttctgataggcactgactctctctgcctat<br>tggtctattttcccacccttaggctgctggtggtctacccttggacccagaggttcttga<br>gtcctttgggatctgtccactcctgatgctgttatgggcaaccctaaggtgaaggctcat<br>ggcaagaaagtgctcggtgcctttagtgatggcctggctcacctggacaacctcaagggca<br>cctttgccacactgagtgagctgcactgtgacaagctgcacgtggatcctgagaacttcag<br>ggtgagtctatgggacgcttgatgtttcttccccttcttttctatggttaagttcatgt<br>cataggaaggggataagtaacagggtacagtttagaatgggaaacagacgaatgattgcat<br>cagtgtggaagtctcaggatcgtttagtttcttttatttgctgttcataacaattgtttt<br>cttttgtttaattcttgctttcttttttttttctctccgcaattttttactattatacttaa<br>tgccttaacattgtgtataacaaaaggaaatatctctgagatacattaagtaacttaaaaa<br>aaaactttacacagtctgcctagtacattactatttggaatatatgtgtgcttatttgcat<br>attcataatctccctactttatttttcttttattttaattgatacataatcattatacata<br>tttatgggttaaagtgtaatgttttaatatgtgtacacatattgaccaaatcagggtaatt<br>ttgcatttgtaattttaaaaaatgctttcttcttttaatatactttttttgtttatcttatt<br>tctaatactttccctaatctctttctttcagggcaataatgatacaatgtatcatgcctct<br>attgcaccattctaaagaataacagtgtaatttctgggttaaggcaatagcaatatctctg<br>catataaatatttctgcatataaattgtaactgatgtaagaggtttcatattgctaatagc<br>agctacaatccagctaccattctgcttttatttatggttgggataaggctggattattct<br>gagtccaagctaggccctttgctaatcatgttcatacctcttatcttcctcccacagctc<br>ctgggcaacgtgctggtctgtgtgctggcccatcactttggcaaagaattcaccccaccag<br>tgcaggctgcctatcagaaagtggtggctggtgtggctaatgccctggcccacaagtatca<br>ctaagctcgctttcttgctgtccaatttctattaaaggttcctttgttccctaagtccaac<br>tactaaactgggggatattatgaagggccttgagcatctggattctgcctaataaaaaaca<br>tttattttcattgcaatgatctcgagggcctatttcccatgattccttcatatttgcatat<br>acgatacaaggctgttagagagataattggaattaatttgactgtaaacacaaagatatta<br>gtacaaaatacgtgacgtagaaagtaataatttcttgggtagtttgcagttttaaaattat<br>gttttaaaatggactatcatatgcttaccgtaacttgaaagtatttcgatttcttggcttt<br>atatatcttgtggaaaggacgaaacaccgccctgtggggcaaggtgaacgttttagtactc<br>tggaaacagaatctactaaaacaaggcaaaatgccgtgtttatctcgtcaacttgttggcg<br>agattttctagagcggccgc |
| SEQ ID NO: 83 | DNA oligo cloned into Plasmid No. 36 (pSaCas9$^{1xms2}$-2x3'UTR) encoding two copies of the human HBB 3' UTR | ggatcctaagctcgctttcttgctgtccaatttctattaaaggttcctttgttccctaagt<br>ccaactactaaactgggggatattatgaagggccttgagcatctggattctgcctaataaa<br>aaacatttattttcattgctagctcgctttcttgctgtccaatttctattaaaggttcctt<br>tgttccctaagtccaactactaaactgggggatattatgaagggccttgagcatctggatt<br>ctgcctaataaaaaacatttattttcattgc |
| SEQ ID NO: 84 | DNA oligo cloned into Plasmid No. 41 (pSaCas9$^{1xMS2}$-2x3'UTR-HBB sgRNA$^{3'PP7}$ 1x3'UTR) | CGGCCGAGGGCCTATTTCCCATGATTCCTTCATATTTGCAT<br>ATACGATACAAGGCTGTTAGAGAGATAATTGGAATTAATT<br>TGACTGTAAACACAAAGATATTAGTACAAAATACGTGACG<br>TAGAAAGTAATAATTTCTTGGGTAGTTTGCAGTTTTAAAAT<br>TATGTTTTAAAATGGACTATCATATGCTTACCGTAACTTGA<br>AAGTATTTCGATTTCTTGGCTTTATATATCTTGTGGAAAGG |

TABLE 10-continued

SEQUENCE LISTING

| SEQ ID NO | Sequence Type | Sequence |
|---|---|---|
| | encoding HBB sgRNA1 with one PP7 aptamer and one copy of HBB 3' UTR downstream of U6 promoter | ACGAAACACCGAGTAACGGCAGACTTCTCCACGTTCTAGT ACTCTGGAAACAGAATCTACTAGAACAAGGCAAAATGCCG TGTTTATCTCGTCAACTTGTTGGCGAGATATCGGAGCAGAC GATATGGCGTCGCTCCAGCGCTCGCTTTCTTGCTGTCCAAT TTCTATTAAAGGTTCCTTTGTTCCCTAAGTCCAACTACTAA ACTGGGGGATATTATGAAGGGCCTTGAGCATCTGGATTCT CG |
| SEQ ID NO: 85 | DNA oligo cloned into Plasmid No. 42 (pSaCas9$^{1xMS2}$-2x3'UTR-HBB sgRNA$^{3'PP7}$ 2x3'UTR) encoding one PP7 aptamer sequence followed by two HBB 3' UTR sequences | GATATCGGAGCAGACGATATGGCGTCGCTCCAGCGCTCGC TTTCTTGCTGTCCAATTTCTATTAAAGGTTCCTTTGTTCCCT AAGTCCAACTACTAAACTGGGGGATATTATGAAGGGCCTT GAGCATCTGGATTCTGCCTAATAAAAAACATTTATTTTCAT TGCGCTCGCTTTCTTGCTGTCCAATTTCTATTAAAGGTTCCT TTGTTCCCTAAGTCCAACTACTAAACTGGGGGATATTATGA AGGGCCTTGAGCATCTGGATTCTGCCTAATAAAAAACATT TATTTTCATTGCTTTTTTTGCGGCCGC |
| SEQ ID NO: 86 | Oligo HBA-5'-F | Ctggctaactaccggctcttctggtccccacagactcagagagaaccggtgccaccatgg |
| SEQ ID NO: 87 | Oligo HBA-5'-R | ccatggtggcaccggttctctctgagtctgtggggaccagaagagccggtagttagccaG |
| SEQ ID NO: 88 | Oligo sp-loop1F | AAAAAAGAAAAGCTTTAGAAAACATGAGGATCACCCAT GTCTGCAGGTCGACTCTAGAATTCCTAGAGCTCG |
| SEQ ID NO: 89 | Oligo sp-loop1R | CGAGCTCTAGGAATTCTAGAGTCGACCTGCAGACATGGGT |
| SEQ ID NO: 90 | Il2RG-sp-g1F1 | ACCGGCGCTTGCTCTTCATTCCCT |
| SEQ ID NO: 91 | Il2RG-sp-g1R | AAACAGGGAATGAAGAGCAAGCGC |
| SEQ ID NO: 92 | MS2-F1 oligo | ACTTGTTGGCGAGATATCTAGAAAACATGAGGATCACCCA TGTCTGCAGAGCGCTCGCTTTCTTGCT |
| SEQ ID NO: 93 | MS2-R1 oligo | AGCAAGAAAGCGAGCGCTCTGCAGACATGGGTGATCCTCA TGTTTTCTAGATATCTCGCCAACAAGT |
| SEQ ID NO: 94 | Human beta hemoglobin DNA sequence (The "T" in the underlined codon is the mutated nucleotide. The underlined codon encodes the sixth amino acid of the β globin protein.) | ACTCCTGTGGAGAAGTCTGCCGTTACT |
| SEQ ID NO: 95 | 119 bp DNA Insertion in human beta hemoglobin (HBB) gene in EGFP reporter cells as described in Javidi-Parsijani, P. et al., PLoS One 2017; 12(5): e0177444 | GAACCCAGGTTCCTGACACAGACAGACTACACCCAGGGAA TGAAGAGCAAGCGCCATACTCCTGTGGAGAAGTCTGCCGT TACTGCCCTGTGGGGCAAGGTGAACGTGGATTGGCTAGC |
| SEQ ID NO: 96 | HBB-1849F | CGATCACGTTGGGAAGCTATAGAG |
| SEQ ID NO: 97 | HBB-5277R | AACATCCTGAGGAAGAATGGGAC |

TABLE 10-continued

SEQUENCE LISTING

| SEQ ID NO | Sequence Type | Sequence |
|---|---|---|
| SEQ ID NO: 98 | Reporter-mut-F1 | TCGTCGGCAGCGTCAGATGTGTATAAGAGACAGTtccatttcagg tgtcgtgag |
| SEQ ID NO: 99 | Reporter-mut-F2 | TCGTCGGCAGCGTCAGATGTGTATAAGAGACAGATtccatttca ggtgtcgtgag |
| SEQ ID NO: 100 | Reporter-mut-F3 | TCGTCGGCAGCGTCAGATGTGTATAAGAGACAGGATtccatttc aggtgtcgtgag |
| SEQ ID NO: 101 | Reporter-mut-F4 | TCGTCGGCAGCGTCAGATGTGTATAAGAGACAGCGATtccatt tcaggtgtcgtgag |
| SEQ ID NO: 102 | Reporter-mut-R1 | GTCTCGTGGGCTCGGAGATGTGTATAAGAGACAGTGAACT TCAGGGTCAGCTTGC |
| SEQ ID NO: 103 | Synthetic DNA sequence (Indel) | GAAGAGCAAGCGCCATA*CTCCT*GTGGAGAAGTCTGCCGTT ACTGCCCTGTGGGGCAAGGTG |
| SEQ ID NO: 104 | Synthetic DNA sequence (Indel) | GAAGAGCAAGCGCCATACTCCTGCCGTTACTGCCCTGTGG GGCAAGGTG |
| SEQ ID NO: 105 | Synthetic DNA sequence (Indel) | GAAGAGCAAGCGCCATACTCCTGTGAGAAGTCTGCCGTTA CTGCCCTGTGGGGCAAGGTG |
| SEQ ID NO: 106 | Synthetic DNA sequence (Indel) | GAAGAGCAAGCGCCATACTCCTGTGAAGTCTGCCGTTACT GCCCTGTGGGGCAAGGTG |
| SEQ ID NO: 107 | Synthetic DNA sequence (Indel) | GAAGAGCAAGCGCCATACTCCTGTCTGCCGTTACTGCCCT GTGGGGCAAGGTG |
| SEQ ID NO: 108 | Synthetic DNA sequence (Indel) | GAAGAGCAAGCGCCATACTCCTGAGAAGTCTGCCGTTACT GCCCTGTGGGGCAAGGTG |
| SEQ ID NO: 109 | Synthetic DNA sequence (Indel) | GAAGAGCAAGCGCCATACTCCTGGAGAAGTCTGCCGTTAC TGCCCTGTGGGGCAAGGTG |
| SEQ ID NO: 110 | Synthetic DNA sequence (Indel) | GAAGAGCAAGCGCCATACTCCTGTGGGCAAGGTG |
| SEQ ID NO: 111 | Synthetic DNA sequence (Indel) | GAAGAGCAAGCGCCATACTCCTGTGTCTGCCGTTACTGCC CTGTGGGGCAAGGTG |
| SEQ ID NO: 112 | Synthetic DNA sequence (Indel) | GAAGAGCAAGCGCCGTTACTGCCCTGTGGGGCAAGGTG |
| SEQ ID NO: 113 | Synthetic fragment containing IL2RG sgRNA2-expression cassette and IL2RG template for homologous recombination. 5' arm and 3' arm flank underlined: IL2RG cDNA; Followed by IL2RG sgRNA2 and sgRNA4 expression cassettes (italicized). | GCGGCCgcTCTCGAACTCCTCAAGCAATCCACCTGCCTTGG CCTCCCAAAGTGCTGGGATTGCAGGCGTGAGTCACTGCAC CCAGCCGAGAGAATAAATTTCTGTTGGTTTAAGCCACTCA GTTTGGGGATAACTTATGGCAGCCCTAGCAAACTAATACA TACTAAAGATACATACTAAATACTAAGCTGGGCCATATAG TCCAGTTTTCCTGAGACTCCCAGGCAAGTGCTGTTTTTCTT TGCTTAATATCCTACACCACTTTCTGTCTGGTAAAATTACA CTCATTCTTTAAGATGCCACTGAAATAGCACCTCTTCAGCA CAGCCTTCACTAAACTATCCCCCTCTCCATCTTGGTAAATT TAGTTACTTCCTCTTCTGTGCTCACATACTTTGTAGTATCTC TACATTTATGCTATAGGACTTGTTACACTATGTTGTATTAC TTGTTTATGTCTTCCCCACTTTTCTGTGAGTGTCTAGAAAT ATGAGGATGTCTTGTTGGTCTATTTCCAGAACATAAGCAC AGTGCCTGGCACATATTAAAAACGTAATAAATGTTTGCTG AATAAATAGTTTCTGTAAGTGGCTTCTCCAATCACCTCTGT GTTTTCGGGGAAGGTAAAACTGGCAACAGGATGAAGAAT GGATTAGAGAGCAGAGGGCCTTTAGAAAGGGAGGCCAGT TGATGGAGTCTAGATAGAATCATGACTAGAGCTAATGAAA GACTGATTTAGCAGAGTGGCTGTGGTAATGGAAAGGAGGA AACCGTTGGGAGAAACACCACAGAAGCAGAGTGGGTTAT ATTCTCTGGGTGAGAGGGGGAGAAATTGAAGCTGATTC TGAGGTTTCAAGTCTGGGTGACTGAGAGGGTGACGATACC ATTGACTGAGGTGGGGAAGGCAGGAAGAGAAGCAGAGTT GGGGGAAGATGGGAAGCTTGAAGCTAGTATTGTTGTTCCT CCATTTCTAGAATATTTTTGTATTATAAGTCACACTTCCTC GCCAGTCTCAACAGGGACCCAGCTCAGGCAGCAGCTAAGG GTGGGTATTCTGGTTTGGATTAGATCAGAGGAAAGACAGC TGTATATGTGCCCACAGGAGCCAAGACGGTATTTTCCATC CTCCCAAAACAGTAGAGCTTTGACAGAGATTTAAGGGTGA |

TABLE 10-continued

SEQUENCE LISTING

| SEQ ID NO | Sequence Type | Sequence |
|---|---|---|
| | | CCAAGTCAAGGAAGAGGCATGGCATAGAACGGTGATGTC<br>GGGGGTGGGGGTTCAGAACTTCCATTATAGAAGGTAATGA<br>TTTAGAGGAGAAGGTGGTTGAGAATGGTGCTAGTGGTAGT<br>GAACAGATCCTTCCCAGGATCTAGGTGGGCTGAGGATTTT<br>TGAGTCTGTGACACTATTGTATATCCAGCTTTAGTTTCTGT<br>TTACCACCTTACAGCAGCACCTAATCTCCTAGAGGACTTA<br>GCCCGTGTCACACAGCACATATTTGCCACACCCTCTGTAA<br>AGCCCTGGTTTATAAGGTTCTTTCCACCGGAAGCTATGACA<br>GAGGAAACGTGTGGGTGGGAGGGGTAGTGGGTGAGGGA<br>CCCAGGTTCCTGccAccatgCtCaaAccTtcCCtGccTttTacCAGcTtG<br>CtGttTctCcagctCccTctCctCggCgtCggActCaaTacAacTatCctGacAcc<br>TaaCggAaaCgaGgaTacAacCgcCgaCttTtttTctCacAacCatgccTacAga<br>TAGcTtGTCCgtGAGcacCctCccTctGccTgaAgtGcagtGCttCgtCttTaa<br>CgtGgaAtaTatgaaCtgTacCtggaaTTCcTCcAGCgaAccTcagccAacAa<br>aTctGacActCcaCtaCtggtaTaaAaaTAGCgaCaaCgaCaaGgtGcagaaAt<br>gTTCccaTtaCTTGttTAGCgaGgaGatTacCAGCggAtgCcagCtCcaGa<br>aGaaAgaAatTcaTctGtaTcaGacCttCgtGgtGcagctGcaggaTccTAgAga<br>GccTagAagGcaggcTacCcagatgTTGaaGctCcagaaCctCgtCatTccTtgg<br>gcCccTgaAaaTctGacCTtGcaTaaGctCTCCgaGAGccagctGgaGctCaa<br>TtggaaTaacagGttTCtgaaTcaTtgCCtggaAcaTCTCgtCcaAtaTAGAac<br>CgaTtgggaTcaTTCctggacCgaGcaGAGCgtCgaCtaCCgGcaCaaAttT<br>AGcCtgccAagCgtCgaCggAcagaaGAgAtaTacCttCAgAgtGAgATCc<br>AgAttCaaTccTctGtgCggCTCCgcAcagcaCtggTCCgaGtggTCCcaTcc<br>TatTcaTtggggATCcaaCacCAGCaaGgaAaaCccAttTctgttCgcTCTgga<br>GgcTgtCgtGatTAGCgtGggAAGcatgggCCtgatCatTTCcTTGctGtgC<br>gtTtaCttTtggctggaGAgAacCatgccTAgGatCccTacActCaaAaaTctGga<br>AgaCTTGgtGacAgaGtaTcaTggAaaTttCAGCgcTtggTCCggaGtCA<br>GCaaAggCctCgcCgaAagCctCcagccTgaTtaTagCgaGAgCctGtgTctG<br>gtGagCgaAatCccTccTaaGggCggAgcTctGggCgaAggAccAggCgCT<br>AGCCCTTGTAATCAGCACTCCCCTTATTGGGCTCCTCCTTG<br>CTATACATTGAAACCAGAGACATAAGGGAACCCAGGAGA<br>CAGGCCACACAGATGCTAAAACTGCAGAATCTGGGTAATT<br>TGGAAAGAAAGGGTCAAGAGACCAGGGATACTGTGGGAC<br>ATTGGAGTCTACAGAGTAGTGTTCTTTTATCATAAGGGTAC<br>ATGGGCAGAAAAGAGGAGGTAGGGGATCATGATGGGAAG<br>GGAGGAGGTATTAGGGGCACTACCTTCAGGATCCTGACTT<br>GTCTAGGCCAGGGGAATGACCACATATGCACACATATCTC<br>CAGTGATCCCCTGGGCTCCAGAGAACCTAACACTTCACAA<br>ACTGAGTGAATCCCAGCTAGAACTGAACTGGAACAACAGA<br>TTCTTGAACCACTGTTTGGAGCACTTGGTGCAGTACCGGAC<br>TGACTGGGACCACAGCTGGACTGTGAGTGACTAGGGACGT<br>GAATGTAGCAGCTAAGGCCAAGAAAGTAGGGCTAAAGGA<br>TTCAACCAGACAGATAGAAGGACCTAATATCAAGCTCCTG<br>TTCTCTGCCTCCCAGCTTCTCTGCTCACCCCCTACCCTCCCT<br>CCTCCAACTCCTTTCCTCGAGGGCCTATTTCCCATGATTCCTT<br>*CATATTTGCATATACGATACAAGGCTGTTAGAGAGATAATTGGA*<br>*ATTAATTTGACTGTAAACACAAAGATATTAGTACAAAATACGTGA*<br>*CGTAGAAAGTAATAATTTCTTGGGTAGTTTGCAGTTTTAAAATTA*<br>*TGTTTTAAAATGGACTATCATATGCTTACCGTAACTTGAAAGTAT*<br>*TTCGATTTCTTGGCTTTATATATCTTGTGGAAAGGACGAAACAC*<br>*CGTGGCCTGTCTCCTGGGTTCCCGTTTTAGTACTCTGGAAACA*<br>*GAATCTACTAAAACAAGGCAAAATGCCGTGTTTATCTCGTCAAC*<br>*TTGTTGGCGAGATTTTTTGTTTTAGAGCTAGAAATAGCAAGT*<br>*TAAAATAAGGCTAGTCCGTTTTTAGCGCGTGCGCCAATTCT*<br>GCAGACAAATGAGGGCCTATTTCCCATGATTCCTTCATATTTG<br>CATATACGATACAAGGCTGTTAGAGAGATAATTGGAATTAATTT<br>GACTGTAAACACAAAGATATTAGTACAAAATACGTGACGTAGAA<br>AGTAATAAATTTCTTGGGTAGTTTGCAGTTTTAAAATTATGTTTTA<br>AAATGGACTATCATATGCTTACCGTAACTTGAAAGTATTTCGAT<br>TTCTTGGCTTTATATATCTTGTGGAAAGGACGAAACACCGGACA<br>CAGACAGATACACCCAGTTTTAGTACTCTGGAAACAGAATCTA<br>CTAAAACAAGGCAAAATGCCGTGTTTATCTCGTCAACTTGTTGG<br>CGAGATTTTTggtAccggtGCGGCCGC |
| SEQ ID NO: 114 | HBB sgRNA1 expression cassette and the wild type template. italicized: HBB 5' arm. underlined: HBB 3' arm Bold: HBB sgRNA1 | GCggccgcttgtgtaatcgtagtttcagagtgttagagctgaaaggaagaagtaggagaaa<br>catgcaaagtaaaagtataacactttccttactaaaccgacatgggtttccaggtaggggc<br>aggattcaggatgactgacagggcccttagggaacactgagacccctacgctgacctcataa<br>atgcttgctacattgctottaattacatcuttaatagcaggaagcagaactctgcacttca<br>aaagtttttcctcacctgaggagttaatttagtacaaggggaaaaagtacaggggatggg<br>agaaaggcgatcacgttgggaagctatagagaaagaagagtaaattttagtaaaggaggtt<br>taaacaaacaaaatataaagagaaataggaacttgaatcaaggaaatgattttaaaacgca<br>gtattcttagtggactagaggaaaaaataatctgagccaagtagaagacctttccccctc<br>ctaccoctactttctaagtcacagaggcttttgttccccagacactcttgcagattagt<br>ccaggcagaaacagttagatgtccccagttaacctcctatttgacaccactgattacccca<br>ttgatagtcacacttttgggttgtaagtgacttttttattttatttgtattttttgactgcatta |

TABLE 10-continued

SEQUENCE LISTING

| SEQ ID NO | Sequence Type | Sequence |
|---|---|---|
| | expression cassette. | agaggtctctagtttttatctcttgtttcccaaaacctaataagtaactaatgcacagag cacattgatttgtatttattctattttagacataatttattagcatgcatgagcaaatta agaaaaacaacaacaaatgaatgcatatatatgtatatgtatgtgtatatatacacaca tatatatatatttttctttcttaccagaaggttttaatccaaataaggagaagatat gcttagaaccgaggtagagttttcatccattctgtcctgtaagtattttgcatattctgga gacgcaggaagagatccatctacatatcccaaagctgaattatggtagacaaaactcttcc acttttagtgcatcaacttcttatttgtgtaataagaaaattgggaaaacgatcttcaata tgcttaccaagctgtgattccaaatattacgtaaatacacttgcaaaggaggatgttttta gtagcaatttgtactgatggtatggggccaagagatatatcttagagggagggctgagggt ttgaagtccaactcctaagccagtgccagaagagccaaggacaggtacggctgtcatcact tagacctcaccctgtggagccacaccctagggttggccaatctactcccaggagcagggag ggcaggagccagggctgggcataaaagtcagggcagagccatctattgcttacatttgctt ctgacacaactgtgttcactagcaacctcaaacagacaccatggtgcatctgactcctgag gagaaaagcgctgtgacagctctctgggaaaagtcaatgtcgacgaagttggtggtgagg ccctgggcaggttggtatcaaggttacaagacaggtttaaggagaccaatagaaactgggc atgtggagacagagaagactcttggatttctgataggcactgactctctctgcctattggt ctattttcccaccctaggctgctggtggtctacccttggacccagagggttctttgagtcc tttgggatctgtccactcctgatgctgttatgggcaacccaaggtgaaggctcatggca agaaagtgctcggtgcctttagtgatggcctggctcacctggacaacctcaagggcacctt tgccacactgagtgagctgcactgtgacaagctgcacgtggatcctgagaacttcagggtg agtctatgggacgcttgatgttttctttcccctctttttctatggttaagttcatgtcata ggaaggggataagtaacagggtacagtttagaatgggaaacagacgaatgattgcatcagt gtggaagtctcaggatcgtttagttttcttttatttgctgttcataacaattgttttctt tgtttaattcttgctttcttttttttttcttctccgcaattttttactattatacttaatgcc ttaacattgtgtataacaaaaggaaatatctctgagatacattaagtaacttaaaaaaaaa ctttacacagtctgcctagtacattactatttggaatatatgtgtgcttatttgcatattc ataatctccctactttattttcttttattttttaattgatacataatcattatacatattta tgggttaaagtgtaatgttttaatatgtgtacacatattgaccaaatcagggtaattttgc atttgtaatttttaaaaaatgctttcttcttttaatatacttttttgtttatcttattcta atactttccctaatctctttctttcagggcaataatgatacaatgtatcatgcctattgca ccattctaaagaataacagtgataatttctgggttaaggcaatagcaatatctctgcatat aaatatttctgcatataaattgtaactgatgtaagaggtttcatattgctaatagcagcta caatccagctaccattctgcttttattttatggttgggataaggctggattattctgagtc caagctaggcccttttgctaatcatgttcatacctcttatcttcctcccacagctcctggg gcaacgtgctggtctgtgtgctggcccatcactttggcaaagaattcaccccaccatgcag gctgcctatcagaaagtggtggctggtgtggctaatgccctggcccacaagtatcactaag ctcgctttcttgctgtccaatttctattaaaggttcctttgttcctaagtccaactacta aactgggggatattatgaagggccttgagcatctggattctgcctaataaaaaacatttat tttcattgcaatgatctcgagggcctatttcccatgattccttcatatttgcatatacgat acaaggctgttagagagataattggaattaatttgactgtaaacacaaagatattagtaca aaatacgtgacgtagaaagtaataatttcttgggtagtttgcagttttaaaatttatgffft aaaatggactatcatatgcttaccgtaacttgaaagtatttcgatttcttggctttatata tcttgtggaaaggacgaaacaccGAGTAACGGCAGACTTCTCCACgttttagtactctgga aacagaatctactaaaacaaggcaaaatgccgtgtttatctcgtcaacttgttggcgagat ttttgcGGCCGC |
| SEQ ID NO: 115 | HBB-F2 | GGGCAGAGCCATCTATTGCTTA |
| SEQ ID NO: 116 | HBB-R3 | TGGGAAAATAGACCAATAGGCAGAG |
| SEQ ID NO: 117 | sgRNA-R2 | CGCCAACAAGTTGACGAGAT |
| SEQ ID NO: 118 | sgRNA-R3 | GATAAACACGGCATTTTGCCTTG |
| SEQ ID NO: 119 | HBB_off-R1 | GTCTCGTGGGCTCGGAGATGTGTATAAGAGACAGTggctgagg tgggagaatcac |
| SEQ ID NO: 120 | HBB_off-F2 | TCGTCGGCAGCGTCAGATGTGTATAAGAGACAGTatttctcctctg cactgccc |
| SEQ ID NO: 121 | HBB_off-R2 | GTCTCGTGGGCTCGGAGATGTGTATAAGAGACAGTggagcctc ggcctagatttc |
| SEQ ID NO: 122 | HBB_off-F3 | TCGTCGGCAGCGTCAGATGTGTATAAGAGACAGTTGATCC CTTCCACCAATGTC |
| SEQ ID NO: 123 | HBB_off-R3 | GTCTCGTGGGCTCGGAGATGTGTATAAGAGACAGTCACGG CTAGGAATAGCAAGG |
| SEQ ID NO: 124 | HBB_off-F4 | TCGTCGGCAGCGTCAGATGTGTATAAGAGACAGTAAAGGA AATTCCATCAGACTAACG |

TABLE 10-continued

SEQUENCE LISTING

| SEQ ID NO | Sequence Type | Sequence |
|---|---|---|
| SEQ ID NO: 125 | HBB_off-R4 | GTCTCGTGGGCTCGGAGATGTGTATAAGAGACAGTCTTTG AAAATGCCGTCCATC |
| SEQ ID NO: 126 | HBB_off-F5 | TCGTCGGCAGCGTCAGATGTGTATAAGAGACAGTAAGACA AAAGCAGAAGGTAAGC |
| SEQ ID NO: 127 | HBB_off-R5 | GTCTCGTGGGCTCGGAGATGTGTATAAGAGACAGTAAGTT GAAGATAGGACCCCACTC |
| SEQ ID NO: 128 | HBB_off-R6 | GTCTCGTGGGCTCGGAGATGTGTATAAGAGACAGTGGCAA CAAGAGCAAAACTCC |
| SEQ ID NO: 129 | HBB_off-F7 | TCGTCGGCAGCGTCAGATGTGTATAAGAGACAGTCCAGAA AGGGAAAACTTGCAC |
| SEQ ID NO: 130 | HBB_off-R7 | GTCTCGTGGGCTCGGAGATGTGTATAAGAGACAGTCCACT GACCCAATCTTTTCC |
| SEQ ID NO: 131 | HBB_off-F8 | TCGTCGGCAGCGTCAGATGTGTATAAGAGACAGTCTGCTC TTTGCCTGTTGGAG |
| SEQ ID NO: 132 | HBB_off-R8 | GTCTCGTGGGCTCGGAGATGTGTATAAGAGACAGTGCTAA AGCTGGAAGGCTGTG |
| SEQ ID NO: 133 | IL2RG-3301R | ATGCCCTCTGTAGTGGGTTG |
| SEQ ID NO: 134 | IL2RG-mut-F1 | GGCAGCTGCAGGAATAAGAG |
| SEQ ID NO: 135 | IL2RG-mut-R4 | TCGTCGGCAGCGTCAGATGTGTATAAGAGACAGTGAAGCT ATGACAGAGGAAACG |

Example 10. System for Packaging SaCas9 mRNA into LVLPs

Described herein is a system to efficiently package SaCas9 mRNA into LVLPs. The LVLPs enabled transient SaCas9 expression and highly efficient genome editing. They generated lower off-target rates compared with AAV and lentiviral delivery. The SaCas9 LVLPs described here have the transient expression feature of RNP-, mRNA- and nanoparticle-delivery strategies, but retain the transduction efficiency of lentiviral vectors. This system can be used for packaging various editor protein-encoding mRNA for genome editing.

Plasmids. pRSV-Rev (Addgene #12253), pMD2.G (Addgene #12259), pMDLg/pRRE (Addgene #12251), psPAX2-D64V (Addgene #63586), pSL-MS2×12 (Addgene #27119), pKanCMV-mRuby3-10aa-H2B (addgene #74258) and pX601-AAV-CMV::NLS-SaCas9-NLS-3×HA-bGHpA; U6::BsaI-sgRNA (Addgene #61591) were purchased from Addgene. pCDH-GFP was purchased from SBI (CD513B-1). The remaining plasmids were generated (see Table 2). Gene synthesis was done by GenScript Inc. All constructs generated were sequence confirmed. Sequence information for primers, oligos, and synthesized DNA fragments is in Table 10.

GFP reporter assay for gene editing activities The EGFP reporter cell line described in Javidi-Parisjani et al. was used to detect gene editing activity of SaCas9/human beta hemoglobin (HBB) sgRNA1 on the target sequences inserted in the GFP-reporter cassette. The GFP-reporter cells (derived from HEK293T cells) expressed no EGFP due to disruption of the EGFP reading frame by the insertion of the HBB sickle mutation and IL2RG target sequences between the start codon and the second codon of EGFP coding sequence. Indels formed after gene editing may restore the reading frame of the EGFP, resulting in EGFP expression. GFP-positive cells were analyzed by fluorescence microscopy or flow cytometry (BD Biosciences, Accuri C6). A single cell suspension was made in PBS/0.5% FBS for analysis. The cells without fluorescent protein expression were used as negative controls and a marker was placed at the position so that 99.9% of the cells were on the left side of the marker. In treated samples, cells on the right side of the marker were considered positive.

AAV6 virus production and transduction Adeno-associated virus expressing SaCas9 and HBB sgRNA1 were made from the AAV vector pSaCas9 (expresses SaCas9) and pSaCas9-HBB-sgRNA1 (expresses HBB sgRNA1, and contains donor template for homologous recombination to change the wild-type HBB gene to the Sickle mutation) respectively. AAV serotype 6 (AAV6) production and concentration were performed by Virovek, Inc. (Hayward, CA). For AAV6 transduction, the cells were changed to serum-free medium or OPTI-MEM, and AAV6 was added to the cells at a titer of $10^3$-$10^4$ virus genome/cell. 24 hours later the medium was changed to serum-containing growth medium.

Lentivirus and LVLP production Lentivirus was produced with the second- or the third-generation packaging systems, as described previously in Javidi-Parisjani et al. Lentiviral vector pCK002-HBB-sgRNA1 expressing both SaCas9 and HBB sgRNA1 was used to produce integration-competent lentivirus (packaged by packaging plasmid pspAX2 or pMDLg/pRRE), and integration-defective lentivirus (IDLV)

packaged by packaging plasmid pspAX2-D64V or pMDLg/pRRE-D64V). To produce LVLPs packaged with SaCas9 mRNA, HEK293T cells were transfected with mixed DNA of the packaging plasmid (NC-MCP or NC-PCP modified), envelope plasmid (pMD2.G), and the SaCas9 expression plasmid with DNA ratio as shown in Table 11. When VPR or NEF fusion proteins were used for packaging, SaCas9 mRNA, plasmid DNA for their expression was also included. Transfection was mediated by polyethylenimine (PEI, Polysciences Inc.) with a DNA:PEI ratio of 1:2. Cell culture and DNA transfection were performed as described in Javidi-Parisjani et al. 24 h after transfection, the medium was changed to Opti-MEM and the lentivirus or LVLPs were collected twice with one collection each 24 h. The supernatant was spun for 10 min at 500 g to remove cell debris before further processing described below.

precipitated according to the manufacturer's instructions so that the soluble p24 peptide was not detected.

Transmission electron microscopy Transmission electron microscopy was performed at the Cellular Imaging Shared Resource of Wake Forest Baptist Health Center (Winston-Salem, NC). For negative staining, 30 ml virus containing supernatant was concentrated to about 1 ml using an ultracentrifuge. Then, plain carbon grids were soaked in 20 µl of virus samples and the particles were stained with phosphotungstic acid. The samples were dried and observed under a FEI Tecnai G2 30 electron microscope (FEI, Hillsboro, OR).

Western blotting analyses To analyze viral proteins from lentivirus and LVLPs, purified lentivirus or LVLPs (200 ng p24 by ELISA) were lysed in 20 µl of 1× Laemmli sample buffer. The proteins in each sample were separated on SDS-PAGE gels and analyzed by Western blotting. The

TABLE 11

Plasmid DNA used to transfect HEK293T cells to make lentiviral particles loaded with SaCas9 mRNA$^a$

| | MCP-fused second generation packaging system | MCP-fused third generation packaging system | PCP-fused second generation packaging system | PCP-fused third generation packaging system | VPR or NEF mediated SaCas9 mRNA packaging |
|---|---|---|---|---|---|
| Gag-pol packaging plasmid (16.5 µg) | pspAX2-D64V-NC-MS2 | pMDLg/pRRE-D64V-NC-MS2 | pspAX2-D64V-NC-PP7 | pMDLg/pRRE-D64V-NC-PP7 | pspAX2-D64V |
| SaCas9 plasmid (12 µg) | pSaCas9$^{1xMS2}$ | pSaCas9$^{1xMS2}$ | pSaCas9$^{1xPP7}$ | pSaCas9$^{1xPP7}$ | pSaCas9$^{1xMS2}$ |
| pMD2G (µg) | 8 | 8 | 8 | 8 | 8 |
| pRSV-REV (µg) | 0 | 4.5 | 0 | 4.5 | 0 |
| VPR or NEF MCP fusion plasmid (µg) | 0 | 0 | 0 | 0 | 12 |

$^a$13 × 10$^6$ cells were seeded in 15-cm dishes 24 hours before transfection.

Concentrating lentivirus and LVLPs Three methods were used to concentrate lentivirus and LVLPs: 1) The supernatant containing the virus or LVLPs was laid on a 10 ml 20% sucrose cushion, and then centrifuged at 20,000 g 4° C. for 4 hours; 2) The supernatant containing the virus or LVLPs was mixed with the Lenti-X™ Concentrator (Takara, Cat. No. 631232) at a ratio of 3:1 (volume/volume), incubated at 4° C. for 30 mins and then centrifuged at 4° C. 1,500×g for 45 minutes; 3) The supernatant was concentrated with the KR2i TFF System (KrosFlo® Research 2i Tangential Flow Filtration System) (Spectrum Lab, Cat. No. SYR2-U20) using the concentration-diafiltration-concentration mode. Typically, 150-300 ml supernatant was first concentrated to about 50 ml, diafiltrated with 500 ml to 1000 ml PBS, and finally concentrated to about 8 ml. The hollow fiber filter modules were made from modified polyethersulfone, with a molecular weight cut-off of 500 kDa. The flow rate and the pressure limit were 80 ml/min and 8 psi for filter module D02-E500-05-N, and 10 ml/min and 5 psi for the filter module CO2-E500-05-N. Since the TFF method produced lentivirus and LVLPs with the best activities, data were generated with virus or LVLPs concentrated by the TFF system, unless otherwise stated.

Lentivirus and LVLP quantification Viral titer was determined by p24 based ELISA (Cell Biolabs, QuickTiter™ Lentivirus Titer Kit Catalog Number VPK-107). When unpurified samples were assayed, the viral particles were antibodies used include HIV1 p17 antibody for MA (ThermoFisher Scientific, Cat No. PA1-4954, 1:1000), HIV1 p15 polyclonal antibody for NC (Abcam, Cat No. ab66951, 1:1000) and p24 monoclonal antibody for CA (Cell Biolabs, Cat No. 310810, 1:1000).

To detect SaCas9 protein, HEK293T cells or GFP reporter cells were transfected with SaCas9 expression plasmid DNA or were co-transduced with 100 ng SaCas9 mRNA packaged LVLPs and 100 ng p24 of IDLV expressing HBB sgRNA1. 48 hours after transfection or transduction, the cells were lysed with 100 µl of 1× Laemmli sample buffer and equal volumes of each sample was loaded for SDS-PAGE separation and Western blotting analysis by anti-HA antibody (ProteinTech, 51064-2-AP, 1:1000) and anti-Cas9 antibody (Millipore Sigma, MAB131872, clone 6F7, 1:1000) to detect the HA-tagged SaCas9. Anti-beta actin (Sigma, A5441, 1:5000) was used to compare the amount of input.

HRP conjugated anti-Mouse IgG (H+L) (ThermoFisher Scientific, Cat No. 31430, 1:5000) and anti-Rabbit IgG (H+L) (Cat No. 31460, 1:5000) secondary antibodies were used in Western blotting. Chemiluminescent reagents (Pierce) were used to visualize the protein signals under the LAS-3000 system (Fujifilm).

RNA isolation from lentivirus or LVLPs An miRNeasy Mini Kit (QIAGEN Cat No./ID: 217004) was used to isolate RNA from concentrated lentivirus or LVLPs. Alternately, RNA was isolated directly from 140 μl particle containing supernatant with the QIAamp Viral RNA Mini Kit (QIA-GEN).

RT-PCR analysis of RNA The QuantiTect Reverse Transcription Kit (QIAGEN) was used to reverse-transcribe the RNA to cDNA. Custom designed Hydrolysis probes specific for SaCas9, HBB sgRNA1 and EGFP (ThermoFisher Scientific) were used in qPCR, together with TaqMan Universal PCR Master Mix (ThermoFisher Scientific). PCR was run on an ABI 7500 instrument.

Lentivirus and LVLP transduction Various amounts of lentivirus or LVLPs (ng p24 protein) were added to $2.5 \times 10^4$ cells grown in 24-well plates, with 8 μg/ml polybrene. The cells were incubated with the particle-containing medium for 12-24 hours, after which normal medium was replaced.

Gene editing in human cells For gene editing with Cas9 expressed from AAV6, the SaCas9 expressing AAV6 and the HBB sgRNA1 expressing AAV6 were co-transduced into GFP reporter cells. For gene editing with LV or IDLV (packaged with packaging plasmids containing a D64V mutation in the integrase) expressing both SaCas9 and HBB sgRNA1, virus equivalent to 10-300 ng p24 was used to transduce $2.5 \times 10^4$ cells in 24 well plates. For gene editing with LVLPs, various amounts of SaCas9 mRNA containing LVLPs were co-transduced into HEK293T cells or the GFP reporter cells with an IDLV expressing HBB sgRNA1. 48-72 hours after transduction, gene editing activity was analyzed by GFP-reporter assay or next-generation sequencing.

To examine gene editing in human lymphoblastoid cells immortalized by Epstein-Barr virus transformation, human lymphoblastoid cell line GM16265 was purchased from the Corrie Institute. The lymphoblasts were cultured in RPMI 1640 with 2 mmol/L L-glutamine and 15% fetal bovine serum at 37° C. under 5% carbon dioxide. For LVLP and IDLV transduction, $2 \times 10^5$ cells were added to 0.5 ml RPMI growth medium. Then, 100 p24 or 500 p24 of SaCas9 LVLP and IL2RG sgRNA IDLV were added to the cells. Polybrene was added in the medium to a final concentration of 8 μg/ml. Fresh medium was replaced twenty hour hours after transduction. The cells were collected 72 hours after transduction for DNA analysis by next-generation sequencing.

Next-generation sequencing and data analyses The following DNA regions were amplified for next-generation sequencing analysis: 1) the endogenous HBB target sequence, 2) the endogenous IL2RG target sequence, and 3) the HBB target sequence in the integrated GFP-expression cassette. To amplify the endogenous HBB target sequence for sequencing, a nested PCR strategy was used to avoid amplifying the sequence from the viral vector template. First, primers HBB-1849F and HBB-5277R were used to amplify the 3.4 kb region from the HBB gene locus. These two primers cannot amplify sequences from the templates in the viral vectors. Then two inside primers HBB-MUT-F and the HBB-MUT-R primers were used to amplify the target DNA for sequencing (Table 10; SEQ ID NOs: 34-40). To amplify the endogenous IL2RG target sequence, primers IL2RG-1029F and IL2RG-3301R were used to amplify the target region from the treated cells (unable to amplify sequences from the templates in the viral vectors), then two inside primers IL2RG-mut-F1 and IL2RG-mut-R4 were used to amplify the target DNA from the first PCR product for sequencing. To amplify the HBB target sequence from the integrated EGFP reporter for sequencing, Reporter-mut-F and Reporter-mut-R primers were used (Table 10; SEQ ID NOs: 98-102). The proofreading HotStart® Ready-Mix from KAPA Biosystems (Wilmington, MA) was used for PCR. In order to increase sequence diversity during next generation sequencing, variant numbers of stagger nucleotide were added after the barcodes in the 5' primers to amplify the same target from different samples. Single-end reads from the 5' of the PCR products were obtained by next-generation sequencing using the Illumina NextSeq 500 as described in Javidi-Parisjani et al. Low quality reads were removed. All sequences were sorted based on the barcodes.

After removing the 3' linker and 5' barcode sequences, the resulting reads were submitted to the online Cas-Analyzer software for mutation analysis. When submitting the reference sequence, the primer sequences were excluded if they were at least 12 nt away from the sgRNA target. Otherwise, primer sequences were included in the reference. Only those readings containing both the 5' 12 nt and 3' 12 nt of the reference sequence were included in Indel analysis. The total Indel rate was the difference between 1 and the percentage of readings without mutation. The top 8-10 most frequently observed readings were presented.

SaCas9 mRNA decay analysis To compare the SaCas9 RNA levels expressed from IDLV and LVLPs, $2.5 \times 10^4$ HEK293 cells were transduced with 35 ng p24 of IDLV or LVLPs. IDLV particles could express SaCas9, and LVLPs were packaged with SaCas9 mRNA. 24 hours after transduction, the cells were maintained in medium containing 0.5% FBS to limit cell division. Fresh medium was changed every 48 hours. The cells were collected 24, 48, 72, and 96 hours post transduction, followed by RNA extraction and RT-qPCR analysis. Three hydrolysis probes, SaCas9, GAPDH and RPLP0 were used for expression analysis. The relative Cas9 mRNA levels of different particles 24 hours after transduction were determined by normalization to RPLP0. Since no new mRNA was generated with LVLPs after transduction, no normalization was performed when evaluating mRNA decay of Cas9 mRNA from the same particle, in order to avoid interference of possible cell proliferation on analysing RNA decay. However, RPLP0 and GAPDH expression were examined for all samples to make sure sample preparation was successful and consistent.

Statistical analysis GraphPad Prism software (version 5.0, GraphPad Software Inc) was used for statistical analyses. T-tests were used to compare the averages of two groups. Analysis of Variance (ANOVA) was performed followed by Tukey post hoc tests to analyze data from more than two groups. Bonferroni post hoc tests were performed following ANOVA in cases of two factors. $p<0.05$ was regarded as statistically significant.

Fusing Nucleocapsid (NC) protein with RNA-binding proteins enabled efficient packaging of SaCas9 mRNA in lentivirus-like particles In order to package SaCas9 mRNA into LVLPs via specific MS2/MCP interaction MS2-binding protein MCP was fused with lentiviral proteins and MCP interacting MS2 aptamer was added after the stop codon of SaCas9 mRNA. To find the MCP fusion partner with the most efficient mRNA packaging, four different lentiviral proteins, viral protein R (VPR), negative regulatory factor (NEF), nucleocapsid protein (NC) and matrix protein (MA), were explored as the recipient proteins for MCP based on the following observation: 1) A mutant NEF (with three mutations: G3C, V153L and G177E) can be incorporated into lentiviral particles for up to 1100 molecules/capsid and has been used as a vehicle for foreign protein delivery; 2) VPR is incorporated into the viral core for up to 550 copies/particle and has also been used as the protein delivery vehicle; 3) NC, which is processed from each one of the 2500-5000 Gag precursors forming a lentiviral particle, is the major RNA binding protein in the viral core; and 4) MA, which is also processed from Gag protein, is shown to bind tRNA.

Figure 2:
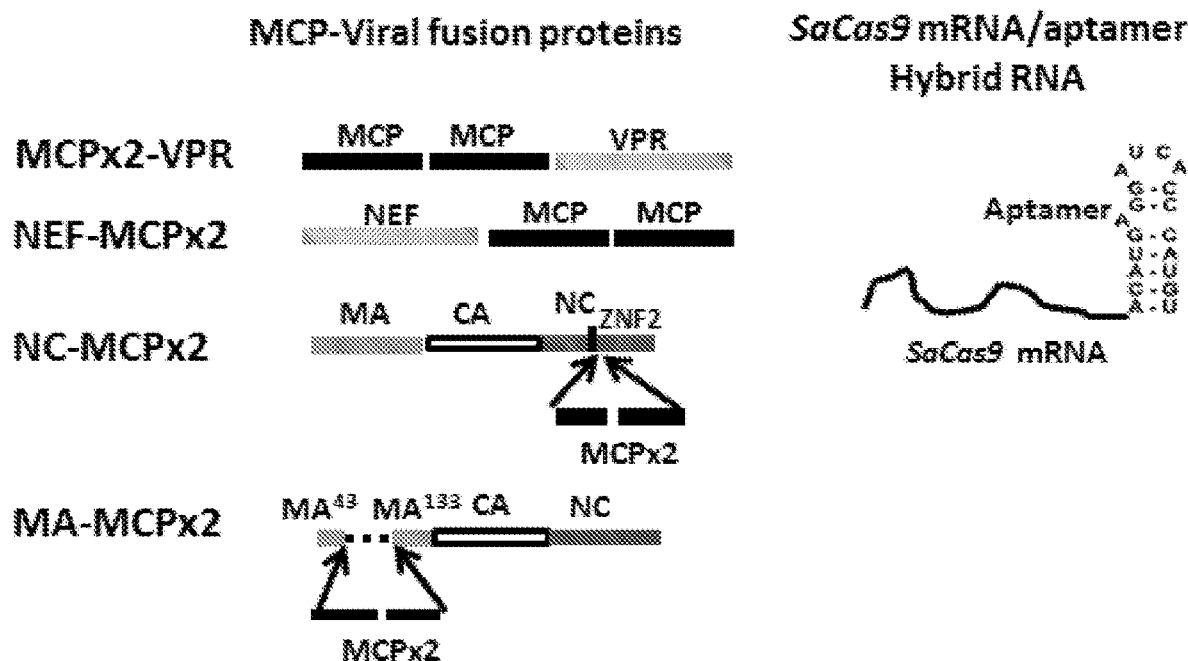
FIG. 2 shows schematic diagrams of MS2 coat protein (MCP) fusion proteins for packaging SaCas9 mRNA in lentivirus-like particles according to some aspects of this disclosure. VPR: Viral Protein R, NEF: Negative Regulatory Factor; NC, Nucleocapsid Protein; MA: Matrix Protein. Dashed line indicates the deleted region.
Figure 7A:
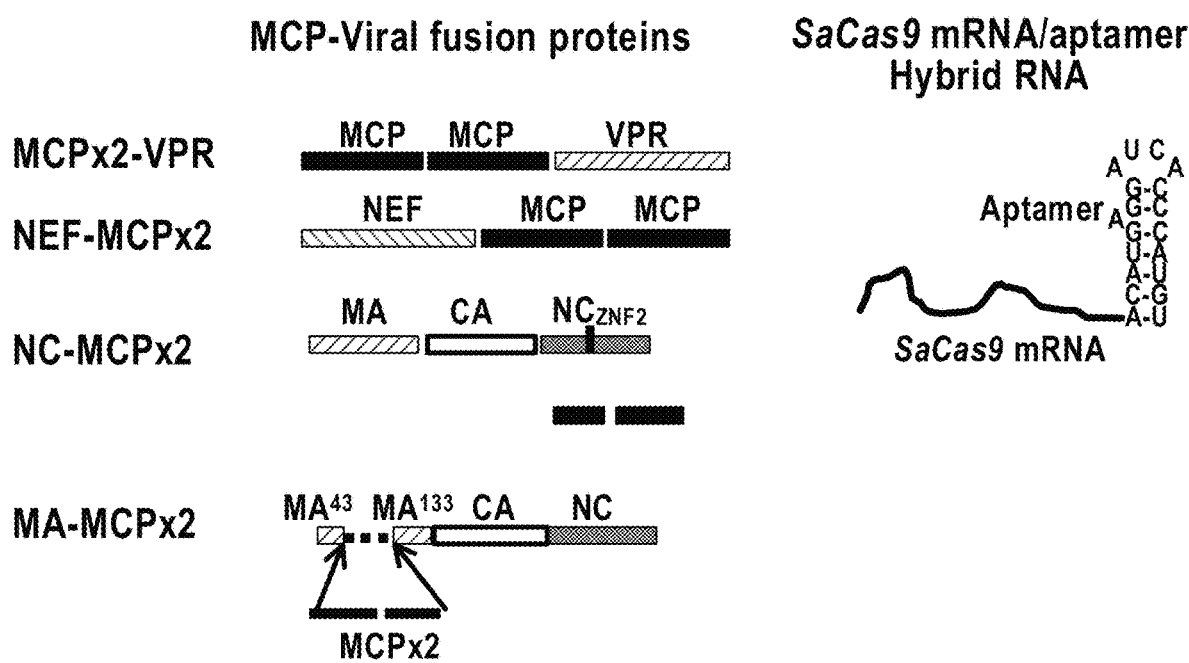
FIGS. 7A-7F show schematics illustrating compositions, systems and results obtained using LVLPs for SaCas9 mRNA packaging.
Figure 7B:
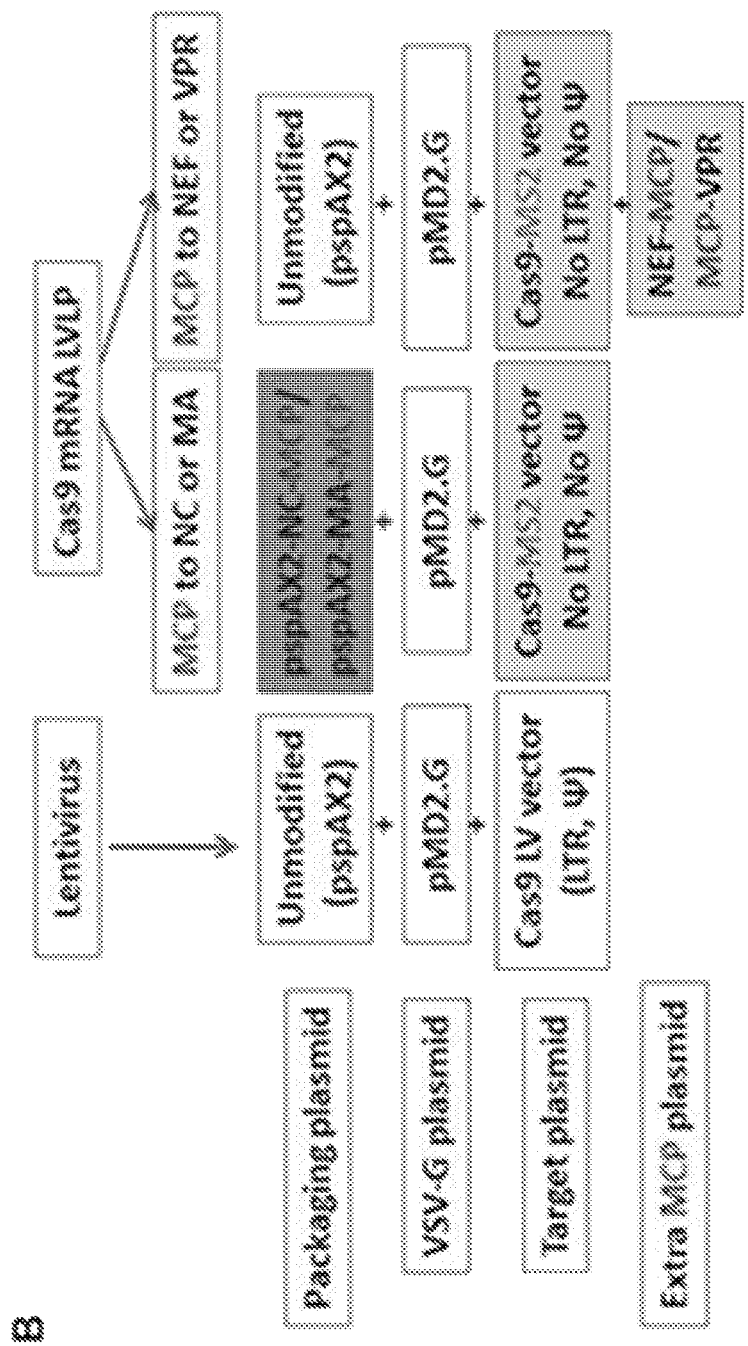

MCP was fused with NEF and VPR in the configuration shown in FIG. 2 and FIG. 7A, which are duplicate figures. MCP-VPR and NEF-MCP were expressed from co-transfected plasmid DNA during LVLP production with the unmodified packaging plasmid (FIG. 7B). To fuse MCP with NC, the packaging plasmid was modified by inserting MCP coding sequence after that of the second zinc finger of NC. Because the second zinc finger of NC is necessary for virion production and deleting this domain reduced virion production 10 fold this domain was preserved rather than replacing it with MCP. To fuse MCP with MA, the coding sequence for MA amino acid 44-132 was replaced in the packaging plasmid with that of MCP, since this region of MA is not necessary for virus production. An MCP coding sequence was inserted into NC or MA of the packaging plasmid in a way that the Gag precursor protein reading frame and the protease processing sites were preserved.

Figures 7C, 7D, 7E, 7F:
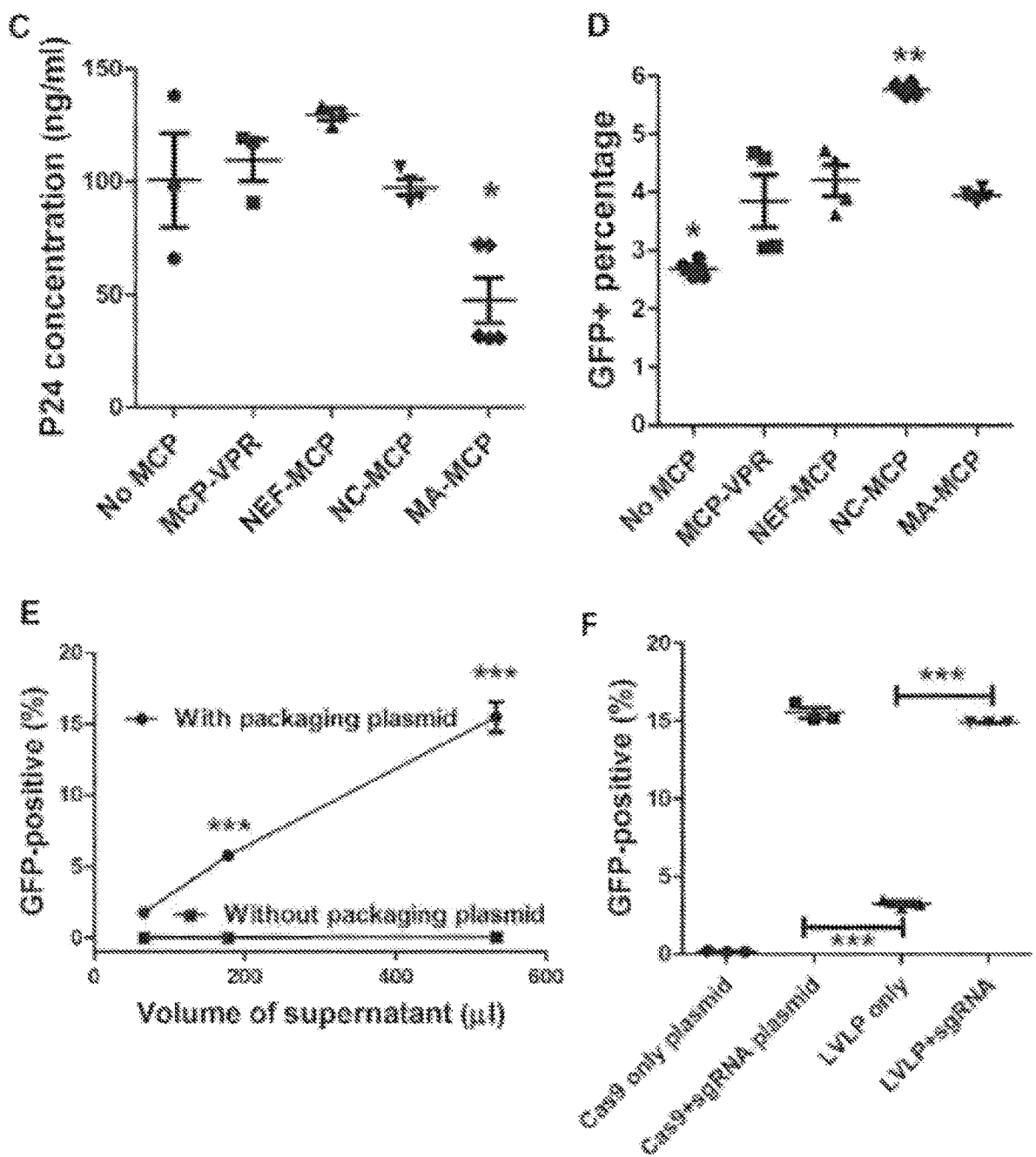

To examine whether the incorporation of MCP affected virion production, GFP-lentivirus production efficiency using these constructs was compared. Expressing MCP-VPR or NEF-MCP in packaging cells did not affect GFP lentivirus production with the original packaging plasmid. NC-MCP modified packaging plasmid generated GFP lentivirus with similar efficiency as the original packaging plasmid, but MA-MCP modified packaging plasmid showed reduced virus production efficiency (FIG. 7C).

In order to have a simple assay to compare genome editing activities, the GFP-reporter cells (derived from HEK293T cells transduced with GFP-reporter lentiviral vectors) were used. These GFP-reporter cells were integrated with a GFP expression cassette, wherein the Sickle mutation sequence of human beta hemoglobin (HBB) targeted by HBB sgRNA1 was inserted between the EGFP start and the second codons, disrupting the reading frame. Insertions or deletions (Indels) in the target sequence resulting from gene editing may restore the EGFP reading frame and GFP expression. To test whether fusing MCP to virus proteins could enhance the packaging of SaCas9 mRNA into LVLPs, SaCas9$^{1 \times MS2}$ (SaCas9 mRNA with 1 copy of MS2 aptamer after the stop codon) was expressed during LVLP generation by the original packaging plasmid (with or without MCP-VPR or NEF-MCP expression), or by the MCP modified packaging plasmid (FIG. 7B). These LVLPs were then co-transduced into the GFP-reporter cells with an integration-defective lentivirus (IDLV) vector expressing HBB sgRNA1 targeting the Sickle mutation of human beta hemoglobin (HBB) (32). LVLPs made from NC-MCP modified packaging plasmid generated significantly more GFP reporter cells than LVLPs generated by all other strategies of MCP incorporation (p<0.01) (FIG. 7D) NC was thus used as the MCP recipient protein for further experiments.

MCP dimers, but not the monomers or oligomers, had RNA aptamer-binding activities. When the performance of packaging plasmids wherein NC was fused with one or two copies of MCP was compared, LVLPs generated by packaging plasmid fused with one copy of MCP produced more GFP+ reporter cells than that fused with two copies of MCP (5.7%±0.1%, N=4, versus 4.4%±0.3%, N=4; p<0.01. Thus, the modified packaging plasmid fused with one copy of MCP was used in subsequent experiments.

Figure 8:
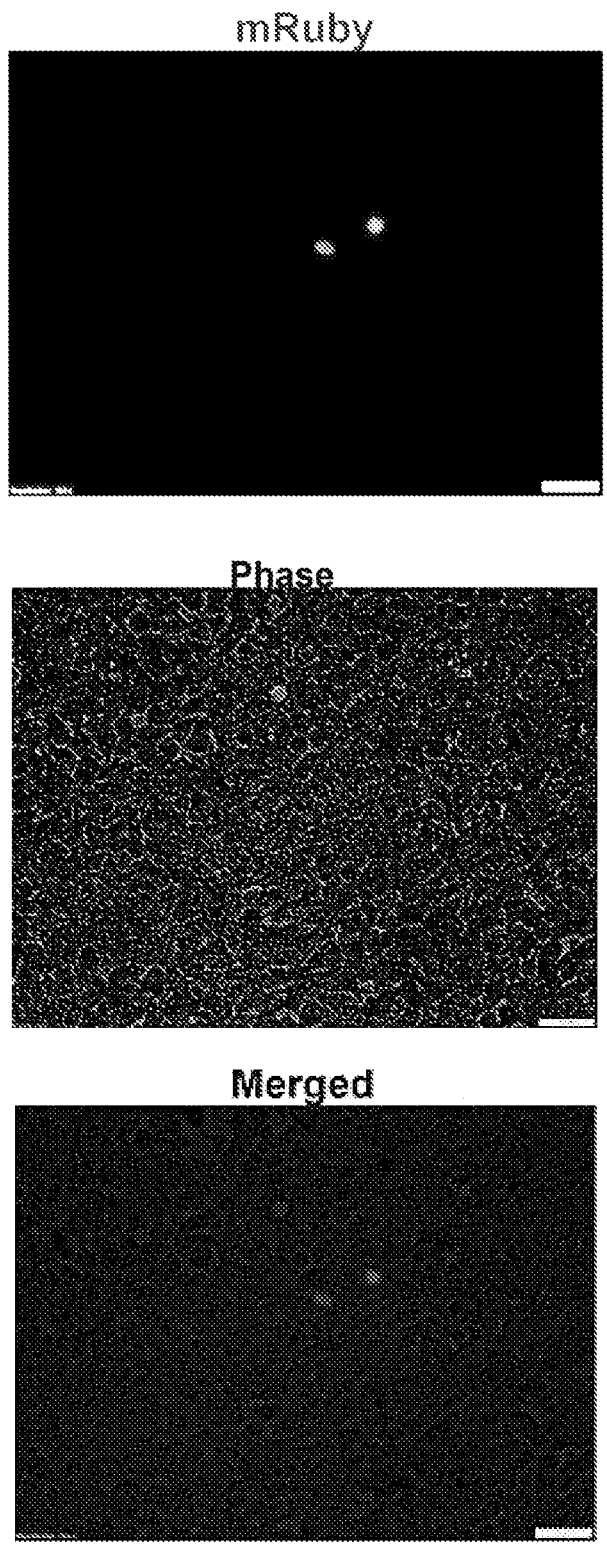
FIG. 8 shows that few mRuby-positive cells could be observed when GFP-reporter cells were transduced with supernatant generated by replacing the packaging plasmid with the (nuclear located) mRuby expressing plasmid. Shown are images from one field of the cells treated with 534 μl of supernatant. Multiple fields were examined and 0-5 positive cells were observed per field. Three fields, with 2, 2 and 3 positive cells respectively, were estimated by imageJ to have 934 cells/field. The average positive rate was 0.0025%.

To test whether the gene editing activity observed was caused by nucleic acid in extracellular vesicles promoted by VSV-G, a control where the NC-MCP modified packaging plasmid was replaced with the plasmid expressing mRuby fluorescent protein, but none of the lentivirus packaging proteins, was included. Equal volumes of supernatants were co-transduced onto GFP-reporter cells with HBB sgRNA1 expressing IDLV, supernatant produced with the packaging plasmid generated up 15% GFP$^+$ reporter cells. Whereas supernatant produced without packaging plasmid generated lower than 0.5% GFP+ reporter cells under all conditions (FIG. 7E) and the mRuby positive rate was lower than 0.5% in cells treated with the highest volume of supernatant (FIG. 8). Since VSV-G was present in both conditions, the data suggested that extracellular vesicles did not having a major role in generating GFP$^+$ reporter cells. The data also suggested that residual plasmid DNA contributed little in the total gene editing activities observed.

To further test the contribution of residual plasmid DNA from LVLP production in generating GFP+ reporter cells, constructs expressing only SaCas9$^{1 \times MS2}$ mRNA (pSaCas9$^{1 \times MS2}$) and expressing both SaCas9$^{1 \times MS2}$ mRNA and HBB sgRNA1 (pSaCas9$^{1 \times MS2}$-HBB sgRNA1) were made. As expected, transfecting pSaCas9$^{1 \times MS2}$-HBB sgRNA1 plasmid DNA into the GFP reporter cells generated significantly more GFP+ reporter cells than transfecting pSaCas9$^{1 \times MS2}$ plasmid DNA (FIG. 7F). Since HBB sgRNA1 without the MS2 aptamer could not be packaged, LVLPs made from pSaCas9$^{1 \times MS2}$-HBB sgRNA1 plasmid DNA were expected to contain insufficient copies of HBB sgRNA1. Indeed, these LVLPs produced significantly less GFP+ reporter cells when transduced alone than when co-transduced with IDLV expressing HBB sgRNA1 (p<0.0001, FIG. 7F). Note that in this experiment, nonspecifically packaged sgRNA in LVLPs also contributed to the background activity, which explains why higher background activity was observed in FIG. 7F than in FIG. 7E. These observations argue against a major contribution from plasmid DNA left over during LVLP production, and support more effective packaging of SaCas9$^{1 \times MS2}$ mRNA when using NC-MCP LVLPs.

Figures 9A, 9B, 9C, 9D, 9E:
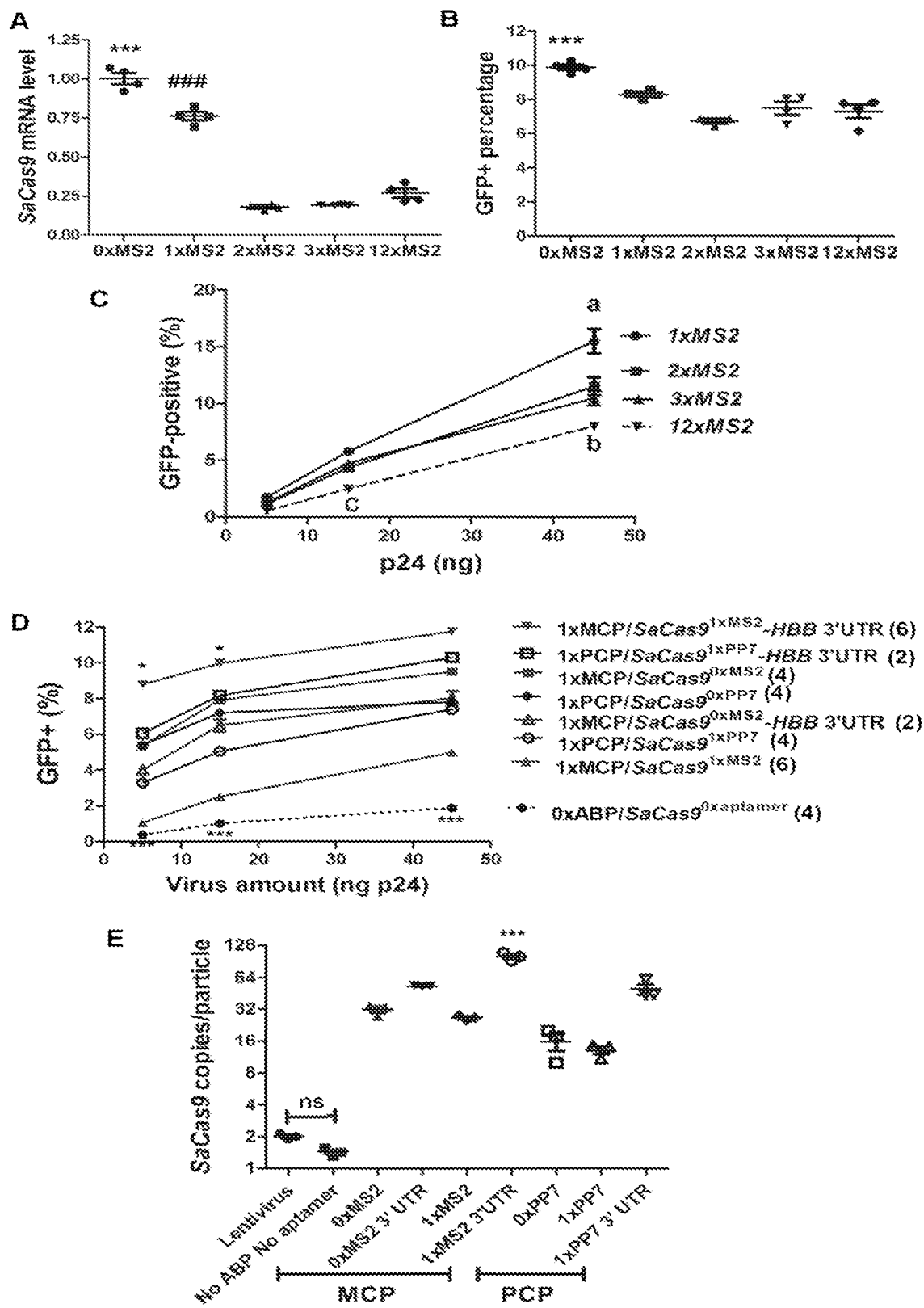
FIGS. 9A-9E show the Gene editing activities of various LVLPs.

Human beta hemoglobin (HBB) 3' untranslated region greatly improved the genome editing activities of SaCas9 mRNA packaged in LVLPs To determine the best copy number of MS2 aptamer for packaging of SaCas9 mRNA, the effects of 0, 1, 2, 3 and 12 copies of MS2 aptamers on SaCas9 mRNA expression were examined. Equal amounts of plasmid DNA expressing SaCas9$^{n \times MS2}$ (n indicates 0, 1, 2, 3 or 12) was transfected into HEK293T cells and the steady-state level of SaCas9 mRNA was compared by RT-qPCR. Addition of 1 aptamer after the stop codon of SaCas9 slightly decreased the steady-state level of SaCas9 mRNA, while adding more than 1 aptamer significantly decreased SaCas9 mRNA (p<0.001, FIG. 9A). Consistent with the decrease in mRNA, when SaCas9$^{n \times MS2}$-expressing DNA was co-transfected into GFP reporter cells with the plasmid expressing the HBB sgRNA1, one aptamer slightly decreased the percentage of GFP$^+$ reporter cells, while more aptamers caused a further decrease (FIG. 9B). Consistently, when LVLPs containing SaCas9$^{1 \times MS2}$, SaCas9$^{2 \times MS2}$, SaCas9$^{3 \times MS2}$, or SaCas9$^{12 \times MS2}$ were co-transduced into GFP-reporter cells with HBB sgRNA1-expressing lentivirus, SaCas9$^{1 \times MS2}$ LVLPs generated the most GFP-positive cells, and SaCas9$^{12 \times MS2}$ LVLPs generated the least at all concentrations tested (FIG. 9C).

To enhance SaCas9 mRNA stability and translatability with or without aptamer, two copies of 3' untranslated region (UTR) sequences from the human HBB gene were added after the SaCas9 stop codon but before the MS2 aptamer. Plasmid DNA transfection in HEK293T cells showed that the steady-state level of SaCas9$^{1\times MS2}$-HBB 3' UTR was 1.3 fold of that of SaCas9$^{0\times MS2}$ (1.3±0.08 versus 1.0±0.03, n=4, p<0.05).

Since more than one MS2 aptamer significantly decreased the gene editing activities of the LVLPs, one copy of MS2 aptamer was further studied. LVLPs containing SaCas9 mRNA with or without MS2 aptamer and HBB 3'UTR (SaCas9$^{0\times MS2}$, SaCas9$^{1\times MS2}$, SaCas9$^{0\times MS2}$-HBB 3'UTR, SaCas9$^{1\times MS2}$-HBB 3'UTR) were made, and each type of particle was transdcued into the GFP-reporter cells with HBB sgRNA1-expressing IDLV. Flow cytometry analysis revealed that without MCP, the LVLP produced GFP-positive cells inefficiently (dashed lines in FIG. 9D). Among LVLPs generated with MCP, the presence of both MS2 and HBB 3'UTR resulted in the highest genome editing activity. Surprisingly, SaCas9 mRNA without MS2 aptamer can also generate appreciable GFP-positive cells. SaCas9$^{1\times MS2}$ LVLPs showed lower activities than SaCas9$^{0\times MS2}$ LVLPs, consistent with a previous observation of MS2 decreasing SaCas9 mRNA stability. HBB 3'UTR significantly improved the performance of SaCas9$^{1\times MS2}$ LVLPs but not that of SaCas9$^{0\times MS2}$ LVLPs, another observation consistent with previous data. These data suggest that 1) MCP is necessary for efficient packaging of SaCas9 mRNA; and 2) MS2 aptamer decreases SaCas9 mRNA stability, although they may increase SaCas9 mRNA/NC-MCP association; and 3) HBB 3'UTR increased SaCa9 mRNA stability, and the presence of MS2 and HBB 3'UTR improved SaCas9 mRNA/NC-MCP association and SaCa9 mRNA stability.

Considering the possible packaging of dCas9 mRNA for CRISPR-mediated gene regulation, where sgRNA may need to be modified with aptamers to enhance gene regulation, more than one aptamer may be used in the same experiment. A PP7/PP7 coat protein (PCP) based packaging system was also developed to enable aptamer combinations. PP7/PCP is another RNA aptamer/ABP pair used in RNA studies. MCP was replaced with PCP in the packaging plasmid and the MS2 aptamer was replaced by the PP7 aptamer in the SaCas9 mRNA expression plasmid (expressing SaCas9$^{1\times PP7}$). PP7/PCP packaged SaCas9 LVLPs could also efficiently generate GFP+ reporter cells when co-transduced into the GFP-reporter cells with the HBB sgRNA1-expressing IDLV (FIG. 9D). Surprisingly, a PCP-modified packaging system can also package PP7-free SaCas9 mRNA, and in this case, the packaging is PCP-dependent.

The GFP-reporter assay data were corroborated by RT-qPCR analysis of SaCas9 mRNA copy numbers per LVLP (FIG. 9E). Consistent with the observation that LVLPs containing SaCas9$^{1\times MS2}$-HBB 3'UTR resulted in the highest percentage of GFP-positive cells, they had the highest SaCas9 mRNA copy number (~50 fold RNA molecules contained in lentiviral vectors with similar p24 protein). Although SaCas9$^{0\times MS2}$ and SaCas9$^{1\times MS2}$ LVLPs had similar copies of Cas9 mRNA/particle, the gene editing activity of Cas9$^{1\times MS2}$ LVLPs was consistently lower than that of Cas9$^{0\times MS2}$ LVLPs (FIG. 9D). This could be the result of the MS2 aptamer decreasing SaCas9 mRNA stability.

Comparing the LVLPs packaged by MCP/MS2 and PCP/PP7 based systems, PCP/PP7 packaged SaCas9 LVLPs had better gene editing activities than those of MCP/MS2 packaged LVLPs when HBB 3'UTR was not added to SaCas9 mRNA. The opposite was true when HBB 3'UTR was added to SaCas9 mRNA (FIG. 9D). SaCas9$^{1\times MS2}$-HBB 3'UTR LVLPs consistently showed the best gene editing activity in multiple repeats.

Figure 10A:
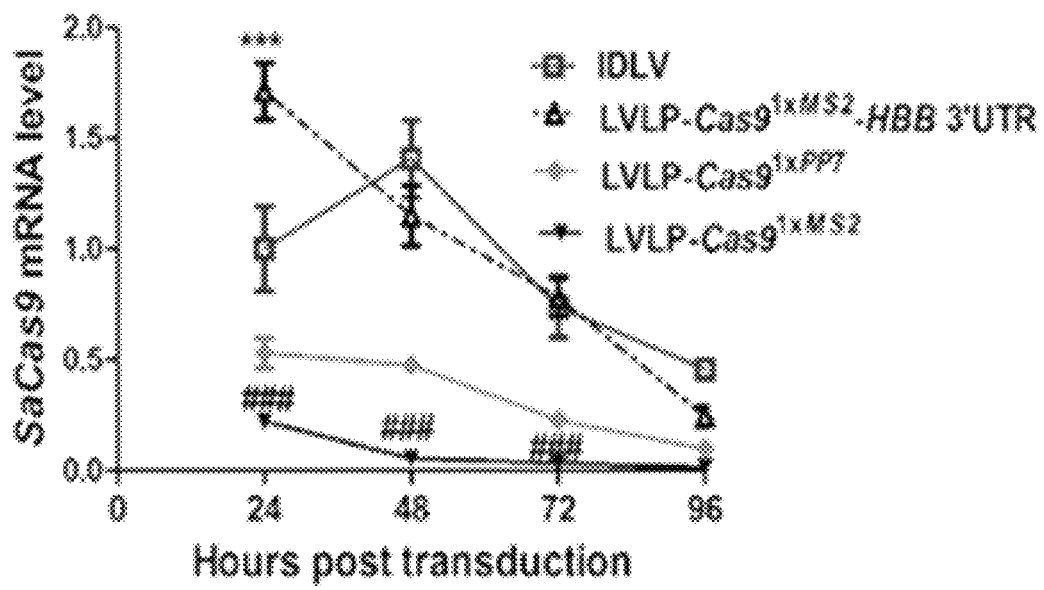
FIGS. 10A-10E show the Characterization of LVLPs.
Figure 10B:
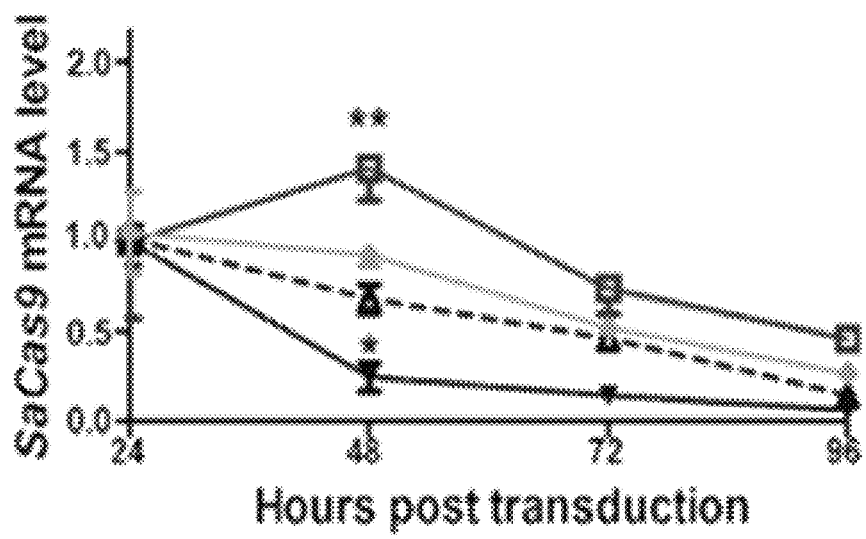

The expression duration of the mRNAs delivered by the LVLPs were examined and compared with that of IDLV. 24 hours after transduction, SaCas9$^{1\times MS2}$-HBB 3'UTR LVLPs showed the highest Cas9 mRNA level, consistent with their high mRNA copy number/particle and mRNA stability (FIG. 10A). SaCas9$^{1\times MS2}$ LVLPs had the lowest mRNA expression, consistent with their low gene editing activity. In contrast to IDLV's increased Cas9 mRNA expression at 48 hours post transduction, suggesting transcription of new Cas9 mRNA, all mRNAs delivered by LVLPs decreased steadily with different speed. Compared with the respective mRNA levels of 24 hours post transduction, SaCas9$^{1\times PP7}$ showed similar decay rates as SaCas9$^{1\times MS2}$-HBB 3'UTR (FIG. 10B), while SaCas9$^{1\times MS2}$ showed much faster decay rates. This could also explain why SaCas9$^{1\times MS2}$-HBB 3'UTR and SaCas9$^{1\times PP7}$ performed better than SaCas9$^{1\times MS2}$ in GFP-reporter assays. Thus, SaCas9$^{1\times MS2}$-HBB 3'UTR LVLPs were able to achieve transient and high expression compared to IDLV virus vectors.

Figure 10C:
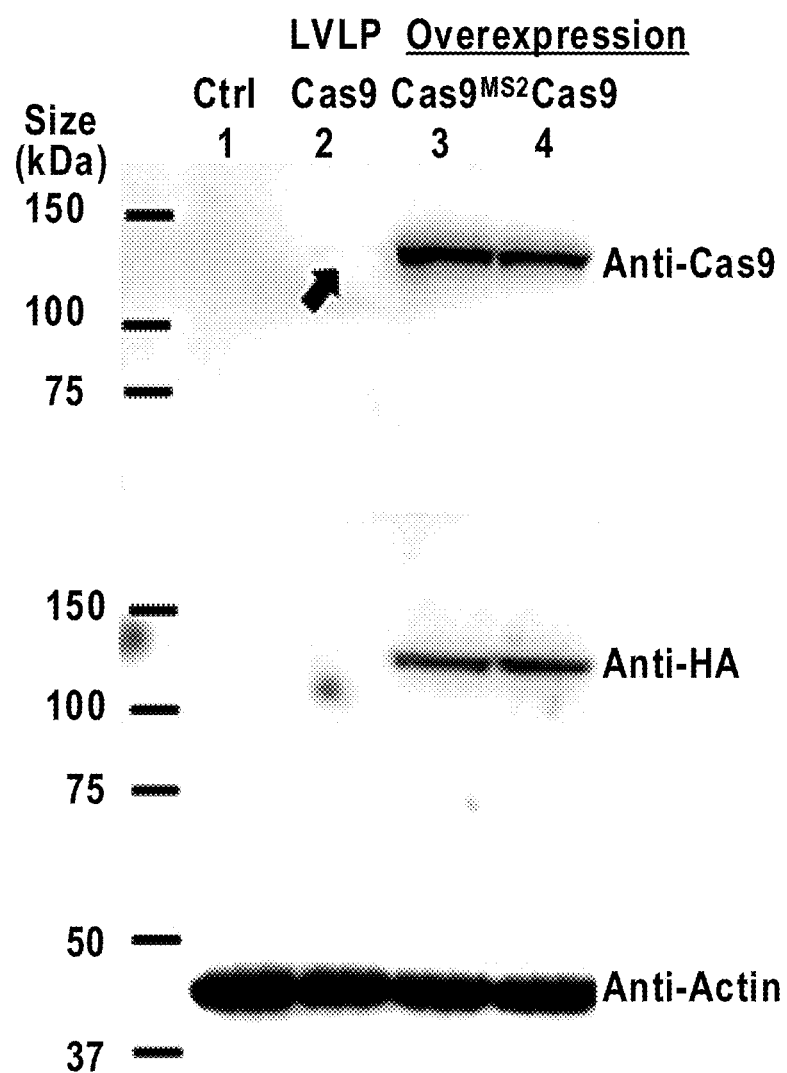

Protein expression from the LVLPs was examined. Cas9 protein expression was readily detected in overexpressed HEK293T cells or GFP reporter cells with either the SaCas9 or HA (the Tag at the C-terminus of Cas9) antibodies, but could hardly detect Cas9 expression in GFP-reporter cells 48 hours after transducing even 300 ng LVLPs (FIG. 10C). These cells were co-transduced with HBB sgRNA1 IDLV and 15% of them were GFP-positive in flow cytometry analysis, suggesting successful gene editing in about 45% of the cells, even though Cas9 protein were difficult to detect in these cells by Western blotting. The data showed that the LVLPs were able to express sufficient Cas9 protein for efficient gene editing, although hardly detectable by the method we used. Since the rate of off-targets increases with increasing Cas9 protein, the relativelylow Cas9 protein from LVLPs will also ensure low off-targets.

Figure 10D:
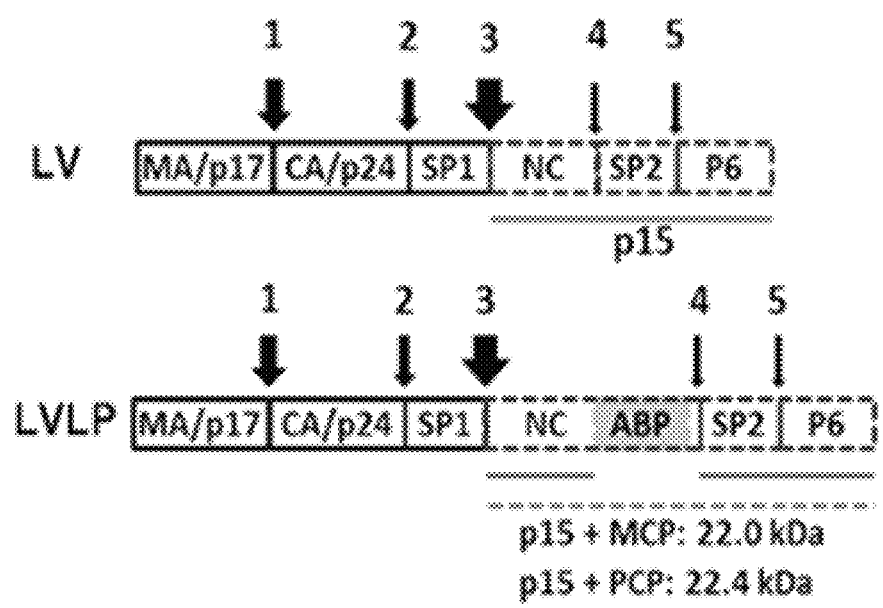
Figure 10E:
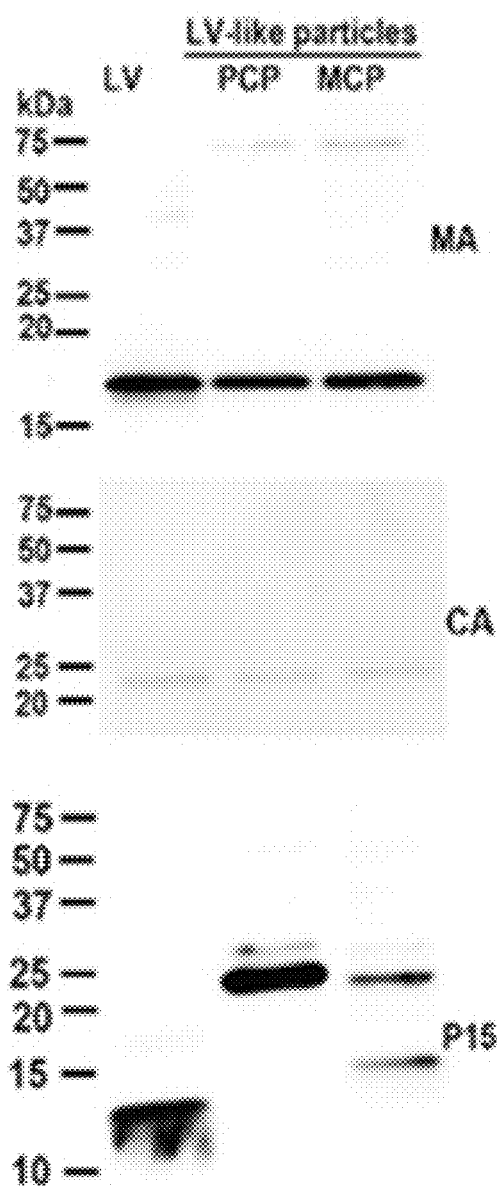
Figure 11:
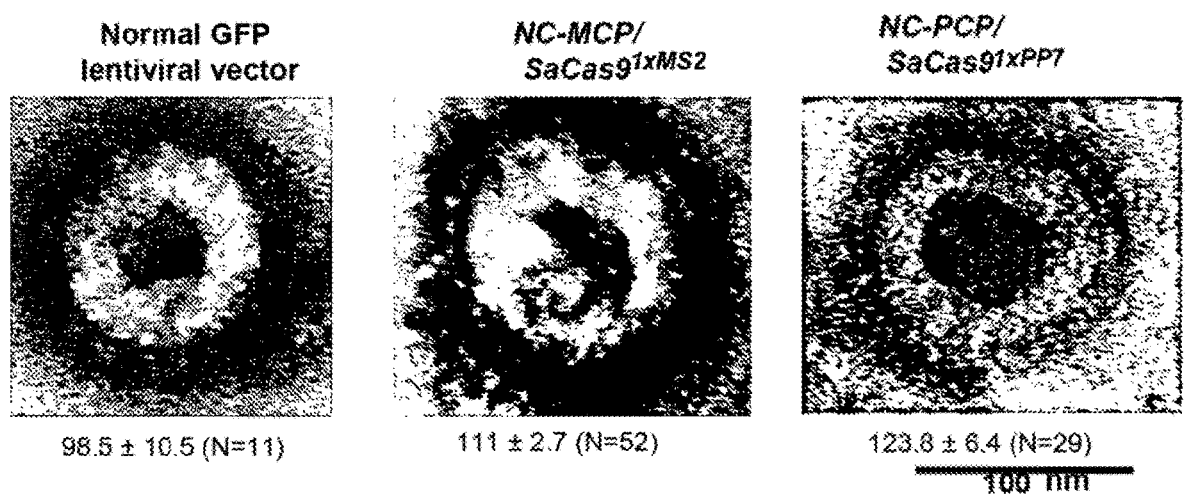
FIG. 11 shows electron microscopy of NC-MCP and NC-PCP modified LVLPs. Shown below the images are the means±SEM with sample numbers in parentheses. No statistical differences were observed between groups.

The Gag precursor protein was processed into mature proteins by sequential protease cleavage with different cleavage speed at different site (FIG. 10D). Antibodies specific for MA (p17), CA (p24) and p15 (from which NC is processed) were used to analyze the sizes of the processed proteins in normal GFP lentiviral vectors, MCP-based SaCas9$^{1\times MS2}$ LVLPs, and PCP-based SaCas9$^{1\times PP7}$ LVLPs. MA and CA protein from all particles showed the same expected size, indicating proper cleavage at the time of analysis (FIG. 10E). Anti-MA antibody detected weak 75 kDa bands in MCP and PCP-based LVLPs. However, similar bands were not detected by anti-CA or anti-p15 antibodies, arguing against the presence of unprocessed Gag precursor proteins. The anti-p15 antibody detected a band slightly smaller than 15 kDa in GFP lentivirus. This size indicates that at the time of analysis, cleavage at sites 4 and 5 did not occur at a detectable level, consistent with their low speed. p15 antibody detected bands between 20-25 kDa in PCP- and MCP-based LVLPs, matching the expected sizes of NC-PCP and NC-MCP fusion proteins in LVLPs (FIG. 10D). In MCP-based LVLPs, an additional small band was detected by the p15 antibody, indicating partial degradation of the p15-MCP fusion protein. These data suggest that the insertion of MCP or PCP in NC had little effect on Gag precursor cleavage at sites 1 (MA/CA), 2 (CA/SP1) and 3 (SP1/NC). The effects on cleavage at sites 4 (NC/SP2) and 5 (SP2/P6) were unknown since at the time of analysis these sites were not cleaved even in normal LV, judged from the size of peptide detected by p15 antibody. Electron microscopy analyses of the MCP- and PCP-based lentiviral-like particles revealed similar particle sizes as GFP lentivirus (FIG. 11).

Figure 12B:
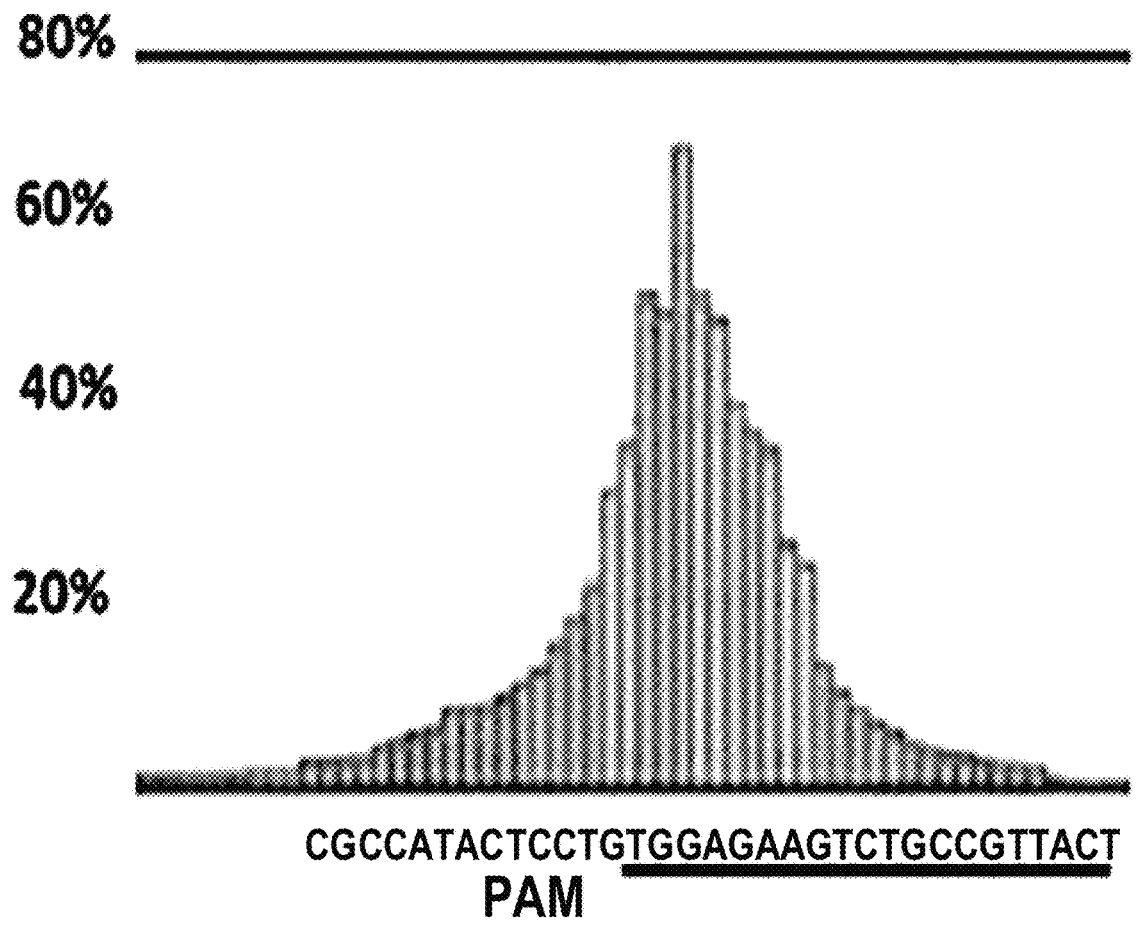

LVLP packaged SaCas9 mRNA enables highly efficient genome editing To further determine the gene editing activity of the SaCas9 mRNA packaged LVLPs, we co-transduced LVLPs (30 ng p24 protein) packaged with SaCas9$^{1\times MS2}$-HBB 3'UTR mRNA into 2.5×10$^4$ GFP reporter cells with 60 ng p24 of HBB sgRNA1-expressing IDLV. 48 hours after transduction, 13% of the reporter cells became GFP-positive. The target DNA for HBB sgRNA1 in the GFP expression cassette was amplified and sequenced by next-generation sequencing. Overall, 86.5% of the alleles had Indels (FIG. 12A), mostly around the predicted cleavage site, which is 3 nt away from the PAM (FIG. 12B). The data demonstrated that delivering SaCas9 mRNA by the LVLPs is highly efficient in generating Indels.

To test the activities of SaCas9 LVLPs on endogenous targets, IDVL expressing sgRNA targeting human IL2RG, a mutation of which causes X-linked severe combined immunodeficiency (SCID-X1), were prepared. In HEK293T cells, 30 ng p24 of SaCas9 LVLPs and 60 ng of IL2RG sgRNA IDLV generated 13% Indels in the target sequence (FIG. 12C). In human lymphoblasts (2×10$^5$ cells), co-transduction of 100 or 500 ng p24 of both types of particles generated 11% or 87.6% Indels in the target sequence (FIG. 12D). Although the Indel rates were different under different conditions, the top most frequently observed mutations were the same. The data showed that the SaCas9 LVLPs could be used to target different target genes in multiple cells.

LVLP packaged SaCas9 mRNA showed lower off-target rates than those of viral vectors. The HBB sgRNA1 was designed to target the HBB Sickle cell mutation and has one nucleotide mismatch with the wild-type HBB sequence (FIG. 12E). As such, the corresponding wild-type HBB gene sequence in the GFP reporter cells can be regarded as the "off-target" for SaCas9/HBB sgRNA1. Indel rates in the wild-type HBB locus were compared when SaCas9 was delivered by LVLP, AAV6, IDLV, or LV expressing SaCas9. To control the percentage of cells having functional SaCas9/HBB sgRNA1, GFP-positive cells were sorted by GFP-activated sorting 48 hours after transduction. At the time of sorting (48 hours after transduction), the percentage of GFP-positive rate was 11.1%, 2.1%, 8.5% and 6.5% for cells treated with LV, LVLP, IDLV, and AAV6 (10$^4$ vg/cell), respectively. Although the cells were treated with the same number of LV, LVLP and IDLV particles based on p24 amount (about 750 ng p24 for 1.25×10$^6$ cells), integration-competent LV treated cells already showed higher GFP-positive rates than IDLV due to continuous CRISPR/Cas9 expression. After sorting, the GFP-positive rates were 95.4%, 88.9%, 93.3%, and 90.8% respectively, suggesting the presence of functional SaCas9/HBB sgRNA1 in most cells under each condition. The DNA from the endogenous HBB locus was then amplified from the sorted cells 1 week after sorting and subjected for next-generation sequencing. The LVLP system had the lowest Indel rate in the endogenous HBB site and LV had the highest (FIG. 12E). These data demonstrate that delivering SaCas9 mRNA by LVLPs for gene editing is safer than other virus delivery systems.

In the cells described above, Indels in 9 possible off-targets predicted by Cas-Offinder) and CRISPOR were searched for. No Indels were detected in 8 of the 9 potential HBB sgRNA1 off-targets even in LV treated cells. However, in off-target 8 (chromosome 20, 33982230 bp-33982337 bp), slightly more Indels were detected in LV-transduced cells than in LVLP transduced cells (FIG. 12F).

Figure 13:
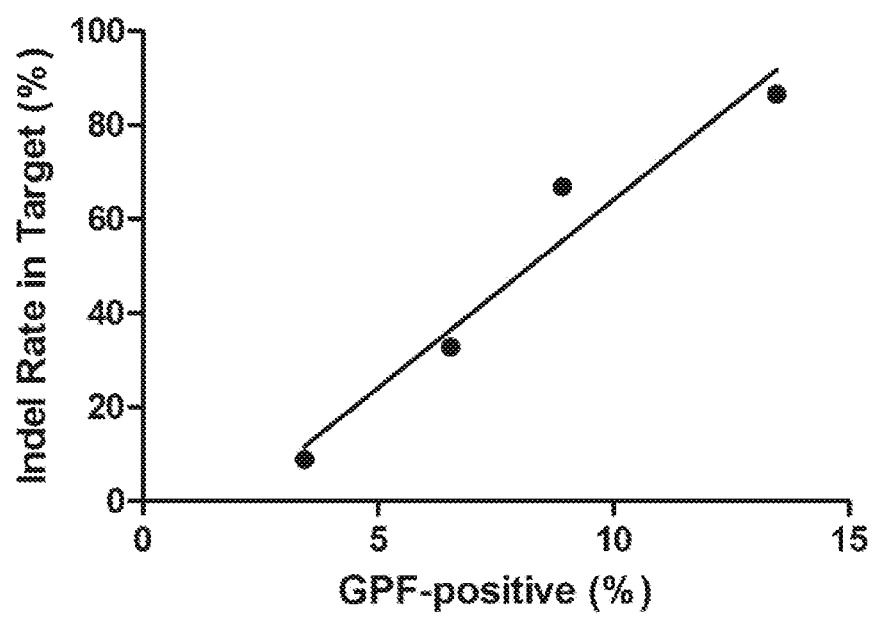
FIG. 13 shows the relationship between target sequence Indel rates and GFP-positive rates in GFP reporter cells. The four data points were from GFP-reporter cells transduced with SaCas9$^{1 \times MS2}$ LVLPs (about 750 ng p24 for 1.25×10$^6$ cells), SaCas9 AAV6 (10$^4$ vg/cell), SaCas9 IDLV (about 750 ng p24 for 1.25×10$^6$ cells), and SaCas9$^{1 \times MS2}$-HBB 3'UTR (30 ng p24 for 2×5×10$^4$ cells). The target sequences in the GFP-expression cassette were amplified and subjected to next generation sequencing. The Indel rates were plotted against the GFP-positive rates obtained by flow cytometry analysis.

Since there were GFP-reporter cells transduced with different particles that showed different percentages of GFP-positive cells (cells used in FIG. 12A and unsorted cells for FIG. 12E), the relationship between GFP-positive percentages and target sequence (in the GFP-expression cassette) Indel rates in these cells was analyzed. It was found that Indel rates increased with the GFP-positive percentage linearly (FIG. 13, $r^2$=0.9497 by linear regression). The data validated the GFP-reporter assay described herein for comparing the genome editing activities of different particle types.

Example 11. Packaging Cas9/sgRNA RNP into Lentivirus-Like Particles

Plasmids pMD2.G (Addgene #12259), psPAX2-D64V (Addgene #63586), pCSII-EF-miRFP709-hCdt (1/100) (Addgene #80007), and pX601-AAV-CMV::NLS-SaCas9-NLS-3×HA-bGHpA; U6::BsaI-sgRNA (Addgene #61591) were purchased from Addgene and have been described previously. Plasmids are described in Example 10 or Table 2. All constructs generated were sequence confirmed. Sequence information for primers, oligoes, and synthesized DNA fragments is in Table 10.

GFP reporter assays for gene editing activities The EGFP reporter cells described above were used to detect gene editing activity of SaCas9/human beta hemoglobin (HBB) sgRNA1 or SaCas9/IL2RG-sgRNA1 on the inserted target sequences in the GFP-reporter cassette. The GFP-reporter cells expressed no EGFP due to the disruption of the EGFP reading frame by the insertion of the HBB sickle mutation and IL2RG target sequences between the start codon and the second codon of EGFP coding sequence. Indels formed after gene editing may restore the EGFP reading frame, resulting in EGFP expression. GFP-positive cells were analyzed by fluorescence microscopy or flow cytometry (BD Biosciences, Accuri C6) as described above and in Lu et al., Nucleic Acids Res. 2019 doi: 10.1093/nar/gkz093.

AAV6 virus production and transduction Adeno-associated virus expressing SaCas9 and HBB sgRNA1 was made from the AAV vector pSaCas9 (expresses SaCas9) and pSaCas9-HBB-sgRNA1 (expresses HBB sgRNA1, and contains donor template for homologous recombination to change the wild-type HBB gene to the Sickle mutation) respectively. AAV serotype 6 (AAV6) production and quantification were performed by Virovek, Inc. (Hayward, CA). AAV6 transduction was performed in serum-free medium or OPTI-MEM at a titer of 10$^3$-10$^4$ virus genome/cell. 24 hours after transduction the cells were returned to serum-containing growth medium.

Lentivirus and LVLP production Lentiviral vector plasmid pCK002-HBB-sgRNA1 expressing both SaCas9 and HBB sgRNA1 was used to produce integration-competent lentiviral vector (packaged by packaging plasmid pspAX2) and integration-defective lentiviral (IDLV) vector (packaged by packaging plasmid pspAX2-D64V) as described above. SaCas9 mRNA LVLP production is also described above. To produce Cas9/sgRNA RNP LVLPs, 13 million actively dividing HEK293T cells, grown in a 15-cm dish were changed to 10 ml Opti-MEM. 16 µg of ABP-modified packaging plasmid pspAX2-D64V-NC-ABP (ABP could be MCP, PCP, λ N22 or COM), 6 µg envelope plasmid (pMD2.G), and 16 µg plasmid DNA co-expressing SaCas9 and the aptamer-modified sgRNA were mixed in 1 ml Opti-MEM. 76 ul of 1 mg/ml polyethylenimine (PEI, Polysciences Inc.) was mixed in 1 ml Opti-MEM. The DNA mixture and the PEI mixture were then mixed and incubated at room temperature for 15 mins. The DNA/PEI mixture was then added to the cells in Opti-MEM. 24 h after transfection, the medium was changed to 15 ml Opti-MEM and the Cas9/sgRNA RNP LVLPs were collected twice with one collection each 24 h. The supernatant was spun for 10 min at 500 g to remove cell debris before further processing described below.

Concentrating lentivirus and LVLPs The collected and cleared supernatant was concentrated with the KR2i TFF System (KrosFlo® Research 2i Tangential Flow Filtration System) (Spectrum Lab, Cat. No. SYR2-U20) using the concentration-diafiltration-concentration mode. Typically, 150-300 ml supernatant was first concentrated to about 50 ml, diafiltrated with 500 ml to 1000 ml PBS, and finally concentrated to about 8 ml. The hollow fiber filter modules were made from modified polyethersulfone, with a molecular weight cut-off of 500 kDa. The flow rate and the pressure limit were 80 ml/min and 8 psi for filter module D02-E500-05-N, and 10 ml/min and 5 psi for the filter module C02-E500-05-N.

Lentiviral vector and LVLP quantification Viral titer was determined by p24 based ELISA (Cell Biolabs, QuickTiter™ Lentivirus Titer Kit Catalog Number VPK-107). When unpurified samples were assayed, the viral particles were precipitated according to the manufacturer's instructions so that the soluble p24 protein was not detected.

Western blotting analysis of viral proteins from lentivirus and LVLPs Purified lentivirus or LVLPs (200 ng p24 by ELISA) were lysed in 20 µl of 1× Laemmli sample buffer. The proteins in each sample were separated on SDS-PAGE gels and analysed by Western blotting. The antibodies used include mouse monoclonal anti-SaCas9 antibody (Millipore Sigma, MAB131872, clone 6F7, 1:1000), rabbit polyclonal HIV1 p17 antibody for MA (ThermoFisher Scientific, Cat No. PA1-4954, 1:1000), rabbit polyclonal HIV1 p15 antibody for NC (Abcam, Cat No. ab66951, 1:1000) and p24 mouse monoclonal antibody for CA (Cell Biolabs, Cat No. 310810, 1:1000). HRP conjugated anti-Mouse IgG (H+L) (ThermoFisher Scientific, Cat No. 31430, 1:5000) and anti-Rabbit IgG (H+L) (Cat No. 31460, 1:5000) secondary antibodies were used in Western blotting. Chemiluminescent reagents (Pierce) were used to visualize the protein signals under the LAS-3000 system (Fujifilm).

RNA isolation from lentivirus or LVLPs and RT-qPCR analysis A miRNeasy Mini Kit (QIAGEN Cat No. 217004) was used to isolate RNA from concentrated lentivirus or LVLPs. The QuantiTect Reverse Transcription Kit (QIAGEN) was used to reverse-transcribe the RNA to cDNA. For sgRNA reverse transcription, half random primers provided in the kit and half sgRNA-specific primers (sgRNA-R2) were used for reverse transcription. Custom designed hydrolysis probes specific for SaCas9 and EGFP (ThermoFisher Scientific) were used in qPCR, together with TaqMan Universal PCR Master Mix (ThermoFisher Scientific). For HBB sgRNA1 and HBB sgRNA1$^{Tetra-com}$ detection, sgRNA-F1 (SEQ ID NO: 30) and s0067RNA-R3 were used as primers in SybrGreen based RT-qPCR. PCR was run on an ABI 7500 instrument.

Removing membrane from LVLP core capsids Lentivirus-like particles were transiently treated with 0.5% Triton X-100 as described in Wiegers et al. J. Virol. 1998, 72: 2846-2854. Briefly, LVLPs were centrifuged with a Sorvall T-890 rotor (2 h at 120 000 g) through step gradients containing a 1 ml layer of 10% sucrose in STE [100 mM NaCl, 50 mM Tris/HCl (pH 7.5), 1 mM EDTA] with or without 0.5% Triton X-100, and a cushion of 2 ml 20% sucrose in STE solution. Pelleted virus was directly lysed for Western blotting or RT-qPCR analysis.

Lentivirus and LVLP transduction Various amounts of concentrated lentivirus or LVLPs (equivalent to 10~300 ng p24 protein) were added to $2.5 \times 10^4$ cells grown in 24-well plates, with 8 µg/ml polybrene. Unconcentrated virus containing supernatant was diluted with fresh medium at a 1:1 ratio to transduce cells. The cells were incubated with the particle containing medium for 12-24 hours, after which normal medium was replaced.

Gene editing in human cells For gene editing with Cas9 expressed from AAV serotype 6, the SaCas9 expressing AAV6 and the HBB sgRNA1 expressing AAV6 were co-transduced into GFP reporter cells. For gene editing with LV or IDLV (packaged with packaging plasmids containing a D64V mutation in the integrase) expressing both SaCas9 and HBB sgRNA1, virus equivalent to 10-300 ng p24 was used to transduce $2.5 \times 10^4$ cells in 24 well plates. For gene editing with SaCas9 mRNA LVLPs, various amounts of SaCas9 mRNA LVLPs (quantified by p24) were co-transduced into HEK293T cells or the GFP reporter cells with an IDLV expressing HBB sgRNA1. For transduction with Cas9/sgRNA RNP LVLPs, various amounts of Cas9/sgRNA RNP LVLPs were transduced into human cells. 48-72 hours after transduction, gene editing activity was analyzed by GFP-reporter assay or next-generation sequencing.

To examine gene editing in human lymphoblastoid cells immortalized by Epstein-Barr virus transformation, human lymphoblastoid cell lines with or without sickle cell mutations were purchased from Corrie Institute (GM16265, with Sickle cell mutation; ID00085, with mutation in IL2RG gene). The lymphoblasts were cultured in RPMI 1640 with 2 mmol/L L-glutamine and 15% fetal bovine serum at 37° C. under 5% carbone dioxide. For LVLP and DLV transduction, $2 \times 10^5$ cells were added to 0.5 ml RPMI growth medium. Then Cas9/sgRNA RNP LVLPs were added to the cells. Polybrene was added in the medium to a final concentration of 8 µg/ml. Fresh medium was replaced twenty hour hours after transduction. The cells were collected 72 hours after transduction for DNA analysis by next-generation sequencing.

Next-generation sequencing and data analysis The endogenous HBB target sequence and IL2RG target sequence, and the HBB and IL2RG target sequence in the integrated GFP-expression cassette were amplified for sequencing analysis. A nested PCR strategy was used to amplify the endogenous HBB target sequence to avoid amplifying the sequence from the viral vector template. First, primers HBB-1849F and HBB-5277R were used to amplify the 3.4 kb region from the HBB gene locus. These two primers cannot amplify sequences from the templates in the viral vectors. Then HBB-F1 and the HBB-F2 primers were used to amplify the target DNA for sequencing. To amplify the endogenous IL2RG target sequence, primers IL2RG-1029F and IL2RG-3301R were used to amplify the target region from the treated cells (unable to amplify sequences from the templates in the viral vectors), then primers IL2RG-F1 (SEQ ID NO: 90) and IL2RG-3301R were used to amplify the target DNA from the first PCR product for sequencing. To amplify the HBB target sequence from the integrated EGFP reporter for sequencing, Reporter-F and Reporter-R1 primers were used. The proofreading HotStart® ReadyMix from KAPA Biosystems (Wilmington, MA) was used for PCR. The purified PCR products were shipped to Genewiz Inc. (Morrisville, NC) to perform next generation sequencing (Amplicon EZ). Usually 50,000 reads/amplicon were obtained.

After removing the 3' linker and 5' barcode sequences, the resulting reads were submitted to the online Cas-Analyzer software for mutation analysis. When submitting the reference sequence, the primer sequences were excluded if they were at least 12 nt away from the sgRNA target. Otherwise, primer sequences were included in the reference. Only those readings containing both the 5' 12 nt and 3' 12 nt of the reference sequence (primer sequences excluded) were included in Indel analysis. The total Indel rate was the difference between 1 and the percentage of readings without mutation. The top 8-10 most frequently observed readings were presented.

Monitoring the speed of GFP-positive cell emergence $2.5 \times 10^4$ GFP-reporter cells seeded in 24-well plates were transduced with 50 ng p24 of Cas9/IL2RG sgRNA1$^{Tetra-com}$ RNP LVLPs, or co-transduced with 100 ng p24 of Cas9 mRNA LVLPs and 100 ng p24 of IDLV expressing IL2RG sgRNA1. The cells were then incubated in the IncuCyte S3 system (Essen BioScience, Inc. Ann Arbor, Michigan) for timed GFP fluorescence scanning. Two wells from each treatment and 9 spots from each well were scanned. The scanning started right after transduction and the cells were scanned once every two hours for 48 hours. The GFP-positive rate of each image was calculated by dividing the GFP-positive area by the phase area (area occupied by cells) in that image.

Statistical analysis GraphPad Prism software was used for statistical analyses. T-tests were used to compare the averages of two groups. Analysis of Variance (ANOVA) was performed followed by Tukey post hoc tests to analyze data from more than two groups. Bonferroni post hoc tests were performed following ANOVA in cases of two factors. $p<0.05$ was regarded as statistically significant.

Replacing the sgRNA Tetraloop with aptamer best preserved the Cas9/sgRNA RNP activity. Packaging Cas9/sgRNA RNP into lentivirus-like particles was tested. The overall strategy was to incorporate ABP into lentivirus-like particles via fusing ABP with the lentiviral nucleocapsid protein (NC) as described above and add the corresponding aptamer into sgRNA, which complexes with Cas9 protein, and forms Cas9/sgRNA RNP during lentiviral capsid assembly. The Cas9/sgRNA RNP is packaged into the lentiviral capsids via the specific aptamer/ABP interaction (FIG. 14A, right diagram). After escaping from the endosomes, the Cas9/sgRNA RNP is released into the cytoplasm, following capsid uncoating, and the RNP complex then enters the nucleus to perform gene editing.

In order for this strategy to work, it is necessary to find a location in the sgRNA scaffold best tolerating aptamer insertion and preserving the nuclease activity after complexing with Cas9. The MS2 aptamer was used, since it mediated efficient Cas9 mRNA packaging. Three locations were tested: inserting MS2 into the Stem loop 2 (ST2), replacing the Tetraloop with MS2, and adding MS2 after the 3' end of the sgRNA (FIG. 14B). When the plasmid DNAs co-expressing SaCas9 and the modified sgRNAs targeting HBB sgRNA1 were transfected into the GFP-reporter cells, Indels in HBB sgRNA1 target sequence may restore GFP expression. It was found that adding one MS2 at any of the three locations preserved gRNA activity in transfection experiments, although replacing the Tetraloop or the ST2 loop slightly decreased the percentage of GFP-positive reporter cells (FIG. 14C). The addition of two MS2 aptamers was also tested. One aptamer replaced the Tetraloop, and the other one was in the ST2 loop or at the 3' end. In both cases, the GFP-positive percentages were consistently decreased, agreeing with observations that more than one copy of MS2 decrease RNA stability. Thus, one copy of aptamer was used in further experiments.

Figures 15A, 15B, 15C:
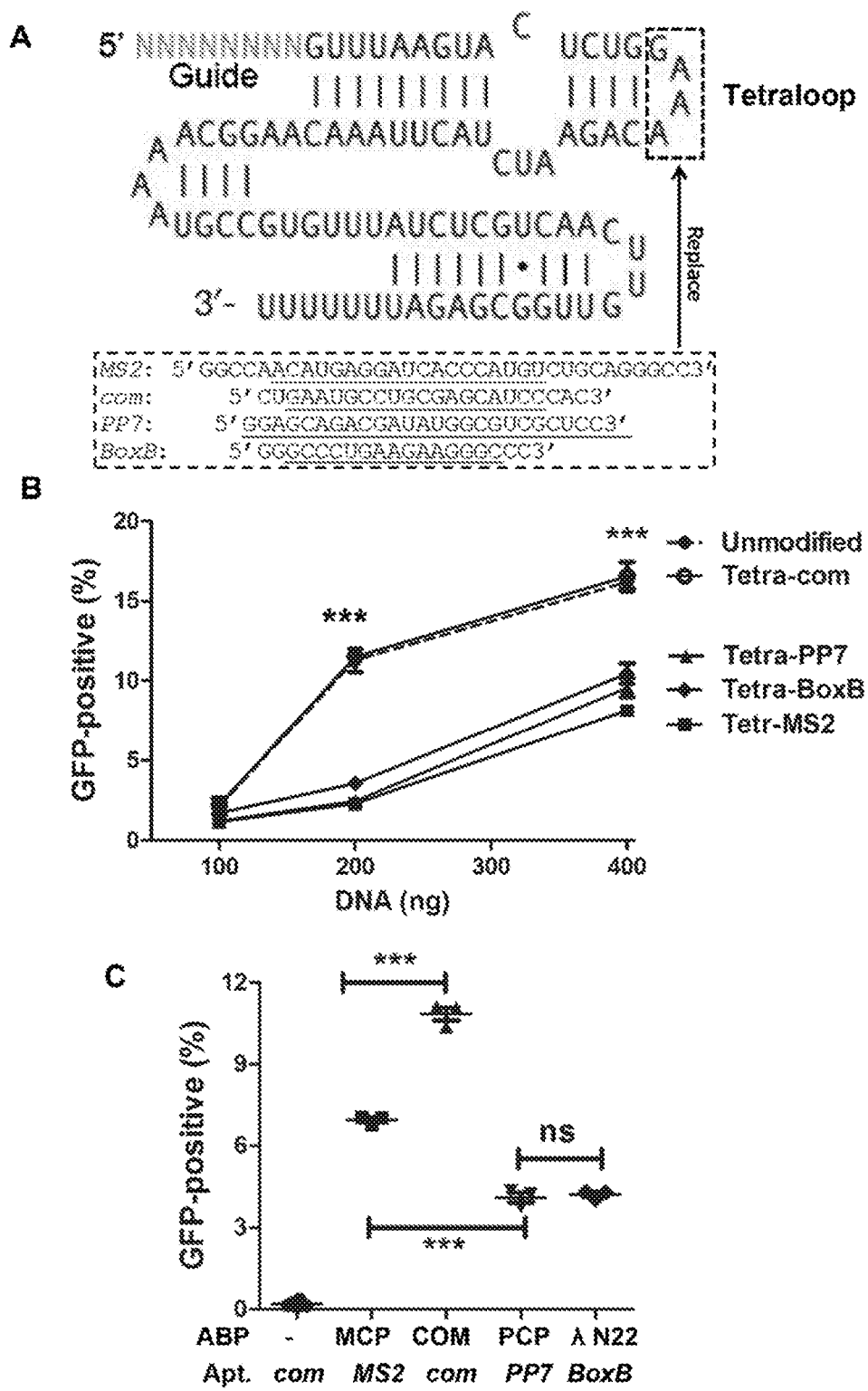
FIGS. 15A-15C provide comparisons for aptamer/ABP pairs for packaging CRISPR/Cas9 RNA in LVLPs.

Whether these MS2-modified sgRNAs could be packaged and delivered by LVLPs was also tested. SaCas9 protein and MS2-modified HBB sgRNA1 were co-expressed during LVLP preparation, and the LVLPs were transduced into our GFP reporter cells. Flow cytometry analysis found that LVLPs containing HBB sgRNA1 with MS2 at the Tetraloop (HBB sgRNA1$^{Tetra\ MS2}$) gave the most GFP-positive cells, LVLPs containing HBB sgRNA1 with MS2 at the 3' end (HBB sgRNA1$^{3'-MS2}$) followed. In contrast with transfection experiments, where MS2 at Stem loop II (HBB sgRNA1$^{ST2\ MS2}$) was active, HBB sgRNA1$^{ST2\ MS2}$ LVLPs had hardly any gene editing activity (FIG. 14D), suggesting that either HBB sgRNA1$^{ST2\ MS2}$ could not be packaged or could not survive the post-transduction process.

com/COM is an aptamer/ABP pair for sgRNA packaging Knowing that replacing the Tetraloop with aptamers performed the best, additional aptamers that could be used to replace the Tetraloop were investigated. Four aptamers, MS2 (23), PP7 (24), BoxB (25) and com (26), have been used in sgRNAs for target-binding purposes (22, 27-29). The activities of HBB sgRNA1 with various aptamers (MS2, PP7, BoxB and corn) replacing the Tetraloop (FIG. 15A) were tested. When plasmid DNA co-expressing SaCas9 and various aptamer-modified HBB sgRNA1 was transfected into GFP reporter cells, replacing Tetraloop with com aptamer generated the same rates of GFP-positive cells as the unmodified sgRNA, while replacing Tetraloop with the other three aptamers significantly reduced the GFP-positive rates (FIG. 15B).

Figure 16:
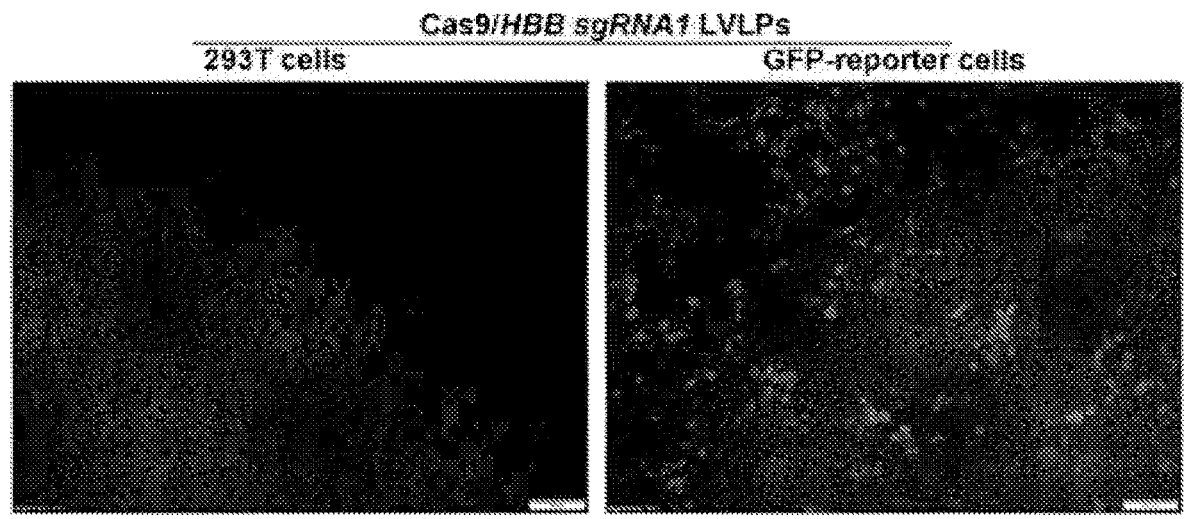
FIG. 16 shows that the LVLPs generated GFP-positive cells in GFP-reporter cells but not in HEK293T cells. $2.5 \times 10^4$ cells were seeded in 24-well plates and 150 ng p24 of Cas9/HBB sgRNA1 RNP LVLPs were transduced into the cells. The cells were analyzed by fluorescent microscopy 48 hours after transduction.

Packaging of HBB sgRNA1 into LVLPs with different aptamers was tested. For this purpose, MCP (MS2 coat protein, binding to MS2), PCP (PP7 coat protein, binding to PP7), λ N22 peptide (binding to BoxB) and COM (binding to corn) modified packaging plasmids, where ABPs were inserted after the second zinc finger domain of nucleocapsid protein (NC) as described above, were used to make LVLPs containing RNPs in which Cas9 complexed with various modified HBB sgRNA1. These LVLPs were transduced into GFP-reporter cells. Flow cytometry found that LVLPs generated by com/COM pair had the most GFP-positive cells, followed by those generated by MS2/MCP. PP7/PCP and BoxB/λ N22 generated LVLPs had the lowest activity (FIG. 15C). GFP-positive cells could only be observed when these LVLPs were used to transduce GFP-reporter cells but not HEK293T cells, excluding possible contamination of GFP-expressing DNA or virus (FIG. 16).

Figure 17:
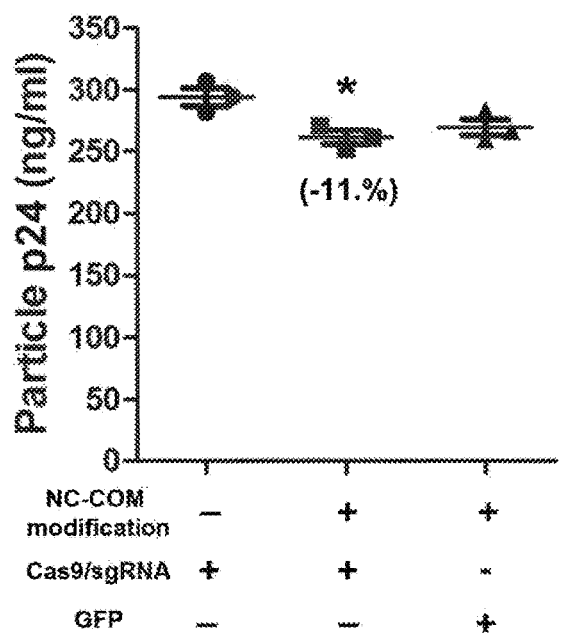
FIG. 17 provides analysis of NC-COM modification on particle assembly efficiency. Packaging plasmid with or without COM modification was used to package Cas9/HBB sgRNA1, or GFP lentiviral vector. Transfection was done in 6-well plates; p24 was assayed in supernatants collected between 24-48 hours after transfection. * indicates p<0.05 by Tukey's Multiple Comparison Test following ANOVA.

Since com-COM combination obtained the best results, whether COM-modification of the packaging plasmid impairs particle assembly was tested. A marginal 11% decrease in particle assembly efficiency compared with the unmodified packaging plasmid (FIG. 17) was observed. This slight decrease should not prevent production of sufficient particles. Through these experiments, the location (Tetraloop) and the aptamer/ABP pair (com/COM) for the most efficient packaging of Cas9 RNPs (or Cas9 mRNA and sgRNA) into lentiviral capsids was identified.

Figure 18A:
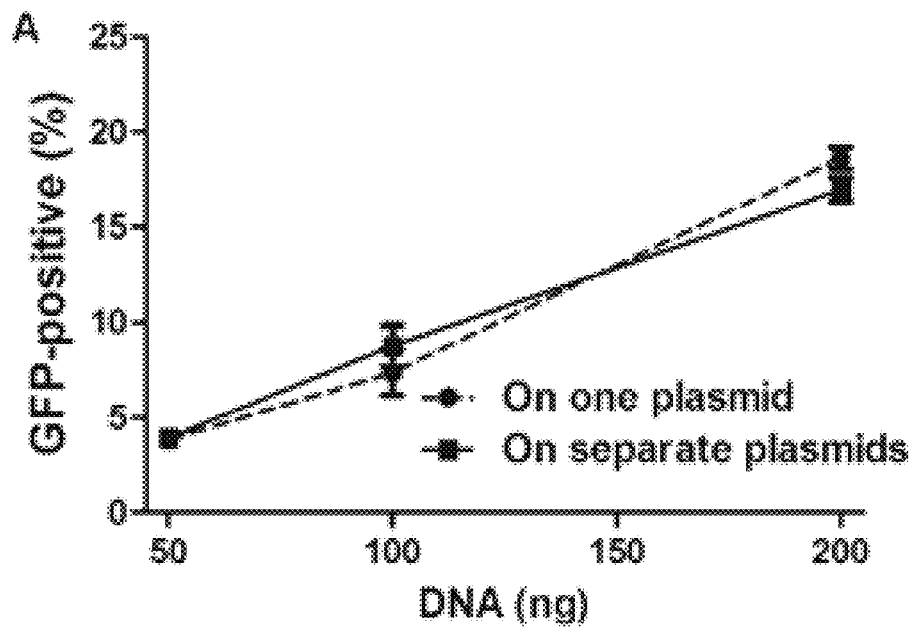
FIG. 18A-18G show that RNP accounted for the gene editing activity.
Figure 18B:
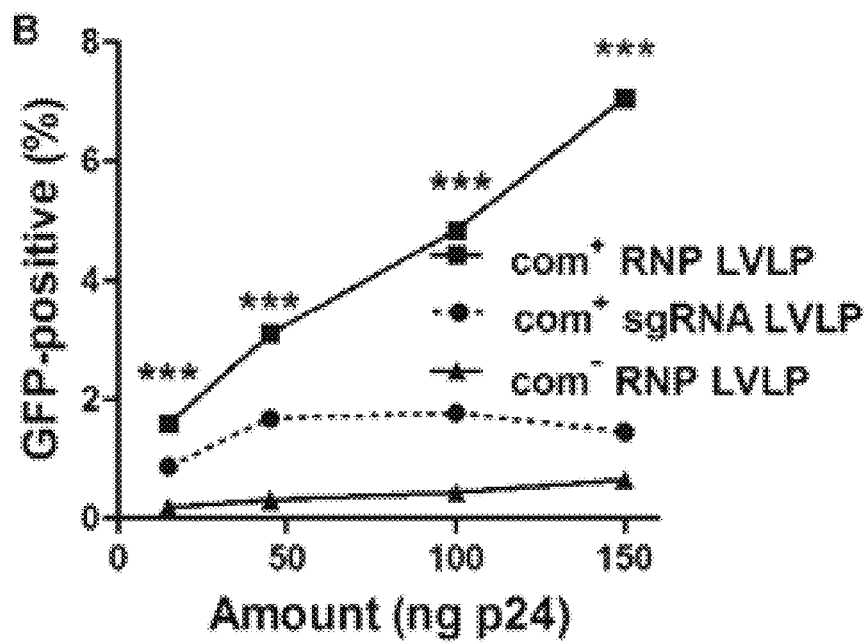

Cas9/sgRNA RNPs in the LVLPs accounted for the observed gene editing activity Although designed to package Cas9/sgRNA RNPs, considering previous observations that aptamer-free SaCas9 mRNA could be packaged for unknown mechanisms, the observed gene editing activity could be from the co-packaged SaCas9 mRNA and sgRNA. To determine whether Cas9/sgRNA RNP or SaCas9 mRNA/sgRNA contributed to the observed gene editing activity, the Cas9 expression cassette was separated from the HHB sgRNA1$^{Tetra-com}$ expression cassette into two different plasmids. When the two plasmids were co-transfected into GFP reporter cells, they generated GFP-positive cells as efficiently as transfecting a single plasmid containing both expression cassettes (FIG. 18A). However, when HHB sgRNA1$^{Tetra-com}$ was packaged into LVLPs, in the absence of Cas9 expression, these LVLPs had little gene editing activity when co-transduced into GFP-reporter cells with validated functional Cas9 mRNA LVLPs (FIG. 18B).

Figure 18C:
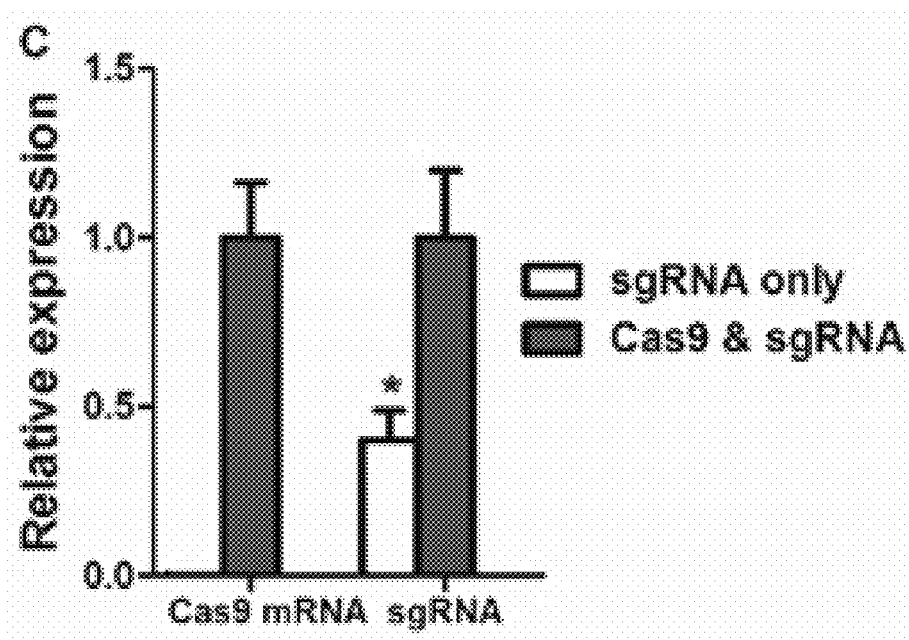

Cas9 protein is needed to protect the stability of sgRNA in cells. This was confirmed by expressing HBB sgRNA1$^{Tetra-com}$ alone or co-expressing sgRNA with Cas9. Co-expressing Cas9 significantly increased the expression of HBB sgRNA1$^{Tetra-com}$ (FIG. 18C). After DNA transfection, the sgRNA was constitutively expressed. Whereas after transduction, the sgRNAs had to complete the post-transduction intracellular traffic and there was no new sgRNA generation. Thus, it is expected that the protective effects of Cas9 protein on sgRNA would be more critical. These data suggest that sgRNA instability, especially sgRNA's inability to survive the post-transduction intracellular traffic, most likely explains why singly packaged HHB sgRNA1$^{Tetra-com}$ LVLPs were inactive after co-transduction with Cas9 mRNA LVLPs.

These experiments show that, in addition to co-packaged Cas9 mRNA and sgRNA, the packaged Cas9/sgRNA RNP-scan also be used for gene editing. To examine the presence of Cas9 protein in the HHB sgRNA1$^{Tetra-com}$ LVLPs packaged with Cas9 expression, Western blotting analyses on the concentrated LVLPs (FIG. 18D) was performed. Viral proteins MA (p17) and CA (p24) were detected, as expected in size and amount, indicating that the processing of MA and CA was unaffected. Detection of p15, from which NC was processed, showed a band between 10 kd and 15 kd in GFP lentivirus (lane 1) and in LVLPs generated with the unmodified packaging plasmid (lane 3). In LVLPs generated by a NC-MCP modified packaging plasmid (lane 2), a strong band between 15~20 kd was detected, which was slightly smaller than the expected 21.8 kd NC-MCP fusion protein. However, in LVLPs generated by NC-COM modified packaging plasmid (lanes 4-6), a band slightly smaller than 15 kd was detected, which was slightly smaller than the expected 18.7 kd of the NC-COM fusion protein. Anti-p15 detected bands slightly smaller than expected in all samples (including GFP lentivirus), which could be caused by the SDS-PAGE system or by partial degradation of the p15 or p15-fusion proteins.

Figure 18D:
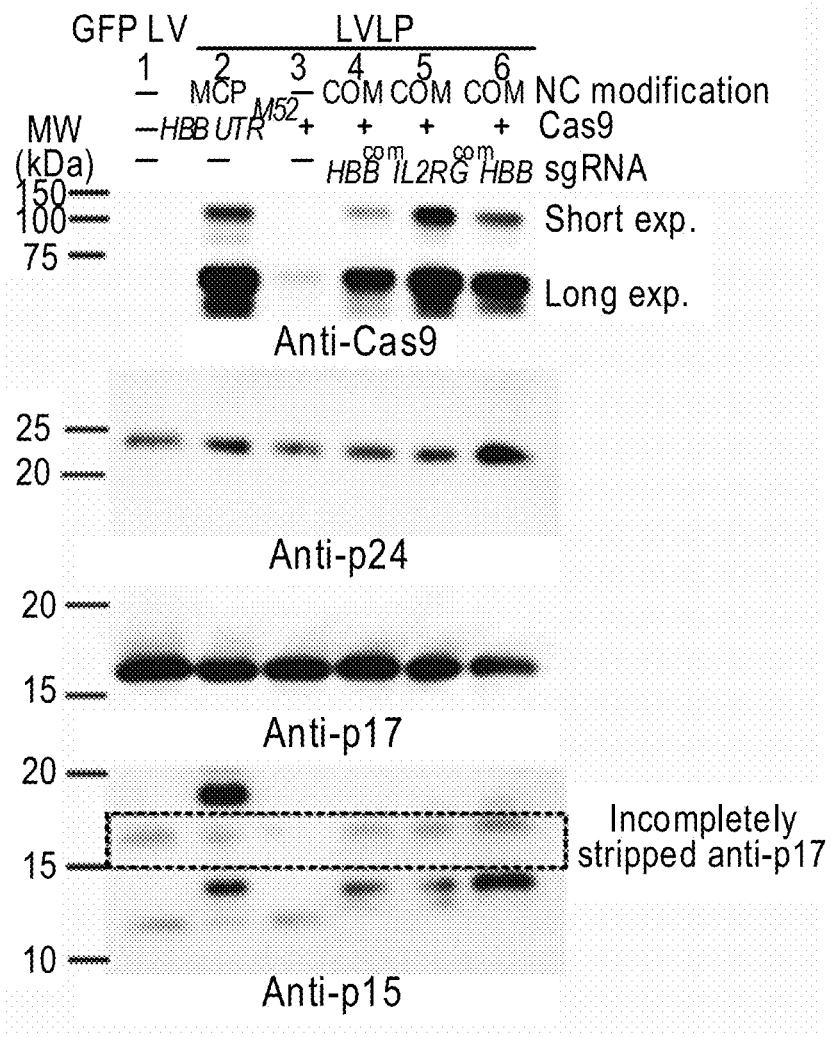
Figure 18E:
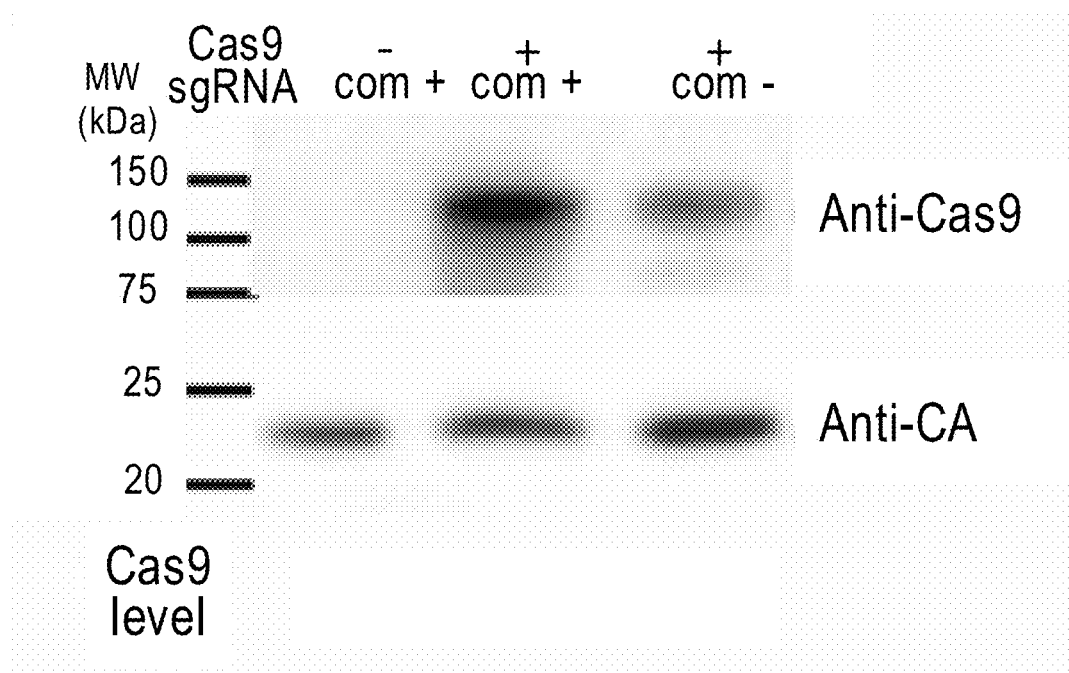

Surprisingly, Cas9 protein was detected in all types of LVLPs produced in cells with Cas9 expression, including samples without sgRNA (lane 3, observed after longer exposure), or without tetra-com aptamer in the sgRNA (lane 6). However, Cas9 was not detected in GFP-expressing lentivirus (FIG. 18D, lane 1). The detection of Cas9 proteins in the LVLPs suggested that Cas9 protein could contribute to the observed gene editing activities, but could not explain the lack of activity from LVLPs containing Cas9 protein and sgRNA without com-modification.

com-modification of sgRNA was necessary for efficiently packaging Cas9/sgRNA RNPs into the core capsid of LVLPs Cas9 protein was detected in LVLPs with HBB sgRNA1 without a com-modification (FIG. 18D, lane 6). These showed little gene editing activity in GFP-reporter assay (FIG. 18B). Therefore, the relative levels of Cas9 protein (normalized to capsid protein CA) in LVLPs with and without com aptamer were compared to determine if the amount of Cas9 protein per particle explains the difference in activity. It was found that the Cas9/HBB sgRNA1$^{Tetra-com}$ LVLPs (com$^+$) contained 2.9 fold Cas9 protein of Cas9/HBB sgRNA1 LVLPs (FIG. 18E, com$^-$).

Figure 18F:
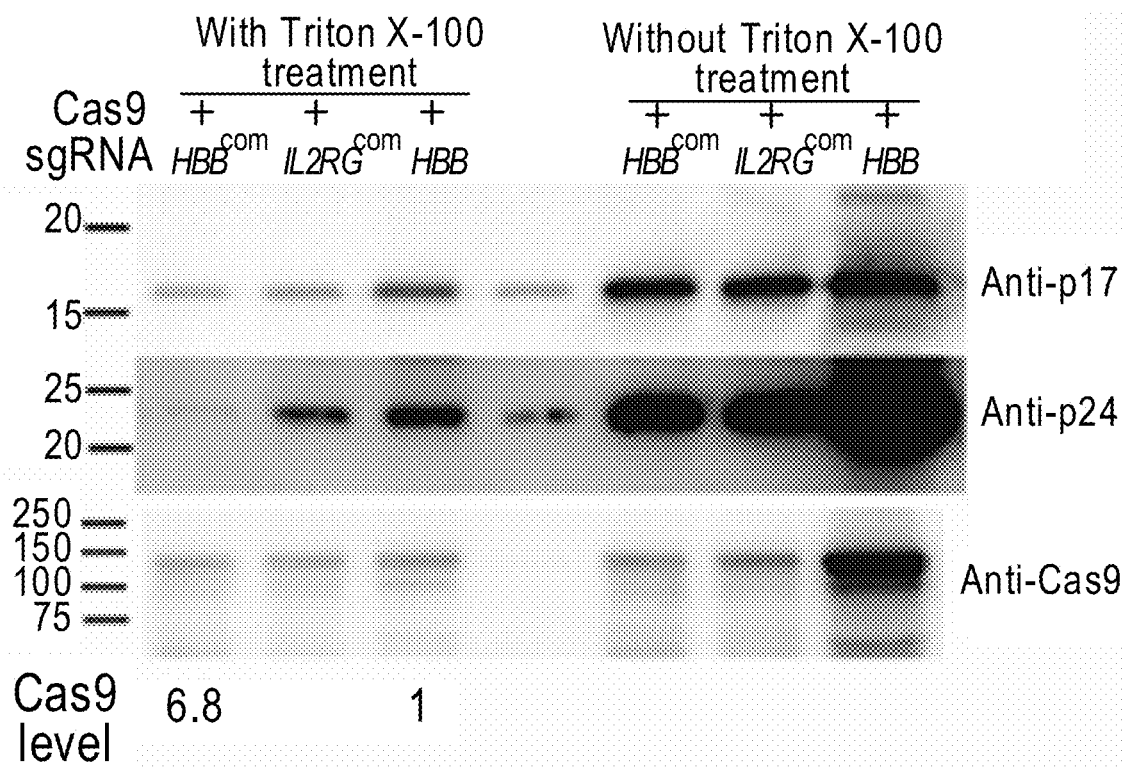

Since there was a less than 3-fold difference in Cas9 protein content, the compartmentalization of Cas9 protein was studied. Since the LVLPs were concentrated by tangential flow filtration, the LVLPs could have membrane structures, including exosomes. It was postulated that RNPs within the capsid core most likely preserve gene editing activity during the post-transduction intracellular traffic, thus the amount of detergent-resistant Cas9 protein matters. To detect Cas9 protein within the capsid core, the particles were transiently treated with 0.5% Triton X-100 to eliminate Cas9 proteins associated with membrane vesicles and capsid envelope. Triton X-100 treatment greatly decreased the amount of MA protein (detected by p17 antibody) associated with the capsid envelope, indicating that the treatment worked (FIG. 18F). The CA protein was reduced to variant degrees, which could reflect different core capsid stability of different types of particles. However, the Cas9 protein amount was greatly reduced in LVLPs with the unmodified sgRNA, but only slightly reduced in the LVLPs with Tetra-com modified sgRNA. Cas9/HBB sgRNA1$^{Tetra-com}$ LVLPs had 6.8 fold detergent-resistant Cas9 protein compared to Cas9/HBB sgRNA1 LVLPs. These data show that Tetra-com modification of sgRNA facilitated the packaging of Cas9 protein in the detergent-resistant capsid core, and the amounts of core-protected Cas9/sgRNA RNPs correlated with gene editing activity.

Figure 18G:
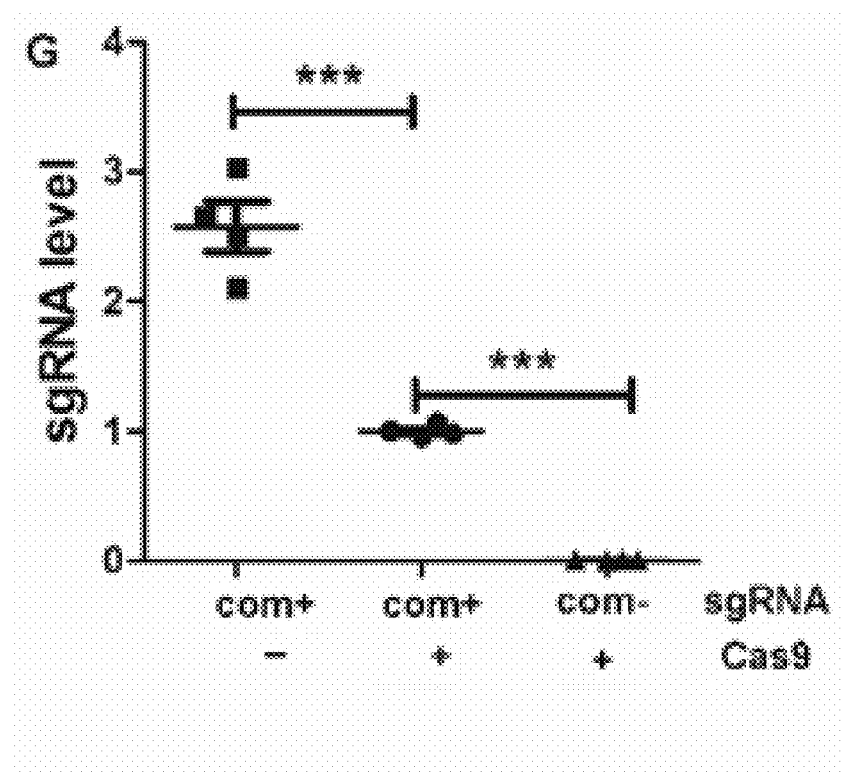
Figure 19:
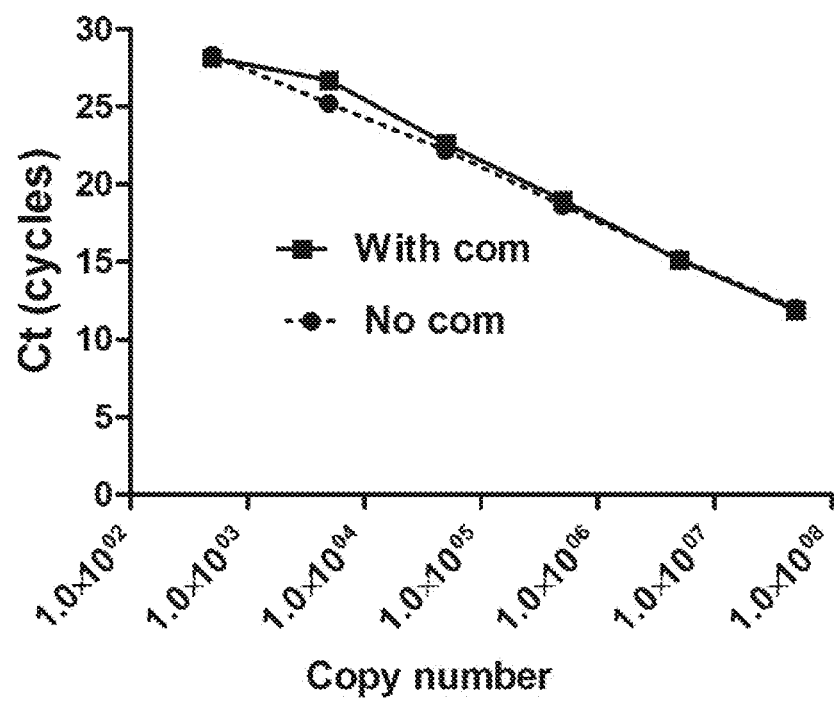
FIG. 19 shows standard curves when the same primer pairs were used to amplify the sgRNA DNA sequence with and without com aptamer.

The importance of com-aptamer on sgRNA packaging was examined by RT-qPCR analysis of sgRNA content in LVLPs. Although the PCR primers used produced amplicons of different sizes from HBB sgRNA1 and HBB sgRNA1$^{Tetra-com}$, due to the presence and absence of the 23 nt com-aptamer, the primers generated very similar standard curves when variant amounts of plasmid DNA were used as the templates for qPCR (FIG. 19), demonstrating similar amplification efficiency for the com-positive and com-negative sgRNA sequences. In LVLPs without Cas9 protein, the HHB sgRNA1$^{Tetra-com}$ level was 2.5 times greater than in LVLPs with Cas9 protein. However, in LVLPs with Cas9 and com-negative HBB sgRNA1, the sgRNA level was less than 1/50 of that in LVLPs with Cas9 and HHB sgRNA1$^{Tetra-com}$ (FIG. 18G). These data showed that the packaging of sgRNA was com-aptamer but not Cas9 protein-dependent. Cas9 protein slightly decreased the amount of com-modified sgRNA packaged, most likely due to the negative effects of Cas9/sgRNA association on com/COM interaction. Thus these data showed that the packaging of Cas9 protein into the capsid core is mediated by sgRNA$^{Tetra-com}$ via com/COM interaction. Although Cas9 protein is not needed for packaging sgRNA into the LVLPs, it is needed to protect the sgRNAs during transduction. Except for experiments described in FIG. 18, where sgRNA with and without com-modification were used for comparison, com-modified sgRNA was used in all subsequent experiments. Hereafter, Cas9/sgRNA RNP was used to indicate Cas9/sgRNA$^{Tetra-com}$ RNP for simplicity.

Cas9/sgRNA RNP LVLPs enabled efficient genome editing and improved discrimination of off-targets The gene editing activities of Cas9 RNP LVLPs described and the Cas9 mRNA LVLPs described above were compared. Cas9/HHB sgRNA1 RNP LVLPs showed comparable gene editing activities as compared to the SaCas9 mRNA LVLPs in GFP-reporter assays (FIG. 20A).

Figure 20D:
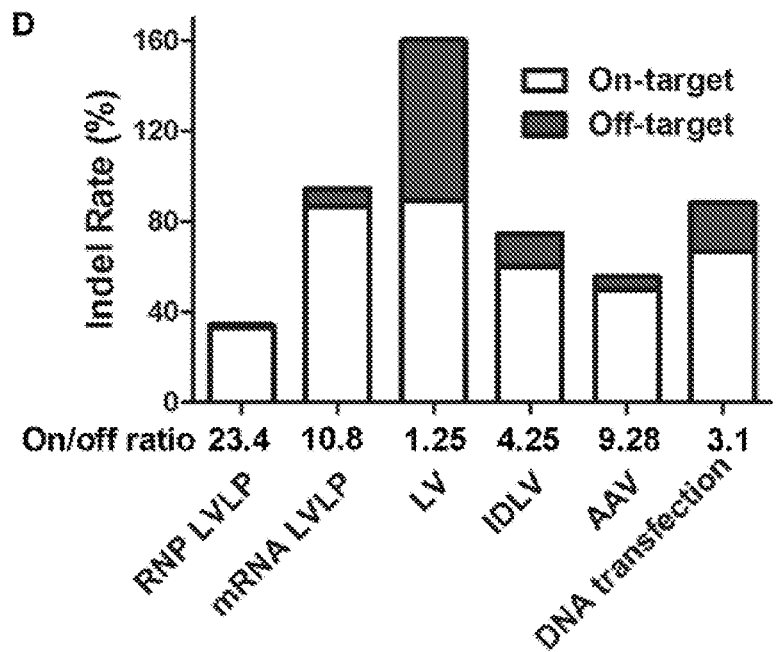
Figure 21:
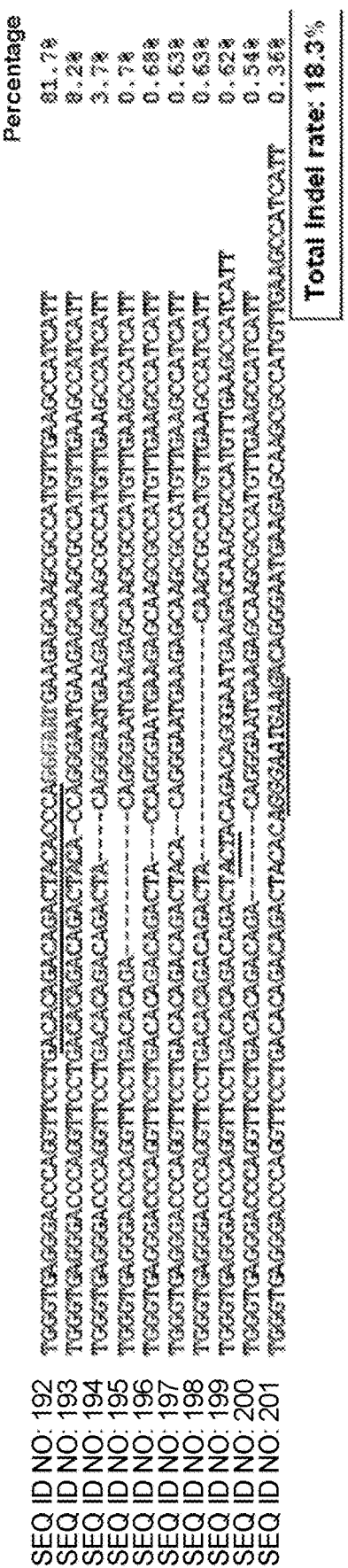
FIG. 21 shows that Indels generated by Cas9/IL2RG RNP LVLPs in lymphocytes. The nucleotides in gray is the PAM. The nucleotides underlined are the target sequence. The underlined Italic nucleotides are insertions.

The gene editing activities of the RNP LVLPs were further examined by next generation sequencing (NGS) on another target, IL2RG, whose mutation causes the X-linked severe combined immunodeficiency, using IL2RG sgRNA1 described above. Cas9/IL2RG sgRNA1 RNP LVLPs were transduced into 2.5×10$^4$ GFP reporter cells. 72 hours after transduction, the endogenous IL2RG region was amplified and subjected to NGS. 15, 45, and 100 ng p24 of these particles generated 4.1%, 8.1% and 21.1% Indels in the endogenous IL2RG gene (FIG. 20B). In the studies described above, 30 ng p24 of SaCas9 mRNA LVLPs and 60 ng of IL2RG sgRNA LV generated 13% Indels in IL2RG of HEK293T cells, thus these RNP LVLPs showed comparable or better gene editing activity. 200 ng p24 of IL2RG sgRNA1 RNP LVLPs were also transduced into $2 \times 10^5$ B lymphoblastoids, and 18.3% Indels were detected (FIG. 21). This activity is also comparable to 100 ng p24 of SaCas9 mRNA LVLPs and 100 ng p24 of IL2RG sgRNA1 expressing IDLV, which generated 11% Indels in the same number of B lymphoblastoids.

These data showed that the RNP LVLPs were as active as Cas9 mRNA LVLPs in gene editing. Delivering Cas9 by RNP should offer better control of the amount of Cas9 protein delivered per cell and more transient Cas9 action. Both would help to reduce off-target rates. The predicted 9 potential HBB sgRNA1 off-targets all had very low Indels, preventing comparison of off-target rates between different delivery methods. However, the wild-type HBB sequence corresponding to the Sickle cell disease mutation has only 1 nucleotide mismatch with HBB sgRNA1 (FIG. 20C) and detectable off-target Indels could be generated by Cas9/HBB sgRNA1. Thus, the on-target Indel rates (in the Sickle cell disease mutation in GFP reporter cassette, shown at the bottom of FIG. 20C) and the off-target Indel rates (in the endogenous wild-type HBB sequence with 1 nucleotide mismatch to HBB sgRNA1, shown on the top of FIG. 20C) in GFP-reporter cells, when Cas9/HBB sgRNA1 was delivered by plasmid transfection, or by LV, IDLV and AAV, were studied. Results showed that Cas9/HBB sgRNA1 RNP LVLP had the highest ratio of on-target to off-target Indel rates, Cas9 mRNA/HBB sgRNA1 LVLPs had the second, and both were higher than those of LV, IDLV and AAV (FIG. 20D). Thus RNP LVLPs best distinguished on-target effects from off-target effects.

Figure 20E:
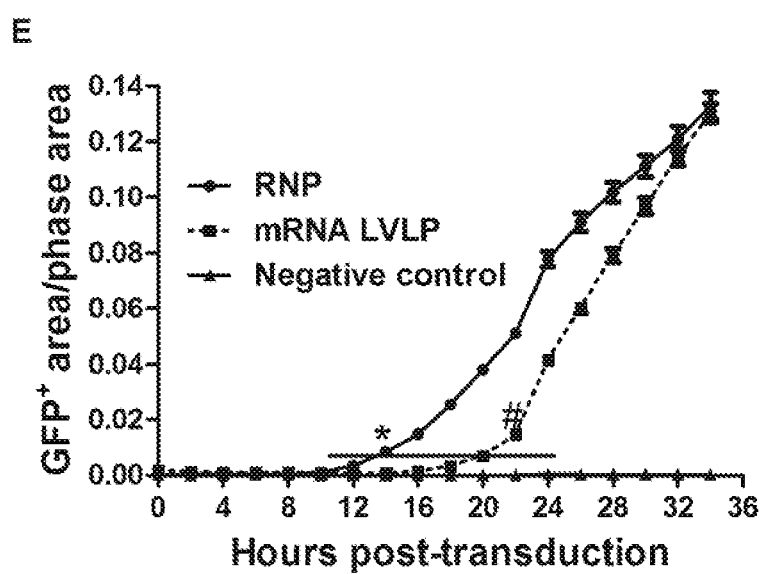

Cas9/sgRNA RNP LVLPs showed faster action than Cas9 mRNA LVLPs after transduction GFP reporter assays were used to compare the kinetics of GFP-positive cell emergence after Cas9/sgRNA RNP LVLP and Cas9 mRNA LVLP treatment. For this purpose, $2.5 \times 10^4$ GFP reporter cells were transduced with 50 ng p24 of Cas9/IL2RG sgRNA1 RNP LVLPs, or co-transduced GFP reporter cells with 100 ng p24 of Cas9 mRNA LVLPs and 100 ng p24 of IDLVs expressing IL2RG sgRNA1. The emergence of GFP-positive cells was monitored every two hours. GFP-positive cells showed up at least 6 hours earlier in the RNP LVLP treated cells than in the mRNA LVLP treated cells (FIG. 20E). 34 hours after transduction, the GFP-positive area rates of the two treatments converged. The data showed that, although mRNA LVLPs can be used effectively, RNP LVLPs have faster actions than mRNA LVLPs and IDLVs. This is likely because the RNPs are available for function in the nucleus soon after escaping from the endosome, while the mRNA LVLPs and IDLVs need more time to express Cas9 protein and sgRNA. The difference in kinetics also indicates that the functional components in Cas9/sgRNA RNP LVLPs are different from those in the Cas9 mRNA LVLPs.

LVLPs mediated efficient homologous recombination in the presence of donor templates One of the applications of CRISPR/Cas9 is to facilitate homologous recombination in the presence of donor template. Integration-defective lentiviral vectors have been used to provide donor template. COM-modification of NC in the packaging plasmid slightly decreased the packaging of a GFP-expressing lentiviral vector (1.0±0.15, N=3 for unmodified packaging plasmid; 0.73±0.15, N=6 for NC-COM modified packaging plasmid; p>0.05), but almost eliminated GFP expression after transduction of these COM-modified GFP lentiviral vectors. In addition, packaging of the Cas9/sgRNA RNP decreased Ψ-mediated lentiviral genome packaging, although the difference did not reach statistical significance (0.53±0.16, N=3 with RNP; 0.93±0.21, N=3 without RNP; p>0.05). In view of these observations, donor template was delivered separately by an integration-defective lentiviral vector (IDLV).

Lentiviral vectors are widely used for ex vivo modification of cells. LVLPs were used to facilitate the insertion of a functional IL2RG cDNA downstream the endogenous IL2RG promoter. This cDNA insertion strategy can be used to treat SCID-X1 regardless of the nature of the disease causing mutations. The donor template contains the 1.5 kb 5' homology arm, the 1.1 kb IL2RG cDNA, and the 3' homology arm. The 3' homology arm was designed so that after homologous recombination, the cDNA replaces similar length of the IL2RG genomic DNA. The IL2RG cDNA was codon optimized to maximize the difference with the original cDNA in order to reduce the chance of cDNA-mediated homologous recombination. In addition to the donor template, the lentiviral vector also contained two U6 promoters driving the expression of IL2RG sgRNA1 and sgRNA2 to facilitate the insertion of the cDNA (FIG. 22A).

Figures 22A, 22B:
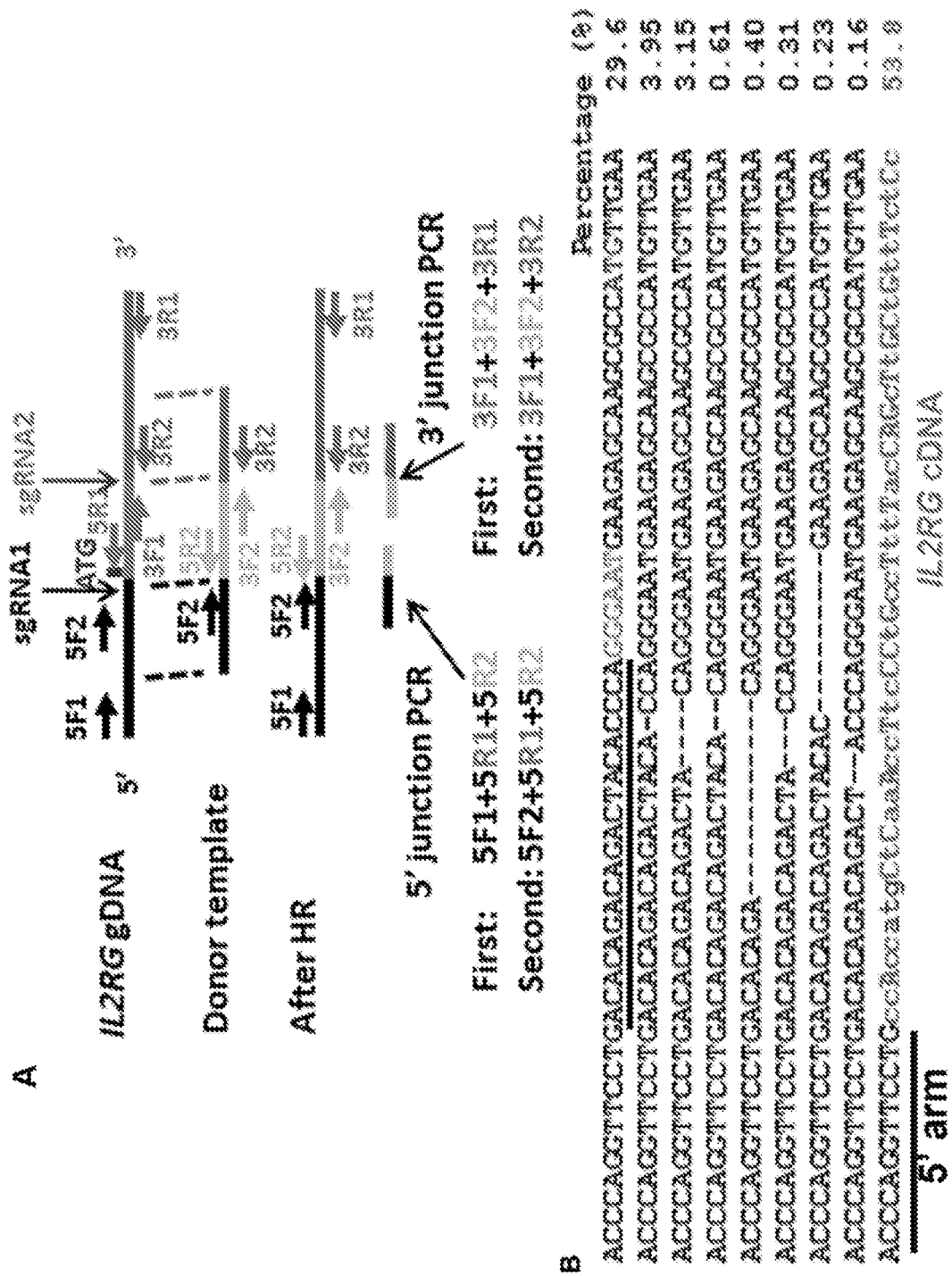
FIGS. 22A and 22B show that Cas9/sgRNA RNP LVLPs facilitated homologous recombination in the presence of donor template delivered by IDLV.

The donor template/sgRNAs were delivered to lymphoblast cells by IDLV, with or without Cas9/IL2RG sgRNA1 RNP LVLPs. 72 hours after transduction, genomic DNA was extracted and the target region was amplified by two rounds of PCR amplification (FIG. 22A). In the first PCRs, one primer was outside the donor template, and thus could not amplify from the template DNA without homologous recombination. The products of the first PCR were purified from the gel and used as the templates in the second PCRs to amplify the 5' and 3' junction DNA for sequencing. Three primers were used in each PCR, in addition to a common primer. One primer matched the inserted cDNA sequence to amplify the DNA with HR, and another primer matched the genomic DNA being replaced to amplify the DNA without HR. 100 ng p24 of LVLP and IDLV were transduced into $2.5 \times 10^4$ HEK293T cells. At the 5' junction, 46.2% sequences without HR (29.6% without Indels and the rest 16.6% with Indels) and 53.8% sequences with HR (FIG. 22B) were observed. In the readings with HR, Indel rate was similar to background since no target sequence was present in the donor templates. The data showed that the Cas9/sgRNA RNPs were active and greatly enhanced the targeted insertion of a 1.1 kb DNA. The observation of 57% readings with HR in the PCR products suggests that these LVLPs can be used together with IDLV to enhance HDR.

What is claimed is:

1. A lentiviral packaging system comprising:
   a) a packaging plasmid comprising a eukaryotic promoter operably linked to a Gag nucleotide sequence, wherein the Gag nucleotide sequence comprises a nucleocapsid (NC) coding sequence and a matrix protein (MA) coding sequence, wherein one or both of the NC coding sequence or the MA coding sequence comprises at least one non-viral aptamer-binding protein (ABP) nucleotide sequence, and wherein the packaging plasmid does not encode a functional integrase protein; and
   b)
   (i) a mammalian expression plasmid comprising a eukaryotic promoter operably linked to a non-viral nucleic acid sequence, wherein the non-viral nucleic acid sequence comprises a CRISPR-associated endonuclease coding sequence and a guide RNA (gRNA) coding sequence, wherein the gRNA coding sequence comprises at least one aptamer coding sequence; or
   (ii) two mammalian expression plasmids wherein each plasmid comprises a eukaryotic promoter operably linked to a non-viral nucleic acid sequence; wherein the non-viral nucleic acid sequence in the first plasmid comprises a CRISPR-associated endonuclease coding sequence, wherein the non-viral nucleic acid sequence in the second plasmid comprises a guide RNA (gRNA) coding sequence, and wherein the gRNA coding sequence comprises at least one aptamer coding sequence.

2. The lentiviral packaging system of claim 1, wherein the CRISPR-associated endonuclease coding sequence encodes a Cas9 protein, a Cpf1 protein, or a derivative of either.

3. The lentiviral packaging system of claim 1, wherein the at least one aptamer coding sequence encodes an aptamer sequence bound specifically by an aptamer binding protein (ABP) selected from the group consisting of MS2 coat protein, PP7 coat protein, lambda N RNA-binding domain, or COM protein.

4. The lentiviral packaging system of claim 1, wherein the gRNA coding sequence comprises at least one aptamer coding sequence.

5. The lentiviral packaging system of claim 4, wherein the at least one aptamer coding sequence is inserted into a tetraloop of the gRNA coding sequence.

6. The lentiviral packaging system of claim 5, wherein the aptamer coding sequence binds to a COM protein.

7. The lentiviral packaging system of claim 1, wherein a polynucleotide sequence encoding a RNA-stabilizing sequence is positioned at the 3' end of the non-viral nucleic acid sequence, and wherein the RNA-stabilizing sequence is at least one 3' UTR of human beta globin gene.

8. The lentiviral packaging system of claim 1, further comprising: c) an envelope plasmid comprising an envelope glycoprotein coding sequence.

9. A lentiviral packaging system comprising:
   a) a packaging plasmid, and wherein the packaging plasmid does not encode a functional integrase protein;
   b) at least one mammalian expression plasmid comprising a eukaryotic promoter operably linked to a Viral Protein R (VPR) coding sequence or a Negative Regulatory Factor (NEF) coding sequence, wherein the VPR coding sequence or the NEF coding sequence comprises at least one non-viral aptamer-binding protein (ABP) nucleotide sequence;
   c) at least one mammalian expression plasmid comprising a eukaryotic promoter operably linked to a non-viral nucleic acid sequence, and wherein the non-viral nucleic acid sequence comprises (i) one or both of a CRISPR-associated endonuclease coding sequence or a guide RNA (gRNA) coding sequence, and (ii) at least one aptamer coding; and
   d) an envelope plasmid comprising an envelope glycoprotein coding sequence.

10. A method of producing a lentiviral particle, the method comprising:
    a) transfecting a plurality of eukaryotic cells with:
       (1) the packaging plasmid;
       (2) (i) the mammalian expression plasmid comprising a eukaryotic promoter operably linked to a non-viral nucleic acid sequence, wherein the non-viral nucleic acid sequence comprises a CRISPR-associated endonuclease coding sequence and a guide RNA (gRNA) coding sequence, wherein the gRNA coding sequence comprises at least one aptamer coding sequence; or
       (ii) two mammalian expression plasmids wherein each plasmid comprises a eukaryotic promoter operably linked to a non-viral nucleic acid sequence; wherein the non-viral nucleic acid sequence in the first plasmid comprises a CRISPR-associated endonuclease coding sequence, wherein the non-viral nucleic acid sequence in the second plasmid comprises a guide RNA (gRNA) coding sequence, and wherein the gRNA coding sequence comprises at least one aptamer coding sequence; and
       (3) the envelope plasmid of the system of claim 8; and
    b) culturing the transfected eukaryotic cells for sufficient time for a lentiviral particle to be produced.

11. The method of claim 10, wherein the lentiviral particle comprises a RNP comprising a ribonucleotide protein (RNP) complex comprising a CRISPR-associated endonuclease and a guide RNA.

12. A method of producing a lentiviral particle, the method comprising:
    a) transfecting a plurality of eukaryotic cells with all of the plasmids of the lentiviral packaging system of claim 9; and
    b) culturing the transfected eukaryotic cells for sufficient time for a lentiviral particle to be produced.

13. An isolated host cell containing the lentiviral packaging system of claim 1.

14. The lentiviral packaging system of claim 1, wherein the NC coding sequence comprises two functional zinc finger protein domains and functional native protease processing sequences.

15. The lentiviral packaging system of claim 8, wherein the NC coding sequence comprises two functional zinc finger protein domains and functional native protease processing sequences.

* * * * *

SEQUENCE LISTING

<160> NUMBER OF SEQ ID NOS: 219

<210> SEQ ID NO 1
<211> LENGTH: 165

```
<212> TYPE: DNA
<213> ORGANISM: Artificial sequence
<220> FEATURE:
<223> OTHER INFORMATION: synthetic construct

<400> SEQUENCE: 1
atacagaaag gcaattttag gaaccaaaga aagactgtta agtgtttcaa ttgtggcaaa      60
gaagggcaca tagccaaaaa ttgcagggcc cctaggaaaa agggctgttg gaaatgtgga    120
aaggaaggac accaaatgaa agattgtact gagagacagg ctaat                   165

<210> SEQ ID NO 2
<211> LENGTH: 55
<212> TYPE: PRT
<213> ORGANISM: Artificial sequence
<220> FEATURE:
<223> OTHER INFORMATION: synthetic construct

<400> SEQUENCE: 2

Ile Gln Lys Gly Asn Phe Arg Asn Gln Arg Lys Thr Val Lys Cys Phe
 1               5                  10                  15

Asn Cys Gly Lys Glu Gly His Ile Ala Lys Asn Cys Arg Ala Pro Arg
                20                  25                  30

Lys Lys Gly Cys Trp Lys Cys Gly Lys Glu Gly His Gln Met Lys Asp
            35                  40                  45

Cys Thr Glu Arg Gln Ala Asn
        50                  55

<210> SEQ ID NO 3
<211> LENGTH: 396
<212> TYPE: DNA
<213> ORGANISM: Artificial sequence
<220> FEATURE:
<223> OTHER INFORMATION: synthetic construct

<400> SEQUENCE: 3
atgggtgcga gagcgtcagt attaagcggg ggagaattag atcgatggga aaaaattcgg     60
ttaaggccag ggggaaagaa aaatataaaa ttaaaacata tagtatgggc aagcagggag    120
ctagaacgat tcgcagttaa tcctggcctg ttagaaacat cagaaggctg tagacaaata    180
ctgggacagc tacaaccatc ccttcagaca ggatcagaag aacttagatc attatataat    240
acagtagcaa ccctctattg tgtgcatcaa aggatagaga taaaagacac caaggaagct    300
ttagacaaga tagaggaaga gcaaaacaaa agtaagaaaa agcacagca agcagcagct    360 gacacaggac acagcaatca ggtcagccaa aattac                             396

<210> SEQ ID NO 4
<211> LENGTH: 131
<212> TYPE: PRT
<213> ORGANISM: Artificial sequence
<220> FEATURE:
<223> OTHER INFORMATION: synthetic construct

<400> SEQUENCE: 4

Gly Ala Arg Ala Ser Val Leu Ser Gly Gly Glu Leu Asp Arg Trp Glu
 1               5                  10                  15

Lys Ile Arg Leu Arg Pro Gly Gly Lys Lys Tyr Lys Leu Lys His
                20                  25                  30

Ile Val Trp Ala Ser Arg Glu Leu Glu Arg Phe Ala Val Asn Pro Gly
            35                  40                  45
```

```
Leu Leu Glu Thr Ser Glu Gly Cys Arg Gln Ile Leu Gly Gln Leu Gln
 50                  55                  60

Pro Ser Leu Gln Thr Gly Ser Glu Glu Leu Arg Ser Leu Tyr Asn Thr
 65                  70                  75                  80

Val Ala Thr Leu Tyr Cys Val His Gln Arg Ile Glu Ile Lys Asp Thr
                 85                  90                  95

Lys Glu Ala Leu Asp Lys Ile Glu Glu Gln Asn Lys Ser Lys Lys
             100                 105                 110

Lys Ala Gln Gln Ala Ala Ala Asp Thr Gly His Ser Asn Gln Val Ser
             115                 120                 125

Gln Asn Tyr
    130

<210> SEQ ID NO 5
<211> LENGTH: 291
<212> TYPE: DNA
<213> ORGANISM: Artificial sequence
<220> FEATURE:
<223> OTHER INFORMATION: synthetic construct

<400> SEQUENCE: 5
atggaacaag cccagaagac ccagggaccg cagagggaac catacaatga atggacacta    60
gaacttttag aggaactcaa gcgggaagca gtcagacact ttcctagacc atggcttcat   120
ggcttaggac aacatatcta tgaaacctat ggagatactt ggacgggggt ggaagctata   180
ataagaattc tgcaacgact actgtttgtc catttcagaa ttgggtgcca gcatagccga   240
ataggcattc taagacagag aagagcaaga aatggagcca gtagatccta a            291

<210> SEQ ID NO 6
<211> LENGTH: 96
<212> TYPE: PRT
<213> ORGANISM: Artificial sequence
<220> FEATURE:
<223> OTHER INFORMATION: synthetic construct

<400> SEQUENCE: 6

Met Glu Gln Ala Pro Glu Asp Gln Gly Pro Gln Arg Glu Pro Tyr Asn
 1               5                  10                  15

Glu Trp Thr Leu Glu Leu Leu Glu Glu Leu Lys Arg Glu Ala Val Arg
             20                  25                  30

His Phe Pro Arg Pro Trp Leu His Gly Leu Gly Gln His Ile Tyr Glu
         35                  40                  45

Thr Tyr Gly Asp Thr Trp Thr Gly Val Glu Ala Ile Ile Arg Ile Leu
     50                  55                  60

Gln Arg Leu Leu Phe Val His Phe Arg Ile Gly Cys Gln His Ser Arg
 65                  70                  75                  80

Ile Gly Ile Leu Arg Gln Arg Arg Ala Arg Asn Gly Ala Ser Arg Ser
             85                  90                  95

<210> SEQ ID NO 7
<211> LENGTH: 618
<212> TYPE: DNA
<213> ORGANISM: Artificial sequence
<220> FEATURE:
<223> OTHER INFORMATION: synthetic construct
```

<400> SEQUENCE: 7

```
atgggttgca agtggtcaaa aagtagtgtg attggatggc ctgctgtaag ggaaagaatg    60
agacgagctg agccagcagc agatggggtg ggagcagtat ctcgagacct agaaaaacat   120
ggagcaatca caagtagcaa tacagcagct aacaatgctg cttgtgcctg gctagaagca   180
caagaggagg aagaggtggg ttttccagtc acacctcagg tacctttaag accaatgact   240
tacaaggcag ctgtagatct tagccacttt ttaaaagaaa aggggggact ggaagggcta   300
attcactccc aaagaagaca agatatcctt gatctgtgga tctaccacac acaaggctac   360
ttccctgatt ggcagaacta cacaccaggg ccagggtca gatatccact gacctttgga   420
tggtgctaca agctagtacc agttgagcca gataagctgg aagaggccaa taaggagag   480
aacaccagct tgttcacccc tgtgagcctg catggaatgg atgaccctgg aagaagtg    540
ttagagtgga ggtttgacag ccgcctagca tttcatcacg tggcccgaga gctgcatccg   600
gagtacttca agaactgc                                                 618
```

<210> SEQ ID NO 8
<211> LENGTH: 206
<212> TYPE: PRT
<213> ORGANISM: Artificial sequence
<220> FEATURE:
<223> OTHER INFORMATION: synthetic construct

<400> SEQUENCE: 8

```
Met Gly Cys Lys Trp Ser Lys Ser Ser Val Ile Gly Trp Pro Ala Val
1               5                   10                  15
Arg Glu Arg Met Arg Arg Ala Glu Pro Ala Ala Asp Gly Val Gly Ala
            20                  25                  30
Val Ser Arg Asp Leu Glu Lys His Gly Ala Ile Thr Ser Ser Asn Thr
        35                  40                  45
Ala Ala Asn Asn Ala Ala Cys Ala Trp Leu Glu Ala Gln Glu Glu Glu
    50                  55                  60
Glu Val Gly Phe Pro Val Thr Pro Gln Val Pro Leu Arg Pro Met Thr
65                  70                  75                  80
Tyr Lys Ala Ala Val Asp Leu Ser His Phe Leu Lys Glu Lys Gly Gly
                85                  90                  95
Leu Glu Gly Leu Ile His Ser Gln Arg Arg Gln Asp Ile Leu Asp Leu
            100                 105                 110
Trp Ile Tyr His Thr Gln Gly Tyr Phe Pro Asp Trp Gln Asn Tyr Thr
        115                 120                 125
Pro Gly Pro Gly Val Arg Tyr Pro Leu Thr Phe Gly Trp Cys Tyr Lys
    130                 135                 140
Leu Val Pro Val Glu Pro Asp Lys Leu Glu Glu Ala Asn Lys Gly Glu
145                 150                 155                 160
Asn Thr Ser Leu Leu His Pro Val Ser Leu His Gly Met Asp Asp Pro
                165                 170                 175
Gly Arg Glu Val Leu Glu Trp Arg Phe Asp Ser Arg Leu Ala Phe His
            180                 185                 190
His Val Ala Arg Glu Leu His Pro Glu Tyr Phe Lys Asn Cys
        195                 200                 205
```

<210> SEQ ID NO 9
<211> LENGTH: 351
<212> TYPE: DNA
<213> ORGANISM: Artificial sequence

```
<220> FEATURE:
<223> OTHER INFORMATION: synthetic construct

<400> SEQUENCE: 9
atggcttcta actttactca gttcgttctc gtcgacaatg gcggaactgg cgacgtgact      60
gtcgccccaa gcaacttcgc taacgggatc gctgaatgga tcagctctaa ctcgcgttca     120
caggcttaca aagtaacctg tagcgttcgt cagagctctg cgcagaatcg caaatacacc     180
atcaaagtcg aggtgcctaa aggcgcctgg cgttcgtact aaatatgga actaaccatt     240 ccaattttcg ccacgaattc cgactgcgag cttattgtta aggcaatgca aggtctccta     300
aaagatggaa acccgattcc ctcagcaatc gcagcaaact ccggcatcta c              351

<210> SEQ ID NO 10
<211> LENGTH: 117
<212> TYPE: PRT
<213> ORGANISM: Artificial sequence
<220> FEATURE:
<223> OTHER INFORMATION: synthetic construct

<400> SEQUENCE: 10

Met Ala Ser Asn Phe Thr Gln Phe Val Leu Val Asp Asn Gly Gly Thr
 1               5                  10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr
        115

<210> SEQ ID NO 11
<211> LENGTH: 363
<212> TYPE: DNA
<213> ORGANISM: Artificial sequence
<220> FEATURE:
<223> OTHER INFORMATION: synthetic construct

<400> SEQUENCE: 11
tccaaaacaa tagtcctctc cgtaggggag gcaacacgga ctttgaccga aatccagtca      60
accgctgacc gacaaatctt tgaagagaaa gtagggcctc ttgtgggccg actgcgcttg     120
actgcaagct tgcgacaaaa cggcgcaaag actgcctata gggtcaacct taaactcgac     180
caagccgacg tggtcgatag cggtctccct aaggttcggt atacgcaggt ctggagtcat     240
gacgtaacaa tcgtagcaaa cagcacagaa gcctcccgaa aaagcctcta cgatctgacg     300
aaatccttgg tggctacgtc acaggtggaa gacctcgttg tcaaccttgt acctctgggt     360
cga                                                                   363

<210> SEQ ID NO 12
<211> LENGTH: 121
<212> TYPE: PRT
```

```
<213> ORGANISM: Artificial sequence
<220> FEATURE:
<223> OTHER INFORMATION: synthetic construct

<400> SEQUENCE: 12

Ser Lys Thr Ile Val Leu Ser Val Gly Glu Ala Thr Arg Thr Leu Thr
1               5                   10                  15

Glu Ile Gln Ser Thr Ala Asp Arg Gln Ile Phe Glu Glu Lys Val Gly
            20                  25                  30

Pro Leu Val Gly Arg Leu Arg Leu Thr Ala Ser Leu Arg Gln Asn Gly
        35                  40                  45

Ala Lys Thr Ala Tyr Arg Val Asn Leu Lys Leu Asp Gln Ala Asp Val
    50                  55                  60

Val Asp Ser Gly Leu Pro Lys Val Arg Tyr Thr Gln Val Trp Ser His
65                  70                  75                  80

Asp Val Thr Ile Val Ala Asn Ser Thr Glu Ala Ser Arg Lys Ser Leu
                85                  90                  95

Tyr Asp Leu Thr Lys Ser Leu Val Ala Thr Ser Gln Val Glu Asp Leu
            100                 105                 110

Val Val Asn Leu Val Pro Leu Gly Arg
        115                 120

<210> SEQ ID NO 13
<211> LENGTH: 66
<212> TYPE: DNA
<213> ORGANISM: Artificial sequence
<220> FEATURE:
<223> OTHER INFORMATION: synthetic construct

<400> SEQUENCE: 13
atggatgcac aaaacacgccg ccgcgaacgt cgcgcagaga aacaggctca atggaaagca     60
gcaaat                                                                66

<210> SEQ ID NO 14
<211> LENGTH: 22
<212> TYPE: PRT
<213> ORGANISM: Artificial sequence
<220> FEATURE:
<223> OTHER INFORMATION: synthetic construct

<400> SEQUENCE: 14

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 15
<211> LENGTH: 193
<212> TYPE: DNA
<213> ORGANISM: Artificial sequence
<220> FEATURE:
<223> OTHER INFORMATION: synthetic construct

<400> SEQUENCE: 15
atgaaatcaa ttcgctgtaa aaactgcaac aaactgttat ttaaggcgga ttcctttgat     60
cacattgaaa tcaggtgtcc gcgttgcaaa cgtcacatca taatgctgaa tgcctgcgag    120
catcccacgg agaaacattg tgggaaaaga gaaaaaatca cgcattctga cgaaaccgtg    180
cgttattgag tat                                                       193
```

<210> SEQ ID NO 16
<211> LENGTH: 62
<212> TYPE: PRT
<213> ORGANISM: Artificial sequence
<220> FEATURE:
<223> OTHER INFORMATION: synthetic construct

<400> SEQUENCE: 16

Met Lys Ser Ile Arg Cys Lys Asn Cys Asn Lys Leu Leu Phe Lys Ala
1               5                   10                  15

Asp Ser Phe Asp His Ile Glu Ile Arg Cys Pro Arg Cys Lys Arg His
            20                  25                  30

Ile Ile Met Leu Asn Ala Cys Glu His Pro Thr Glu Lys His Cys Gly
        35                  40                  45

Lys Arg Glu Lys Ile Thr His Ser Asp Glu Thr Val Arg Tyr
    50                  55                  60

<210> SEQ ID NO 17
<211> LENGTH: 19
<212> TYPE: RNA
<213> ORGANISM: Artificial sequence
<220> FEATURE:
<223> OTHER INFORMATION: synthetic construct

<400> SEQUENCE: 17
acaugaggau cacccaugu                                              19

<210> SEQ ID NO 18
<211> LENGTH: 19
<212> TYPE: DNA
<213> ORGANISM: Artificial sequence
<220> FEATURE:
<223> OTHER INFORMATION: synthetic construct

<400> SEQUENCE: 18
acatgaggat cacccatgt                                              19

<210> SEQ ID NO 19
<211> LENGTH: 25
<212> TYPE: RNA
<213> ORGANISM: Artificial sequence
<220> FEATURE:
<223> OTHER INFORMATION: synthetic construct

<400> SEQUENCE: 19
ggagcagacg auauggcguc gcucc                                       25

<210> SEQ ID NO 20
<211> LENGTH: 25
<212> TYPE: DNA
<213> ORGANISM: Artificial sequence
<220> FEATURE:
<223> OTHER INFORMATION: synthetic construct

<400> SEQUENCE: 20
ggagcagacg atatggcgtc gctcc                                       25

<210> SEQ ID NO 21
<211> LENGTH: 19
<212> TYPE: RNA
<213> ORGANISM: Artificial sequence
<220> FEATURE:
<223> OTHER INFORMATION: synthetic construct

```
<400> SEQUENCE: 21
gggcccugaa gaagggccc                                                    19

<210> SEQ ID NO 22
<211> LENGTH: 19
<212> TYPE: DNA
<213> ORGANISM: Artificial sequence
<220> FEATURE:
<223> OTHER INFORMATION: synthetic construct

<400> SEQUENCE: 22
gggccctgaa gaagggccc                                                    19

<210> SEQ ID NO 23
<211> LENGTH: 19
<212> TYPE: RNA
<213> ORGANISM: Artificial sequence
<220> FEATURE:
<223> OTHER INFORMATION: synthetic construct

<400> SEQUENCE: 23
cugaaugccu gcgagcauc                                                    19

<210> SEQ ID NO 24
<211> LENGTH: 18
<212> TYPE: DNA
<213> ORGANISM: Artificial sequence
<220> FEATURE:
<223> OTHER INFORMATION: synthetic construct

<400> SEQUENCE: 24
ctgaatgcct gcgagcat                                                     18

<210> SEQ ID NO 25
<211> LENGTH: 132
<212> TYPE: DNA
<213> ORGANISM: Artificial sequence
<220> FEATURE:
<223> OTHER INFORMATION: synthetic construct

<400> SEQUENCE: 25
gctcgctttc ttgctgtcca atttctatta aaggttcctt tgttccctaa gtccaactac       60
taaactgggg gatattatga agggccttga gcatctggat tctgcctaat aaaaaacatt      120
tattttcatt gc                                                          132

<210> SEQ ID NO 26
<211> LENGTH: 132
<212> TYPE: RNA
<213> ORGANISM: Artificial sequence
<220> FEATURE:
<223> OTHER INFORMATION: synthetic construct

<400> SEQUENCE: 26
gcucgcuuuc uugcugucca auucuauua aagguuccuu uguccccuaa guccaacuac        60
uaaacugggg gauauuauga agggccuuga gcaucuggau ucugccuaau aaaaaacauu      120
uauuuucauu gc                                                          132

<210> SEQ ID NO 27
<211> LENGTH: 31
<212> TYPE: DNA
<213> ORGANISM: Artificial sequence
<220> FEATURE:
```

<223> OTHER INFORMATION: synthetic construct

<400> SEQUENCE: 27
ctcttctggt ccccacagac tcagagagaa c                          31

<210> SEQ ID NO 28
<211> LENGTH: 20
<212> TYPE: DNA
<213> ORGANISM: Artificial sequence
<220> FEATURE:
<223> OTHER INFORMATION: synthetic construct

<400> SEQUENCE: 28
aaaccgggaa ctacctgacc                                       20

<210> SEQ ID NO 29
<211> LENGTH: 20
<212> TYPE: DNA
<213> ORGANISM: Artificial sequence
<220> FEATURE:
<223> OTHER INFORMATION: synthetic construct

<400> SEQUENCE: 29
tcacgacctt gtttctgctg                                       20

<210> SEQ ID NO 30
<211> LENGTH: 21
<212> TYPE: DNA
<213> ORGANISM: Artificial sequence
<220> FEATURE:
<223> OTHER INFORMATION: synthetic construct

<400> SEQUENCE: 30
gagtaacggc agacttctcc a                                     21

<210> SEQ ID NO 31
<211> LENGTH: 21
<212> TYPE: DNA
<213> ORGANISM: Artificial sequence
<220> FEATURE:
<223> OTHER INFORMATION: synthetic construct

<400> SEQUENCE: 31
cggcattttg ccttgtttaa g                                     21

<210> SEQ ID NO 32
<211> LENGTH: 20
<212> TYPE: DNA
<213> ORGANISM: Artificial sequence
<220> FEATURE:
<223> OTHER INFORMATION: synthetic construct

<400> SEQUENCE: 32
cagtgcttca gccgctaccc                                       20

<210> SEQ ID NO 33
<211> LENGTH: 20
<212> TYPE: DNA
<213> ORGANISM: Artificial sequence
<220> FEATURE:
<223> OTHER INFORMATION: synthetic construct

<400> SEQUENCE: 33
agctcgatgc ggttcaccag                                       20

```
<210> SEQ ID NO 34
<211> LENGTH: 56
<212> TYPE: DNA
<213> ORGANISM: Artificial sequence
<220> FEATURE:
<223> OTHER INFORMATION: synthetic construct

<400> SEQUENCE: 34
tcgtcggcag cgtcagatgt gtataagaga cagtgttcac tagcaacctc aaacag        56

<210> SEQ ID NO 35
<211> LENGTH: 57
<212> TYPE: DNA
<213> ORGANISM: Artificial sequence
<220> FEATURE:
<223> OTHER INFORMATION: synthetic construct

<400> SEQUENCE: 35
tcgtcggcag cgtcagatgt gtataagaga cagatgttca ctagcaacct caaacag       57

<210> SEQ ID NO 36
<211> LENGTH: 58
<212> TYPE: DNA
<213> ORGANISM: Artificial sequence
<220> FEATURE:
<223> OTHER INFORMATION: synthetic construct

<400> SEQUENCE: 36
tcgtcggcag cgtcagatgt gtataagaga caggatgttc actagcaacc tcaaacag      58

<210> SEQ ID NO 37
<211> LENGTH: 59
<212> TYPE: DNA
<213> ORGANISM: Artificial sequence
<220> FEATURE:
<223> OTHER INFORMATION: synthetic construct

<400> SEQUENCE: 37
tcgtcggcag cgtcagatgt gtataagaga cagcgatgtt cactagcaac ctcaaacag     59

<210> SEQ ID NO 38
<211> LENGTH: 60
<212> TYPE: DNA
<213> ORGANISM: Artificial sequence
<220> FEATURE:
<223> OTHER INFORMATION: synthetic construct

<400> SEQUENCE: 38
tcgtcggcag cgtcagatgt gtataagaga cagtcgatgt tcactagcaa cctcaaacag    60

<210> SEQ ID NO 39
<211> LENGTH: 61
<212> TYPE: DNA
<213> ORGANISM: Artificial sequence
<220> FEATURE:
<223> OTHER INFORMATION: synthetic construct

<400> SEQUENCE: 39
tcgtcggcag cgtcagatgt gtataagaga cagatcgatg ttcactagca acctcaaaca    60
g                                                                    61

<210> SEQ ID NO 40
<211> LENGTH: 58
<212> TYPE: DNA
<213> ORGANISM: Artificial sequence
<220> FEATURE:
```

<223> OTHER INFORMATION: synthetic construct

<400> SEQUENCE: 40
gtctcgtggg ctcggagatg tgtataagag acagtccaat aggcagagag agtcagtg    58

<210> SEQ ID NO 41
<211> LENGTH: 75
<212> TYPE: DNA
<213> ORGANISM: Artificial sequence
<220> FEATURE:
<223> OTHER INFORMATION: synthetic construct

<400> SEQUENCE: 41
ttacgcttaa gaattctaga aaacatgagg atcacccatg tctgcaggtc gactctagaa    60
aattcctaga gctcg    75

<210> SEQ ID NO 42
<211> LENGTH: 75
<212> TYPE: DNA
<213> ORGANISM: Artificial sequence
<220> FEATURE:
<223> OTHER INFORMATION: synthetic construct

<400> SEQUENCE: 42
cgagctctag gaattttcta gagtcgacct gcagacatgg gtgatcctca tgttttctag    60
aattcttaag cgtaa    75

<210> SEQ ID NO 43
<211> LENGTH: 101
<212> TYPE: DNA
<213> ORGANISM: Artificial sequence
<220> FEATURE:
<223> OTHER INFORMATION: synthetic construct

<400> SEQUENCE: 43
ttacgcttaa gaattctaga aaacatgagg atcacccatg tctgcaggtc gactctagaa    60
aacatgagga tcacccatgt ctgcaaaatt cctagagctc g    101

<210> SEQ ID NO 44
<211> LENGTH: 101
<212> TYPE: DNA
<213> ORGANISM: Artificial sequence
<220> FEATURE:
<223> OTHER INFORMATION: synthetic construct

<400> SEQUENCE: 44
cgagctctag gaattttgca gacatgggtg atcctcatgt tttctagagt cgacctgcag    60
acatgggtga tcctcatgtt ttctagaatt cttaagcgta a    101

<210> SEQ ID NO 45
<211> LENGTH: 101
<212> TYPE: DNA
<213> ORGANISM: Artificial sequence
<220> FEATURE:
<223> OTHER INFORMATION: synthetic construct

<400> SEQUENCE: 45
ttacgcttaa gaattctaga aaacatgagg atcacccatg tctgcaggtc gactctagaa    60
aacatgagga tcacccatgt ctgcaaaatt ctagaaaaca t    101

<210> SEQ ID NO 46
<211> LENGTH: 101

```
<212> TYPE: DNA
<213> ORGANISM: Artificial sequence
<220> FEATURE:
<223> OTHER INFORMATION: synthetic construct

<400> SEQUENCE: 46
atgttttcta gaattttgca gacatgggtg atcctcatgt tttctagagt cgacctgcag    60
acatgggtga tcctcatgtt ttctagaatt cttaagcgta a                      101

<210> SEQ ID NO 47
<211> LENGTH: 25
<212> TYPE: DNA
<213> ORGANISM: Artificial sequence
<220> FEATURE:
<223> OTHER INFORMATION: synthetic construct

<400> SEQUENCE: 47
caccgccctg tggggcaagg tgaac                                         25

<210> SEQ ID NO 48
<211> LENGTH: 25
<212> TYPE: DNA
<213> ORGANISM: Artificial sequence
<220> FEATURE:
<223> OTHER INFORMATION: synthetic construct

<400> SEQUENCE: 48
aaacgttcac cttgccccac agggc                                         25

<210> SEQ ID NO 49
<211> LENGTH: 26
<212> TYPE: DNA
<213> ORGANISM: Artificial sequence
<220> FEATURE:
<223> OTHER INFORMATION: synthetic construct

<400> SEQUENCE: 49
caccgagtaa cggcagactt ctccac                                        26

<210> SEQ ID NO 50
<211> LENGTH: 26
<212> TYPE: DNA
<213> ORGANISM: Artificial sequence
<220> FEATURE:
<223> OTHER INFORMATION: synthetic construct

<400> SEQUENCE: 50
aaacgtggag aagtctgccg ttactc                                        26

<210> SEQ ID NO 51
<211> LENGTH: 57
<212> TYPE: DNA
<213> ORGANISM: Artificial sequence
<220> FEATURE:
<223> OTHER INFORMATION: synthetic construct

<400> SEQUENCE: 51
ttacgcttaa gaattcggag cagacgatat ggcgtcgctc cgaattccta gagctcg      57

<210> SEQ ID NO 52
<211> LENGTH: 57
<212> TYPE: DNA
<213> ORGANISM: Artificial sequence
<220> FEATURE:
<223> OTHER INFORMATION: synthetic construct
```

<400> SEQUENCE: 52
cgagctctag gaattcggag cgacgccata tcgtctgctc cgaattctta agcgtaa    57

<210> SEQ ID NO 53
<211> LENGTH: 26
<212> TYPE: DNA
<213> ORGANISM: Artificial sequence
<220> FEATURE:
<223> OTHER INFORMATION: synthetic construct

<400> SEQUENCE: 53
caccgagtaa cggcagactt ctccac    26

<210> SEQ ID NO 54
<211> LENGTH: 26
<212> TYPE: DNA
<213> ORGANISM: Artificial sequence
<220> FEATURE:
<223> OTHER INFORMATION: synthetic construct

<400> SEQUENCE: 54
gaacgtggag aagtctgccg ttactc    26

<210> SEQ ID NO 55
<211> LENGTH: 35
<212> TYPE: DNA
<213> ORGANISM: Artificial sequence
<220> FEATURE:
<223> OTHER INFORMATION: synthetic construct

<400> SEQUENCE: 55
ttgcaatgat ctcgagggcc tatttcccat gattc    35

<210> SEQ ID NO 56
<211> LENGTH: 36
<212> TYPE: DNA
<213> ORGANISM: Artificial sequence
<220> FEATURE:
<223> OTHER INFORMATION: synthetic construct

<400> SEQUENCE: 56
ctgcggccgc tctagaaaaa tctcgccaac aagttg    36

<210> SEQ ID NO 57
<211> LENGTH: 85
<212> TYPE: DNA
<213> ORGANISM: Artificial sequence
<220> FEATURE:
<223> OTHER INFORMATION: synthetic construct

<400> SEQUENCE: 57
catggtgcat ctgacacctg tggagaagtc tgccgttact gccctgtggg gcaaggtgaa    60
cgtggatgaa gttggtggtg aggcc    85

<210> SEQ ID NO 58
<211> LENGTH: 84
<212> TYPE: DNA
<213> ORGANISM: Artificial sequence
<220> FEATURE:
<223> OTHER INFORMATION: synthetic construct

<400> SEQUENCE: 58
cagggcctca ccaccaactt catccacgtt caccttgccc cacagggcag taacggcaga    60
cttctccaca ggtgtcagat gcac    84

<210> SEQ ID NO 59
<211> LENGTH: 38
<212> TYPE: DNA
<213> ORGANISM: Artificial sequence
<220> FEATURE:
<223> OTHER INFORMATION: synthetic construct

<400> SEQUENCE: 59
cttctgattt tctagattgt gtaatcgtag tttcagag                              38

<210> SEQ ID NO 60
<211> LENGTH: 39
<212> TYPE: DNA
<213> ORGANISM: Artificial sequence
<220> FEATURE:
<223> OTHER INFORMATION: synthetic construct

<400> SEQUENCE: 60
gcttgatatc gaattaaaaa atctcgccaa caagttgac                             39

<210> SEQ ID NO 61
<211> LENGTH: 1041
<212> TYPE: DNA
<213> ORGANISM: Artificial sequence
<220> FEATURE:
<223> OTHER INFORMATION: synthetic construct

<400> SEQUENCE: 61
gctagccacc atggcttcta actttactca gttcgttctc gtcgacaatg gcggaactgg      60
cgacgtgact gtcgcccaa gcaacttcgc taacgggatc gctgaatgga tcagctctaa     120
ctcgcgttca caggcttaca aagtaacctg tagcgttcgt cagagctctg cgcagaatcg     180
caaatacacc atcaaagtcg aggtgcctaa aggcgcctgg cgttcgtact aaatatgga     240 actaaccatt ccaattttcg ccacgaattc cgactgcgag cttattgtta aggcaatgca     300
aggtctccta aaagatggaa acccgattcc ctcagcaatc gcagcaaact ccggcatcta     360
cggtggtgga ggaggaatgg cgtccaattt cacgcagttc gtcctggttg acaacggggg     420
gactggggac gttacggtcg ctccgagcaa cttttgccaat ggtattgcgg agtggatttc     480
ttctaattca cggtcccaag cttacaaagt gacctgttcc gtgcggcaaa gttctgctca     540
gaatagaaag tacactataa aggtcgaagt ccctaagggg gcctggcgat catatctcaa     600
tatggagctt accatcccaa tatttgccac taattctgat tgtgaattga ttgtcaaagc     660
aatgcaagga ctcttgaaag acggaaaccc aatcccagc gcaatcgcag ccaactccgg     720
tatatacgga ggtggtggag gaatggaaca agccccagaa gaccagggac cgcagaggga     780
accatacaat gaatggacac tagaactttt agaggaactc aagcgggaag cagtcagaca     840
ctttcctaga ccatggcttc atggcttagg acaacatatc tatgaaacct atggagatac     900
ttggacgggg gtggaagcta taataagaat tctgcaacga ctactgtttg tccatttcag     960
aattgggtgc cagcatagcc gaataggcat tctaagacag agaagagcaa gaaatggagc    1020
cagtagatcc taagcggccg c                                             1041

<210> SEQ ID NO 62
<211> LENGTH: 340
<212> TYPE: PRT
<213> ORGANISM: Artificial sequence
<220> FEATURE:
<223> OTHER INFORMATION: synthetic construct

<400> SEQUENCE: 62

```
Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Ile Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Gly Ala Trp Arg Ser Tyr Leu Asn Met Glu Leu Thr Ile
65                  70                  75                  80

Pro Ile Phe Ala Thr Asn Ser Asp Cys Glu Leu Ile Val Lys Ala Met
                85                  90                  95

Gln Gly Leu Leu Lys Asp Gly Asn Pro Ile Pro Ser Ala Ile Ala Ala
            100                 105                 110

Asn Ser Gly Ile Tyr Gly Gly Gly Gly Met Ala Ser Asn Phe Thr
        115                 120                 125

Gln Phe Val Leu Val Asp Asn Gly Gly Thr Gly Asp Val Thr Val Ala
    130                 135                 140

Pro Ser Asn Phe Ala Asn Gly Ile Ala Glu Trp Ile Ser Ser Asn Ser
145                 150                 155                 160

Arg Ser Gln Ala Tyr Lys Val Thr Cys Ser Val Arg Gln Ser Ser Ala
                165                 170                 175

Gln Asn Arg Lys Tyr Thr Ile Lys Val Glu Val Pro Lys Gly Ala Trp
            180                 185                 190

Arg Ser Tyr Leu Asn Met Glu Leu Thr Ile Pro Ile Phe Ala Thr Asn
        195                 200                 205

Ser Asp Cys Glu Leu Ile Val Lys Ala Met Gln Gly Leu Leu Lys Asp
    210                 215                 220

Gly Asn Pro Ile Pro Ser Ala Ile Ala Ala Asn Ser Gly Ile Tyr Gly
225                 230                 235                 240

Gly Gly Gly Gly Met Glu Gln Ala Pro Glu Asp Gln Gly Pro Gln Arg
                245                 250                 255

Glu Pro Tyr Asn Glu Trp Thr Leu Glu Leu Leu Glu Glu Leu Lys Arg
            260                 265                 270

Glu Ala Val Arg His Phe Pro Arg Pro Trp Leu His Gly Leu Gly Gln
        275                 280                 285

His Ile Tyr Glu Thr Tyr Gly Asp Thr Trp Thr Gly Val Glu Ala Ile
    290                 295                 300

Ile Arg Ile Leu Gln Arg Leu Leu Phe Val His Phe Arg Ile Gly Cys
305                 310                 315                 320

Gln His Ser Arg Ile Gly Ile Leu Arg Gln Arg Ala Arg Asn Gly
                325                 330                 335

Ala Ser Arg Ser
            340
```

<210> SEQ ID NO 63
<211> LENGTH: 1371
<212> TYPE: DNA
<213> ORGANISM: Artificial sequence
<220> FEATURE:
<223> OTHER INFORMATION: synthetic construct

<400> SEQUENCE: 63

```
gctagccacc atgggttgca agtggtcaaa aagtagtgtg attggatggc ctgctgtaag      60
ggaaagaatg agacgagctg agccagcagc agatggggtg ggagcagtat ctcgagacct     120
agaaaaacat ggagcaatca caagtagcaa tacagcagct aacaatgctg cttgtgcctg     180
gctagaagca caagaggagg aagaggtggg ttttccagtc acacctcagg tacctttaag     240
accaatgact tacaaggcag ctgtagatct tagccacttt ttaaaagaaa agggggggact    300
ggaagggcta attcactccc aaagaagaca agatatcctt gatctgtgga tctaccacac     360
acaaggctac ttccctgatt ggcagaacta cacaccaggg ccaggggtca gatatccact     420
gacctttgga tggtgctaca agctagtacc agttgagcca gataagctgg aagaggccaa     480
taaaggagag aacaccagct tgttacaccc tgtgagcctg catggaatgg atgaccctgg     540
aagagaagtg ttagagtgga ggtttgacag ccgcctagca tttcatcacg tggcccgaga     600
gctgcatccg gagtacttca gaactgcgag aggtggtgga ggaatggctt ctaactttac     660
tcagttcgtt ctcgtcgaca atggcggaac tggcgacgtg actgtcgccc aagcaacttt     720
cgctaacggg atcgctgaat ggatcagctc taactcgcgt tcacaggctt acaaagtaac     780
ctgtagcgtt cgtcagagct ctgcgcagaa tcgcaaatac accatcaaag tcgaggtgcc     840
taaaggcgcc tggcgttcgt acttaaatat ggaactaacc attccaattt cgccacgaa      900
ttccgactgc gagcttattg ttaaggcaat gcaaggtctc ctaaaagatg gaaacccgat     960
tccctcagca atcgcagcaa actccggcat ctacggtggt ggaggaggaa tggcgtccaa    1020
tttcacgcag ttcgtcctgg ttgacaacgg ggggactggg gacgttacgg tcgctccgag    1080
caactttgcc aatggtattg cggagtggat ttcttctaat tcacggtccc aagcttacaa    1140
agtgacctgt tccgtgcggc aaagttctgc tcagaataga aagtacacta taaaggtcga    1200
agtccctaag ggggcctggc gatcatatct caatatggag cttaccatcc caatatttgc    1260
cactaattct gattgtgaat tgattgtcaa agcaatgcaa ggactcttga agacggaaa     1320
cccaatcccc agcgcaatcg cagccaactc cggtatatac tgagcggccg c            1371
```

<210> SEQ ID NO 64
<211> LENGTH: 451
<212> TYPE: PRT
<213> ORGANISM: Artificial sequence
<220> FEATURE:
<223> OTHER INFORMATION: synthetic construct

<400> SEQUENCE: 64

```
Thr Met Gly Cys Lys Trp Ser Lys Ser Ser Val Ile Gly Trp Pro Ala
1               5                   10                  15

Val Arg Glu Arg Met Arg Arg Ala Glu Pro Ala Ala Asp Gly Val Gly
            20                  25                  30

Ala Val Ser Arg Asp Leu Glu Lys His Gly Ala Ile Thr Ser Ser Asn
        35                  40                  45

Thr Ala Ala Asn Asn Ala Ala Cys Ala Trp Leu Glu Ala Gln Glu Glu
    50                  55                  60

Glu Glu Val Gly Phe Pro Val Thr Pro Gln Val Pro Leu Arg Pro Met
65                  70                  75                  80

Thr Tyr Lys Ala Ala Val Asp Leu Ser His Phe Leu Lys Glu Lys Gly
                85                  90                  95

Gly Leu Glu Gly Leu Ile His Ser Gln Arg Arg Gln Asp Ile Leu Asp
            100                 105                 110
```

Leu Trp Ile Tyr His Thr Gln Gly Tyr Phe Pro Asp Trp Gln Asn Tyr
            115                 120                 125

Thr Pro Gly Pro Gly Val Arg Tyr Pro Leu Thr Phe Gly Trp Cys Tyr
130                 135                 140

Lys Leu Val Pro Val Glu Pro Asp Lys Leu Glu Ala Asn Lys Gly
145                 150                 155                 160

Glu Asn Thr Ser Leu Leu His Pro Val Ser Leu His Gly Met Asp Asp
                165                 170                 175

Pro Gly Arg Glu Val Leu Glu Trp Arg Phe Asp Ser Arg Leu Ala Phe
            180                 185                 190

His His Val Ala Arg Glu Leu His Pro Glu Tyr Phe Lys Asn Cys Gly
            195                 200                 205

Gly Gly Gly Gly Met Ala Ser Asn Phe Thr Gln Phe Val Leu Val Asp
210                 215                 220

Asn Gly Gly Thr Gly Asp Val Thr Val Ala Pro Ser Asn Phe Ala Asn
225                 230                 235                 240

Gly Ile Ala Glu Trp Ile Ser Ser Asn Ser Arg Ser Gln Ala Tyr Lys
            245                 250                 255

Val Thr Cys Ser Val Arg Gln Ser Ser Ala Gln Asn Arg Lys Tyr Thr
            260                 265                 270

Ile Lys Val Glu Val Pro Lys Gly Ala Trp Arg Ser Tyr Leu Asn Met
            275                 280                 285

Glu Leu Thr Ile Pro Ile Phe Ala Thr Asn Ser Asp Cys Glu Leu Ile
            290                 295                 300

Val Lys Ala Met Gln Gly Leu Leu Lys Asp Gly Asn Pro Ile Pro Ser
305                 310                 315                 320

Ala Ile Ala Ala Asn Ser Gly Ile Tyr Gly Gly Gly Gly Met Ala
            325                 330                 335

Ser Asn Phe Thr Gln Phe Val Leu Val Asp Asn Gly Gly Thr Gly Asp
            340                 345                 350

Val Thr Val Ala Pro Ser Asn Phe Ala Asn Gly Ile Ala Glu Trp Ile
            355                 360                 365

Ser Ser Asn Ser Arg Ser Gln Ala Tyr Lys Val Thr Cys Ser Val Arg
370                 375                 380

Gln Ser Ser Ala Gln Asn Arg Lys Tyr Thr Ile Lys Val Glu Val Pro
385                 390                 395                 400

Lys Gly Ala Trp Arg Ser Tyr Leu Asn Met Glu Leu Thr Ile Pro Ile
            405                 410                 415

Phe Ala Thr Asn Ser Asp Cys Glu Leu Ile Val Lys Ala Met Gln Gly
            420                 425                 430

Leu Leu Lys Asp Gly Asn Pro Ile Pro Ser Ala Ile Ala Ala Asn Ser
            435                 440                 445

Gly Ile Tyr
450

<210> SEQ ID NO 65
<211> LENGTH: 1234
<212> TYPE: DNA
<213> ORGANISM: Artificial sequence
<220> FEATURE:
<223> OTHER INFORMATION: synthetic construct

<400> SEQUENCE: 65

```
cctaggaaaa agggctgttg gaaatgtgga aaggaaggac accaaatgaa agattgttcc      60
ggtggaggtg gatccggtgg aggttccatg gcgtccaatt tcacgcagtt cgtcctggtt     120
gacaacgggg ggactgggga cgttacggtc gctccgagca actttgccaa tggtattgcg     180
gagtggattt cttctaattc acggtcccaa gcttacaaag tgacctgttc cgtgcggcaa     240
agttctgctc agaatagaaa gtacactata aaggtcgaag tccctaaggg ggcctggcga     300
tcatatctca atatggagct taccatccca atatttgcca ctaattctga ttgtgaattg     360
attgtcaaag caatgcaagg actcttgaaa gacggaaacc caatcccag cgcaatcgca      420
gccaactccg gtatatactc cggaggtgga ggtggaactg agagacaggc taatttttta    480
gggaagatct ggccttccca caagggaagg ccagggaatt tcttcagag cagaccagag     540
ccaacagccc caccagaaga gagcttcagg tttggggaag agacaacaac tccctctcag    600
aagcaggagc cgatagacaa ggaactgtat cctttagctt ccctcagatc actctttggc    660
agcgacccct cgtcacaata aagatagggg ggcaattaaa ggaagctcta ttagatacag    720
gagcagatga tacagtatta gaagaaatga atttgccagg aagatggaaa ccaaaaatga    780
tagggggaat tggaggtttt atcaaagtaa gacagtatga tcagatactc atagaaatct    840
gcggacataa agctataggt acagtattag taggacctac acctgtcaac ataattggaa    900
gaaatctgtt gactcagatt ggctgcactt taaattttcc cattagtcct attgagactg    960
taccagtaaa attaaagcca ggaatggatg gcccaaaagt taaacaatgg ccattgacag   1020
aagaaaaaat aaaagcatta gtagaaattt gtacagaaat ggaaaaggaa ggaaaaattt   1080
caaaaattgg gcctgaaaat ccatacaata ctccagtatt tgccataaag aaaaagaca    1140
gtactaaatg gagaaaatta gtagatttca gagaacttaa taagagaact caagatttct   1200
gggaagttca attaggaata ccacatcctg cagg                               1234
```

<210> SEQ ID NO 66
<211> LENGTH: 226
<212> TYPE: PRT
<213> ORGANISM: Artificial sequence
<220> FEATURE:
<223> OTHER INFORMATION: synthetic construct

<400> SEQUENCE: 66

```
Pro Arg Lys Lys Gly Cys Trp Lys Cys Gly Lys Glu Gly His Gln Met
1               5                   10                  15
Lys Asp Cys Ser Gly Gly Gly Ser Gly Gly Ser Met Ala Ser
            20                  25                  30
Asn Phe Thr Gln Phe Val Leu Val Asp Asn Gly Gly Thr Gly Asp Val
                35                  40                  45
Thr Val Ala Pro Ser Asn Phe Ala Asn Gly Ile Ala Glu Trp Ile Ser
        50                  55                  60
Ser Asn Ser Arg Ser Gln Ala Tyr Lys Val Thr Cys Ser Val Arg Gln
65                  70                  75                  80
Ser Ser Ala Gln Asn Arg Lys Tyr Thr Ile Lys Val Glu Val Pro Lys
                85                  90                  95
Gly Ala Trp Arg Ser Tyr Leu Asn Met Glu Leu Thr Ile Pro Ile Phe
            100                 105                 110
Ala Thr Asn Ser Asp Cys Glu Leu Ile Val Lys Ala Met Gln Gly Leu
        115                 120                 125
```

```
Leu Lys Asp Gly Asn Pro Ile Pro Ser Ala Ile Ala Ala Asn Ser Gly
    130                 135                 140
Ile Tyr Ser Gly Gly Gly Gly Thr Glu Arg Gln Ala Asn Phe Leu
145                 150                 155                 160
Gly Lys Ile Trp Pro Ser His Lys Gly Arg Pro Gly Asn Phe Leu Gln
                165                 170                 175
Ser Arg Pro Glu Pro Thr Ala Pro Pro Glu Glu Ser Phe Arg Phe Gly
            180                 185                 190
Glu Glu Thr Thr Thr Pro Ser Gln Lys Gln Glu Pro Ile Asp Lys Glu
                195                 200                 205
Leu Tyr Pro Leu Ala Ser Leu Arg Ser Leu Phe Gly Ser Asp Pro Ser
    210                 215                 220

Ser Gln
225

<210> SEQ ID NO 67
<211> LENGTH: 1591
<212> TYPE: DNA
<213> ORGANISM: Artificial sequence
<220> FEATURE:
<223> OTHER INFORMATION: synthetic construct

<400> SEQUENCE: 67
cctaggaaaa agggctgttg gaaatgtgga aaggaaggac accaaatgaa agattgttcc      60
ggtggaggtg gatccatggc ttctaacttt actcagttcg ttctcgtcga caatggcgga     120
actggcgacg tgactgtcgc cccaagcaac ttcgctaacg ggatcgctga atggatcagc     180
tctaactcgc gttcacaggc ttacaaagta acctgtagcg ttcgtcagag ctctgcgcag     240
aatcgcaaat acaccatcaa agtcgaggtg cctaaaggcg cctggcgttc gtacttaaat     300
atggaactaa ccattccaat tttcgccacg aattccgact gcgagcttat tgttaaggca     360
atgcaaggtc tcctaaaaga tggaaacccg attccctcag caatcgcagc aaactccggc     420
atctacggat ccggtggagg ttccatggcg tccaatttca cgcagttcgt cctggttgac     480
aacgggggga ctggggacgt tacggtcgct ccgagcaact tgccaatgg tattgcggag     540 tggatttctt ctaattcacg gtcccaagct tacaaagtga cctgttccgt gcggcaaagt     600
tctgctcaga atagaaagta cactataaag gtcgaagtcc ctaaggggc ctggcgatca     660 tatctcaata tggagcttac catcccaata tttgccacta attctgattg tgaattgatt     720
gtcaaagcaa tgcaaggact cttgaaagac ggaaacccaa tccccagcgc aatcgcagcc     780
aactccggta tatactccgg aggtggaggt ggaactgaga acaggctaa ttttttaggg     840 aagatctggc cttcccacaa gggaaggcca gggaattttc ttcagagcag accagagcca     900
acagccccac cagaagagag cttcaggttt gggaagagaa caacactcc ctctcagaag     960 caggagccga tagacaagga actgtatcct ttagcttccc tcagatcact ctttggcagc    1020 gaccccttcgt cacaataaag ataggggggc aattaaagga agctctatta gatacaggag    1080
cagatgatac agtattagaa gaaatgaatt tgccaggaag atggaaacca aaaatgatag    1140
ggggaattgg aggttttatc aaagtaagac agtatgatca gatactcata gaaatctgcg    1200
gacataaagc tataggtaca gtattagtag gacctacacc tgtcaacata attggaagaa    1260
atctgttgac tcagattggc tgcactttaa attttcccat tagtcctatt gagactgtac    1320
cagtaaaatt aaagccagga atggatggcc caaaagttaa acaatggcca ttgacagaag    1380
aaaaaataaa agcattagta gaaatttgta cagaaatgga aaggaagga aaaatttcaa    1440
```
aaattgggcc tgaaaatcca tacaatactc cagtatttgc cataaagaaa aaagacagta 1500
ctaaatggag aaaattagta gatttcagag aacttaataa gagaactcaa gatttctggg 1560
aagttcaatt aggaatacca catcctgcag g 1591

```
<210> SEQ ID NO 68
<211> LENGTH: 345
<212> TYPE: PRT
<213> ORGANISM: Artificial sequence
<220> FEATURE:
<223> OTHER INFORMATION: synthetic construct

<400> SEQUENCE: 68

Pro Arg Lys Lys Gly Cys Trp Lys Cys Gly Lys Glu Gly His Gln Met
1               5                   10                  15

Lys Asp Cys Ser Gly Gly Gly Ser Met Ala Ser Asn Phe Thr Gln
            20                  25                  30

Phe Val Leu Val Asp Asn Gly Gly Thr Gly Asp Val Thr Val Ala Pro
        35                  40                  45

Ser Asn Phe Ala Asn Gly Ile Ala Glu Trp Ile Ser Ser Asn Ser Arg
    50                  55                  60

Ser Gln Ala Tyr Lys Val Thr Cys Ser Val Arg Gln Ser Ser Ala Gln
65                  70                  75                  80

Asn Arg Lys Tyr Thr Ile Lys Val Glu Val Pro Lys Gly Ala Trp Arg
                85                  90                  95

Ser Tyr Leu Asn Met Glu Leu Thr Ile Pro Ile Phe Ala Thr Asn Ser
            100                 105                 110

Asp Cys Glu Leu Ile Val Lys Ala Met Gln Gly Leu Leu Lys Asp Gly
        115                 120                 125

Asn Pro Ile Pro Ser Ala Ile Ala Ala Asn Ser Gly Ile Tyr Gly Ser
    130                 135                 140

Gly Gly Gly Ser Met Ala Ser Asn Phe Thr Gln Phe Val Leu Val Asp
145                 150                 155                 160

Asn Gly Gly Thr Gly Asp Val Thr Val Ala Pro Ser Asn Phe Ala Asn
                165                 170                 175

Gly Ile Ala Glu Trp Ile Ser Ser Asn Ser Arg Ser Gln Ala Tyr Lys
            180                 185                 190

Val Thr Cys Ser Val Arg Gln Ser Ser Ala Gln Asn Arg Lys Tyr Thr
        195                 200                 205

Ile Lys Val Glu Val Pro Lys Gly Ala Trp Arg Ser Tyr Leu Asn Met
    210                 215                 220

Glu Leu Thr Ile Pro Ile Phe Ala Thr Asn Ser Asp Cys Glu Leu Ile
225                 230                 235                 240

Val Lys Ala Met Gln Gly Leu Leu Lys Asp Gly Asn Pro Ile Pro Ser
                245                 250                 255

Ala Ile Ala Ala Asn Ser Gly Ile Tyr Ser Gly Gly Gly Gly Thr
            260                 265                 270

Glu Arg Gln Ala Asn Phe Leu Gly Lys Ile Trp Pro Ser His Lys Gly
        275                 280                 285

Arg Pro Gly Asn Phe Leu Gln Ser Arg Pro Glu Pro Thr Ala Pro Pro
    290                 295                 300

Glu Glu Ser Phe Arg Phe Gly Glu Glu Thr Thr Thr Pro Ser Gln Lys
305                 310                 315                 320

Gln Glu Pro Ile Asp Lys Glu Leu Tyr Pro Leu Ala Ser Leu Arg Ser
                325                 330                 335
```

Leu Phe Gly Ser Asp Pro Ser Ser Gln
          340                 345

<210> SEQ ID NO 69
<211> LENGTH: 1234
<212> TYPE: DNA
<213> ORGANISM: Artificial sequence
<220> FEATURE:
<223> OTHER INFORMATION: synthetic construct

<400> SEQUENCE: 69

```
cctaggaaaa agggctgttg aaatgtgga aggaaggac ccaaatgaa agattgttcc      60
ggtggaggtg atcctccaa acaatagtc ctctccgtag gggaggcaac acggactttg    120
accgaaatcc agtcaaccgc tgaccgacaa atctttgaag agaaagtagg gcctcttgtg   180
ggccgactgc gcttgactgc aagcttgcga caaaacggcg caaagactgc ctatagggtc   240
aaccttaaac tcgaccaagc cgacgtggtc gatagcggtc tccctaaggt tcggtatacg   300
caggtctgga gtcatgacgt aacaatcgta gcaaacagca cagaagcctc ccgaaaaagc   360
ctctacgatc tgacgaaatc cttggtggct acgtcacagg tggaagacct cgttgtcaac   420
cttgtacctc tgggtcggtc cggaggtgga ggtggaactg agacacaggc taatttttta   480
gggaagatct ggccttccca caagggaagg ccagggaatt ttcttcagag cagaccagag   540
ccaacagccc caccagaaga gagcttcagg tttggggaag agacaacaac tccctctcag   600
aagcaggagc cgatagacaa ggaactgtat cctttagctt ccctcagatc actctttggc   660
agcgacccct cgtcacaata aagataggg ggcaattaaa ggaagctcta ttagatacag   720
gagcagatga tacagtatta aagaaatga atttgccagg aagatggaaa ccaaaaatga   780
tagggggaat tggaggtttt atcaaagtaa gacagtatga tcagatactc atagaaatct   840
gcggacataa agctataggt acagtattag taggacctac acctgtcaac ataattggaa   900
gaaatctgtt gactcagatt ggctgcactt taaattttcc cattagtcct attgagactg   960
taccagtaaa attaaagcca ggaatggatg gcccaaaagt taaacaatgg ccattgacag  1020
aagaaaaaat aaaagcatta gtagaaattt gtacagaaat ggaaaaggaa ggaaaaattt  1080
caaaaattgg gcctgaaaat ccatacaata ctccagtatt tgccataaag aaaaaagaca  1140
gtactaaatg gagaaaatta gtagatttca gagaacttaa taagagaact caagatttct  1200
gggaagttca attaggaata ccacatcctg cagg                              1234
```

<210> SEQ ID NO 70
<211> LENGTH: 226
<212> TYPE: PRT
<213> ORGANISM: Artificial sequence
<220> FEATURE:
<223> OTHER INFORMATION: synthetic construct

<400> SEQUENCE: 70

Pro Arg Lys Lys Gly Cys Trp Lys Cys Gly Lys Glu Gly His Gln Met
1               5                   10                  15

Lys Asp Cys Ser Gly Gly Gly Ser Ser Lys Thr Ile Val Leu Ser
            20                  25                  30

Val Gly Glu Ala Thr Arg Thr Leu Thr Glu Ile Gln Ser Thr Ala Asp
        35                  40                  45

Arg Gln Ile Phe Glu Glu Lys Val Gly Pro Leu Val Gly Arg Leu Arg
    50                  55                  60

Leu Thr Ala Ser Leu Arg Gln Asn Gly Ala Lys Thr Ala Tyr Arg Val
65                  70                  75                  80

```
Asn Leu Lys Leu Asp Gln Ala Asp Val Val Asp Ser Gly Leu Pro Lys
             85                  90                  95
Val Arg Tyr Thr Gln Val Trp Ser His Asp Val Thr Ile Val Ala Asn
            100                 105                 110
Ser Thr Glu Ala Ser Arg Lys Ser Leu Tyr Asp Leu Thr Lys Ser Leu
        115                 120                 125
Val Ala Thr Ser Gln Val Glu Asp Leu Val Val Asn Leu Val Pro Leu
    130                 135                 140
Gly Arg Ser Gly Gly Gly Gly Thr Glu Arg Gln Ala Asn Phe Leu
145                 150                 155                 160
Gly Lys Ile Trp Pro Ser His Lys Gly Arg Pro Gly Asn Phe Leu Gln
                165                 170                 175
Ser Arg Pro Glu Pro Thr Ala Pro Pro Glu Glu Ser Phe Arg Phe Gly
            180                 185                 190
Glu Glu Thr Thr Thr Pro Ser Gln Lys Gln Glu Pro Ile Asp Lys Glu
        195                 200                 205
Leu Tyr Pro Leu Ala Ser Leu Arg Ser Leu Phe Gly Ser Asp Pro Ser
    210                 215                 220
Ser Gln
225

<210> SEQ ID NO 71
<211> LENGTH: 1176
<212> TYPE: DNA
<213> ORGANISM: Artificial sequence
<220> FEATURE:
<223> OTHER INFORMATION: synthetic construct

<400> SEQUENCE: 71
cacgtgagat ctgaattcga gatctgccgc cgccatgggt gcgagagcgt cagtattaag      60
cgggggagaa ttagatcgat gggaaaaaat tcggttaagg ccagggggaa agaaaaaata     120
taaattaaaa catatagtat gggcaagcag ggagctagaa cgaggaggtg gtggaggaat     180
ggcttctaac tttactcagt tcgttctcgt cgacaatggc ggaactggcg acgtgactgt     240
cgccccaagc aacttcgcta acgggatcgc tgaatggatc agctctaact cgcgttcaca     300
ggcttacaaa gtaacctgta gcgttcgtca gagctctgcg cagaatcgca atacaccat     360 caaagtcgag gtgcctaaag gcgcctggcg ttcgtactta aatatggaac taaccattcc     420
aattttcgcc acgaattccg actgcgagct tattgttaag gcaatgcaag gtctcctaaa     480
agatggaaac ccgattccct cagcaatcgc agcaaactcc ggcatctacg gtggtggagg     540
aggaatggcg tccaatttca cgcagttcgt cctggttgac aacgggggga ctggggacgt     600
tacggtcgct ccgagcaact tgccaatgg tattgcggag tggatttctt ctaattcacg     660
gtcccaagct tacaaagtga cctgttccgt gcggcaaagt tctgctcaga atagaaagta     720
cactataaag gtcgaagtcc ctaaggggc ctggcgatca tatctcaata tggagcttac     780
catcccaata tttgccacta attctgattg tgaattgatt gtcaaagcaa tgcaaggact     840
cttgaaagac ggaaacccaa tccccagcgc aatcgcagcc aactccggta tataccaggt     900
cagccaaaat taccctatag tgcagaacat ccaggggcaa atggtacatc aggccatatc     960
acctagaact ttaaatgcat gggtaaaagt agtagaagag aaggctttca gcccagaagt    1020
gatacccatg ttttcagcat tatcagaagg agccaccccca caagatttaa acaccatgct    1080
```

```
aaacacagtg gggggacatc aagcagccat gcaaatgtta aaagagacca tcaatgagga   1140
agctgcagaa tgggatagag tgcatccagt gcatgc                             1176
```

<210> SEQ ID NO 72
<211> LENGTH: 380
<212> TYPE: PRT
<213> ORGANISM: Artificial sequence
<220> FEATURE:
<223> OTHER INFORMATION: synthetic construct

<400> SEQUENCE: 72

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Gly Gly Gly Gly
        35                  40                  45

Met Ala Ser Asn Phe Thr Gln Phe Val Leu Val Asp Asn Gly Gly Thr
50                  55                  60

Gly Asp Val Thr Val Ala Pro Ser Asn Phe Ala Asn Gly Ile Ala Glu
65                  70                  75                  80

Trp Ile Ser Ser Asn Ser Arg Ser Gln Ala Tyr Lys Val Thr Cys Ser
                85                  90                  95

Val Arg Gln Ser Ser Ala Gln Asn Arg Lys Tyr Thr Ile Lys Val Glu
            100                 105                 110

Val Pro Lys Gly Ala Trp Arg Ser Tyr Leu Asn Met Glu Leu Thr Ile
        115                 120                 125

Pro Ile Phe Ala Thr Asn Ser Asp Cys Glu Leu Ile Val Lys Ala Met
    130                 135                 140

Gln Gly Leu Leu Lys Asp Gly Asn Pro Ile Pro Ser Ala Ile Ala Ala
145                 150                 155                 160

Asn Ser Gly Ile Tyr Gly Gly Gly Gly Met Ala Ser Asn Phe Thr
                165                 170                 175

Gln Phe Val Leu Val Asp Asn Gly Gly Thr Gly Asp Val Thr Val Ala
            180                 185                 190

Pro Ser Asn Phe Ala Asn Gly Ile Ala Glu Trp Ile Ser Ser Asn Ser
        195                 200                 205

Arg Ser Gln Ala Tyr Lys Val Thr Cys Ser Val Arg Gln Ser Ser Ala
    210                 215                 220

Gln Asn Arg Lys Tyr Thr Ile Lys Val Glu Val Pro Lys Gly Ala Trp
225                 230                 235                 240

Arg Ser Tyr Leu Asn Met Glu Leu Thr Ile Pro Ile Phe Ala Thr Asn
                245                 250                 255

Ser Asp Cys Glu Leu Ile Val Lys Ala Met Gln Gly Leu Leu Lys Asp
            260                 265                 270

Gly Asn Pro Ile Pro Ser Ala Ile Ala Ala Asn Ser Gly Ile Tyr Gln
        275                 280                 285

Val Ser Gln Asn Tyr Pro Ile Val Gln Asn Ile Gln Gly Gln Met Val
    290                 295                 300

His Gln Ala Ile Ser Pro Arg Thr Leu Asn Ala Trp Val Lys Val Val
305                 310                 315                 320

Glu Glu Lys Ala Phe Ser Pro Glu Val Ile Pro Met Phe Ser Ala Leu
                325                 330                 335
```

Ser Glu Gly Ala Thr Pro Gln Asp Leu Asn Thr Met Leu Asn Thr Val
                340                 345                 350

Gly Gly His Gln Ala Ala Met Gln Met Leu Lys Glu Thr Ile Asn Glu
            355                 360                 365

Glu Ala Ala Glu Trp Asp Arg Val His Pro Val His
        370                 375                 380

<210> SEQ ID NO 73
<211> LENGTH: 861
<212> TYPE: DNA
<213> ORGANISM: Artificial sequence
<220> FEATURE:
<223> OTHER INFORMATION: synthetic construct

<400> SEQUENCE: 73
cacgtgagat ctgaattcga gatctgccgc cgccatgggt gcgagagcgt cagtattaag    60
cgggggagaa ttagatcgat gggaaaaaat tcggttaagg ccaggggaa agaaaaaata   120 taaattaaaa catatagtat gggcaagcag ggagctagaa cgaggaggtg gtggaggaat   180
ggcttctaac tttactcagt tcgttctcgt cgactccaaa acaatagtcc tctccgtagg   240
ggaggcaaca cggactttga ccgaaatcca gtcaaccgct gaccgacaaa tctttgaaga   300
gaaagtaggg cctcttgtgg gccgactgcg cttgactgca agcttgcgac aaaacggcgc   360
aaagactgcc tatagggtca accttaaact cgaccaagcc gacgtggtcg atagcggtct   420
ccctaaggtt cggtatacgc aggtctggag tcatgacgta acaatcgtag caaacagcac   480
agaagcctcc cgaaaaagcc tctacgatct gacgaaatcc ttggtggcta cgtcacaggt   540
ggaagacctc gttgtcaacc ttgtacctct gggtcgaaac caggtcagcc aaaattaccc   600
tatagtgcag aacatccagg ggcaaatggt acatcaggcc atatcaccta gaactttaaa   660
tgcatgggta aaagtagtag aagagaaggc tttcagccca gaagtgatac ccatgttttc   720
agcattatca gaaggagcca ccccacaaga tttaaacacc atgctaaaca cagtgggggg   780
acatcaagca gccatgcaaa tgttaaaaga gaccatcaat gaggaagctg cagaatggga   840
tagagtgcat ccagtgcatg c                                             861

<210> SEQ ID NO 74
<211> LENGTH: 275
<212> TYPE: PRT
<213> ORGANISM: Artificial sequence
<220> FEATURE:
<223> OTHER INFORMATION: synthetic construct

<400> SEQUENCE: 74

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Gly Gly Gly Gly
        35                  40                  45

Met Ala Ser Asn Phe Thr Gln Phe Val Leu Val Asp Ser Lys Thr Ile
    50                  55                  60

Val Leu Ser Val Gly Glu Ala Thr Arg Thr Leu Thr Glu Ile Gln Ser
65                  70                  75                  80

Thr Ala Asp Arg Gln Ile Phe Glu Glu Lys Val Gly Pro Leu Val Gly
                85                  90                  95

```
Arg Leu Arg Leu Thr Ala Ser Leu Arg Gln Asn Gly Ala Lys Thr Ala
            100                 105                 110

Tyr Arg Val Asn Leu Lys Leu Asp Gln Ala Asp Val Asp Ser Gly
            115                 120             125

Leu Pro Lys Val Arg Tyr Thr Gln Val Trp Ser His Asp Val Thr Ile
        130                 135                 140

Val Ala Asn Ser Thr Glu Ala Ser Arg Lys Ser Leu Tyr Asp Leu Thr
145                 150                 155                 160

Lys Ser Leu Val Ala Thr Ser Gln Val Glu Asp Leu Val Val Asn Leu
                165                 170                 175

Val Pro Leu Gly Arg Asn Gln Val Ser Gln Asn Tyr Pro Ile Val Gln
                180                 185                 190

Asn Ile Gln Gly Gln Met Val His Gln Ala Ile Ser Pro Arg Thr Leu
            195                 200                 205

Asn Ala Trp Val Lys Val Val Glu Glu Lys Ala Phe Ser Pro Glu Val
            210                 215                 220

Ile Pro Met Phe Ser Ala Leu Ser Glu Gly Ala Thr Pro Gln Asp Leu
225                 230                 235                 240

Asn Thr Met Leu Asn Thr Val Gly Gly His Gln Ala Ala Met Gln Met
                245                 250                 255

Leu Lys Glu Thr Ile Asn Glu Glu Ala Ala Glu Trp Asp Arg Val His
                260                 265                 270

Pro Val His
        275

<210> SEQ ID NO 75
<211> LENGTH: 1239
<212> TYPE: DNA
<213> ORGANISM: Artificial sequence
<220> FEATURE:
<223> OTHER INFORMATION: synthetic construct

<400> SEQUENCE: 75
cacgtgagat ctgaattcga gatctgccgc cgccatgggt gcgagagcgt cagtattaag      60
cgggggagaa ttagatcgat gggaaaaaat tcggttaagg ccagggggaa agaaaaaata     120
taaattaaaa catatagtat gggcaagcag ggagctagaa cgaggaggtg gtggaggaat     180
ggcttctaac tttactcagt tcgttctcgt cgactccaaa acaatagtcc tctccgtagg     240
ggaggcaaca cggactttga ccgaaatcca gtcaaccgct gaccgacaaa tctttgaaga     300
gaaagtaggg cctcttgtgg gccgactgcg cttgactgca agcttgcgac aaaacggcgc     360
aaagactgcc tatagggtca accttaaact cgaccaagcc gacgtggtcg atagcggtct     420
ccctaaggtt cggtatacgc aggtctggag tcatgacgta acaatcgtag caaacagcac     480
agaagcctcc cgaaaaagcc tctacgatct gacgaaatcc ttggtggcta cgtcacaggt     540
ggaagacctc gttgtcaacc ttgtacctct gggtcgagcg gatccgctcg catcaaaaac     600
tattgtgctc tccgtgggag aagccacccg cacgcttacc gaaattcaat caacggcaga     660
cagacaaatc tttgaggaga agtaggtcc gttggtgggt cggttgcgct tgaccgcaag     720
cctccgccaa aacggagcga aaaccgcata ccgcgtaaac ttgaagctgg accagccga     780 tgttgttgac tccggcttgc ccaaagtgcg atatactcag gtctggtctc atgatgtcac     840
aatcgtcgct aattccactg aggctagtcg caaaagtctg tatgacttga caaagtcctt     900
ggtagccacg tcacaggtgg aagatttggt ggtgaacctc gttccactgg gaagaaacca     960
```

```
ggtcagccaa aattacccta tagtgcagaa catccagggg caaatggtac atcaggccat   1020
atcacctaga actttaaatg catgggtaaa agtagtagaa gagaaggctt tcagcccaga   1080
agtgataccc atgttttcag cattatcaga aggagccacc ccacaagatt taaacaccat   1140
gctaaacaca gtgggggggac atcaagcagc catgcaaatg ttaaaagaga ccatcaatga   1200
ggaagctgca gaatgggata gagtgcatcc agtgcatgc                         1239
```

```
<210> SEQ ID NO 76
<211> LENGTH: 401
<212> TYPE: PRT
<213> ORGANISM: Artificial sequence
<220> FEATURE:
<223> OTHER INFORMATION: synthetic construct

<400> SEQUENCE: 76
```

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Gly Gly Gly Gly Gly
        35                  40                  45

Met Ala Ser Asn Phe Thr Gln Phe Val Leu Val Asp Ser Lys Thr Ile
    50                  55                  60

Val Leu Ser Val Gly Glu Ala Thr Arg Thr Leu Thr Glu Ile Gln Ser
65                  70                  75                  80

Thr Ala Asp Arg Gln Ile Phe Glu Glu Lys Val Gly Pro Leu Val Gly
                85                  90                  95

Arg Leu Arg Leu Thr Ala Ser Leu Arg Gln Asn Gly Ala Lys Thr Ala
            100                 105                 110

Tyr Arg Val Asn Leu Lys Leu Asp Gln Ala Asp Val Val Asp Ser Gly
        115                 120                 125

Leu Pro Lys Val Arg Tyr Thr Gln Val Trp Ser His Asp Val Thr Ile
    130                 135                 140

Val Ala Asn Ser Thr Glu Ala Ser Arg Lys Ser Leu Tyr Asp Leu Thr
145                 150                 155                 160

Lys Ser Leu Val Ala Thr Ser Gln Val Glu Asp Leu Val Val Asn Leu
                165                 170                 175

Val Pro Leu Gly Arg Ala Asp Pro Leu Ala Ser Lys Thr Ile Val Leu
            180                 185                 190

Ser Val Gly Glu Ala Thr Arg Thr Leu Thr Glu Ile Gln Ser Thr Ala
        195                 200                 205

Asp Arg Gln Ile Phe Glu Glu Lys Val Gly Pro Leu Val Gly Arg Leu
    210                 215                 220

Arg Leu Thr Ala Ser Leu Arg Gln Asn Gly Ala Lys Thr Ala Tyr Arg
225                 230                 235                 240

Val Asn Leu Lys Leu Asp Gln Ala Asp Val Val Asp Ser Gly Leu Pro
                245                 250                 255

Lys Val Arg Tyr Thr Gln Val Trp Ser His Asp Val Thr Ile Val Ala
            260                 265                 270

Asn Ser Thr Glu Ala Ser Arg Lys Ser Leu Tyr Asp Leu Thr Lys Ser
        275                 280                 285

Leu Val Ala Thr Ser Gln Val Glu Asp Leu Val Val Asn Leu Val Pro
    290                 295                 300

Leu Gly Arg Asn Gln Val Ser Gln Asn Tyr Pro Ile Val Gln Asn Ile
305                 310                 315                 320

```
Gln Gly Gln Met Val His Gln Ala Ile Ser Pro Arg Thr Leu Asn Ala
            325                 330                 335

Trp Val Lys Val Glu Glu Lys Ala Phe Ser Pro Glu Val Ile Pro
            340                 345                 350

Met Phe Ser Ala Leu Ser Glu Gly Ala Thr Pro Gln Asp Leu Asn Thr
            355                 360                 365

Met Leu Asn Thr Val Gly Gly His Gln Ala Ala Met Gln Met Leu Lys
            370                 375                 380

Glu Thr Ile Asn Glu Glu Ala Ala Glu Trp Asp Arg Val His Pro Val
385                 390                 395                 400

His

<210> SEQ ID NO 77
<211> LENGTH: 159
<212> TYPE: DNA
<213> ORGANISM: Artificial sequence
<220> FEATURE:
<223> OTHER INFORMATION: synthetic construct

<400> SEQUENCE: 77
ggtctcgcac cgagtaacgg cagacttctc cacgtttaag tactctggaa acagaatcta      60
cttaaacaag gcaaaatgcc gtgtttatct cgtcaacttg ttggcgagat ggccaacatg     120
aggatcaccc atgtctgcag ggcctttttt tgcggccgc                            159

<210> SEQ ID NO 78
<211> LENGTH: 154
<212> TYPE: DNA
<213> ORGANISM: Artificial sequence
<220> FEATURE:
<223> OTHER INFORMATION: synthetic construct

<400> SEQUENCE: 78
ggtctcgcac cgagtaacgg cagacttctc cacgtttaag tactctgggc aacatgagg      60 atcacccatg tctgcagggc ccagaatcta cttaaacaag gcaaaatgcc gtgtttatct    120
cgtcaacttg ttggcgagat ttttttgcgg ccgc                                154

<210> SEQ ID NO 79
<211> LENGTH: 154
<212> TYPE: DNA
<213> ORGANISM: Artificial sequence
<220> FEATURE:
<223> OTHER INFORMATION: synthetic construct

<400> SEQUENCE: 79
ggtctcgcac cgagtaacgg cagacttctc cacgtttaag tactctggaa acagaatcta     60
cttaaacaag gcaaaatgcc gtgtttatct cgtcaaggcc aacatgagga tcacccatgt    120
ctgcagggcc ttggcgagat ttttttgcgg ccgc                                154

<210> SEQ ID NO 80
<211> LENGTH: 184
<212> TYPE: DNA
<213> ORGANISM: Artificial sequence
<220> FEATURE:
<223> OTHER INFORMATION: synthetic construct

<400> SEQUENCE: 80
ggtctcgcac cgagtaacgg cagacttctc cacgtttaag tactctgggc aacatgagg      60 atcacccatg tctgcagggc ccagaatcta cttaaacaag gcaaaatgcc gtgtttatct    120
```

```
cgtcaaggcc aacatgagga tcacccatgt ctgcagggcc ttggcgagat ttttttgcgg    180
ccgc                                                                 184
```

<210> SEQ ID NO 81
<211> LENGTH: 394
<212> TYPE: DNA
<213> ORGANISM: Artificial sequence
<220> FEATURE:
<223> OTHER INFORMATION: synthetic construct

<400> SEQUENCE: 81

```
ggtaccgagg gcctatttcc catgattcct tcatatttgc atatacgata caaggctgtt     60
agagagataa ttggaattaa tttgactgta aacacaaaga tattagtaca aaatacgtga    120
cgtagaaagt aataatttct gggtagtttt gcagttttaa aattatgttt taaaatggac    180
tatcatatgc ttaccgtaac ttgaaagtat ttcgatttct tggctttata tatcttgtgg    240
aaaggacgaa acaccgagta acggcagact tctccacgtt ctagtactct ggaaacagaa    300
tctactagaa caaggcaaaa tgccgtgttt atctcgtcaa cttgttggcg agatggagca    360
gacgatatgg cgtcgctcct tttttgcgg ccgc                                 394
```

<210> SEQ ID NO 82
<211> LENGTH: 3376
<212> TYPE: DNA
<213> ORGANISM: Artificial sequence
<220> FEATURE:
<223> OTHER INFORMATION: synthetic construct

<400> SEQUENCE: 82

```
gcggccgctt gtgtaatcgt agtttcagag tgttagagct gaaaggaaga agtaggagaa     60
acatgcaaag taaaagtata acactttcct tactaaaccg catgggtttt ccaggtaggg    120
gcaggattca ggatgactga cagggcccct agggaacact gagacccctac gctgacctca   180 taaatgcttg ctacctttgc tgtttttaatt acatctttta atagcaggaa gcagaactct    240
gcacttcaaa agttttttcct cacctgagga gttaatttag tacaagggga aaaagtacag    300
ggggatggga gaaaggcgat cacgttggga agctatagag aaagaagagt aaattttagt    360
aaaggaggtt taaacaaaca aaatataaag agaaatagga acttgaatca aggaaatgat    420
tttaaaacgc agtattctta gtggactaga ggaaaaaaat aatctgagcc aagtagaaga    480 cctttttcccc tcctacccct actttctaag tcacagaggc ttttgttcc cccagacact     540 cttgcagatt agtccaggca gaaacagtta gatgtcccca gttaacctcc tatttgacac    600
cactgattac cccattgata gtcacacttt gggttgtaag tgactttta tttatttgta     660 tttttgactg cattaagagg tctctagttt tttatctctt gtttcccaaa acctaataag    720
taactaatgc acagagcaca ttgatttgta tttattctat ttttagacat aatttattag    780
catgcatgag caaattaaga aaaacaacaa caaatgaatg catatatatg tatatgtatg    840
tgtgtatata tacacacata tatatatata ttttttcttt tcttaccaga aggttttaat    900
ccaaataagg agaagatatg cttagaaccg aggtagagtt ttcatccatt ctgtcctgta    960
agtattttgc atattctgga gacgcaggaa gagatccatc tacatatccc aaagctgaat   1020
tatggtagac aaaactcttc cacttttagt gcatcaactt cttatttgtg taataagaaa   1080
attgggaaaa cgatcttcaa tatgcttacc aagctgtgat tccaaatatt acgtaaaatac  1140 acttgcaaag gaggatgttt ttagtagcaa tttgtactga tggtatgggg ccaagagata   1200
```

-continued

```
tatcttagag ggagggctga gggtttgaag tccaactcct aagccagtgc cagaagagcc    1260
aaggacaggt acggctgtca tcacttagac ctcaccctgt ggagccacac cctaggttg     1320 gccaatctac tcccaggagc agggagggca ggagccaggg ctgggcataa aagtcagggc    1380
agagccatct attgcttaca tttgcttctg acacaactgt gttcactagc aacctcaaac    1440
agacaccatg gtgcatctga ctcctgagga gaaaagcgct gtgacagctc tctggggaaa    1500
agtcaatgtc gacgaagttg gtggtgaggc cctgggcagg ttggtatcaa ggttacaaga    1560
caggtttaag gagaccaata gaaactgggc atgtggagac agagaagact cttgggtttc    1620
tgataggcac tgactctctc tgcctattgg tctatttttcc cacccttagg ctgctggtgg    1680 tctaccccttg gacccagagg ttctttgagt cctttgggga tctgtccact cctgatgctg    1740
ttatgggcaa ccctaaggtg aaggctcatg gcaagaaagt gctcggtgcc tttagtgatg    1800
gcctggctca cctggacaac ctcaagggca cctttgccac actgagtgag ctgcactgtg    1860
acaagctgca cgtggatcct gagaacttca gggtgagtct atgggacgct tgatgttttc    1920
tttccccttc ttttctatgg ttaagttcat gtcataggaa ggggataagt aacagggtac    1980
agtttagaat gggaaacaga cgaatgattg catcagtgtg gaagtctcag gatcgtttta    2040 gtttcttttta tttgctgttc ataacaattg tttttctttttg tttaattctt gctttctttt    2100 ttttttcttct ccgcaatttt tactattata cttaatgcct taacattgtg tataacaaaa    2160
ggaaatatct ctgagataca ttaagtaact taaaaaaaaa ctttacacag tctgcctagt    2220
acattactat ttggaatata tgtgtgctta tttgcatatt cataatctcc ctactttatt    2280
ttcttttatt tttaattgat acataatcat tatacatatt tatgggttaa agtgtaatgt    2340
tttaatatgt gtacacatat tgaccaaatc agggtaattt tgcatttgta atttttaaaaa    2400 atgctttctt cttttaatat acttttttgt ttatcttatt tctaatactt tccctaatct    2460
ctttctttca gggcaataat gatacaatgt atcatgcctc tttgcaccat tctaaagaat    2520
aacagtgata atttctgggt taaggcaata gcaatatctc tgcatataaa tatttctgca    2580
tataaattgt aactgatgta agaggtttca tattgctaat agcagctaca atccagctac    2640
cattctgctt ttattttatg gttgggataa ggctggatta ttctgagtcc aagctaggcc    2700
cttttgctaa tcatgttcat acctcttatc ttcctcccac agctcctggg caacgtgctg    2760
gtctgtgtgc tggcccatca ctttggcaaa gaattcaccc caccagtgca ggctgcctat    2820
cagaaagtgg tggctggtgt ggctaatgcc ctggcccaca gtatcacta agctcgcttt    2880 cttgctgtcc aatttctatt aaaggttcct ttgttcccta agtccaacta ctaaactggg    2940
ggatattatg aagggccttg agcatctgga ttctgcctaa taaaaaacat ttattttcat    3000
tgcaatgatc tcgagggcct atttcccatg attccttcat atttgcatat acgatacaag    3060
gctgttagag agataattgg aattaatttg actgtaaaca caagatatt agtacaaaat    3120 acgtgacgta gaaagtaata atttcttggg tagtttgcag ttttaaaatt atgttttaaa    3180
atggactatc atatgcttac cgtaacttga aagtatttcg atttcttggc tttatatatc    3240
ttgtggaaag gacgaaacac cgccctgtgg ggcaaggtga acgttttagt actctggaaa    3300
cagaatctac taaaacaagg caaaatgccg tgtttatctc gtcaacttgt tggcgagatt    3360
tttctagagc ggccgc                                                   3376
```

<210> SEQ ID NO 83
<211> LENGTH: 275
<212> TYPE: DNA
<213> ORGANISM: Artificial sequence
<220> FEATURE:
<223> OTHER INFORMATION: synthetic construct

<400> SEQUENCE: 83

```
ggatcctaag ctcgctttct tgctgtccaa tttctattaa aggttccttt gttccctaag      60
tccaactact aaactggggg atattatgaa gggccttgag catctggatt ctgcctaata     120
aaaaacattt attttcattg ctagctcgct ttcttgctgt ccaatttcta ttaaaggttc     180
ctttgttccc taagtccaac tactaaactg ggggatatta tgaagggcct tgagcatctg     240
gattctgcct aataaaaaac atttattttc attgc                                275
```

<210> SEQ ID NO 84
<211> LENGTH: 530
<212> TYPE: DNA
<213> ORGANISM: Artificial sequence
<220> FEATURE:
<223> OTHER INFORMATION: synthetic construct

<400> SEQUENCE: 84

```
cggccgaggg cctatttccc atgattcctt catatttgca tatacgatac aaggctgtta      60
gagagataat tggaattaat ttgactgtaa acacaaagat attagtacaa atacgtgac     120 gtagaaagta ataatttctt gggtagtttg cagttttaaa attatgtttt aaaatggact     180
atcatatgct taccgtaact tgaaagtatt tcgatttctt ggcttatat atcttgtgga     240 aaggacgaaa caccgagtaa cggcagactt ctccacgttc tagtactctg gaaacagaat     300
ctactagaac aaggcaaaat gccgtgttta tctcgtcaac ttgttggcga gatatcggag     360
cagacgatat ggcgtcgctc cagcgctcgc tttcttgctg tccaatttct attaaaggtt     420
cctttgttcc ctaagtccaa ctactaaact gggggatatt atgaagggcc ttgagcatct     480
ggattctgcc taataaaaaa catttatttt cattgctttt tttgcggccg                530
```

<210> SEQ ID NO 85
<211> LENGTH: 313
<212> TYPE: DNA
<213> ORGANISM: Artificial sequence
<220> FEATURE:
<223> OTHER INFORMATION: synthetic construct

<400> SEQUENCE: 85

```
gatatcggag cagacgatat ggcgtcgctc cagcgctcgc tttcttgctg tccaatttct      60
attaaaggtt cctttgttcc ctaagtccaa ctactaaact gggggatatt atgaagggcc     120
ttgagcatct ggattctgcc taataaaaaa catttatttt cattgcgctc gctttcttgc     180
tgtccaattt ctattaaagg ttcctttgtt ccctaagtcc aactactaaa ctggggata     240 ttatgaaggg ccttgagcat ctggattctg cctaataaaa aacatttatt ttcattgctt     300
tttttgcggc cgc                                                        313
```

<210> SEQ ID NO 86
<211> LENGTH: 60
<212> TYPE: DNA
<213> ORGANISM: Artificial sequence
<220> FEATURE:
<223> OTHER INFORMATION: synthetic construct

<400> SEQUENCE: 86

```
ctggctaact accggctctt ctggtcccca cagactcaga gagaaccggt gccaccatgg      60
```

<210> SEQ ID NO 87

```
<211> LENGTH: 60
<212> TYPE: DNA
<213> ORGANISM: Artificial sequence
<220> FEATURE:
<223> OTHER INFORMATION: synthetic construct

<400> SEQUENCE: 87
ccatggtggc accggttctc tctgagtctg tggggaccag aagagccggt agttagccag    60

<210> SEQ ID NO 88
<211> LENGTH: 73
<212> TYPE: DNA
<213> ORGANISM: Artificial sequence
<220> FEATURE:
<223> OTHER INFORMATION: synthetic construct

<400> SEQUENCE: 88
aaaaaagaaa aagctttaga aaacatgagg atcacccatg tctgcaggtc gactctagaa    60
ttcctagagc tcg                                                       73

<210> SEQ ID NO 89
<211> LENGTH: 73
<212> TYPE: DNA
<213> ORGANISM: Artificial sequence
<220> FEATURE:
<223> OTHER INFORMATION: synthetic construct

<400> SEQUENCE: 89
cgagctctag gaattctaga gtcgacctgc agacatgggt gatcctcatg ttttctaaag    60
cttttctttt ttt                                                       73

<210> SEQ ID NO 90
<211> LENGTH: 24
<212> TYPE: DNA
<213> ORGANISM: Artificial sequence
<220> FEATURE:
<223> OTHER INFORMATION: synthetic construct

<400> SEQUENCE: 90
accggcgctt gctcttcatt ccct                                           24

<210> SEQ ID NO 91
<211> LENGTH: 24
<212> TYPE: DNA
<213> ORGANISM: Artificial sequence
<220> FEATURE:
<223> OTHER INFORMATION: synthetic construct

<400> SEQUENCE: 91
aaacagggaa tgaagagcaa gcgc                                           24

<210> SEQ ID NO 92
<211> LENGTH: 67
<212> TYPE: DNA
<213> ORGANISM: Artificial sequence
<220> FEATURE:
<223> OTHER INFORMATION: synthetic construct

<400> SEQUENCE: 92
acttgttggc gagatatcta gaaaacatga ggatcaccca tgtctgcaga gcgctcgctt    60
tcttgct                                                              67

<210> SEQ ID NO 93
<211> LENGTH: 67
```

```
<212> TYPE: DNA
<213> ORGANISM: Artificial sequence
<220> FEATURE:
<223> OTHER INFORMATION: synthetic construct

<400> SEQUENCE: 93
agcaagaaag cgagcgctct gcagacatgg gtgatcctca tgttttctag atatctcgcc    60
aacaagt                                                              67

<210> SEQ ID NO 94
<211> LENGTH: 27
<212> TYPE: DNA
<213> ORGANISM: Artificial sequence
<220> FEATURE:
<223> OTHER INFORMATION: synthetic construct

<400> SEQUENCE: 94
actcctgtgg agaagtctgc cgttact                                        27

<210> SEQ ID NO 95
<211> LENGTH: 119
<212> TYPE: DNA
<213> ORGANISM: Artificial sequence
<220> FEATURE:
<223> OTHER INFORMATION: synthetic construct

<400> SEQUENCE: 95
gaacccaggt tcctgacaca gacagactac acccagggaa tgaagagcaa gcgccatact    60
cctgtggaga agtctgccgt tactgccctg tggggcaagg tgaacgtgga ttggctagc    119

<210> SEQ ID NO 96
<211> LENGTH: 24
<212> TYPE: DNA
<213> ORGANISM: Artificial sequence
<220> FEATURE:
<223> OTHER INFORMATION: synthetic construct

<400> SEQUENCE: 96
cgatcacgtt gggaagctat agag                                           24

<210> SEQ ID NO 97
<211> LENGTH: 23
<212> TYPE: DNA
<213> ORGANISM: Artificial sequence
<220> FEATURE:
<223> OTHER INFORMATION: synthetic construct

<400> SEQUENCE: 97
aacatcctga ggaagaatgg gac                                            23

<210> SEQ ID NO 98
<211> LENGTH: 54
<212> TYPE: DNA
<213> ORGANISM: Artificial sequence
<220> FEATURE:
<223> OTHER INFORMATION: synthetic construct

<400> SEQUENCE: 98
tcgtcggcag cgtcagatgt gtataagaga cagttccatt tcaggtgtcg tgag          54

<210> SEQ ID NO 99
<211> LENGTH: 55
<212> TYPE: DNA
<213> ORGANISM: Artificial sequence
<220> FEATURE:
```

<223> OTHER INFORMATION: synthetic construct

<400> SEQUENCE: 99
tcgtcggcag cgtcagatgt gtataagaga cagattccat ttcaggtgtc gtgag    55

<210> SEQ ID NO 100
<211> LENGTH: 56
<212> TYPE: DNA
<213> ORGANISM: Artificial sequence
<220> FEATURE:
<223> OTHER INFORMATION: synthetic construct

<400> SEQUENCE: 100
tcgtcggcag cgtcagatgt gtataagaga caggattcca tttcaggtgt cgtgag    56

<210> SEQ ID NO 101
<211> LENGTH: 57
<212> TYPE: DNA
<213> ORGANISM: Artificial sequence
<220> FEATURE:
<223> OTHER INFORMATION: synthetic construct

<400> SEQUENCE: 101
tcgtcggcag cgtcagatgt gtataagaga cagcgattcc atttcaggtg tcgtgag    57

<210> SEQ ID NO 102
<211> LENGTH: 55
<212> TYPE: DNA
<213> ORGANISM: Artificial sequence
<220> FEATURE:
<223> OTHER INFORMATION: synthetic construct

<400> SEQUENCE: 102
gtctcgtggg ctcggagatg tgtataagag acagtgaact tcagggtcag cttgc    55

<210> SEQ ID NO 103
<211> LENGTH: 61
<212> TYPE: DNA
<213> ORGANISM: Artificial sequence
<220> FEATURE:
<223> OTHER INFORMATION: synthetic construct

<400> SEQUENCE: 103
gaagagcaag cgccatactc ctgtggagaa gtctgccgtt actgccctgt ggggcaaggt    60
g    61

<210> SEQ ID NO 104
<211> LENGTH: 49
<212> TYPE: DNA
<213> ORGANISM: Artificial sequence
<220> FEATURE:
<223> OTHER INFORMATION: synthetic construct

<400> SEQUENCE: 104
gaagagcaag cgccatactc ctgccgttac tgccctgtgg ggcaaggtg    49

<210> SEQ ID NO 105
<211> LENGTH: 60
<212> TYPE: DNA
<213> ORGANISM: Artificial sequence
<220> FEATURE:
<223> OTHER INFORMATION: synthetic construct

<400> SEQUENCE: 105
gaagagcaag cgccatactc ctgtgagaag tctgccgtta ctgccctgtg gggcaaggtg    60

<210> SEQ ID NO 106
<211> LENGTH: 58
<212> TYPE: DNA
<213> ORGANISM: Artificial sequence
<220> FEATURE:
<223> OTHER INFORMATION: synthetic construct

<400> SEQUENCE: 106
gaagagcaag cgccatactc ctgtgaagtc tgccgttact gccctgtggg gcaaggtg    58

<210> SEQ ID NO 107
<211> LENGTH: 53
<212> TYPE: DNA
<213> ORGANISM: Artificial sequence
<220> FEATURE:
<223> OTHER INFORMATION: synthetic construct

<400> SEQUENCE: 107
gaagagcaag cgccatactc ctgtctgccg ttactgccct gtggggcaag gtg    53

<210> SEQ ID NO 108
<211> LENGTH: 58
<212> TYPE: DNA
<213> ORGANISM: Artificial sequence
<220> FEATURE:
<223> OTHER INFORMATION: synthetic construct

<400> SEQUENCE: 108
gaagagcaag cgccatactc ctgagaagtc tgccgttact gccctgtggg gcaaggtg    58

<210> SEQ ID NO 109
<211> LENGTH: 59
<212> TYPE: DNA
<213> ORGANISM: Artificial sequence
<220> FEATURE:
<223> OTHER INFORMATION: synthetic construct

<400> SEQUENCE: 109
gaagagcaag cgccatactc ctggagaagt ctgccgttac tgccctgtgg ggcaaggtg    59

<210> SEQ ID NO 110
<211> LENGTH: 35
<212> TYPE: DNA
<213> ORGANISM: Artificial sequence
<220> FEATURE:
<223> OTHER INFORMATION: synthetic construct

<400> SEQUENCE: 110
gaagagcaag cgccatactc ctgtggggca aggtg    35

<210> SEQ ID NO 111
<211> LENGTH: 55
<212> TYPE: DNA
<213> ORGANISM: Artificial sequence
<220> FEATURE:
<223> OTHER INFORMATION: synthetic construct

<400> SEQUENCE: 111
gaagagcaag cgccatactc ctgtgtctgc cgttactgcc ctgtggggca aggtg    55

<210> SEQ ID NO 112
<211> LENGTH: 38
<212> TYPE: DNA
<213> ORGANISM: Artificial sequence
<220> FEATURE:

<223> OTHER INFORMATION: synthetic construct

<400> SEQUENCE: 112

```
gaagagcaag cgccgttact gccctgtggg gcaaggtg                           38
```

<210> SEQ ID NO 113
<211> LENGTH: 4004
<212> TYPE: DNA
<213> ORGANISM: Artificial sequence
<220> FEATURE:
<223> OTHER INFORMATION: synthetic construct

<400> SEQUENCE: 113

```
gcggccgctc tcgaactcct caagcaatcc acctgccttg gcctcccaaa gtgctgggat     60
tgcaggcgtg agtcactgca cccagccgag agaataaatt tctgttggtt taagccactc    120
agtttgggga taacttatgg cagccctagc aaactaatac atactaaaga tacatactaa    180
atactaagct gggccatata gtccagtttt cctgagactc ccaggcaagt gctgtttttc    240
tttgcttaat atcctacacc actttctgtc tggtaaaatt acactcattc tttaagatgc    300
cactgaaata gcacctcttc agcacagcct tcactaaact atcccctct ccatcttggt    360 aaatttagtt acttcctctt ctgtgctcac atactttgta gtatctctac atttatgcta    420
taggacttgt tacactatgt tgtattactt gtttatgtct tccccacttt tctgtgagtg    480
tctagaaata tgaggatgtc ttgttggtct atttccagaa cataagcaca gtgcctggca    540
catattaaaa acgtaataaa tgtttgctga ataaatagtt tctgtaagtg cttctccaa    600 tcacctctgt gttttcgggg aaggtaaaac tggcaacagg atgaagaatg gattagagag    660
cagagggcct ttagaaaggg aggccagttg atggagtcta gatagaatca tgactagagc    720
taatgaaaga ctgatttagc agagtggctg tggtaatgaa aggaggaaa ccgttgggag    780 aaacaccaca gaagcagagt gggttatatt ctctgggtga gagagggga gaaattgaag    840 ctgattctga ggtttcaagt ctgggtgact gagagggtga cgataccatt gactgaggtg    900
gggaaggcag gaagagaagc agagttgggg gaagatggga agcttgaagc tagtattgtt    960
gttcctccat ttctagaata tttttgtatt ataagtcaca cttcctcgcc agtctcaaca   1020
gggacccagc tcaggcagca gctaagggtg ggtattctgg tttggattag atcagaggaa   1080
agacagctgt atatgtgccc acaggagcca agacggtatt ttccatcctc ccaaaacagt   1140
agagctttga cagagattta agggtgacca agtcaaggaa gaggcatggc atagaacggt   1200
gatgtcgggg gtgggggttc agaacttcca ttatagaagg taatgattta gaggagaagg   1260
tggttgagaa tggtgctagt ggtagtgaac agatccttcc caggatctag gtgggctgag   1320
gatttttgag tctgtgacac tattgtatat ccagctttag tttctgttta ccaccttaca   1380
gcagcaccta atctcctaga ggacttagcc cgtgtcacac agcacatatt tgccacaccc   1440
tctgtaaagc cctggtttat aaggttcttt ccaccggaag ctatgacaga ggaaacgtgt   1500
gggtggggag gggtagtggg tgaggaccc aggttcctgc caccatgctc aaaccttccc   1560
tgccttttac cagcttgctg tttctccagc tccctctcct cggcgtcgga ctcaatacaa   1620
ctatcctgac acctaacgga aacgaggata caaccgccga cttttttctc acaaccatgc   1680
ctacagatag cttgtccgtg agcaccctcc ctctgcctga agtgcagtgc ttcgtcttta   1740
acgtggaata tatgaactgt acctggaatt cctccagcga acctcagcca acaaatctga   1800
cactccacta ctggtataaa aatagcgaca acgacaaggt gcagaaatgt tcccattact   1860 tgttttagcga ggagattacc agcggatgcc agctccagaa gaaagaaatt catctgtatc   1920
```

```
agaccttcgt ggtgcagctg caggatccta gagagcctag aaggcaggct acccagatgt    1980
tgaagctcca gaacctcgtc attccttggg cccctgaaaa tctgaccttg cataagctct    2040
ccgagagcca gctggagctc aattggaata acaggtttct gaatcattgc ctggaacatc    2100
tcgtccaata tagaaccgat tgggatcatt cctggaccga gcagagcgtc gactaccggc    2160
acaaatttag cctgccaagc gtcgacggac agaagagata taccttcaga gtgagatcca    2220
gattcaatcc tctgtgcggc tccgcacagc actggtccga gtggtcccat cctattcatt    2280
ggggatccaa caccagcaag gaaaacccat ttctgttcgc tctggaggct gtcgtgatta    2340
gcgtgggaag catgggcctg atcatttcct tgctgtgcgt ttacttttgg ctggagagaa    2400
ccatgcctag gatccctaca ctcaaaaatc tggaagactt ggtgacagag tatcatggaa    2460
atttcagcgc ttggtccgga gtcagcaaag gcctcgccga aagcctccag cctgattata    2520
gcgagaggct gtgtctggtg agcgaaatcc ctcctaaggg cggagctctg ggcgaaggac    2580
caggcgctag cccttgtaat cagcactccc cttattgggc tcctccttgc tatacattga    2640
aaccagagac ataagggaac ccaggagaca ggccacacag atgctaaaac tgcagaatct    2700
gggtaatttg gaaagaaagg gtcaagagac cagggatact gtgggacatt ggagtctaca    2760
gagtagtgtt cttttatcat aagggtacat gggcagaaaa gaggaggtag gggatcatga    2820
tgggaaggga ggaggtatta ggggcactac cttcaggatc ctgacttgtc taggccaggg    2880
gaatgaccac atatgcacac atatctccag tgatccctg gctccagag aacctaacac    2940 ttcacaaact gagtgaatcc cagctagaac tgaactggaa caacagattc ttgaaccact    3000
gtttggagca cttggtgcag taccggactg actgggacca cagctggact gtgagtgact    3060
agggacgtga atgtagcagc taaggccaag aaagtagggc taaaggattc aaccagacag    3120
atagaaggac ctaatatcaa gctcctgttc tctgcctccc agcttctctg ctcaccccct    3180
accctccctc ctccaactcc tttcctcgag ggcctatttc ccatgattcc ttcatatttg    3240
catatacgat acaaggctgt tagagagata attggaatta atttgactgt aaacacaaag    3300
atattagtac aaaatacgtg acgtagaaag taataatttc ttgggtagtt tgcagtttta    3360
aaattatgtt ttaaaatgga ctatcatatg cttaccgtaa cttgaaagta tttcgatttc    3420
ttggctttat atatcttgtg gaaaggacga acaccgtgg cctgtctcct gggttcccgt    3480
tttagtactc tggaaacaga atctactaaa acaaggcaaa atgccgtgtt tatctcgtca    3540
acttgttggc gagatttttt gttttagagc tagaaatagc aagttaaaat aaggctagtc    3600 cgttttagc gcgtgcgcca attctgcaga caaatgaggg cctatttccc atgattcctt    3660
catatttgca tatacgatac aaggctgtta gagagataat tggaattaat ttgactgtaa    3720
acacaaagat attagtacaa atacgtgac gtagaaagta ataatttctt gggtagtttg    3780
cagttttaaa attatgtttt aaaatggact atcatatgct taccgtaact tgaaagtatt    3840
tcgatttctt ggctttatat atcttgtgga aaggacgaaa caccggacac agacagacta    3900
cacccagttt tagtactctg gaaacagaat ctactaaaac aaggcaaaat gccgtgttta    3960
tctcgtcaac ttgttggcga gattttttggt accggtgcgg ccgc                   4004
```

<210> SEQ ID NO 114
<211> LENGTH: 3372
<212> TYPE: DNA
<213> ORGANISM: Artificial sequence
<220> FEATURE:
<223> OTHER INFORMATION: synthetic construct

<400> SEQUENCE: 114

```
gcggccgctt gtgtaatcgt agtttcagag tgttagagct gaaaggaaga agtaggagaa      60
acatgcaaag taaaagtata acactttcct tactaaaccg acatgggttt ccaggtaggg     120
gcaggattca ggatgactga cagggccctt agggaacact gagaccctac gctgacctca     180
taaatgcttg ctacctttgc tgttttaatt acatctttta atagcaggaa gcagaactct     240
gcacttcaaa agttttcct cacctgagga gttaatttag tacaagggga aaaagtacag     300
ggggatggga gaaaggcgat cacgttggga agctatagag aaagaagagt aaattttagt     360
aaaggaggtt taaacaaaca aaatataaag agaaatagga acttgaatca aggaaatgat     420
tttaaaacgc agtattctta gtggactaga ggaaaaaaat aatctgagcc aagtagaaga     480
ccttttcccc tcctacccct actttctaag tcacagaggc tttttgttcc cccagacact     540
cttgcagatt agtccaggca gaaacagtta gatgtcccca gttaacctcc tatttgacac     600
cactgattac cccattgata gtcacacttt gggttgtaag tgactttta tttatttgta     660
tttttgactg cattaagagg tctctagttt tttatctctt gtttcccaaa acctaataag     720
taactaatgc acagagcaca ttgatttgta tttattctat ttttagacat aatttattag     780
catgcatgag caaattaaga aaaacaacaa caaatgaatg catatatatg tatatgtatg     840
tgtgtatata tacacacata tatatatata tttttctttt tcttaccaga aggttttaat     900
ccaataaagg agaagatatg cttagaaccg aggtagagtt ttcatccatt ctgtcctgta     960
agtattttgc atattctgga gacgcaggaa gagatccatc tacatatccc aaagctgaat    1020
tatggtagac aaaactcttc cacttttagt gcatcaactt cttatttgtg taataagaaa    1080
attgggaaaa cgatcttcaa tatgcttacc aagctgtgat tccaaatatt acgtaaatac    1140
acttgcaaag gaggatgttt ttagtagcaa tttgtactga tggtatgggg ccaagagata    1200
tatcttagag ggagggctga gggtttgaag tccaactcct aagccagtgc cagaagagcc    1260
aaggacaggt acggctgtca tcacttagac ctcaccctgt ggagccacac cctagggttg    1320
gccaatctac tcccaggagc agggagggca ggagccaggg ctgggcataa aagtcagggc    1380
agagccatct attgcttaca tttgcttctg acacaactgt gttcactagc aacctcaaac    1440
agacaccatg gtgcatctga ctcctgagga gaaaagcgct gtgacagctc tctgggaaa     1500
agtcaatgtc gacgaagttg gtggtgaggc cctgggcagg ttggtatcaa ggttacaaga    1560
caggtttaag gagaccaata gaaactgggc atgtggagac agagaagact cttgggtttc    1620
tgataggcac tgactctctc tgcctattgg tctattttcc cacccttagg ctgctggtgg    1680
tctacccttg gacccagagg ttctttgagt cctttgggga tctgtccact cctgatgctg    1740
ttatgggcaa ccctaaggtg aaggctcatg gcaagaaagt gctcggtgcc tttagtgatg    1800
gcctggctca cctggacaac ctcaagggca cctttgccac actgagtgag ctgcactgtg    1860
acaagctgca cgtggatcct gagaacttca gggtgagtct atgggacgct tgatgttttc    1920
tttccccttc ttttctatgg ttaagttcat gtcataggaa ggggataagt aacagggtac    1980
agtttagaat gggaaacaga cgaatgattg catcagtgtg gaagtctcag gatcgtttta    2040
gtttctttta tttgctgttc ataacaattg ttttctttg tttaattctt gctttctttt    2100
tttttcttct ccgcaatttt tactattata cttaatgcct taacattgtg tataacaaaa    2160
ggaaatatct ctgagataca ttaagtaact taaaaaaaaa ctttacacag tctgcctagt    2220
acattactat ttggaatata tgtgtgctta tttgcatatt cataatctcc ctactttatt    2280
ttcttttatt tttaattgat acataatcat tatacatatt tatgggttaa agtgtaatgt    2340
```

```
tttaatatgt gtacacatat tgaccaaatc agggtaattt tgcatttgta attttaaaaa    2400
atgctttctt cttttaatat acttttttgt ttatcttatt tctaatactt tccctaatct    2460
ctttctttca gggcaataat gatacaatgt atcatgcctc tttgcaccat tctaaagaat    2520
aacagtgata atttctgggt taaggcaata gcaatatctc tgcatataaa tatttctgca    2580
tataaattgt aactgatgta agaggtttca tattgctaat agcagctaca atccagctac    2640
cattctgctt ttattttatg gttgggataa ggctggatta ttctgagtcc aagctaggcc    2700
cttttgctaa tcatgttcat acctcttatc ttcctcccac agctcctggg caacgtgctg    2760
gtctgtgtgc tggcccatca ctttggcaaa gaattcaccc caccagtgca ggctgcctat    2820
cagaaagtgg tggctggtgt ggctaatgcc ctggcccaca gtatcacta agctcgcttt      2880 cttgctgtcc aatttctatt aaaggttcct ttgttcccta agtccaacta ctaaactggg    2940
ggatattatg aagggccttg agcatctgga ttctgcctaa taaaaaacat ttattttcat    3000
tgcaatgatc tcgagggcct atttcccatg attccttcat atttgcatat acgatacaag    3060
gctgttagag agataattgg aattaatttg actgtaaaca caaagatatt agtacaaaat    3120
acgtgacgta gaaagtaata atttcttggg tagtttgcag ttttaaaatt atgttttaaa    3180
atggactatc atatgcttac cgtaacttga aagtatttcg atttcttggc tttatatatc    3240
ttgtggaaag gacgaaacac cgagtaacgg cagacttctc cacgttttag tactctggaa    3300
acagaatcta ctaaaacaag gcaaaatgcc gtgtttatct cgtcaacttg ttggcgagat    3360
ttttgcggcc gc                                                        3372

<210> SEQ ID NO 115
<211> LENGTH: 22
<212> TYPE: DNA
<213> ORGANISM: Artificial sequence
<220> FEATURE:
<223> OTHER INFORMATION: synthetic construct

<400> SEQUENCE: 115
gggcagagcc atctattgct ta                                              22

<210> SEQ ID NO 116
<211> LENGTH: 25
<212> TYPE: DNA
<213> ORGANISM: Artificial sequence
<220> FEATURE:
<223> OTHER INFORMATION: synthetic construct

<400> SEQUENCE: 116
tgggaaaata gaccaatagg cagag                                           25

<210> SEQ ID NO 117
<211> LENGTH: 20
<212> TYPE: DNA
<213> ORGANISM: Artificial sequence
<220> FEATURE:
<223> OTHER INFORMATION: synthetic construct

<400> SEQUENCE: 117
cgccaacaag ttgacgagat                                                 20

<210> SEQ ID NO 118
<211> LENGTH: 23
<212> TYPE: DNA
<213> ORGANISM: Artificial sequence
<220> FEATURE:
```

<223> OTHER INFORMATION: synthetic construct

<400> SEQUENCE: 118
gataaacacg gcattttgcc ttg                                        23

<210> SEQ ID NO 119
<211> LENGTH: 55
<212> TYPE: DNA
<213> ORGANISM: Artificial sequence
<220> FEATURE:
<223> OTHER INFORMATION: synthetic construct

<400> SEQUENCE: 119
gtctcgtggg ctcggagatg tgtataagag acagtggctg aggtgggaga atcac     55

<210> SEQ ID NO 120
<211> LENGTH: 54
<212> TYPE: DNA
<213> ORGANISM: Artificial sequence
<220> FEATURE:
<223> OTHER INFORMATION: synthetic construct

<400> SEQUENCE: 120
tcgtcggcag cgtcagatgt gtataagaga cagtatttct cctctgcact gccc      54

<210> SEQ ID NO 121
<211> LENGTH: 55
<212> TYPE: DNA
<213> ORGANISM: Artificial sequence
<220> FEATURE:
<223> OTHER INFORMATION: synthetic construct

<400> SEQUENCE: 121
gtctcgtggg ctcggagatg tgtataagag acagtggagc ctcggcctag atttc     55

<210> SEQ ID NO 122
<211> LENGTH: 54
<212> TYPE: DNA
<213> ORGANISM: Artificial sequence
<220> FEATURE:
<223> OTHER INFORMATION: synthetic construct

<400> SEQUENCE: 122
tcgtcggcag cgtcagatgt gtataagaga cagttgatcc cttccaccaa tgtc      54

<210> SEQ ID NO 123
<211> LENGTH: 55
<212> TYPE: DNA
<213> ORGANISM: Artificial sequence
<220> FEATURE:
<223> OTHER INFORMATION: synthetic construct

<400> SEQUENCE: 123
gtctcgtggg ctcggagatg tgtataagag acagtcacgg ctaggaatag caagg     55

<210> SEQ ID NO 124
<211> LENGTH: 58
<212> TYPE: DNA
<213> ORGANISM: Artificial sequence
<220> FEATURE:
<223> OTHER INFORMATION: synthetic construct

<400> SEQUENCE: 124
tcgtcggcag cgtcagatgt gtataagaga cagtaaagga aattccatca gactaacg  58

```
<210> SEQ ID NO 125
<211> LENGTH: 55
<212> TYPE: DNA
<213> ORGANISM: Artificial sequence
<220> FEATURE:
<223> OTHER INFORMATION: synthetic construct

<400> SEQUENCE: 125
gtctcgtggg ctcggagatg tgtataagag acagtctttg aaaatgccgt ccatc       55

<210> SEQ ID NO 126
<211> LENGTH: 56
<212> TYPE: DNA
<213> ORGANISM: Artificial sequence
<220> FEATURE:
<223> OTHER INFORMATION: synthetic construct

<400> SEQUENCE: 126
tcgtcggcag cgtcagatgt gtataagaga cagtaagaca aaagcagaag gtaagc      56

<210> SEQ ID NO 127
<211> LENGTH: 58
<212> TYPE: DNA
<213> ORGANISM: Artificial sequence
<220> FEATURE:
<223> OTHER INFORMATION: synthetic construct

<400> SEQUENCE: 127
gtctcgtggg ctcggagatg tgtataagag acagtaagtt gaagatagga ccccactc    58

<210> SEQ ID NO 128
<211> LENGTH: 55
<212> TYPE: DNA
<213> ORGANISM: Artificial sequence
<220> FEATURE:
<223> OTHER INFORMATION: synthetic construct

<400> SEQUENCE: 128
gtctcgtggg ctcggagatg tgtataagag acagtggcaa caagagcaaa actcc       55

<210> SEQ ID NO 129
<211> LENGTH: 55
<212> TYPE: DNA
<213> ORGANISM: Artificial sequence
<220> FEATURE:
<223> OTHER INFORMATION: synthetic construct

<400> SEQUENCE: 129
tcgtcggcag cgtcagatgt gtataagaga cagtccagaa agggaaaact tgcac       55

<210> SEQ ID NO 130
<211> LENGTH: 55
<212> TYPE: DNA
<213> ORGANISM: Artificial sequence
<220> FEATURE:
<223> OTHER INFORMATION: synthetic construct

<400> SEQUENCE: 130
gtctcgtggg ctcggagatg tgtataagag acagtccact gacccaatct tttcc       55

<210> SEQ ID NO 131
<211> LENGTH: 54
<212> TYPE: DNA
<213> ORGANISM: Artificial sequence
<220> FEATURE:
<223> OTHER INFORMATION: synthetic construct
```

```
<400> SEQUENCE: 131
tcgtcggcag cgtcagatgt gtataagaga cagtctgctc tttgcctgtt ggag     54

<210> SEQ ID NO 132
<211> LENGTH: 55
<212> TYPE: DNA
<213> ORGANISM: Artificial sequence
<220> FEATURE:
<223> OTHER INFORMATION: synthetic construct

<400> SEQUENCE: 132
gtctcgtggg ctcggagatg tgtataagag acagtgctaa agctggaagg ctgtg    55

<210> SEQ ID NO 133
<211> LENGTH: 20
<212> TYPE: DNA
<213> ORGANISM: Artificial sequence
<220> FEATURE:
<223> OTHER INFORMATION: synthetic construct

<400> SEQUENCE: 133
atgccctctg tagtgggttg                                            20

<210> SEQ ID NO 134
<211> LENGTH: 20
<212> TYPE: DNA
<213> ORGANISM: Artificial sequence
<220> FEATURE:
<223> OTHER INFORMATION: synthetic construct

<400> SEQUENCE: 134
ggcagctgca ggaataagag                                            20

<210> SEQ ID NO 135
<211> LENGTH: 55
<212> TYPE: DNA
<213> ORGANISM: Artificial sequence
<220> FEATURE:
<223> OTHER INFORMATION: synthetic construct

<400> SEQUENCE: 135
tcgtcggcag cgtcagatgt gtataagaga cagtgaagct atgacagagg aaacg     55

<210> SEQ ID NO 136
<211> LENGTH: 40
<212> TYPE: DNA
<213> ORGANISM: Artificial sequence
<220> FEATURE:
<223> OTHER INFORMATION: Synthetic construct

<400> SEQUENCE: 136
agcgccatac tcctgtggag aagtctgccg ttactgccct                      40

<210> SEQ ID NO 137
<211> LENGTH: 40
<212> TYPE: DNA
<213> ORGANISM: ARTIFICIAL SEQUENCE
<220> FEATURE:
<223> OTHER INFORMATION: Synthetic construct

<400> SEQUENCE: 137
agcgccatac tcctgtggag aagtctgccg ttactgccct                      40

<210> SEQ ID NO 138
<211> LENGTH: 27
```

```
<212> TYPE: DNA
<213> ORGANISM: ARTIFICIAL SEQUENCE
<220> FEATURE:
<223> OTHER INFORMATION: Synthetic construct

<400> SEQUENCE: 138
agcgccatac tcctgccgtt actgcct                                              27

<210> SEQ ID NO 139
<211> LENGTH: 39
<212> TYPE: DNA
<213> ORGANISM: ARTIFICIAL SEQUENCE
<220> FEATURE:
<223> OTHER INFORMATION: Synthetic construct

<400> SEQUENCE: 139
agcgccatac tcctgtgaga agtctgccgt tactgccct                                 39

<210> SEQ ID NO 140
<211> LENGTH: 38
<212> TYPE: DNA
<213> ORGANISM: ARTIFICIAL SEQUENCE
<220> FEATURE:
<223> OTHER INFORMATION: Synthetic construct

<400> SEQUENCE: 140
agccgccata ctcctgtgaa gtctgccgtt actgccct                                  38

<210> SEQ ID NO 141
<211> LENGTH: 32
<212> TYPE: DNA
<213> ORGANISM: ARTIFICIAL SEQUENCE
<220> FEATURE:
<223> OTHER INFORMATION: Synthetic construct

<400> SEQUENCE: 141
agcgccatac tcctgtctgc cgttactgcc ct                                        32

<210> SEQ ID NO 142
<211> LENGTH: 37
<212> TYPE: DNA
<213> ORGANISM: ARTIFICIAL SEQUENCE
<220> FEATURE:
<223> OTHER INFORMATION: Synthetic construct

<400> SEQUENCE: 142
agcgccatac tcctgagaag tctgccgtta ctgccct                                   37

<210> SEQ ID NO 143
<211> LENGTH: 38
<212> TYPE: DNA
<213> ORGANISM: ARTIFICIAL SEQUENCE
<220> FEATURE:
<223> OTHER INFORMATION: Synthetic construct

<400> SEQUENCE: 143
agcgccatac tcctggagaa gtctgccgtt actgccct                                  38

<210> SEQ ID NO 144
<211> LENGTH: 14
<212> TYPE: DNA
<213> ORGANISM: ARTIFICIAL SEQUENCE
<220> FEATURE:
<223> OTHER INFORMATION: Synthetic construct
```

```
<400> SEQUENCE: 144
agcgccatac tcct                                                         14

<210> SEQ ID NO 145
<211> LENGTH: 34
<212> TYPE: DNA
<213> ORGANISM: ARTIFICIAL SEQUENCE
<220> FEATURE:
<223> OTHER INFORMATION: Synthetic construct

<400> SEQUENCE: 145
agcgccatac tcctgtgtct gccgttactg ccct                                   34

<210> SEQ ID NO 146
<211> LENGTH: 17
<212> TYPE: DNA
<213> ORGANISM: ARTIFICIAL SEQUENCE
<220> FEATURE:
<223> OTHER INFORMATION: Synthetic construct

<400> SEQUENCE: 146
agcgccgtta ctgccct                                                      17

<210> SEQ ID NO 147
<211> LENGTH: 33
<212> TYPE: DNA
<213> ORGANISM: ARTIFICIAL SEQUENCE
<220> FEATURE:
<223> OTHER INFORMATION: Synthetic construct

<400> SEQUENCE: 147
cgccatactc ctgtggagaa gtctgccgtt act                                    33

<210> SEQ ID NO 148
<211> LENGTH: 39
<212> TYPE: DNA
<213> ORGANISM: ARTIFICIAL SEQUENCE
<220> FEATURE:
<223> OTHER INFORMATION: Synthetic construct

<400> SEQUENCE: 148
ttcctgacac agacagacta cacccaggga atgaagagc                              39

<210> SEQ ID NO 149
<211> LENGTH: 38
<212> TYPE: DNA
<213> ORGANISM: ARTIFICIAL SEQUENCE
<220> FEATURE:
<223> OTHER INFORMATION: Synthetic construct

<400> SEQUENCE: 149
ttcctgacac agacagacta caccagggaa tgaagagc                               38

<210> SEQ ID NO 150
<211> LENGTH: 35
<212> TYPE: DNA
<213> ORGANISM: ARTIFICIAL SEQUENCE
<220> FEATURE:
<223> OTHER INFORMATION: Synthetic construct

<400> SEQUENCE: 150
ttcctgacac agacagacta cagggaatga agagc                                  35

<210> SEQ ID NO 151
```

```
<211> LENGTH: 37
<212> TYPE: DNA
<213> ORGANISM: ARTIFICIAL SEQUENCE
<220> FEATURE:
<223> OTHER INFORMATION: Synthetic construct

<400> SEQUENCE: 151
ttcctgacac agacagacta cacagggaat gaagagc                          37

<210> SEQ ID NO 152
<211> LENGTH: 28
<212> TYPE: DNA
<213> ORGANISM: ARTIFICIAL SEQUENCE
<220> FEATURE:
<223> OTHER INFORMATION: Synthetic construct

<400> SEQUENCE: 152
ttcctgacac agacagggaa tgaagagc                                    28

<210> SEQ ID NO 153
<211> LENGTH: 36
<212> TYPE: DNA
<213> ORGANISM: ARTIFICIAL SEQUENCE
<220> FEATURE:
<223> OTHER INFORMATION: Synthetic construct

<400> SEQUENCE: 153
ttcctgacac agacagacta ccagggaatg aagagc                           36

<210> SEQ ID NO 154
<211> LENGTH: 30
<212> TYPE: DNA
<213> ORGANISM: ARTIFICIAL SEQUENCE
<220> FEATURE:
<223> OTHER INFORMATION: Synthetic construct

<400> SEQUENCE: 154
ttcctgacac agacagacta cacgaagagc                                  30

<210> SEQ ID NO 155
<211> LENGTH: 32
<212> TYPE: DNA
<213> ORGANISM: ARTIFICIAL SEQUENCE
<220> FEATURE:
<223> OTHER INFORMATION: Synthetic construct

<400> SEQUENCE: 155
ttcctgacac agacagacag ggaatgaaga gc                               32

<210> SEQ ID NO 156
<211> LENGTH: 39
<212> TYPE: DNA
<213> ORGANISM: ARTIFICIAL SEQUENCE
<220> FEATURE:
<223> OTHER INFORMATION: Synthetic construct

<400> SEQUENCE: 156
ttcctgacac agacagacta cacccaggga atgaagagc                        39

<210> SEQ ID NO 157
<211> LENGTH: 38
<212> TYPE: DNA
<213> ORGANISM: ARTIFICIAL SEQUENCE
<220> FEATURE:
<223> OTHER INFORMATION: Synthetic construct
```

<400> SEQUENCE: 157
ttcctgacac agacagacta caccagggaa tgaagagc                                38

<210> SEQ ID NO 158
<211> LENGTH: 35
<212> TYPE: DNA
<213> ORGANISM: ARTIFICIAL SEQUENCE
<220> FEATURE:
<223> OTHER INFORMATION: Synthetic construct

<400> SEQUENCE: 158
ttcctgacac agacagacta cagggaatga agagc                                   35

<210> SEQ ID NO 159
<211> LENGTH: 37
<212> TYPE: DNA
<213> ORGANISM: ARTIFICIAL SEQUENCE
<220> FEATURE:
<223> OTHER INFORMATION: Synthetic construct

<400> SEQUENCE: 159
ttcctgacac agacagacta cacagggaat gaagagc                                 37

<210> SEQ ID NO 160
<211> LENGTH: 28
<212> TYPE: DNA
<213> ORGANISM: ARTIFICIAL SEQUENCE
<220> FEATURE:
<223> OTHER INFORMATION: Synthetic construct

<400> SEQUENCE: 160
ttcctgacac agacagggaa tgaagagc                                           28

<210> SEQ ID NO 161
<211> LENGTH: 36
<212> TYPE: DNA
<213> ORGANISM: ARTIFICIAL SEQUENCE
<220> FEATURE:
<223> OTHER INFORMATION: Synthetic construct

<400> SEQUENCE: 161
ttcctgacac agacagacta ccagggaatg aagagc                                  36

<210> SEQ ID NO 162
<211> LENGTH: 30
<212> TYPE: DNA
<213> ORGANISM: ARTIFICIAL SEQUENCE
<220> FEATURE:
<223> OTHER INFORMATION: Synthetic construct

<400> SEQUENCE: 162
ttcctgacac agacagacta cacgaagagc                                         30

<210> SEQ ID NO 163
<211> LENGTH: 32
<212> TYPE: DNA
<213> ORGANISM: ARTIFICIAL SEQUENCE
<220> FEATURE:
<223> OTHER INFORMATION: Synthetic construct

<400> SEQUENCE: 163
ttcctgacac agacagacag ggaatgaaga gc                                      32

<210> SEQ ID NO 164

```
<211> LENGTH: 21
<212> TYPE: RNA
<213> ORGANISM: Artificial sequence
<220> FEATURE:
<223> OTHER INFORMATION: Synthetic construct

<400> SEQUENCE: 164
caccucuuca gacggcaaug a                                         21

<210> SEQ ID NO 165
<211> LENGTH: 40
<212> TYPE: DNA
<213> ORGANISM: ARTIFICIAL SEQUENCE
<220> FEATURE:
<223> OTHER INFORMATION: Synthetic construct

<400> SEQUENCE: 165
atggtgcacc tgactcctga ggagaagtct gccgttactg                     40

<210> SEQ ID NO 166
<211> LENGTH: 37
<212> TYPE: DNA
<213> ORGANISM: ARTIFICIAL SEQUENCE
<220> FEATURE:
<223> OTHER INFORMATION: Synthetic construct

<400> SEQUENCE: 166
atggtgcacc tgactcctga gaagtctgcc gttactg                        37

<210> SEQ ID NO 167
<211> LENGTH: 39
<212> TYPE: DNA
<213> ORGANISM: ARTIFICIAL SEQUENCE
<220> FEATURE:
<223> OTHER INFORMATION: Synthetic construct

<400> SEQUENCE: 167
atggtgcacc tgactcctga gagaagtctg ccgttactg                      39

<210> SEQ ID NO 168
<211> LENGTH: 35
<212> TYPE: DNA
<213> ORGANISM: ARTIFICIAL SEQUENCE
<220> FEATURE:
<223> OTHER INFORMATION: Synthetic construct

<400> SEQUENCE: 168
atggtgcacc tgactcctga agtctgccgt tactg                          35

<210> SEQ ID NO 169
<211> LENGTH: 38
<212> TYPE: DNA
<213> ORGANISM: ARTIFICIAL SEQUENCE
<220> FEATURE:
<223> OTHER INFORMATION: Synthetic construct

<400> SEQUENCE: 169
atggtgcacc tgactcctgg agaagtctgc cgttactg                       38

<210> SEQ ID NO 170
<211> LENGTH: 34
<212> TYPE: DNA
<213> ORGANISM: ARTIFICIAL SEQUENCE
<220> FEATURE:
<223> OTHER INFORMATION: Synthetic construct
```

```
<400> SEQUENCE: 170
atggtgcacc tgactcctga gtctgccgtt actg                                34

<210> SEQ ID NO 171
<211> LENGTH: 28
<212> TYPE: DNA
<213> ORGANISM: ARTIFICIAL SEQUENCE
<220> FEATURE:
<223> OTHER INFORMATION: Synthetic construct

<400> SEQUENCE: 171
atggtgcacc tgactcctgc cgttactg                                       28

<210> SEQ ID NO 172
<211> LENGTH: 30
<212> TYPE: DNA
<213> ORGANISM: ARTIFICIAL SEQUENCE
<220> FEATURE:
<223> OTHER INFORMATION: Synthetic construct

<400> SEQUENCE: 172
atggtgcacc tgagaagtct gccgttactg                                     30

<210> SEQ ID NO 173
<211> LENGTH: 35
<212> TYPE: DNA
<213> ORGANISM: ARTIFICIAL SEQUENCE
<220> FEATURE:
<223> OTHER INFORMATION: Synthetic construct

<400> SEQUENCE: 173
atggtgcacc tgactcgaga agtctgccgt tactg                               35

<210> SEQ ID NO 174
<211> LENGTH: 35
<212> TYPE: DNA
<213> ORGANISM: ARTIFICIAL SEQUENCE
<220> FEATURE:
<223> OTHER INFORMATION: Synthetic construct

<400> SEQUENCE: 174
atggtgcacc tgactcctga ggtctgccgt tactg                               35

<210> SEQ ID NO 175
<211> LENGTH: 32
<212> TYPE: DNA
<213> ORGANISM: ARTIFICIAL SEQUENCE
<220> FEATURE:
<223> OTHER INFORMATION: Synthetic construct

<400> SEQUENCE: 175
atggtgcacc tgactcctga gtgccgttac tg                                  32

<210> SEQ ID NO 176
<211> LENGTH: 28
<212> TYPE: DNA
<213> ORGANISM: ARTIFICIAL SEQUENCE
<220> FEATURE:
<223> OTHER INFORMATION: Synthetic construct

<400> SEQUENCE: 176
agtcacaggc agacttctcc acggggag                                       28

<210> SEQ ID NO 177
```

```
<211> LENGTH: 21
<212> TYPE: RNA
<213> ORGANISM: Artificial sequence
<220> FEATURE:
<223> OTHER INFORMATION: Synthetic construct

<400> SEQUENCE: 177
aguaacggca gacuucucca c                                              21

<210> SEQ ID NO 178
<211> LENGTH: 62
<212> TYPE: DNA
<213> ORGANISM: ARTIFICIAL SEQUENCE
<220> FEATURE:
<223> OTHER INFORMATION: Synthetic construct

<400> SEQUENCE: 178
gacccaggtt cctgacacag acagactaca cccagggaat gaagagcaag cgccatgttg    60
aa                                                                   62

<210> SEQ ID NO 179
<211> LENGTH: 61
<212> TYPE: DNA
<213> ORGANISM: ARTIFICIAL SEQUENCE
<220> FEATURE:
<223> OTHER INFORMATION: Synthetic construct

<400> SEQUENCE: 179
gacccaggtt cctgacacag acagactaca ccagggaatg aagagcaagc gccatgttga    60
a                                                                    61

<210> SEQ ID NO 180
<211> LENGTH: 58
<212> TYPE: DNA
<213> ORGANISM: ARTIFICIAL SEQUENCE
<220> FEATURE:
<223> OTHER INFORMATION: Synthetic construct

<400> SEQUENCE: 180
gacccaggtt cctgacacag acagactaca gggaatgaag agcaagcgcc atgttgaa     58

<210> SEQ ID NO 181
<211> LENGTH: 60
<212> TYPE: DNA
<213> ORGANISM: ARTIFICIAL SEQUENCE
<220> FEATURE:
<223> OTHER INFORMATION: Synthetic construct

<400> SEQUENCE: 181
gacccaggtt cctgacacag acagactaca cagggaatga agagcaagcg ccatgttgaa   60

<210> SEQ ID NO 182
<211> LENGTH: 60
<212> TYPE: DNA
<213> ORGANISM: ARTIFICIAL SEQUENCE
<220> FEATURE:
<223> OTHER INFORMATION: Synthetic construct

<400> SEQUENCE: 182
gacccaggtt cctgacacag acagactacc cagggaatga agagcaagcg ccatgttgaa   60

<210> SEQ ID NO 183
<211> LENGTH: 60
<212> TYPE: DNA
<213> ORGANISM: ARTIFICIAL SEQUENCE
```

```
<220> FEATURE:
<223> OTHER INFORMATION: Synthetic construct

<400> SEQUENCE: 183
gacccaggtt cctgacacag acagactacc cagggaatga agagcaagcg ccatgttgaa        60

<210> SEQ ID NO 184
<211> LENGTH: 51
<212> TYPE: DNA
<213> ORGANISM: ARTIFICIAL SEQUENCE
<220> FEATURE:
<223> OTHER INFORMATION: Synthetic construct

<400> SEQUENCE: 184
gacccaggtt cctgacacag acagggaatg aagagcaagc gccatgttga a                 51

<210> SEQ ID NO 185
<211> LENGTH: 56
<212> TYPE: DNA
<213> ORGANISM: ARTIFICIAL SEQUENCE
<220> FEATURE:
<223> OTHER INFORMATION: Synthetic construct

<400> SEQUENCE: 185
gacccaggtt cctgacacag acagactaca caatgaagag caagcgccat gttgaa           56

<210> SEQ ID NO 186
<211> LENGTH: 53
<212> TYPE: DNA
<213> ORGANISM: ARTIFICIAL SEQUENCE
<220> FEATURE:
<223> OTHER INFORMATION: Synthetic construct

<400> SEQUENCE: 186
gacccaggtt cctgacacag acagactaca cgaagagcaa gcgccatgtt gaa              53

<210> SEQ ID NO 187
<211> LENGTH: 34
<212> TYPE: DNA
<213> ORGANISM: ARTIFICIAL SEQUENCE
<220> FEATURE:
<223> OTHER INFORMATION: Synthetic construct

<400> SEQUENCE: 187
gacccaggga atgaagagca agcgccatgt tgaa                                   34

<210> SEQ ID NO 188
<211> LENGTH: 54
<212> TYPE: DNA
<213> ORGANISM: ARTIFICIAL SEQUENCE
<220> FEATURE:
<223> OTHER INFORMATION: Synthetic construct

<400> SEQUENCE: 188
gacccaggtt cctgacacag gaaccaggga atgaagagca agcgccatgt tgaa             54

<210> SEQ ID NO 189
<211> LENGTH: 29
<212> TYPE: DNA
<213> ORGANISM: ARTIFICIAL SEQUENCE
<220> FEATURE:
<223> OTHER INFORMATION: Synthetic construct

<400> SEQUENCE: 189
actcctgagg agaagtctgc cgttactgc                                         29
```

<210> SEQ ID NO 190
<211> LENGTH: 21
<212> TYPE: RNA
<213> ORGANISM: Artificial sequence
<220> FEATURE:
<223> OTHER INFORMATION: synthetic construct

<400> SEQUENCE: 190
caccucuuca gacggcaaug a                                           21

<210> SEQ ID NO 191
<211> LENGTH: 29
<212> TYPE: DNA
<213> ORGANISM: ARTIFICIAL SEQUENCE
<220> FEATURE:
<223> OTHER INFORMATION: Synthetic construct

<400> SEQUENCE: 191
actcctgtgg agaagtctgc cgttactgc                                   29

<210> SEQ ID NO 192
<211> LENGTH: 80
<212> TYPE: DNA
<213> ORGANISM: ARTIFICIAL SEQUENCE
<220> FEATURE:
<223> OTHER INFORMATION: Synthetic construct

<400> SEQUENCE: 192
tgggtgaggg acccaggttc ctgacacaga cagactacac ccagggaatg aagagcaagc    60
gccatgttga agccatcatt                                               80

<210> SEQ ID NO 193
<211> LENGTH: 79
<212> TYPE: DNA
<213> ORGANISM: ARTIFICIAL SEQUENCE
<220> FEATURE:
<223> OTHER INFORMATION: Synthetic construct

<400> SEQUENCE: 193
tgggtgaggg acccaggttc ctgacacaga cagactacac cagggaatga agagcaagcg    60
ccatgttgaa gccatcatt                                                79

<210> SEQ ID NO 194
<211> LENGTH: 76
<212> TYPE: DNA
<213> ORGANISM: ARTIFICIAL SEQUENCE
<220> FEATURE:
<223> OTHER INFORMATION: Synthetic construct

<400> SEQUENCE: 194
tgggtgaggg acccaggttc ctgacacaga cagactacag ggaatgaaga gcaagcgcca    60
tgttgaagcc atcatt                                                   76

<210> SEQ ID NO 195
<211> LENGTH: 69
<212> TYPE: DNA
<213> ORGANISM: ARTIFICIAL SEQUENCE
<220> FEATURE:
<223> OTHER INFORMATION: Synthetic construct

<400> SEQUENCE: 195
tgggtgaggg acccaggttc ctgacacaga cagggaatga agagcaagcg ccatgttgaa    60
gccatcatt                                                           69

<210> SEQ ID NO 196
<211> LENGTH: 77
<212> TYPE: DNA
<213> ORGANISM: ARTIFICIAL SEQUENCE
<220> FEATURE:
<223> OTHER INFORMATION: Synthetic construct

<400> SEQUENCE: 196
tgggtgaggg acccaggttc ctgacacaga cagactacca gggaatgaag agcaagcgcc      60
atgttgaagc catcatt                                                    77

<210> SEQ ID NO 197
<211> LENGTH: 78
<212> TYPE: DNA
<213> ORGANISM: ARTIFICIAL SEQUENCE
<220> FEATURE:
<223> OTHER INFORMATION: Synthetic construct

<400> SEQUENCE: 197
tgggtgaggg acccaggttc ctgacacaga cagactacac agggaatgaa gagcaagcgc      60
catgttgaag ccatcatt                                                   78

<210> SEQ ID NO 198
<211> LENGTH: 62
<212> TYPE: DNA
<213> ORGANISM: ARTIFICIAL SEQUENCE
<220> FEATURE:
<223> OTHER INFORMATION: Synthetic construct

<400> SEQUENCE: 198
tgggtgaggg acccaggttc ctgacacaga cagactacaa gcgccatgtt gaagccatca      60
tt                                                                    62

<210> SEQ ID NO 199
<211> LENGTH: 83
<212> TYPE: DNA
<213> ORGANISM: ARTIFICIAL SEQUENCE
<220> FEATURE:
<223> OTHER INFORMATION: Synthetic construct

<400> SEQUENCE: 199
tgggtgaggg acccaggttc ctgacacaga cagactacta cagacaggga atgaagagca      60
agcgccatgt tgaagccatc att                                             83

<210> SEQ ID NO 200
<211> LENGTH: 73
<212> TYPE: DNA
<213> ORGANISM: ARTIFICIAL SEQUENCE
<220> FEATURE:
<223> OTHER INFORMATION: Synthetic construct

<400> SEQUENCE: 200
tgggtgaggg acccaggttc ctgacacaga cagacaggga atgaagagca agcgccatgt      60
tgaagccatc att                                                        73

<210> SEQ ID NO 201
<211> LENGTH: 91
<212> TYPE: DNA
<213> ORGANISM: ARTIFICIAL SEQUENCE
<220> FEATURE:
<223> OTHER INFORMATION: Synthetic construct

<400> SEQUENCE: 201
tgggtgaggg acccaggttc ctgacacaga cagactacac agggaatgaa gacagggaat       60
gaagagcaag cgccatgttg aagccatcat t                                     91

<210> SEQ ID NO 202
<211> LENGTH: 61
<212> TYPE: DNA
<213> ORGANISM: ARTIFICIAL SEQUENCE
<220> FEATURE:
<223> OTHER INFORMATION: Synthetic construct

<400> SEQUENCE: 202
acccaggttc ctgacacaga cagactacac ccagggaatg aagagcaagc gccatgttga       60
a                                                                      61

<210> SEQ ID NO 203
<211> LENGTH: 60
<212> TYPE: DNA
<213> ORGANISM: ARTIFICIAL SEQUENCE
<220> FEATURE:
<223> OTHER INFORMATION: Synthetic construct

<400> SEQUENCE: 203
acccaggttc ctgacacaga cagactacac cagggaatga agagcaagcg ccatgttgaa       60

<210> SEQ ID NO 204
<211> LENGTH: 57
<212> TYPE: DNA
<213> ORGANISM: ARTIFICIAL SEQUENCE
<220> FEATURE:
<223> OTHER INFORMATION: Synthetic construct

<400> SEQUENCE: 204
acccaggttc ctgacacaga cagactacag ggaatgaaga gcaagcgcca tgttgaa         57

<210> SEQ ID NO 205
<211> LENGTH: 59
<212> TYPE: DNA
<213> ORGANISM: ARTIFICIAL SEQUENCE
<220> FEATURE:
<223> OTHER INFORMATION: Synthetic construct

<400> SEQUENCE: 205
acccaggttc ctgacacaga cagactacac agggaatgaa gagcaagcgc catgttgaa       59

<210> SEQ ID NO 206
<211> LENGTH: 50
<212> TYPE: DNA
<213> ORGANISM: ARTIFICIAL SEQUENCE
<220> FEATURE:
<223> OTHER INFORMATION: Synthetic construct

<400> SEQUENCE: 206
acccaggttc ctgacacaga cagggaatga agagcaagcg ccatgttgaa                 50

<210> SEQ ID NO 207
<211> LENGTH: 58
<212> TYPE: DNA
<213> ORGANISM: ARTIFICIAL SEQUENCE
<220> FEATURE:
<223> OTHER INFORMATION: Synthetic construct

<400> SEQUENCE: 207
acccaggttc ctgacacaga cagactacca gggaatgaag agcaagcgcc atgttgaa        58

<210> SEQ ID NO 208
<211> LENGTH: 52
<212> TYPE: DNA
<213> ORGANISM: ARTIFICIAL SEQUENCE
<220> FEATURE:
<223> OTHER INFORMATION: Synthetic construct

<400> SEQUENCE: 208
acccaggttc ctgacacaga cagactacac gaagagcaag cgccatgttg aa                52

<210> SEQ ID NO 209
<211> LENGTH: 59
<212> TYPE: DNA
<213> ORGANISM: ARTIFICIAL SEQUENCE
<220> FEATURE:
<223> OTHER INFORMATION: Synthetic construct

<400> SEQUENCE: 209
acccaggttc ctgacacaga cagactaccc agggaatgaa gagcaagcgc catgttgaa         59

<210> SEQ ID NO 210
<211> LENGTH: 61
<212> TYPE: DNA
<213> ORGANISM: ARTIFICIAL SEQUENCE
<220> FEATURE:
<223> OTHER INFORMATION: Synthetic construct

<400> SEQUENCE: 210
acccaggttc ctgccaccat gctcaaacct tccctgcctt ttaccagctt gctgtttctc        60
c                                                                        61

<210> SEQ ID NO 211
<211> LENGTH: 19
<212> TYPE: RNA
<213> ORGANISM: Artificial sequence
<220> FEATURE:
<223> OTHER INFORMATION: Synthetic construct

<400> SEQUENCE: 211
acaugaggau cacccaugu                                                     19

<210> SEQ ID NO 212
<211> LENGTH: 93
<212> TYPE: RNA
<213> ORGANISM: Artificial sequence
<220> FEATURE:
<223> OTHER INFORMATION: synthetic construct
<220> FEATURE:
<221> NAME/KEY: misc_feature
<222> LOCATION: (1)..(8)
<223> OTHER INFORMATION: n is a, c, g, or u

<400> SEQUENCE: 212
nnnnnnnngu uuaaguacuc uggaaacaga aucuacuuaa acaaaggcaa aaugccgugu        60
uuaucucguc aacuuguuuu uuuagagcgg uug                                     93

<210> SEQ ID NO 213
<211> LENGTH: 34
<212> TYPE: RNA
<213> ORGANISM: Artificial sequence
<220> FEATURE:
<223> OTHER INFORMATION: synthetic construct

```
<400> SEQUENCE: 213
ggccaacaug aggaucaccc augucugcag ggcc                          34

<210> SEQ ID NO 214
<211> LENGTH: 34
<212> TYPE: RNA
<213> ORGANISM: Artificial sequence
<220> FEATURE:
<223> OTHER INFORMATION: Synthetic construct

<400> SEQUENCE: 214
ggccaacaug aggaucaccc augucugcag ggcc                          34

<210> SEQ ID NO 215
<211> LENGTH: 91
<212> TYPE: RNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(8)
<223> OTHER INFORMATION: n is a, c, g, or u

<400> SEQUENCE: 215
nnnnnnnngu uuaaguacuc uggaaacaga aucuacuuaa acaaggcaaa augccuguu    60 uaucucguca acuuguuggc gagauuuuuu u                                 91

<210> SEQ ID NO 216
<211> LENGTH: 34
<212> TYPE: RNA
<213> ORGANISM: Artificial sequence
<220> FEATURE:
<223> OTHER INFORMATION: synthetic construct

<400> SEQUENCE: 216
ggccaacaug aggaucaccc augucugcag ggcc                          34

<210> SEQ ID NO 217
<211> LENGTH: 23
<212> TYPE: RNA
<213> ORGANISM: Artificial sequence
<220> FEATURE:
<223> OTHER INFORMATION: synthetic construct

<400> SEQUENCE: 217
cugaaugccu gcgagcaucc cac                                      23

<210> SEQ ID NO 218
<211> LENGTH: 25
<212> TYPE: RNA
<213> ORGANISM: Artificial sequence
<220> FEATURE:
<223> OTHER INFORMATION: synthetic construct

<400> SEQUENCE: 218
ggagcagacg auauggcguc gcucc                                    25

<210> SEQ ID NO 219
<211> LENGTH: 19
<212> TYPE: RNA
<213> ORGANISM: Artificial sequence
<220> FEATURE:
<223> OTHER INFORMATION: Synthetic construct
```

```
<400> SEQUENCE: 219
gggcccugaa gaagggccc                                              19
```